United States Patent [19]

Luciw et al.

[11] Patent Number: 5,156,949
[45] Date of Patent: Oct. 20, 1992

[54] IMMUNOASSAYS FOR ANTIBODY TO HUMAN IMMUNODEFICIENCY VIRUS USING RECOMBINANT ANTIGENS

[75] Inventors: Paul A. Luciw, Davis; Dino Dina, San Francisco, both of Calif.

[73] Assignee: Chiron Corporation, Emeryville, Calif.

[21] Appl. No.: 138,894

[22] Filed: Dec. 24, 1987

Related U.S. Application Data

[63] Continuation-in-part of Ser. No. 773,447, Sep. 6, 1985, abandoned, which is a continuation-in-part of Ser. No. 696,534, Jan. 30, 1985, abandoned, which is a continuation-in-part of Ser. No. 667,501, Oct. 31, 1984, abandoned.

[51] Int. Cl.$^5$ ............... G01N 33/53; C12P 21/06; C12N 15/00; C12N 1/20
[52] U.S. Cl. .................. 435/5; 435/7.2; 435/69.1; 435/172.3; 435/252.33; 435/810; 435/820; 435/974; 935/60; 935/66; 935/69; 935/71
[58] Field of Search ............ 435/5, 7, 68, 172.3, 435/235–239, 810, 820, 948, 69.1, 974; 935/60, 81, 66, 69, 71

[56] References Cited

U.S. PATENT DOCUMENTS

| | | |
|---|---|---|
| 4,520,113 | 5/1985 | Gallo et al. |
| 4,708,818 | 11/1987 | Montagnier .............. 435/5 |
| 4,716,102 | 12/1987 | Levy ........................ 435/5 |
| 4,725,669 | 2/1988 | Essex et al. ............. 530/395 |
| 4,751,180 | 6/1988 | Cousens et al. .......... 435/255 |

FOREIGN PATENT DOCUMENTS

| | | |
|---|---|---|
| 136798 | 4/1985 | European Pat. Off. |
| 138667 | 4/1985 | European Pat. Off. |
| 0139216 | 5/1985 | European Pat. Off. |
| 0152030 | 8/1985 | European Pat. Off. |
| 165120 | 12/1985 | European Pat. Off. |
| 173529 | 3/1986 | European Pat. Off. |
| 178978 | 4/1986 | European Pat. Off. |
| 181150 | 5/1986 | European Pat. Off. |
| 185444 | 6/1986 | European Pat. Off. |
| 8504897 | 11/1985 | PCT Int'l Appl. |
| 8504903 | 11/1985 | PCT Int'l Appl. |
| 8602383 | 4/1986 | World Int. Prop. O. |

OTHER PUBLICATIONS

Wain-Hobson, S. *AIDS* 3(Suppl 1): S13–S18 (1989).
Fenyo, E. M. et al. *AIDS* 3(Suppl 1):S5–S12 (1989).
Meyerhans, A. et al. *Cell* 58:901–910 (Sep. 8, 1989).
Popovic et al., Science 24:497–500 (May 4, 1984).
Barre-Sinoussi et al., May 20 (1983) Science 220:868–871.
Saxinger et al., (1983) Laboratory Investigation 49:371–377.
Gallo et al., (May 4, 1984) Science 224:497–504.
Schupbach et al., (May 4, 1984) Science 224:607–609.
Sarngadharan et al., (May 4, 1984) Science 224:506–508.
Safai et al., (Jun. 30, 1984) Lancet, pp. 1438–1440.
Shaw et al. in *AIDS: Papers from Science, 1982–1985*, pp. 356–268 (R. Kulstad ed. 1986).
Looney et al., Science 241:357–359 (1988).
Culliton in *AIDS: Papers from Science, 1982–1985*, pp. 266–277 (R. Kulstad ed. 1986).
Gurgo et al., Virology 164:531–536.

(List continued on next page.)

Primary Examiner—Christine M. Nucker
Assistant Examiner—M. P. Woodward
Attorney, Agent, or Firm—Robert P. Blackburn; Barbara G. McClung; Debra A. Shetka

[57] ABSTRACT

Polynucleotide sequences are provided for the diagnosis of the presence of retroviral infection in a human host associated with lymphadenopathy syndrome and/or acquired immune deficiency syndrome, for expression of polypeptides and use of the polypeptides to prepare antibodies, where both the polypeptides and antibodies may be employed as diagnostic reagents or in therapy, e.g., vaccines and passive immunization. The sequences provide detection of the viral infectious agents associated with the indicated syndromes and can be used for expression of antigenic polypeptides.

22 Claims, 59 Drawing Sheets

OTHER PUBLICATIONS

Montagnier et al., (Jul. 6, 1984) Science 225:63–66.
Kalyanaraman et al., (Jul. 20, 1984) Science 224:321–323.
Levy et al., (Aug. 24, 1984) Science 225:840–842.
Melbye et al., (Sep. 8, 1984) British Medical Journal 289:573–575.
Ho et al., (Oct. 1984) Science 226:451–453.
Shoeman et al, "Comparison of Recombinant Human Immunodeficiency Virus gag Precursor and gag/env Fusion Proteins and a Synthetic env Peptide as Diagnostic Reagents", Anal. Biochem. 161 (1987) 370–379.
Feorino, et al, Science (Jul. 6, 1984) 225:69–72.
Montagomier, et al., Human T-cell Leukemia/lymphoma Virus Cold Spring Harbor Conference Sep. 14–16, 1983 (1984) 363–379.
Vilmer, et al, *Lancet* (Apr. 7, 1984) 1:753.
Gallo, et al, *Science* (May 4, 1984) 224:500.
Klatzmann, et al, *Science* (Jul. 6, 1984) 225:59–62.
Marx, *Science* (May 4, 1984) 224:475–477.
Levy, et al, *Science* (Aug. 24, 1984) 225:840–842.
Sinkovics, et al, *Reviews of Infectious Diseases* (Sep.–Oct. 1984) 6:745–760.
Fauci, et al, *Annals of Internal Medicine* (1984) 100:92–106, Conference held Jun. 23, 1983 in U.S.
Lee, et al, *Science* (Oct. 5, 1984) 226:57–61.
Arya, et al, *Science* (Aug. 31, 1984) 225:927–930.
Samuel, et al, *Science* (Nov. 30, 1984) 226:1094–1097.
Shaw, et al, *Science* (Dec. 7, 1984) 226:1165–1171.
Klatzmann, et al, *Nature* (Dec. 20/27 1984) 312:767–768.
Alizon, et al, *Nature* (Dec. 20/27 1984) 312:757–760.
Leciw, et al, *Nature* (Dec. 20/27 1984) 312:760–763.
Sanchez-Pescador, et al, *Science* (Feb. 1, 1985) 227:484–492.
Chang, et al, *Nature* (May 9, 1985) 315:151–154.
Crowl, R., et al, *Cell* (Jul. 1985) 41:979–986.

```
Argument Map in DNA Strand ssarv2
from the '/v/lib/6mers'file.
Translation shown at open reading frames.

_!!___!___!_____!!_____ !!_!!_____!_!_____!_____!_!!
  mboll-1  mboll-1              bglll    narl         xmnl   pstl
   binI       aval-2             sacl     sacl               binI
    binI      scal                aflll                       mboll-1
    ecor5                         hindlll ___!!!_!_____!!____!___!_!_____!____!___!_!_____!_
   hindlll  ahalll   pstl       bstXI    ahalll       apal
   mboll-1  ava3 ahalll            hindlll            avr2
            mboll-1  sphl                 mboll-1
    mboll-1
     pvull
     pstl
     pvull
     tthIII1-2

___!_!_!_____!!_____!!_!__!!_____!_____!____!!!__
   mboll-2      mboll-1    mboll-1       scal     ava3   tthIII1-2
    mboll-1     bstXI      ahalll                        ecor5
   mboll-1                 tthIII1-2                     bstXI
   bglll                   ball                          binI
                           mboll-1

___!__!___!___!_____!_____!___!__!_____!_____!__!___!_
     bstXI      mboll-1 ahalll       kpnl  mboll-1
   binI    pvull              hpal               mboll-1
     tthIII1-2                 ahalll                    ava3

____!___!_!_____!_!_!_!___!__!!_!_!_____!_!_____!___!____
    kpnl mboll-1 bstXI  mboll-1    aflll     hindlll
     scal    pvull  xmnl scal         ahalll          mboll-1
             ava3        ball
              xbal        binI
```

FIG. 4A

```
_!__!!_!_____!__!_____!__!_!____!____!!_!___!__!!_!____
 ndeI  avr2         avr2       mboII-1  ecorI   avr2    mboII-1
   scaI                binI       afIII          mboII-1  mboII-1
                                    avr2          xbaI     sacI
                                    ncoI                mluI  hindIII
                                                         mstII _!____!_____!_____!__!__!_____!__!_____!!_!__
 scaI              ndeI    binI  mboII-1   stuI         mboII-1
  mboII-1                   ahaIII   scaI                mboII-1
                                                          bgIII
                                                           pvuII ___!_____!_____!_____!_____!!_____!____
 mboII-1              mboII-2           mstII
    mstII               mboII-1          binI
                                         avr2
                                               mboII-1

!_____!!!___!!_____!_____!_____!_!____!_!__!_!_!_
 mboII-1    avaI-2      pstI      mboII-1  avaI-1    ahaIII
             mboII-1                        tthIII1-2  mboII-1
              mboII-1                        xhoI   mstII  binI
                mboII-1                              mboII-1
                  bgIII                                kpnI
                  mboII-2

_!!__!_____!!_____!__!!!!_____
 ecor5   avaI-2  pvuII
   mboII-1        bgIII
            scaI   sacI
 binI              afIII
                    hindIII
```

FIG. 4B

1 CTGGAAGGGCTAATTTGGTCCCAAAGAAGACAAGAGATCCTTGATCTGTGGATCTACCACAC
  GACCTTCCCGATTAAACCAGGGTTTCTTCTGTTCTCTAGGAACTAGACACCTAGATGGTGTG 26 mboII, 50 binI, 63 ACAAGGCTACTTCCCTGATTGGCAGAATTACACACCAGGGCCAGGGATCAGATATCCACT
   TGTTCCGATGAAGGGACTAACCGTCTTAATGTGTGGTCCCGGTCCCTAGTCTATAGGTGA 107 binI, 113 ecor5, 123 GACCTTTGGATGGTGCTTCAAGCTAGTACCAGTTGAGCCAGAGAAGGTAGAAGAGGCCAA
    CTGGAAACCTACCACGAAGTTCGATCATGGTCAACTCGGTCTCTTCCATCTTCTCCGGTT 172 mboII, 183 TGAAGGAGAGAACAACAGCTTGTTACACCCTATGAGCCTGCATGGGATGGAGGACGCGGA
    ACTTCCTCTCTTGTTGTCGAACAATGTGGGATACTCGGACGTACCCTACCTCCTGCGCCT 243 GAAAGAAGTGTTAGTGTGGAGGTTTGACAGCAAACTAGCATTTCATCACATGGCCCGAGA
    CTTTCTTCACAATCACACCTCCAAACTGTCGTTTGATCGTAAAGTAGTGTACCGGGCTCT 296 avaI, 303 GCTGCATCCGGAGTACTACAAAGACTGCTGACATCGAGCTTTCTACAAGGGACTTTCCGC
    CGACGTAGGCCTCATGATGTTTCTGACGACTGTAGCTCGAAAGATGTTCCCTGAAAGGCG 314 scaI, 363 TGGGGACTTTCCAGGGAGGCGTGGCCTGGGCGGGACTGGGGAGTGGCGTCCCTCAGATGC
    ACCCCTGAAAGGTCCCTCCGCACCGGACCCGCCCTGACCCCTCACCGCAGGGAGTCTACG 423 TGCATATAAGCAGACTGCTTTTTGCCTGTACTGGGTCTCTCTGGTTAGACCAGATCTGAG
    ACGTATATTCGTCTGACGAAAAACGGACATGACCCAGAGAGACCAATCTGGTCTAGACTC 474 bglII, 483 CCTGGGAGCTCTCTGGCTAACTAGGGAACCCACTGCTTAAGCCTCAATAAAGCTTGCCTT
    GGACCCTCGAGAGACCGATTGATCCCTTGGGTGACGAATTCGGAGTTATTTCGAACGGAA 488 sacI, 518 aflII, 532 hindIII, 543 GAGTGCTTCAAGTAGTGTGTGCCCGTCTGTTGTGTGACTCTGGTAACTAGAGATCCCTCA
    CTCACGAAGTTCATCACACACGGGCAGACAACACACTGAGACCATTGATCTCTAGGGAGT 603 GACCCTTTTAGTCAGTGTGGAAAAATCTCTAGCAGTGGCGCCCGAACAGGGACGCGAAAG
    CTGGGAAAATCAGTCACACCTTTTTAGAGATCGTCACCGCGGGCTTGTCCCTGCGCTTTC 639 narI, 663 CGAAAGTAGAACCAGAGGAGCTCTCTCGACGCAGGACTCGGCTTGCTGAAGCGCGCACAG
    GCTTTCATCTTGGTCTCCTCGAGAGAGCTGCGTCCTGAGCCGAACGACTTCGCGCGTGTC 680 sacI, 723 CAAGAGGCGAGGGGCGGCGACTGGTGAGTACGCCAATTTTTGACTAGCGGAGGCTAGAAG
    GTTCTCCGCTCCCCGCCGCTGACCACTCATGCGGTTAAAAACTGATCGCCTCCGATCTTC MetGlyAlaArgAlaSerValLeuSerGlyGlyGluLeuAspLysTrpGlu |GAG
783 GAGAGAGAGATGGGTGCGAGAGCGTCGGTATTAAGCGGGGAGAATTAGATAAATGGGAA
    CTCTCTCTCTACCCACGCTCTCGCAGCCATAATTCGCCCCTCTTAATCTATTTACCCTT

FIG. 4C

```
       LysIleArgLeuArgProGlyGlyLysLysLysTyrLysLeuLysHisIleValTrpAla
 843   AAAATTCGGTTAAGGCCAGGGGGAAAGAAAAAATATAAGTTAAAACATATAGTATGGGCA
       TTTTAAGCCAATTCCGGTCCCCCTTTCTTTTTTATATTCAATTTTGTATATCATACCCGT

SerArgGluLeuGluArgPheAlaValAsnProGlyLeuLeuGluThrSerGluGlyCys
 903   AGCAGGGAGCTAGAACGATTCGCAGTCAATCCTGGCCTGTTAGAAACATCAGAAGGCTGC
       TCGTCCCTCGATCTTGCTAAGCGTCAGTTAGGACCGGACAATCTTTGTAGTCTTCCGACG
                                                                 ^
       959 pst1, ArgGlnIleLeuGlyGlnLeuGlnProSerLeuGlnThrGlySerGluGluLeuArgSer
 963   AGACAAATATTGGGACAGCTACAGCCATCCCTTCAGACAGGATCAGAAGAACTTAGATCA
       TCTGTTTATAACCCTGTCGATGTCGGTAGGGAAGTCTGTCCTAGTCTTCTTGAATCTAGT
                                            ^          ^
       1002 binI, 1008 mboII, LeuTyrAsnThrValAlaThrLeuTyrCysValHisGlnArgIleAspValLysAspThr
1023   TTATATAATACAGTAGCAACCCTCTATTGTGTACATCAAAGGATAGATGTAAAAGACACC
       AATATATTATGTCATCGTTGGGAGATAACACATGTAGTTTCCTATCTACATTTTCTGTGG LysGluAlaLeuGluLysIleGluGluGluGlnAsnLysSerLysLysLysAlaGlnGln
1083   AAGGAAGCTTTAGAGAAGATAGAGGAAGAGCAAAACAAAAGTAAGAAAAAGGCACAGCAA
       TTCCTTCGAAATCTCTTCTATCTCCTTCTCGTTTTGTTTTCATTCTTTTTCCGTGTCGTT
                 ^      ^                       ^                               p25
       1087 hindIII, 1097 mboII, 1107 mboII, AlaAlaAlaAlaAlaGlyThrGlyAsnSerSerGlnValSerGlnAsnTyrProIleVal
1143   GCAGCAGCTGCAGCTGGCACAGGAAACAGCAGCCAGGTCAGCCAAAATTACCCTATAGTG
       CGTCGTCGACGTCGACCGTGTCCTTTGTCGTCGGTCCAGTCGGTTTTAATGGGATATCAC
            ^  ^  ^                ^
       1147 pvuII, 1150 pst1, 1153 pvuII, 1156 tthIII1, GlnAsnLeuGlnGlyGlnMetValHisGlnAlaIleSerProArgThrLeuAsnAlaTrp
1203   CAGAACCTACAGGGGCAAATGGTACATCAGGCCATATCACCTAGAACTTTAAATGCATGG
       GTCTTGGATGTCCCCGTTTACCATGTAGTCCGGTATAGTGGATCTTGAAATTTACGTACC
                                                  ^       ^
       1250 ahaIII, 1255 ava3, ValLysValValGluGluLysAlaPheSerProGluValIleProMetPheSerAlaLeu
1263   GTAAAAGTAGTAGAAGAAAAGGCTTTCAGCCCAGAAGTAATACCCATGTTTTCAGCATTA
       CATTTTCATCATCTTCTTTTCCGAAAGTCGGGTCTTCATTATGGGTACAAAAGTCGTAAT
                     ^
       1275 mboII, SerGluGlyAlaThrProGlnAspLeuAsnThrMetLeuAsnThrValGlyGlyHisGln
1323   TCAGAAGGAGCCACCCCACAAGATTTAAACACCATGCTAAACACAGTGGGGGGACATCAA
       AGTCTTCCTCGGTGGGGTGTTCTAAATTTGTGGTACGATTTGTGTCACCCCCCTGTAGTT
                                ^
       1346 ahaIII, AlaAlaMetGlnMetLeuLysGluThrIleAsnGluGluAlaAlaGluTrpAspArgVal
1383   GCAGCCATGCAAATGTTAAAAGAGACTATCAATGAGGAAGCTGCAGAATGGGATAGAGTG
       CGTCGGTACGTTTACAATTTTCTCTGATAGTTACTCCTTCGACGTCTTACCCTATCTCAC
                                                      ^
       1423 pst1, HisProValHisAlaGlyProIleAlaProGlyGlnMetArgGluProArgGlySerAsp
1443   CATCCAGTGCATGCAGGGCCTATTGCACCAGGCCAAATGAGAGAACCAAGGGGAAGTGAC
       GTAGGTCACGTACGTCCCGGATAACGTGGTCCGGTTTACTCTCTTGGTTCCCCTTCACTG
                    ^
       1451 sph1,
```

FIG. 4D

```
       IleAlaGlyThrThrSerThrLeuGlnGluGlnIleGlyTrpMetThrAsnAsnProPro
1503   ATAGCAGGAACTACTAGTACCCTTCAGGAACAAATAGGATGGATGACAAATAATCCACCT
       TATCGTCCTTGATGATCATGGGAAGTCCTTGTTTATCCTACCTACTGTTTATTAGGTGGA

IleProValGlyGluIleTyrLysArgTrpIleIleLeuGlyLeuAsnLysIleValArg
1563   ATCCCAGTAGGAGAAATCTATAAAAGATGGATAATCCTGGGATTAAATAAAATAGTAAGA
       TAGGGTCATCCTCTTTAGATATTTTCTACCTATTAGGACCCTAATTTATTTTATCATTCT

MetTyrSerProThrSerIleLeuAspIleArgGlnGlyProLysGluProPheArgAsp
1623   ATGTATAGCCCTACCAGCATTCTGGACATAAGACAAGGACCAAAGGAACCCTTTAGAGAT
       TACATATCGGGATGGTCGTAAGACCTGTATTCTGTTCCTGGTTTCCTTGGGAAATCTCTA
                                   ^
       1636 bstXI, TyrValAspArgPheTyrLysThrLeuArgAlaGluGlnAlaSerGlnAspValLysAsn
1683   TATGTAGACCGGTTCTATAAAACTCTAAGAGCCGAACAAGCTTCACAGGATGTAAAAAAT
       ATACATCTGGCCAAGATATTTTGAGATTCTCGGCTTGTTCGAAGTGTCCTACATTTTTTA
                                          ^
       1720 hindIII, TrpMetThrGluThrLeuLeuValGlnAsnAlaAsnProAspCysLysThrIleLeuLys
1743   TGGATGACAGAAACCTTGTTGGTCCAAAATGCAAACCCAGATTGTAAGACTATTTTAAAA
       ACCTACTGTCTTTGGAACAACCAGGTTTTACGTTTGGGTCTAACATTCTGATAAAATTTT
                                                              ^
       1796 ahaIII, AlaLeuGlyProAlaAlaThrLeuGluGluMetMetThrAlaCysGlnGlyValGlyGly
1803   GCATTGGGACCAGCAGCTACACTAGAAGAAATGATGACAGCATGTCAGGGAGTGGGGGGA
       CGTAACCCTGGTCGTCGATGTGATCTTCTTTACTACTGTCGTACAGTCCCTCACCCCCCT
                                    ^
       1827 mboII, ProGlyHisLysAlaArgValLeuAlaGluAlaMetSerGlnValThrAsnProAlaAsn
1863   CCCGGCCATAAAGCAAGAGTTTTGGCTGAAGCCATGAGCCAAGTAACAAATCCAGCTAAC
       GGGCCGGTATTTCGTTCTCAAAACCGACTTCGGTACTCGGTTCATTGTTTAGGTCGATTG
                          p18
       IleMetMetGlnArgGlyAsnPheArgAsnGlnArgLysThrValLysCysPheAsnCys
1923   ATAATGATGCAGAGAGGCAATTTTAGGAACCAAAGAAAGACTGTTAAGTGTTTCAATTGT
       TATTACTACGTCTCTCCGTTAAAATCCTTGGTTTCTTTCTGACAATTCACAAAGTTAACA GlyLysGluGlyHisIleAlaLysAsnCysArgAlaProArgLysLysGlyCysTrpArg
1983   GGCAAAGAAGGGCACATAGCCAAAAATTGCAGGGCCCCTAGGAAAAAGGGCTGTTGGAGA
       CCGTTTCTTCCCGTGTATCGGTTTTTAACGTCCCGGGGATCCTTTTTCCCGACAACCTCT
                                        ^         ^
       2014 apaI, 2019 avr2, CysGlyArgGluGlyHisGlnMetLysAspCysThrGluArgGlnAlaAsnPheLeuGly
2043   TGTGGAAGGGAAGGACACCAAATGAAAGATTGCACTGAGAGACAGGCTAATTTTTTAGGG
       ACACCTTCCCTTCCTGTGGTTTACTTTCTAACGTGACTCTCTGTCCGATTAAAAAATCCC
                                                              ^
       2102 mboII, LysIleTrpProSerTyrLysGlyArgProGlyAsnPheLeuGlnSerArgProGluPro
2103   AAGATCTGGCCTTCCTACAAGGGAAGGCCAGGGAATTTTCTTCAGAGCAGACCAGAGCCA
       TTCTAGACCGGAAGGATGTTCCCTTCCGGTCCCTTAAAAGAAGTCTCGTCTGGTCTCGGT
         ^                                ^
       2104 bgIII, 2141 mboII,
```

FIG. 4E

```
      ThrAlaProProGluGluSerPheArgPheGlyGluGluLysThrThrProSerGlnLys
2163  ACAGCCCCACCAGAAGAGAGCTTCAGGTTTGGGGAGGAGAAAACAACTCCCTCTCAGAAG
      TGTCGGGGTGGTCTTCTCTCGAAGTCCAAACCCCTCCTCTTTTGTTGAGGGAGAGTCTTC
                   ^
      2175 mboII, GlnGluProIleAspLysGluLeuTyrProLeuThrSerLeuArgSerLeuPheGlyAsn
2223  CAGGAGCCGATAGACAAGGAACTGTATCCTTTAACTTCCCTCAGATCACTCTTTGGCAAC
      GTCCTCGGCTATCTGTTCCTTGACATAGGAAATTGAAGGGAGTCTAGTGAGAAACCGTTG AspProSerSerGlnOC
2283  GACCCCTCGTCACAATAAGGATAGGGGGGCAACTAAAGGAAGCTCTATTAGATACAGGA
      CTGGGGAGCAGTGTTATTCCTATCCCCCGTTGATTTCCTTCGAGATAATCTATGTCCT MetAsnLeuProGlyLysTrpLysProLysMetIle
2342  GCAGATGATACAGTATTAGAAGAAATGAATTTGCCAGGAAAATGGAAACCAAAAATGATA
      CGTCTACTATGTCATAATCTTCTTTACTTAAACGGTCCTTTTACCTTTGGTTTTTACTAT
                       ^                                ^
      2360 mboII,  2375 bstXI, GlyGlyIleGlyGlyPheIleLysValArgGlnTyrAspGlnIleProValGluIleCys
2402  GGGGGAATTGGAGGTTTTATCAAAGTAAGACAGTACGATCAGATACCTGTAGAAATCTGT
      CCCCCTTAACCTCCAAAATAGTTTCATTCTGTCATGCTAGTCTATGGACATCTTTAGACA GlyHisLysAlaIleGlyThrValLeuValGlyProThrProValAsnIleIleGlyArg
2462  GGACATAAAGCTATAGGTACAGTATTAGTAGGACCTACACCTGTCAACATAATTGGAAGA
      CCTGTATTTCGATATCCATGTCATAATCATCCTGGATGTGGACAGTTGTATTAACCTTCT
                                                           ^
      2517 mboII, AsnLeuLeuThrGlnIleGlyCysThrLeuAsnPheProIleSerProIleGluThrVal
2522  AATCTGTTGACTCAGATTGGTTGTACTTTAAATTTCCCCATTAGTCCTATTGAAACTGTA
      TTAGACAACTGAGTCTAACCAACATGAAATTTAAAGGGGTAATCAGGATAACTTTGACAT
                    ^                                ^
      2548 ahaIII,  2577 tthIII1, ProValLysLeuLysProGlyMetAspGlyProLysValLysGlnTrpProLeuThrGlu
2582  CCAGTAAAATTAAAGCCAGGAATGGATGGCCCAAAAGTTAAGCAATGGCCATTGACAGAA
      GGTCATTTTAATTTCGGTCCTTACCTACCGGGTTTTCAATTCGTTACCGGTAACTGTCTT
                                ^             ^
      2627 baII,  2639 mboII, GluLysIleLysAlaLeuValGluIleCysThrGluMetGluLysGluGlyLysIleSer
2642  GAAAAAATAAAAGCATTAGTAGAGATATGTACAGAAATGGAAAAGGAAGGGAAAATTTCA
      CTTTTTTATTTTCGTAATCATCTCTATACATGTCTTTACCTTTTCCTTCCCTTTTAAAGT LysIleGlyProGluAsnProTyrAsnThrProValPheAlaIleLysLysLysAspSer
2702  AAAATTGGGCCTGAAAATCCATACAATACTCCAGTATTTGCTATAAAGAAAAAGACAGT
      TTTTAACCCGGACTTTTAGGTATGTTATGAGGTCATAAACGATATTTCTTTTTTCTGTCA
                                                              ^
      2759 scaI, ThrLysTrpArgLysLeuValAspPheArgGluLeuAsnLysArgThrGlnAspPheTrp
2762  ACTAAATGGAGAAAACTAGTAGATTTCAGAGAACTTAATAAAAGAACTCAAGACTTCTGG
      TGATTTACCTCTTTTGATCATCTAAAGTCTCTTGAATTATTTTCTTGAGTTCTGAAGACC GluValGlnLeuGlyIleProHisProGlnGlyOC
2822  GAAGTTCAGTTAGGAATACCACACCCGCAGGGTTAAAAAAGAAAAAATCAGTAACAGTA
      CTTCAAGTCAATCCTTATGGTGTGGGCGTCCCAATTTTTTTCTTTTTAGTCATTGTCAT
```

FIG. 4F

2882 TTGGATGTGGGTGATGCATACTTTTCAGTTCCCTTAGATAAAGACTTTAGAAAGTATACTG
     AACCTACACCCACTACGTATGAAAAGTCAAGGGAATCTATTTCTGAAATCTTTCATATGAC 2895 ava3, MetArgHisGlnGlyLeuAspIleSerThrMetTrp  POL
2943 CATTTACCATACCTAGTATAAACAATGAGACACCAGGGATTAGATATCAGTACAATGTGG
     GTAAATGGTATGGATCATATTTGTTACTCTGTGGTCCCTAATCTATAGTCATGTTACACC 2985 ecor5, LeuProGlnGlyTrpLysGlySerProAlaIlePheGlnSerSerMetThrLysIleLeu
3003 CTGCCACAGGGATGGAAAGGATCACCAGCAATATTCCAAAGTAGCATGACAAAAATCTTA
     GACGGTGTCCCTACCTTTCCTAGTGGTCGTTATAAGGTTTCATCGTACTGTTTTTAGAAT 3003 tthIII1, 3006 bstXI, 3021 binI, GluProPheArgLysGlnAsnProAspIleValIleTyrGlnTyrMetAspAspLeuTyr
3063 GAGCCTTTTAGAAAACAGAATCCAGACATAGTTATCTATCAATACATGGATGATTTGTAT
     CTCGGAAAATCTTTTGTCTTAGGTCTGTATCAATAGATAGTTATGTACCTACTAAACATA ValGlySerAspLeuGluIleGlyGlnHisArgThrLysIleGluGluLeuArgGlnHis
3123 GTAGGATCTGACTTAGAAATAGGGCAGCATAGAACAAAAATAGAGGAACTGAGACAGCAT
     CATCCTAGACTGAATCTTTATCCCGTCGTATCTTGTTTTTATCTCCTTGACTCTGTCGTA 3126 binI, 3171 tthIII1, LeuLeuArgTrpGlyPheThrThrProAspLysLysHisGlnLysGluProProPheLeu
3183 CTGTTGAGGTGGGGATTTACCACACCAGACAAAAAACATCAGAAAGAACCTCCATTCCTT
     GACAACTCCACCCCTAAATGGTGTGGTCTGTTTTTTGTAGTCTTTCTTGGAGGTAAGGAA 3234 bstXI, TrpMetGlyTyrGluLeuHisProAspLysTrpThrValGlnProIleMetLeuProGlu
3243 TGGATGGGTTATGAACTCCATCCTGATAAATGGACAGTACAGCCTATAATGCTGCCAGAA
     ACCTACCCAATACTTGAGGTAGGACTATTTACCTGTCATGTCGGATATTACGACGGTCTT LysAspSerTrpThrValAsnAspIleGlnLysLeuValGlyLysLeuAsnTrpAlaSer
3303 AAAGACAGCTGGACTGTCAATGACATACAGAAGTTAGTGGGAAAATTGAATTGGGCAAGT
     TTTCTGTCGACCTGACAGTTACTGTATGTCTTCAATCACCCTTTTAACTTAACCCGTTCA 3308 pvuII, GlnIleTyrAlaGlyIleLysValLysGlnLeuCysLysLeuLeuArgGlyThrLysAla
3363 CAGATTTATGCAGGGATTAAAGTAAAGCAGTTATGTAAACTCCTTAGAGGAACCAAAGCA
     GTCTAAATACGTCCCTAATTTCATTTCGTCAATACATTTGAGGAATCTCCTTGGTTTCGT LeuThrGluValIleProLeuThrGluGluAlaGluLeuGluLeuAlaGluAsnArgGlu
3423 CTAACAGAAGTAATACCACTAACAGAAGAAGCAGAGCTAGAACTGGCAGAAAACAGGGAG
     GATTGTCTTCATTATGGTGATTGTCTTCTTCGTCTCGATCTTGACCGTCTTTTGTCCCTC 3447 mboII, IleLeuLysGluProValHisGluValTyrTyrAspProSerLysAspLeuValAlaGlu
3483 ATTCTAAAAGAACCAGTACATGAAGTATATTATGACCCATCAAAAGACTTAGTAGCAGAA
     TAAGATTTTCTTGGTCATGTACTTCATATAATACTGGGTAGTTTTCTGAATCATCGTCTT IleGlnLysGlnGlyGlnGlyGlnTrpThrTyrGlnIleTyrGlnGluProPheLysAsn
3543 ATACAGAAGCAGGGGCAAGGCCAATGGACATATCAAATTTATCAAGAGCCATTTAAAAAT
     TATGTCTTCGTCCCCGTTCCGGTTACCTGTATAGTTTAAATAGTTCTCGGTAAATTTTTA 3594 ahaII1,

FIG. 4G

```
       LeuLysThrGlyLysTyrAlaArgMetArgGlyAlaHisThrAsnAspValLysGlnLeu
3603   CTGAAAACAGGAAAGTATGCAAGGATGAGGGGTGCCCACACTAATGATGTAAAACAGTTA
       GACTTTTGTCCTTTCATACGTTCCTACTCCCCACGGGTGTGATTACTACATTTTGTCAAT
                                                               ^
       3659 hpa1, ThrGluAlaValGlnLysValSerThrGluSerIleValIleTrpGlyLysIleProLys
3663   ACAGAGGCAGTGCAAAAAGTATCCACAGAAAGCATAGTAATATGGGGAAAGATTCCTAAA
       TGTCTCCGTCACGTTTTTCATAGGTGTCTTTCGTATCATTATACCCCTTTCTAAGGATTT PheLysLeuProIleGlnLysGluThrTrpGluAlaTrpTrpMetGluTyrTrpGlnAla
3723   TTTAAACTACCCATACAAAAGGAAACATGGGAAGCATGGTGGATGGAGTATTGGCAAGCT
       AAATTTGATGGGTATGTTTTCCTTTGTACCCTTCGTACCACCTACCTCATAACCGTTCGA
       ^
       3723 aha111, ThrTrpIleProGluTrpGluPheValAsnThrProProLeuValLysLeuTrpTyrGln
3783   ACCTGGATTCCTGAGTGGGAGTTTGTCAATACCCCTCCCTTAGTGAAATTATGGTACCAG
       TGGACCTAAGGACTCACCCTCAAACAGTTATGGGGAGGGAATCACTTTAATACCATGGTC
                                                             ^
       3835 kpn1, LeuGluLysGluProIleValGlyAlaGluThrPheTyrValAspGlyAlaAlaAsnArg
3843   TTAGAGAAAGAACCCATAGTAGGAGCAGAAACTTTCTATGTAGATGGGGCAGCTAATAGG
       AATCTCTTTCTTGGGTATCATCCTCGTCTTTGAAAGATACATCTACCCCGTCGATTATCC GluThrLysLeuGlyLysAlaGlyTyrValThrAspArgGlyArgGlnLysValValSer
3903   GAGACTAAATTAGGAAAAGCAGGATATGTTACTGACAGAGGAAGACAAAAAGTTGTCTCC
       CTCTGATTTAATCCTTTTCGTCCTATACAATGACTGTCTCCTTCTGTTTTTCAACAGAGG
                                                     ^
       3943 mbo11, IleAlaAspThrThrAsnGlnLysThrGluLeuGlnAlaIleHisLeuAlaLeuGlnAsp
3963   ATAGCTGACACAACAAATCAGAAGACTGAATTACAAGCAATTCATCTAGCTTTGCAGGAT
       TATCGACTGTGTTGTTTAGTCTTCTGACTTAATGTTCGTTAAGTAGATCGAAACGTCCTA
                                ^
       3983 mbo11, SerGlyLeuGluValAsnIleValThrAspSerGlnTyrAlaLeuGlyIleIleGlnAla
4023   TCGGGATTAGAAGTAAACATAGTAACAGACTCACAATATGCATTAGGAATCATTCAAGCA
       AGCCCTAATCTTCATTTGTATCATTGTCTGAGTGTTATACGTAATCCTTAGTAAGTTCGT
                                                 ^
       4060 ava3, GlnProAspLysSerGluSerGluLeuValSerGlnIleIleGluGlnLeuIleLysLys
4083   CAACCAGATAAGAGTGAATCAGAGTTAGTCAGTCAAATAATAGAGCAGTTAATAAAAAAG
       GTTGGTCTATTCTCACTTAGTCTCAATCAGTCAGTTTATTATCTCGTCAATTATTTTTTC GluLysValTyrLeuAlaTrpValProAlaHisLysGlyIleGlyGlyAsnGluGlnVal
4143   GAAAAGGTCTACCTGGCATGGGTACCAGCACACAAAGGAATTGGAGGAAATGAACAAGTA
       CTTTTCCAGATGGACCGTACCCATGGTCGTGTGTTTCCTTAACCTCCTTTACTTGTTCAT
                          ^
       4163 kpn1, AspLysLeuValSerAlaGlyIleArgLysValLeuPheLeuAsnGlyIleAspLysAla
4203   GATAAATTAGTCAGTGCTGGAATCAGGAAAGTACTATTTTTGAATGGAATAGATAAGGCC
       CTATTTAATCAGTCACGACCTTAGTCCTTTCATGATAAAAACTTACCTTATCTATTCCGG
                                         ^
       4232 sca1,
```

FIG. 4H

```
       GlnGluGluHisGluLysTyrHisSerAsnTrpArgAlaMetAlaSerAspPheAsnLeu
4263 CAAGAAGAACATGAGAAATATCACAGTAATTGGAGAGCAATGGCTAGTGATTTTAACCTG
     GTTCTTCTTGTACTCTTTATAGTGTCATTAACCTCTCGTTACCGATCACTAAAATTGGAC 4266 mboII, ProProValValAlaLysGluIleValAlaSerCysAspLysCysGlnLeuLysGlyGlu
4323 CCACCTGTAGTAGCAAAAGAAATAGTAGCCAGCTGTGATAAATGTCAGCTAAAAGGAGAA
     GGTGGACATCATCGTTTTCTTTATCATCGGTCGACACTATTTACAGTCGATTTTCCTCTT 4352 pvuII, AlaMetHisGlyGlnValAspCysSerProGlyIleTrpGlnLeuAspCysThrHisLeu
4383 GCCATGCATGGACAAGTAGACTGTAGTCCAGGAATATGGCAACTAGATTGTACACATCTA
     CGGTACGTACCTGTTCATCTGACATCAGGTCCTTATACCGTTGATCTAACATGTGTAGAT 4386 ava3, 4410 bstXI, 4439 xbaI, GluGlyLysIleIleLeuValAlaValHisValAlaSerGlyTyrIleGluAlaGluVal
4443 GAAGGAAAAATTATCCTGGTAGCAGTTCATGTAGCCAGTGGATATATAGAAGCAGAAGTT
     CTTCCTTTTTAATAGGACCATCGTCAAGTACATCGGTCACCTATATATCTTCGTCTTCAA 4497 xmnI, IleProAlaGluThrGlyGlnGluThrAlaTyrPheLeuLeuLysLeuAlaGlyArgTrp
4503 ATTCCAGCAGAGACAGGGCAGGAAACAGCATATTTTCTCTTAAAATTAGCAGGAAGATGG
     TAAGGTCGTCTCTGTCCCGTCCTTTGTCGTATAAAAGAGAATTTTAATCGTCCTTCTACC 4555 mboII, 4560 balI, ProValLysThrIleHisThrAspAsnGlySerAsnPheThrSerThrThrValLysAla
4563 CCAGTAAAAACAATACATACAGACAATGGCAGCAATTTCACCAGTACTACGGTTAAGGCC
     GGTCATTTTGTTATGTATGTCTGTTACCGTCGTTAAAGTGGTCATGATGCCAATTCCGG 4605 scaI, AlaCysTrpTrpAlaGlyIleLysGlnGluPheGlyIleProTyrAsnProGlnSerGln
4623 GCCTGTTGGTGGGCAGGGATCAAGCAGGAATTTGGCATTCCCTACAATCCCCAAAGTCAA
     CGGACAACCACCCGTCCCTAGTTCGTCCTTAAACCGTAAGGGATGTTAGGGGTTTCAGTT 4639 binI, GlyValValGluSerMetAsnAsnGluLeuLysLysIleIleGlyGlnValArgAspGln
4683 GGAGTAGTAGAATCTATGAATAATGAATTAAAGAAAATTATAGGACAGGTAAGAGATCAG
     CCTCATCATCTTAGATACTTATTACTTAATTTCTTTTAATATCCTGTCCATTCTCTAGTC AlaGluHisLeuLysThrAlaValGlnMetAlaValPheIleHisAsnPheLysArgLys
4743 GCTGAACACCTTAAGACAGCAGTACAAATGGCAGTATTCATCCACAATTTTAAAAGAAAA
     CGACTTGTGGAATTCTGTCGTCATGTTTACCGTCATAAGTAGGTGTTAAAATTTTCTTTT 4752 alfII, 4791 ahaIII, GlyGlyIleGlyGlyTyrSerAlaGlyGluArgIleValAspIleIleAlaThrAspIle
4803 GGGGGGATTGGGGGATACAGTGCAGGGGAAAGAATAGTAGACATAATAGCAACAGACATA
     CCCCCCTAACCCCCTATGTCACGTCCCCTTTCTTATCATCTGTATTATCGTTGTCTGTAT GlnThrLysGluLeuGlnLysGlnIleThrLysIleGlnAsnPheArgValTyrTyrArg
4863 CAAACTAAAGAACTACAAAAGCAAATTACAAAAATTCAAAATTTTCGGGTTTATTACAGG
     GTTTGATTTCTTGATGTTTTCGTTTAATGTTTTTAAGTTTTAAAAGCCCAAATAATGTCC
```

FIG. 4I

```
           AspAsnLysAspProLeuTrpLysGlyProAlaLysLeuLeuTrpLysGlyGluGlyAla
     4923  GACAACAAAGATCCCCTTTGGAAAGGACCAGCAAAGCTTCTCTGGAAAGGTGAAGGGGCA
           CTGTTGTTTCTAGGGGAAACCTTTCCTGGTCGTTTCGAAGAGACCTTTCCACTTCCCCGT
                                          ^
           4956 hindlll, ValValIleGlnAspAsnSerAspIleLysValValProArgArgLysAlaLysIleIle
     4983  GTAGTAATACAAGATAATAGTGACATAAAAGTAGTGCCAAGAAGAAAAGCAAAAATCATT
           CATCATTATGTTCTATTATCACTGTATTTTCATCACGGTTCTTCTTTTCGTTTTTAGTAA
                                                   ^
           5023 mboII, MetGluAsnArgTrpGlnValMetIleValTrpGlnValAspArgMetArgIle
           ArgAspTyrGlyLysGlnMetAlaGlyAspAspCysValAlaSerArgGlnAspGluAsp
     5043  AGGGATTATGGAAAACAGATGGCAGGTGATGATTGTGTGGCAAGTAGACAGGATGAGGAT
           TCCCTAATACCTTTTGTCTACCGTCCACTACTAACACACCGTTCATCTGTCCTACTCCTA ArgTreTrpLysSerLeuValLysHisHisMetTyrIleSerLysLysAlaLysGlyTrp
           AM
     5103  TAGAACATGGAAAAGTTTAGTAAAACACCATATGTATATTTCAAAGAAAGCTAAAGGATGG
           ATCTTGTACCTTTTCAAATCATTTTGTGGTATACATATAAAGTTTCTTTCGATTTCCTACC
                                         ^
           5131 ndeI, PheTyrArgHisHisTyrGluSerThrHisProArgValSerSerGluValHisIle
     5163      TTTTATAGACATCACTATGAAAGTACTCATCCAAGAGTAAGTTCAGAAGTACACATC
               AAAATATCTGTAGTGATACTTTCATGAGTAGGTTCTCATTCAAGTCTTCATGTGTAG
                                    ^
           5185 scaI, ProLeuGlyAspAlaLysLeuValIleThrThrTyrTrpGlyLeuHisThrGlyGluArg
     5221  CCCCTAGGGGATGCTAAATTGGTAATAACAACATATTGGGGTCTGCATACAGGAGAAAGA
           GGGGATCCCCTACGATTTAACCATTATTGTTGTATAACCCCAGACGTATGTCCTCTTTCT
              ^
           5223 avr2, GluTrpHisLeuGlyGlnGlyValAlaIleGluTrpArgLysLysLysTyrSerThrGln
     5281  GAATGGCATTTGGGCCAGGGAGTCGCCATAGAATGGAGGAAAAAGAAATATAGCACACAA
           CTTACCGTAAACCCGGTCCCTCAGCGGTATCTTACCTCCTTTTTCTTTATATCGTGTGTT ValAspProGlyLeuAlaAspGlnLeuIleHisLeuHisTyrPheAspCysPheSerGlu
     5341  GTAGACCCTGGCCTAGCAGACCAACTAATTCATCTGCATTATTTTGATTGTTTTTCAGAA
           CATCTGGGACCGGATCGTCTGGTTGATTAAGTAGACGTAATAAAACTAACAAAAAGTCTT SerAlaIleLysAsnAlaIleLeuGlyTyrArgValSerProArgCysGluTyrGlnAla
     5401  TCTGCTATAAAAAATGCCATATTAGGATATAGAGTTAGTCCTAGGTGTGAATATCAAGCA
           AGACGATATTTTTTACGGTATAATCCTATATCTCAATCAGGATCCACACTTATAGTTCGT
                                                           ^
           5440 avr2, GlyHisAsnLysValGlySerLeuGlnTyrLeuAlaLeuAlaAlaLeuIleThrProLys
     5461  GGACATAACAAGGTAGGATCTCTACAATACTTGGCACTAGCAGCATTAATAACACCAAAA
           CCTGTATTGTTCCATCCTAGAGATGTTATGAACCGTGATCGTCGTAATTATTGTGGTTTT
                          ^
           5476 binI, LysThrLysProProLeuProSerValLysLysLeuThrGluAspArgTrpAsnLysPro
     5521  AAGACAAAGCCACCTTTGCCTAGTGTTAAGAAACTGACAGAGGATAGATGGAACAAGCCC
           TTCTGTTTCGGTGGAAACGGATCACAATTCTTTGACTGTCTCCTATCTACCTTGTTCGGG
```

FIG. 4J

```
               GlnLysThrLysGlyHisArgGlySerHisThrMetAsnGlyHisAM
       5581    CAGAAGACCAAGGGCCACAGAGGGAGCCATACAATGAATGGACACTAGAGCTTTTAGAGG
               GTCTTCTGGTTCCCGGTGTCTCCCTCGGTATGTTACTTACCTGTGATCTCGAAAATCTCC 5583 mboII, 5641    AGCTTAAGAGAGAAGCTGTTAGACATTTTCCTAGGCCATGGCTCCATAGCTTAGGACAAT
               TCGAATTCTCTCTTCGACAATCTGTAAAAGGATCCGGTACCGAGGTATCGAATCCTGTTA 5643 afIII, 5670 avr2, 5676 ncoI, 5701    ATATCTATGAAACTTATGGGGATACTTGGGCAGGAGTGGAAGCCATAATAAGAATTCTGC
               TATAGATACTTTGAATACCCCTATGAACCCGTCCTCACCTTCGGTATTATTCTTAAGACG 5752 ecorI, 5761    AACAACTGCTGTTTATTCATTTCAGAATTGGGTGTCAACATAGCAGAATAGGCATTATTC
               TTGTTGACGACAAATAAGTAAAGTCTTAACCCACAGTTGTATCGTCTTATCCGTAATAAG 5821    AACAGAGGAGAGCAAGAAGAAATGGAGCCAGTAGATCCTAATCTAGAGCCCTGGAAGCAT
               TTGTCTCCTCTCGTTCTTCTTTACCTCGGTCATCTAGGATTAGATCTCGGGACCTTCGTA 5836 mboII, 5862 xbaI, 5881    CCAGGAAGTCAGCCTAGGACTGCTTGTAACAATTGCTATTGTAAAAAGTGTTGCTTTCAT
               GGTCCTTCAGTCGGATCCTGACGAACATTGTTAACGATAACATTTTTCACAACGAAAGTA 5893 avr2, 5941    TGCTACGCGTGTTTCACAAGAAAAGGCTTAGGCATCTCCTATGGCAGGAAGAAGCGGAGA
               ACGATGCGCACAAAGTGTTCTTTTCCGAATCCGTAGAGGATACCGTCCTTCTTCGCCTCT 5945 mluI, 5988 mboII, 6001    CAGCGACGAAGAGCTCCTCAGGACAGTCAGACTCATCAAGCTTCTCTATCAAAGCAGTAA
               GTCGCTGCTTCTCGAGGAGTCCTGTCAGTCTGAGTAGTTCGAAGAGATAGTTTCGTCATT 6008 mboII, 6011 sacI, 6016 mstII, 6038 hindIII, 6061    GTAGTAAATGTAATGCAATCTTTACAAATATTAGCAATAGTATCATTAGTAGTAGTAGCA
               CATCATTTACATTACGTTAGAAATGTTTATAATCGTTATCATAGTAATCATCATCATCGT 6121    ATAATAGCAATAGTTGTGTGGACCATAGTACTCATAGAATATAGGAAAATATTAAGACAA
               TATTATCGTTATCAACACACCTGGTATCATGAGTATCTTATATCCTTTTATAATTCTGTT 6147 scaI, MetLys   ENV
       6181    AGAAAATAGACAGATTAATTGATAGAATAAGAGAAAAAGCAGAAGACAGTGGCAATGAAA
               TCTTTTATCTGTCTAATTAACTATCTTATTCTCTTTTTCGTCTTCTGTCACCGTTACTTT 6222 mboII, ValLysGlyThrArgArgAsnTyrGlnHisLeuTrpArgTrpGlyThrLeuLeuLeuGly
       6241    GTGAAGGGGACCAGGAGGAATTATCAGCACTTGTGGAGATGGGGCACCTTGCTCCTTGGG
               CACTTCCCCTGGTCCTCCTTAATAGTCGTGAACACCTCTACCCCGTGGAACGAGGAACCC MetLeuMetIleCysSerAlaThrGluLysLeuTrpValThrValTyrTyrGlyValPro
       6301    ATGTTGATGATCTGTAGTGCTACAGAAAAATTGTGGGTCACAGTTTATTATGGAGTACCT
               TACAACTACTAGACATCACGATGTCTTTTTAACACCCAGTGTCAAATAATACCTCATGGA
```

FIG. 4K

```
     ValTrpLysGluAlaThrThrThrLeuPheCysAlaSerAspAlaArgAlaTyrAspThr
6361 GTGTGGAAAGAAGCAACTACCACTCTATTTTGTGCATCAGATGCTAGAGCATATGATACA
     CACACCTTTCTTCGTTGATGGTGAGATAAAACACGTAGTCTACGATCTCGTATACTATGT 6410 ndel, GluValHisAsnValTrpAlaThrHisAlaCysValProThrAspProAsnProGlnGlu
6421 GAGGTACATAATGTTTGGGCCACACATGCCTGTGTACCCACAGACCCCAACCCACAAGAA
     CTCCATGTATTACAAACCCGGTGTGTACGGACACATGGGTGTCTGGGGTTGGGTGTTCTT ValValLeuGlyAsnValThrGluAsnPheAsnMetTrpLysAsnAsnMetValGluGln
6481 GTAGTATTGGGAAATGTGACAGAAAATTTTAACATGTGGAAAAATAACATGGTAGAACAG
     CATCATAACCCTTTACACTGTCTTTTAAAATTGTACACCTTTTTATTGTACCATCTTGTC MetGlnGluAspIleIleSerLeuTrpAspGlnSerLeuLysProCysValLysLeuThr
6541 ATGCAGGAGGATATAATCAGTTTATGGGATCAAAGCCTAAAGCCATGTGTAAAATTAACC
     TACGTCCTCCTATATTAGTCAAATACCCTAGTTTCGGATTTCGGTACACATTTTAATTGG 6567 binI, ProLeuCysValThrLeuAsnCysThrAspLeuGlyLysAlaThrAsnThrAsnSerSer
6601 CCACTCTGTGTTACTTTAAATTGCACTGATTTGGGGAAGGCTACTAATACCAATAGTAGT
     GGTGAGACACAATGAAATTTAACGTGACTAAACCCCTTCCGATGATTATGGTTATCATCA 6615 ahaIII, AsnTrpLysGluGluIleLysGlyGluIleLysAsnCysSerPheAsnIleThrThrSer
6661 AATTGGAAAGAAGAAATAAAAGGAGAAATAAAAAACTGCTCTTTCAATATCACCACAAGC
     TTAACCTTTCTTCTTTATTTTCCTCTTTATTTTTTGACGAGAAAGTTATAGTGGTGTTCG 6670 mboII, IleArgAspLysIleGlnLysGluAsnAlaLeuPheArgAsnLeuAspValValProIle
6721 ATAAGAGATAAGATTCAGAAAGAAAATGCACTTTTTCGTAACCTTGATGTAGTACCAATA
     TATTCTCTATTCTAAGTCTTTCTTTTACGTGAAAAAGCATTGGAACTACATCATGGTTAT AspAsnAlaSerThrThrThrAsnTyrThrAsnTyrArgLeuIleHisCysAsnArgSer
6781 GATAATGCTAGTACTACTACCAACTATACCAACTATAGGTTGATACATTGTAACAGATCA
     CTATTACGATCATGATGATGGTTGATATGGTTGATATCCAACTATGTAACATTGTCTAGT 6790 scaI, ValIleThrGlnAlaCysProLysValSerPheGluProIleProIleHisTyrCysThr
6841 GTCATTACACAGGCCTGTCCAAAGGTATCATTTGAGCCAATTCCCATACATTATTGTACC
     CAGTAATGTGTCCGGACAGGTTTCCATAGTAAACTCGGTTAAGGGTATGTAATAACATGG 6851 stuI, ProAlaGlyPheAlaIleLeuLysCysAsnAsnLysThrPheAsnGlyLysGlyProCys
6901 CCGGCTGGTTTTGCGATTCTAAAGTGTAATAATAAAACGTTCAATGGAAAAGGACCATGT
     GGCCGACCAAAACGCTAAGATTTCACATTATTATTTTGCAAGTTACCTTTTCCTGGTACA ThrAsnValSerThrValGlnCysThrHisGlyIleArgProIleValSerThrGlnLeu
6961 ACAAATGTCAGCACAGTACAATGTACACATGGAATTAGGCCAATAGTGTCAACTCAACTG
     TGTTTACAGTCGTGTCATGTTACATGTGTACCTTAATCCGGTTATCACAGTTGAGTTGAC LeuLeuAsnGlySerLeuAlaGluGluGluValValIleArgSerAspAsnPheThrAsn
7021 CTGTTAAATGGCAGTCTAGCAGAAGAAGAGGTAGTAATTAGATCTGACAATTTCACGAAC
     GACAATTTACCGTCAGATCGTCTTCTTCTCCATCATTAATCTAGACTGTTAAAGTGCTTG 7042 mboII, 7045 mboII, 7060 bglII,
```

FIG. 4L

```
             AsnAlaLysThrIleIleValGlnLeuAsnGluSerValAlaIleAsnCysThrArgPro
      7081   AATGCTAAAACCATAATAGTACAGCTGAATGAATCTGTAGCAATTAACTGTACAAGACCC
             TTACGATTTTGGTATTATCATGTCGACTTACTTAGACATCGTTAATTGACATGTTCTGGG
                                         ^
                7102 pvuII, AsnAsnAsnThrArgLysSerIleTyrIleGlyProGlyArgAlaPheHisThrThrGly
      7141   AACAACAATACAAGAAAAAGTATCTATATAGGACCAGGGAGAGCATTTCATACAACAGGA
             TTGTTGTTATGTTCTTTTTCATAGATATATCCTGGTCCCTCTCGTAAAGTATGTTGTCCT
                                                                        ^
                7199 mboII, ArgIleIleGlyAspIleArgLysAlaHisCysAsnIleSerArgAlaGlnTrpAsnAsn
      7201   AGAATAATAGGAGATATAAGAAAAGCACATTGTAACATTAGTAGAGCACAATGGAATAAC
             TCTTATTATCCTCTATATTCTTTTCGTGTAACATTGTAATCATCTCGTGTTACCTTATTG ThrLeuGluGlnIleValLysLysLeuArgGluGlnPheGlyAsnAsnLysThrIleVal
      7261   ACTTTAGAACAGATAGTTAAAAAATTAAGAGAACAGTTTGGGAATAATAAAACAATAGTC
             TGAAATCTTGTCTATCAATTTTTTAATTCTCTTGTCAAACCCTTATTATTTTGTTATCAG PheAsnGlnSerSerGlyGlyAspProGluIleValMetHisSerPheAsnCysArgGly
      7321   TTTAATCAATCCTCAGGAGGGGACCCAGAAATTGTAATGCACAGTTTTAATTGTAGAGGG
             AAATTAGTTAGGAGTCCTCCCCTGGGTCTTTAACATTACGTGTCAAAATTAACATCTCCC
                             ^
                7331 mstII, GluPhePheTyrCysAsnThrThrGlnLeuPheAsnAsnThrTrpArgLeuAsnHisThr
      7381   GAATTTTCTACTGTAATACAACACAACTGTTTAATAATACATGGAGGTTAAATCACACT
             CTTAAAAAGATGACATTATGTTGTGTTGACAAATTATTATGTACCTCCAATTTAGTGTGA GluGlyThrLysGlyAsnAspThrIleIleLeuProCysArgIleLysGlnIleIleAsn
      7441   GAAGGAACTAAAGGAAATGACACAATCATACTCCCATGTAGAATAAAACAAATTATAAAC
             CTTCCTTGATTTCCTTTACTGTGTTAGTATGAGGGTACATCTTATTTTGTTTAATATTTG MetTrpGlnGluValGlyLysAlaMetTyrAlaProProIleGlyGlyGlnIleSerCys
      7501   ATGTGGCAGGAAGTAGGAAAAGCAATGTATGCCCCTCCCATTGGAGGACAAATTAGTTGT
             TACACCGTCCTTCATCCTTTTCGTTACATACGGGGAGGGTAACCTCCTGTTTAATCAACA SerSerAsnIleThrGlyLeuLeuLeuThrArgAspGlyGlyThrAsnValThrAsnAsp
      7561   TCATCAAATATTACAGGGCTGCTATTAACAAGAGATGGTGGTACAAATGTAACTAATGAC
             AGTAGTTTATAATGTCCCGACGATAATTGTTCTCTACCACCATGTTTACATTGATTACTG ThrGluValPheArgProGlyGlyGlyAspMetArgAspAsnTrpArgSerGluLeuTyr
      7621   ACCGAGGTCTTCAGACCTGGAGGAGGAGATATGAGGGACAATTGGAGAAGTGAATTATAT
             TGGCTCCAGAAGTCTGGACCTCCTCCTCTATACTCCCTGTTAACCTCTTCACTTAATATA
                   ^
                7628 mboII, LysTyrLysValIleLysIleGluProLeuGlyIleAlaProThrLysAlaLysArgArg
      7681   AAATATAAAGTAATAAAAATTGAACCATTAGGAATAGCACCCACCAAGGCAAAGAGAAGA
             TTTATATTTCATTATTTTTAACTTGGTAATCCTTATCGTGGGTGGTTCCGTTTCTCTTCT
                                                                      ^
                7736 mboII, ValValGlnArgGluLysArgAlaValGlyIleValGlyAlaMetPheLeuGlyPheLeu
      7741   GTGGTGCAGAGAGAAAAAAGAGCAGTGGGAATAGTAGGAGCTATGTTCCTTGGGTTCTTG
             CACCACGTCTCTCTTTTTTCTCGTCACCCTTATCATCCTCGATACAAGGAACCCAAGAAC GlyAlaAlaGlySerThrMetGlyAlaValSerLeuThrLeuThrValGlnAlaArgGln
      7801   GGAGCAGCAGGAAGCACTATGGGCGCAGTGTCATTGACGCTGACGGTACAGGCCAGACAA
             CCTCGTCGTCCTTCGTGATACCCGCGTCACAGTAACTGCGACTGCCATGTCCGGTCTGTT
```

FIG. 4M

```
      LeuLeuSerGlyIleValGlnGlnGlnAsnAsnLeuLeuArgAlaIleGluAlaGlnGln
7861  TTATTGTCTGGTATAGTGCAACAGCAGAACAATTTGCTGAGGGCTATTGAGGCGCAACAA
      AATAACAGACCATATCACGTTGTCGTCTTGTTAAACGACTCCCGATAACTCCGCGTTGTT

HisLeuLeuGlnLeuThrValTrpGlyIleLysGlnLeuGlnAlaArgValLeuAlaVal
7921  CATCTGTTGCAACTCACAGTCTGGGGCATCAAGCAGCTCCAGGCAAGAGTCCTGGCTGTG
      GTAGACAACGTTGAGTGTCAGACCCCGTAGTTCGTCGAGGTCCGTTCTCAGGACCGACAC

GluArgTyrLeuArgAspGlnGlnLeuLeuGlyIleTrpGlyCysSerGlyLysLeuIle
7981  GAAAGATACCTAAGGGATCAACAGCTCCTAGGGATTTGGGGTTGCTCTGGAAAACTCATT
      CTTTCTATGGATTCCCTAGTTGTCGAGGATCCCTAAACCCCAACGAGACCTTTTGAGTAA 7989 mstII, 7995 binI, 8007 avr2, CysThrThrAlaValProTrpAsnAlaSerTrpSerAsnLysSerLeuGluAspIleTrp
8041  TGCACCACTGCTGTGCCTTGGAATGCTAGTTGGAGTAATAAATCTCTGGAAGACATTTGG
      ACGTGGTGACGACACGGAACCTTACGATCAACCTCATTATTTAGAGACCTTCTGTAAACC 8089 mboII, AspAsnMetThrTrpMetGlnTrpGluArgGluIleAspAsnTyrThrAsnThrIleTyr
8101  GATAACATGACCTGGATGCAGTGGGAAAGAGAAATTGACAATTACACAAACACAATATAC
      CTATTGTACTGGACCTACGTCACCCTTTCTCTTTAACTGTTAATGTGTTTGTGTTATATG ThrLeuLeuGluGluSerGlnAsnGlnGlnGluLysAsnGluGlnGluLeuLeuGluLeu
8161  ACCTTACTTGAAGAATCGCAGAACCAACAAGAAAAGAATGAACAAGAATTATTAGAATTG
      TGGAATGAACTTCTTAGCGTCTTGGTTGTTCTTTTCTTACTTGTTCTTAATAATCTTAAC 8170 mboII, AspLysTrpAlaSerLeuTrpAsnTrpPheSerIleThrAsnTrpLeuTrpTyrIleLys
8221  GATAAGTGGGCAAGTTTGTGGAATTGGTTTAGCATAACAAACTGGCTGTGGTATATAAAG
      CTATTCACCCGTTCAAACACCTTAACCAAATCGTATTGTTTGACCGACACCATATATTTC IlePheIleMetIleValGlyGlyLeuValGlyLeuArgIleValPheAlaValLeuSer
8281  ATATTCATAATGATAGTAGGAGGCTTGGTAGGTTTAAGAATAGTTTTTGCTGTGCTTTCT
      TATAAGTATTACTATCATCCTCCGAACCATCCAAATTCTTATCAAAAACGACACGAAAGA IleValAsnArgValArgGlnGlyTyrSerProLeuSerPheGlnThrArgLeuProVal
8341  ATAGTGAATAGAGTTAGGCAGGGATACTCACCATTGTCATTTCAGACCCGCCTCCCAGTC
      TATCACTTATCTCAATCCGTCCCTATGAGTGGTAACAGTAAAGTCTGGGCGGAGGGTCAG 8400 aval, ProArgGlyProAspArgProAspGlyIleGluGluGluGlyGlyGluArgAspArgAsp
8401  CCGAGGGGACCCGACAGGCCCGACGGAATCGAAGAAGAAGGTGGAGAGAGAGACAGAGAC
      GGCTCCCCTGGGCTGTCCGGGCTGCCTTAGCTTCTTCTTCCACCTCTCTCTCTGTCTCTG 8431 mboII, 8434 mboII, ArgSerValArgLeuValAspGlyPheLeuAlaLeuIleTrpGluAspLeuArgSerLeu
8461  AGATCCGTTCGATTAGTGGATGGATTCTTAGCACTTATCTGGGAAGATCTGCGGAGCCTG
      TCTAGGCAAGCTAATCACCTACCTAAGAATCGTGAATAGACCCTTCTAGACGCCTCGGAC 8503 mboII, 8505 bglII, CysLeuPheSerTyrArgArgLeuArgAspLeuLeuLeuIleAlaAlaArgThrValGlu
8521  TGCCTCTTCAGCTACCGCCGCTTGAGAGACTTACTCTTGATTGCAGCGAGGACTGTGGAA
      ACGGAGAAGTCGATGGCGGCGAACTCTCTGAATGAGAACTAACGTCGCTCCTGACACCTT 8525 mboII,
```

FIG. 4N

```
         IleLeuGlyHisArgGlyTrpGluAlaLeuLysTyrTrpTrpSerLeuLeuGlnTyrTrp
   8581  ATTCTGGGGCACAGGGGGTGGGAAGCCCTCAAATATTGGTGGAGTCTCCTGCAGTATTGG
         TAAGACCCCGTGTCCCCCACCCTTCGGGAGTTTATAACCACCTCAGAGGACGTCATAACC 8629 pst1, IleGlnGluLeuLysAsnSerAlaValSerTrpLeuAsnAlaThrAlaIleAlaValThr
   8641  ATTCAGGAACTAAAGAATAGTGCTGTTAGCTGGCTCAACGCCACAGCTATAGCAGTAACT
         TAAGTCCTTGATTTCTTATCACGACAATCGACCGAGTTGCGGTGTCGATATCGTCATTGA GluGlyThrAspArgValIleGluValAlaGlnArgAlaTyrArgAlaIleLeuHisIle
   8701  GAGGGGACAGATAGGGTTATAGAAGTAGCACAAAGAGCTTATAGAGCTATTCTCCACATA
         CTCCCCTGTCTATCCCAATATCTTCATCGTGTTTCTCGAATATCTCGATAAGAGGTGTAT HisArgArgIleArgGlnGlyLeuGluArgLeuLeuLeuOC  MetGlyGlyLysTrpSer
   8761  CATAGAAGAATTAGACAGGGCTTGGAAAGGCTTTTGCTATAAGATGGGTGGCAAGTGGTCA
         GTATCTTCTTAATCTGTCCCGAACCTTTCCGAAAACGATATTCTACCCACCGTTCACCAGT 8765 mbol1, LysArgSerMetGlyGlyTrpSerAlaIleArgGluArgMetArgArgAlaGluProArg
   8822  AAACGTAGTATGGGTGGATGGTCTGCTATAAGGGAAAGAATGAGACGAGCTGAGCCACGA
         TTTGCATCATACCCACCTACCAGACGATATTCCCTTTCTTACTCTGCTCGACTCGGTGCT AlaGluProAlaAlaAspGlyValGlyAlaValSerArgAspLeuGluLysHisGlyAla
   8882  GCTGAGCCAGCAGCAGATGGGGTGGGAGCAGTATCTCGAGACCTGGAAAAACATGGAGCA
         CGACTCGGTCGTCGTCTACCCCACCCTCGTCATAGAGCTCTGGACCTTTTTGTACCTCGT 8883 tthIII1, 8916 aval xhol, IleThrSerSerAsnThrAlaAlaThrAsnAlaAspCysAlaTrpLeuGluAlaGlnGlu
   8942  ATCACAAGTAGCAATACAGCAGCTACTAATGCTGATTGTGCCTGGCTAGAAGCACAAGAG
         TAGTGTTCATCGTTATGTCGTCGATGATTACGACTAACACGGACCGATCTTCGTGTTCTC GluGluGluValGlyPheProValArgProGlnValProLeuArgProMetThrTyrLys
   9002  GAGGAAGAGGTGGGTTTTCCAGTCAGACCTCAGGTACCTTTAAGACCAATGACTTACAAG
         CTCCTTCTCCACCCAAAAGGTCAGTCTGGAGTCCATGGAAATTCTGGTTACTGAATGTTC 9005 mbol1, 9029 mstII, 9034 kpn1, AlaAlaLeuAspIleSerHisPheLeuLysGluLysGlyGlyLeuGluGlyLeuIleTrp
   9062  GCAGCTTTAGATATTAGCCACTTTTTAAAAGAAAAGGGGGGACTGGAAGGGCTAATTTGG
         CGTCGAAATCTATAATCGGTGAAAAATTTTCTTTTCCCCCCTGACCTTCCCGATTAAACC 9085 ahaIII, SerGlnArgArgGlnGluIleLeuAspLeuTrpIleTyrHisThrGlnGlyTyrPhePro
   9122  TCCCAAAGAAGACAAGAGATCCTTGATCTGTGGATCTACCACACACAAGGCTACTTCCCT
         AGGGTTTCTTCTGTTCTCTAGGAACTAGACACCTAGATGGTGTGTGTTCCGATGAAGGGA 9129 mbol1, 9153 bin1, AspTrpGlnAsnTyrThrProGlyProGlyIleArgTyrProLeuThrPheGlyTrpCys
   9182  GATTGGCAGAATTACACACCAGGGCCAGGGATCAGATATCCACTGACCTTTGGATGGTGC
         CTAACCGTCTTAATGTGTGGTCCCGGTCCCTAGTCTATAGGTGACTGGAAACCTACCACG 9210 bin1, 9216 ecor5,
```

FIG. 40

```
         PheLysLeuValProValGluProGluLysValGluGluAlaAsnGluGlyGluAsnAsn
9242 TTCAAGCTAGTACCAGTTGAGCCAGAGAAGGTAGAAGAGGCCAATGAAGGAGAGAACAAC
     AAGTTCGATCATGGTCAACTCGGTCTCTTCCATCTTCTCCGGTTACTTCCTCTCTTGTTG
                                       ^
     9275 mboII, SerLeuLeuHisProMetSerLeuHisGlyMetGluAspAlaGluLysGluValLeuVal
9302 AGCTTGTTACACCCTATGAGCCTGCATGGGATGGAGGACGCGGAGAAAGAAGTGTTAGTG
     TCGAACAATGTGGGATACTCGGACGTACCCTACCTCCTGCGCCTCTTTCTTCACAATCAC TrpArgPheAspSerLysLeuAlaPheHisHisMetAlaArgGluLeuHisProGluTyr
9362 TGGAGGTTTGACAGCAAACTAGCATTTCATCACATGGCCCGAGAGCTGCATCCGGAGTAC
     ACCTCCAAACTGTCGTTTGATCGTAAAGTAGTGTACCGGGCTCTCGACGTAGGCCTCATG
                                         ^                ^
     9399 avaI,  9417 scaI, TyrLysAspCysOP
9422 TACAAAGACTGCTGACATCGAGCTTTCTACAAGGGACTTTCCGCTGGGGACTTTCCAGGG
     ATGTTTCTGACGACTGTAGCTCGAAAGATGTTCCCTGAAAGGCGACCCCTGAAAGGTCCC 9482 AGGCGTGGCCTGGGCGGGACTGGGGAGTGGCGTCCCTCAGATGCTGCATATAAGCAGCTG
     TCCGCACCGGACCCGCCCTGACCCCTCACCGCAGGGAGTCTACGACGTATATTCGTCGAC
                                                              ^
     9536 pvuII, 9542 CTTTTTGCCTGTACTGGGTCTCTCTGGTTAGACCAGATCTGAGCCTGGGAGCTCTCTGGC
     GAAAAACGGACATGACCCAGAGAGACCAATCTGGTCTAGACTCGGACCCTCGAGAGACCG
                                        ^            ^
     9576 bgIII, 9590 sacI, 9602 TAACTAGGGAACCCACTGCTTAAGCCTCAATAAAGCTTGCCTTGAGTGCTTCAAGTAGTG
     ATTGATCCCTTGGGTGACGAATTCGGAGTTATTTCGAACGGAACTCACGAAGTTCATCAC
                            ^           ^
     9620 afIII, 9634 hindIII, 9662 TGTGCCCGTCTGTTGTGTGACTCTGGTAACTAGAGATCCCTCAGACCCTTTTAGTCAGTG
     ACACGGGCAGACAACACACTGAGACCATTGATCTCTAGGGAGTCTGGGAAAATCAGTCAC

9722 TGGAAAAATCTCTAGCAG
     ACCTTTTTAGAGATCGTC
```

FIG. 4P

```
            U3→
       -453 CTGGAAGGGCTAATTTGGTCCCAAAGAAGACAAGAGATCCTTGATCTGTGGATCTACCAC

ACACAAGGCTACTTCCCTGATTGGCAGAATTACACACCAGGGCCAGGGATCAGATATCCA

-333 CTGACCTTTGGATGGTGCTTCAAGCTAGTACCAGTTGAGCCAGAGAAGGTAGAAGAGGCC

AATGAAGGAGAGAACAACAGCTTGTTACACCCTATGAGCCTGCATGGGATGGAGGACGCG        L

-214 GAGAAAGAAGTGTTAGTGTGGAGGTTTGACAGCAAACTAGCATTTCATCACATGGCCCGA

GAGCTGCATCCGGAGTACTACAAAGACTGCTGACATCGAGCTTTCTACAAGGGACTTTCCG      T

-93 CTGGGGACTTTCCAGGGAGGCGTGGCCTGGGCGGGACTGGGGAGTGGCGTCCCTCAGATG
                                ←U3  R→
            CTGCATATAAGCAGCTGCTTTTTGCCTGTACTG  GGTCTCTCTGGTTAGACCAGATCTGAG     R

28 CCTGGGAGCTCTCTGGCTAACTAGGGAACCCACTGCTTAAGCCTCAATAAAGCTTGCCTT
              ←R  U5→
            GAGTGCTTCA AGTAGTGTGTGCCCGTCTGTTGTGTGACTCTGGTAACTAGAGATCCCTCA
                                        ←U5
        148 GACCCTTTTAGTCAGTGTGGAAAAATCTCTAGCAG TGGCGCCCGAACAGGGACGCGAAA

GCGAAAGTAGAACCAGAGGAGCTCTCTCGACGCAGGACTCGGCTTGCTGAAGCGCGCACAG

268 CAAGAGGCGAGGGGCGGCGACTGGTGAGTACGCCAATTTTTGACTAGCGGAGGCTAGAAG
                       MetGlyAlaArgAlaSerValLeuSerGlyGlyGluLeuAspLysTrpGlu      17
            GAGAGAGAGATGGGTGCGAGAGCGTCGGTATTAAGCGGGGGAGAATTAGATAAATGGGAA

LysIleArgLeuArgProGlyGlyLysLysLysTyrLysLeuLysHisIleValTrpAla
        388 AAAATTCGGTTAAGGCCAGGGGGAAAGAAAAAATATAAGTTAAAACATATAGTATGGGCA

SerArgGluLeuGluArgPheAlaValAsnProGlyLeuLeuGluThrSerGluGlyCys       57
            AGCAGGGAGCTAGAACGATTCGCAGTCAATCCTGGCCTGTTAGAAACATCAGAAGGCTGC

ArgGlnIleLeuGlyGlnLeuGlnProSerLeuGlnThrGlySerGluGluLeuArgSer
        508 AGACAAATATTGGGACAGCTACAGCCATCCCTTCAGACAGGATCAGAAGAACTTAGATCA

LeuTyrAsnThrValAlaThrLeuTyrCysValHisGlnArgIleAspValLysAspThr      97
            TTATATAATACAGTAGCAACCCTCTATTGTGTACATCAAAGGATAGATGTAAAAGACACC

LysGluAlaLeuGluLysIleGluGluGluGlnAsnLysSerLysLysLysAlaGlnGln
        628 AAGGAAGCTTTAGAGAAGATAGAGGAAGAGCAAAACAAAAGTAAGAAAAAGGCACAGCAA

AlaAlaAlaAlaAlaGlyThrGlyAsnSerSerGlnValSerGlnAsnTyrProIleVal    137
            GCAGCAGCTGCAGCTGGCACAGGAAACAGCAGCCAGGTCAGCCAAAATTACCCTATAGTG

GlnAsnLeuGlnGlyGlnMetValHisGlnAlaIleSerProArgThrLeuAsnAlaTrp
        748 CAGAACCTACAGGGGCAAATGGTACATCAGGCCATATCACCTAGAACTTTAAATGCATGG

ValLysValValGluGluLysAlaPheSerProGluValIleProMetPheSerAlaLeu    177
            GTAAAAGTAGTAGAAGAAAAGGCTTTCAGCCCAGAAGTAATACCCATGTTTTCAGCATTA

SerGluGlyAlaThrProGlnAspLeuAsnThrMetLeuAsnThrValGlyGlyHisGln
        868 TCAGAAGGAGCCACCCCACAAGATTTAAACACCATGCTAAACACAGTGGGGGGACATCAA
```

FIG. 5A

```
           AlaAlaMetGlnMetLeuLysGluThrIleAsnGluGluAlaAlaGluTrpAspArgVal   217
       GCAGCCATGCAAATGTTAAAAGAGACTATCAATGAGGAAGCTGCAGAATGGGATAGAGTG
           HisProValHisAlaGlyProIleAlaProGlyGlnMetArgGluProArgGlySerAsp
   988 CATCCAGTGCATGCAGGGCCTATTGCACCAGGCCAAATGAGAGAACCAAGGGGAAGTGAC
           IleAlaGlyThrThrSerThrLeuGlnGluGlnIleGlyTrpMetThrAsnAsnProPro   257
       ATAGCAGGAACTACTAGTACCCTTCAGGAACAAATAGGATGGATGACAAATAATCCACCT
           IleProValGlyGluIleTyrLysArgTrpIleIleLeuGlyLeuAsnLysIleValArg
  1108 ATCCCAGTAGGAGAAATCTATAAAAGATGGATAATCCTGGGATTAAATAAAATAGTAAGA
           MetTyrSerProThrSerIleLeuAspIleArgGlnGlyProLysGluProPheArgAsp   297
       ATGTATAGCCCTACCAGCATTCTGGACATAAGACAAGGACCAAAGGAACCCTTTAGAGAT
           TyrValAspArgPheTyrLysThrLeuArgAlaGluGlnAlaSerGlnAspValLysAsn
  1228 TATGTAGACCGGTTCTATAAAACTCTAAGAGCCGAACAAGCTTCACAGGATGTAAAAAAT
           TrpMetThrGluThrLeuLeuValGlnAsnAlaAsnProAspCysLysThrIleLeuLys   337
       TGGATGACAGAAACCTTGTTGGTCCAAAATGCAAACCCAGATTGTAAGACTATTTTAAAA
           AlaLeuGlyProAlaAlaThrLeuGluGluMetMetThrAlaCysGlnGlyValGlyGly
  1348 GCATTGGGACCAGCAGCTACACTAGAAGAAATGATGACAGCATGTCAGGGAGTGGGGGGA
           ProGlyHisLysAlaArgValLeuAlaGluAlaMetSerGlnValThrAsnProAlaAsn   377
       CCCGGCCATAAAGCAAGAGTTTTGGCTGAAGCCATGAGCCAAGTAACAAATCCAGCTAAC
           IleMetMetGlnArgGlyAsnPheArgAsnGlnArgLysThrValLysCysPheAsnCys
  1468 ATAATGATGCAGAGAGGCAATTTTAGGAACCAAAGAAAGACTGTTAAGTGTTTCAATTGT
           GlyLysGluGlyHisIleAlaLysAsnCysArgAlaProArgLysLysGlyCysTrpArg   417
       GGCAAAGAAGGGCACATAGCCAAAAATTGCAGGGCCCCTAGGAAAAAGGGCTGTTGGAGA
           CysGlyArgGluGlyHisGlnMetLysAspCysThrGluArgGlnAlaAsnPheLeuGly
                                                              PhePheArgG
  1588 TGTGGAAGGGAAGGACACCAAATGAAAGATTGCACTGAGAGACAGGCTAATTTTTTAGGG
           LysIleTrpProSerTyrLysGlyArgProGlyAsnPheLeuGlnSerArgProGluPro   457
           luAspLeuAlaPheLeuGlnGlyLysAlaArgGluPheSerSerGluGlnThrArgAla   23
       AAGATCTGGCCTTCCTACAAGGGAAGGCCAGGGAATTTTCTTCAGAGCAGACCAGAGCCA
           ThrAlaProProGluGluSerPheArgPheGlyGluGluLysThrThrProSerGlnLys
           AsnSerProThrArgArgGluLeuGlnValTrpGlyGlyGluAsnAsnSerLeuSerGluA
  1708 ACAGCCCCACCAGAAGAGAGCTTCAGGTTTGGGGAGGAGAAAACAACTCCCTCTCAGAAG
           GlnGluProIleAspLysGluLeuTyrProLeuThrSerLeuArgSerLeuPheGlyAsn   497
           laGlyAlaAspArgGlnGlyThrValSerPheAsnPheProGlnIleThrLeuTrpGln   63
       CAGGAGCCGATAGACAAGGAACTGTATCCTTTAACTTCCCTCAGATCACTCTTTGGCAAC
           AspProSerSerGlnOC
           ArgProLeuValThrIleArgIleGlyGlyGlnLeuLysGluAlaLeuLeuAspThrGlyA
  1828 GACCCCTCGTCACAATAAGGATAGGGGGGCAACTAAAGGAAGCTCTATTAGATACAGGAG
           laAspAspThrValLeuGluGluMetAsnLeuProGlyLysTrpLysProLysMetIle   103
       CAGATGATACAGTATTAGAAGAAATGAATTTGCCAGGAAAATGGAAACCAAAAATGATAG
           GlyGlyIleGlyGlyPheIleLysValArgGlnTyrAspGlnIleProValGluIleCysG
  1948 GGGGAATTGGAGGTTTTATCAAAGTAAGACAGTACGATCAGATACCTGTAGAAATCTGTG
```

FIG. 5B

```
        lyHisLysAlaIleGlyThrValLeuValGlyProThrProValAsnIleIleGlyArg 143
        GACATAAAGCTATAGGTACAGTATTAGTAGGACCTACACCTGTCAACATAATTGGAAGAA

AsnLeuLeuThrGlnIleGlyCysThrLeuAsnPheProIleSerProIleGluThrValP
2068   ATCTGTTGACTCAGATTGGTTGTACTTTAAATTTCCCCATTAGTCCTATTGAAACTGTAC roValLysLeuLysProGlyMetAspGlyProLysValLysGlnTrpProLeuThrGlu 183
       CAGTAAAATTAAAGCCAGGAATGGATGGCCCAAAAGTTAAGCAATGGCCATTGACAGAAG

GluLysIleLysAlaLeuValGluIleCysThrGluMetGluLysGluGlyLysIleSerL
2188    AAAAAAATAAAAGCATTAGTAGAGATATGTACAGAAATGGAAAAGGAAGGGAAAATTTCAA ysIleGlyProGluAsnProTyrAsnThrProValPheAlaIleLysLysLysAspSer 223
         AAATTGGGCCTGAAAATCCATACAATACTCCAGTATTTGCTATAAAGAAAAAAGACAGTA

ThrLysTrpArgLysLeuValAspPheArgGluLeuAsnLysArgThrGlnAspPheTrpG
2308   CTAAATGGAGAAAACTAGTAGATTTCAGAGAACTTAATAAAAGAACTCAAGACTTCTGGG luValGlnLeuGlyIleProHisProAlaGlyLeuLysLysLysLysSerValThrVal 263
         AAGTTCAGTTAGGAATACCACACCCCGCAGGGTTAAAAAAGAAAAAATCAGTAACAGTAT

LeuAspValGlyAspAlaTyrPheSerValProLeuAspLysAspPheArgLysTyrThrA
2428      TGGATGTGGGTGATGCATACTTTTCAGTTCCCTTAGATAAAGACTTTAGAAAGTATACTG laPheThrIleProSerIleAsnAsnGluThrProGlyIleArgTyrGlnTyrAsnVal 303
         CATTTACCATACCTAGTATAAACAATGAGACACCAGGGATTAGATATCAGTACAATGTGC

LeuProGlnGlyTrpLysGlySerProAlaIlePheGlnSerSerMetThrLysIleLeuG
2548    TGCCACAGGGATGGAAAGGATCACCAGCAATATTCCAAAGTAGCATGACAAAAATCTTAG luProPheArgLysGlnAsnProAspIleValIleTyrGlnTyrMetAspAspLeuTyr 343
        AGCCTTTTAGAAAACAGAATCCAGACATAGTTATCTATCAATACATGGATGATTTGTATG

ValGlySerAspLeuGluIleGlyGlnHisArgThrLysIleGluGluLeuArgGlnHisL
2668   TAGGATCTGACTTAGAAATAGGGCAGCATAGAACAAAAATAGAGGAACTGAGACAGCATC euLeuArgTrpGlyPheThrThrProAspLysLysHisGlnLysGluProProPheLeu 383
         TGTTGAGGTGGGGATTTACCACACCAGACAAAAAACATCAGAAAGAACCTCCATTCCTTT

TrpMetGlyTyrGluLeuHisProAspLysTrpThrValGlnProIleMetLeuProGluL
2788    GGATGGGTTATGAACTCCATCCTGATAAATGGACAGTACAGCCTATAATGCTGCCAGAAA ysAspSerTrpThrValAsnAspIleGlnLysLeuValGlyLysLeuAsnTrpAlaSer 423
        AAGACAGCTGGACTGTCAATGACATACAGAAGTTAGTGGGAAAATTGAATTGGGCAAGTC

GlnIleTyrAlaGlyIleLysValLysGlnLeuCysLysLeuLeuArgGlyThrLysAlaL
2908     AGATTTATGCAGGGATTAAAGTAAAGCAGTTATGTAAACTCCTTAGAGGAACCAAAGCAC euThrGluValIleProLeuThrGluGluAlaGluLeuGluLeuAlaGluAsnArgGlu 463   P
        TAACAGAAGTAATACCACTAACAGAAGAAGCAGAGCTAGAACTGGCAGAAAACAGGGAGA

IleLeuLysGluProValHisGluValTyrTyrAspProSerLysAspLeuValAlaGluI
3028    TTCTAAAAGAACCAGTACATGAAGTATATTATGACCCATCAAAAGACTTAGTAGCAGAAA leGlnLysGlnGlyGlnGlyGlnTrpThrTyrGlnIleTyrGlnGluProPheLysAsn 503   O
         TACAGAAGCAGGGGCAAGGCCAATGGACATATCAAATTTATCAAGAGCCATTTAAAAATC

LeuLysThrGlyLysTyrAlaArgMetArgGlyAlaHisThrAsnAspValLysGlnLeuT
3148    TGAAAACAGGAAAGTATGCAAGGATGAGGGGTGCCCACACTAATGATGTAAAACAGTTAA hrGluAlaValGlnLysValSerThrGluSerIleValIleTrpGlyLysIleProLys 543   L
         CAGAGGCAGTGCAAAAAGTATCCACAGAAAGCATAGTAATATGGGGAAAGATTCCTAAAT
```

FIG. 5C

```
      PheLysLeuProIleGlnLysGluThrTrpGluAlaTrpTrpMetGluTyrTrpGlnAlaT
3268 TTAAACTACCCATACAAAAGGAAACATGGGAAGCATGGTGGATGGAGTATTGGCAAGCTA hrTrpIleProGluTrpGluPheValAsnThrProProLeuValLysLeuTrpTyrGln 583
     CCTGGATTCCTGAGTGGGAGTTTGTCAATACCCCTCCCTTAGTGAAATTATGGTACCAGT

LeuGluLysGluProIleValGlyAlaGluThrPheTyrValAspGlyAlaAlaAsnArgG
3388 TAGAGAAAGAACCCATAGTAGGAGCAGAAACTTTCTATGTAGATGGGGCAGCTAATAGGG luThrLysLeuGlyLysAlaGlyTyrValThrAspArgGlyArgGlnLysValValSer 623
     AGACTAAATTAGGAAAAGCAGGATATGTTACTGACAGAGGAAGACAAAAAGTTGTCTCCA

IleAlaAspThrThrAsnGlnLysThrGluLeuGlnAlaIleHisLeuAlaLeuGlnAspS
3508 TAGCTGACACAACAAATCAGAAGACTGAATTACAAGCAATTCATCTAGCTTTGCAGGATT erGlyLeuGluValAsnIleValThrAspSerGlnTyrAlaLeuGlyIleIleGlnAla 663
     CGGGATTAGAAGTAAACATAGTAACAGACTCACAATATGCATTAGGAATCATTCAAGCAC

GlnProAspLysSerGluSerGluLeuValSerGlnIleIleGluGlnLeuIleLysLysG
3628 AACCAGATAAGAGTGAATCAGAGTTAGTCAGTCAAATAATAGAGCAGTTAATAAAAAAGG luLysValTyrLeuAlaTrpValProAlaHisLysGlyIleGlyGlyAsnGluGlnVal 703
     AAAAGGTCTACCTGGCATGGGTACCAGCACACAAAGGAATTGGAGGAAATGAACAAGTAG

AspLysLeuValSerAlaGlyIleArgLysValLeuPheLeuAsnGlyIleAspLysAlaG
3748 ATAAATTAGTCAGTGCTGGAATCAGGAAAGTACTATTTTTGAATGGAATAGATAAGGCCC lnGluGluHisGluLysTyrHisSerAsnTrpArgAlaMetAlaSerAspPheAsnLeu 743
     AAGAAGAACATGAGAAATATCACAGTAATTGGAGAGCAATGGCTAGTGATTTTAACCTGC

ProProValValAlaLysGluIleValAlaSerCysAspLysCysGlnLeuLysGlyGluA
3868 CACCTGTAGTAGCAAAAGAAATAGTAGCCAGCTGTGATAAATGTCAGCTAAAAGGAGAAG laMetHisGlyGlnValAspCysSerProGlyIleTrpGlnLeuAspCysThrHisLeu 783
     CCATGCATGGACAAGTAGACTGTAGTCCAGGAATATGGCAACTAGATTGTACACATCTAG

GluGlyLysIleIleLeuValAlaValHisValAlaSerGlyTyrIleGluAlaGluValI
3988 AAGGAAAAATTATCCTGGTAGCAGTTCATGTAGCCAGTGGATATATAGAAGCAGAAGTTA leProAlaGluThrGlyGlnGluThrAlaTyrPheLeuLeuLysLeuAlaGlyArgTrp 823
     TTCCAGCAGAGACAGGGCAGGAAACAGCATATTTTCTCTTAAAATTAGCAGGAAGATGGC

ProValLysThrIleHisThrAspAsnGlySerAsnPheThrSerThrThrValLysAlaA
4108 CAGTAAAAACAATACATACAGACAATGGCAGCAATTTCACCAGTACTACGGTTAAGGCCG laCysTrpTrpAlaGlyIleLysGlnGluPheGlyIleProTyrAsnProGlnSerGln 863
     CCTGTTGGTGGGCAGGGATCAAGCAGGAATTTGGCATTCCCTACAATCCCCAAAGTCAAG

GlyValValGluSerMetAsnAsnGluLeuLysLysIleIleGlyGlnValArgAspGlnA
4228 GAGTAGTAGAATCTATGAATAATGAATTAAAGAAAATTATAGGACAGGTAAGAGATCAGG laGluHisLeuLysThrAlaValGlnMetAlaValPheIleHisAsnPheLysArgLys 903
     CTGAACACCTTAAGACAGCAGTACAAATGGCAGTATTCATCCACAATTTTAAAAGAAAAG

GlyGlyIleGlyGlyTyrSerAlaGlyGluArgIleValAspIleIleAlaThrAspIleG
4348 GGGGGATTGGGGGGATACAGTGCAGGGGAAAGAATAGTAGACATAATAGCAACAGACATAC lnThrLysGluLeuGlnLysGlnIleThrLysIleGlnAsnPheArgValTyrTyrArg 943
     AAAACTAAAGAACTACAAAAGCAAATTACAAAAATTCAAAATTTTCGGGTTTATTACAGGG
```

FIG. 5D

```
      AspAsnLysAspProLeuTrpLysGlyProAlaLysLeuLeuTrpLysGlyGluGlyAlaV
4468  ACAACAAAGATCCCCTTTGGAAAGGACCAGCAAAGCTTCTCTGGAAAGGTGAAGGGGCAG alValIleGlnAspAsnSerAspIleLysValValProArgArgLysAlaLysIleIle  983
      TAGTAATACAAGATAATAGTGACATAAAAGTAGTGCCAAGAAGAAAAGCAAAAATCATTA

ArgAspTyrGlyLysGlnMetAlaGlyAspAspCysValAlaSerArgGlnAspGluAspA
4588  GGGATTATGGAAAACAGATGGCAGGTGATGATTGTGTGGCAAGTAGACAGGATGAGGATT

M
      AGAACATGGAAAAGTTTAGTAAAACACCATATGTATATTTCAAAGAAAGCTAAAGGATGG
4708  TTTTATAGACATCACTATGAAAGTACTCATCCAAGAGTAAGTTCAGAAGTACACATCCCC

CTAGGGGATGCTAAATTGGTAATAACAACATATTGGGGTCTGCATACAGGAGAAAGAGAA
4828  TGGCATTTGGGCCAGGGAGTCGCCATAGAATGGAGGAAAAAGAAATATAGCACACAAGTA

GACCCTGGCCTAGCAGACCAACTAATTCATCTGCATTATTTTGATTGTTTTTCAGAATCT
4948  GCTATAAAAAATGCCATATTAGGATATAGAGTTAGTCCTAGGTGTGAATATCAAGCAGGA

CATAACAAGGTAGGATCTCTACAATACTTGGCACTAGCAGCATTAATAACACCAAAAAAG
5068  ACAAAGCCACCTTTGCCTAGTGTTAAGAAACTGACAGAGGATAGATGGAACAAGCCCCAG

AAGACCAAGGGCCACAGAGGGAGCCATACAATGAATGGACACTAGAGCTTTTAGAGGAGC
5188  TTAAGAGAGAAGCTGTTAGACATTTTCCTAGGCCATGGCTCCATAGCTTAGGACAATATA

TCTATGAAACTTATGGGGATACTTGGGCAGGAGTGGAAGCCATAATAAGAATTCTGCAAC
5308  AACTGCTGTTTATTCATTTCAGAATTGGGTGTCAACATAGCAGAATAGGCATTATTCAAC

AGAGGAGAGCAAGAAGAAATGGAGCCAGTAGATCCTAATCTAGAGCCCTGGAAGCATCCA
5428  GGAAGTCAGCCTAGGACTGCTTGTAACAATTGCTATTGTAAAAAGTGTTGCTTTCATTGC

TACGCGTGTTTCACAAGAAAAGGCTTAGGCATCTCCTATGGCAGGAAGAAGCGGAGACAG
5548  CGACGAAGAGCTCCTCAGGACAGTCAGACTCATCAAGCTTCTCTATCAAAGCAGTAAGTA

GTAAATGTAATGCAATCTTTACAAATATTAGCAATAGTATCATTAGTAGTAGTAGCAATA
5668  ATAGCAATAGTTGTGTGGACCATAGTACTCATAGAATATAGGAAAATATTAAGACAAAGA

MetLysVal    3
      AAATAGACAGATTAATTGATAGAATAAGAGAAAAAGCAGAAGACAGTGGCAATGAAAGTG

LysGlyThrArgArgAsnTyrGlnHisLeuTrpArgTrpGlyThrLeuLeuLeuGlyMet
5788  AAGGGGACCAGGAGGAATTATCAGCACTTGTGGAGATGGGGCACCTTGCTCCTTGGGATG

LeuMetIleCysSerAlaThrGluLysLeuTrpValThrValTyrTyrGlyValProVal  43
      TTGATGATCTGTAGTGCTACAGAAAAATTGTGGGTCACAGTTTATTATGGAGTACCTGTG

TrpLysGluAlaThrThrThrLeuPheCysAlaSerAspAlaArgAlaTyrAspThrGlu
5908  TGGAAAGAAGCAACTACCACTCTATTTTGTGCATCAGATGCTAGAGCATATGATACAGAG

ValHisAsnValTrpAlaThrHisAlaCysValProThrAspProAsnProGlnGluVal  83
      GTACATAATGTTTGGGCCACACATGCCTGTGTACCCACAGACCCCAACCCACAAGAAGTA
```

FIG. 5E

```
           ValLeuGlyAsnValThrGluAsnPheAsnMetTrpLysAsnAsnMetValGluGlnMet
     6028  GTATTGGGAAATGTGACAGAAAATTTTAACATGTGGAAAAATAACATGGTAGAACAGATG

GlnGluAspIleIleSerLeuTrpAspGlnSerLeuLysProCysValLysLeuThrPro  123
           CAGGAGGATATAATCAGTTTATGGGATCAAAGCCTAAAGCCATGTGTAAAATTAACCCCA

LeuCysValThrLeuAsnCysThrAspLeuGlyLysAlaThrAsnThrAsnSerSerAsn
     6148  CTCTGTGTTACTTTAAATTGCACTGATTTGGGGAAGGCTACTAATACCAATAGTAGTAAT

TrpLysGluGluIleLysGlyGluIleLysAsnCysSerPheAsnIleThrThrSerIle  163
           TGGAAAGAAGAAATAAAAGGAGAAATAAAAAACTGCTCTTTCAATATCACCACAAGCATA

ArgAspLysIleGlnLysGluAsnAlaLeuPheArgAsnLeuAspValValProIleAsp
     6268  AGAGATAAGATTCAGAAAGAAAATGCACTTTTTCGTAACCTTGATGTAGTACCAATAGAT

AsnAlaSerThrThrThrAsnTyrThrAsnTyrArgLeuIleHisCysAsnArgSerVal  203
           AATGCTAGTACTACTACCAACTATACCAACTATAGGTTGATACATTGTAACAGATCAGTC

IleThrGlnAlaCysProLysValSerPheGluProIleProIleHisTyrCysThrPro
     6388  ATTACACAGGCCTGTCCAAAGGTATCATTTGAGCCAATTCCCATACATTATTGTACCCCG

AlaGlyPheAlaIleLeuLysCysAsnAsnLysThrPheAsnGlyLysGlyProCysThr  243   E
           GCTGGTTTTGCGATTCTAAAGTGTAATAATAAAACGTTCAATGGAAAAGGACCATGTACA

AsnValSerThrValGlnCysThrHisGlyIleArgProIleValSerThrGlnLeuLeu
     6508  AATGTCAGCACAGTACAATGTACACATGGAATTAGGCCAATAGTGTCAACTCAACTGCTG

LeuAsnGlySerLeuAlaGluGluGluValValIleArgSerAspAsnPheThrAsnAsn  283   N
           TTAAATGGCAGTCTAGCAGAAGAAGAGGTAGTAATTAGATCTGACAATTTCACGAACAAT

AlaLysThrIleIleValGlnLeuAsnGluSerValAlaIleAsnCysThrArgProAsn
     6628  GCTAAAACCATAATAGTACAGCTGAATGAATCTGTAGCAATTAACTGTACAAGACCCAAC

AsnAsnThrArgLysSerIleTyrIleGlyProGlyArgAlaPheHisThrThrGlyArg  323   V
           AACAATACAAGAAAAAGTATCTATATAGGACCAGGGAGAGCATTTCATACAACAGGAAGA

IleIleGlyAspIleArgLysAlaHisCysAsnIleSerArgAlaGlnTrpAsnAsnThr
     6748  ATAATAGGAGATATAAGAAAAGCACATTGTAACATTAGTAGAGCACAATGGAATAACACT

LeuGluGlnIleValLysLysLeuArgGluGlnPheGlyAsnAsnLysThrIleValPhe  363
           TTAGAACAGATAGTTAAAAAATTAAGAGAACAGTTTGGGAATAATAAAACAATAGTCTTT

AsnGlnSerSerGlyGlyAspProGluIleValMetHisSerPheAsnCysArgGlyGlu
     6868  AATCAATCCTCAGGAGGGGACCCAGAAATTGTAATGCACAGTTTTAATTGTAGAGGGGAA

PhePheTyrCysAsnThrThrGlnLeuPheAsnAsnThrTrpArgLeuAsnHisThrGlu  403
           TTTTTCTACTGTAATACAACACAACTGTTTAATAATACATGGAGGTTAAATCACACTGAA

GlyThrLysGlyAsnAspThrIleIleLeuProCysArgIleLysGlnIleIleAsnMet
     6988  GGAACTAAAGGAAATGACACAATCATACTCCCATGTAGAATAAAACAAATTATAAACATG

TrpGlnGluValGlyLysAlaMetTyrAlaProProIleGlyGlyGlnIleSerCysSer  443
           TGGCAGGAAGTAGGAAAAGCAATGTATGCCCCTCCCATTGGAGGACAAATTAGTTGTTCA

SerAsnIleThrGlyLeuLeuLeuThrArgAspGlyGlyThrAsnValThrAsnAspThr
     7108  TCAAATATTACAGGGCTGCTATTAACAAGAGATGGTGGTACAAATGTAACTAATGACACC

GluValPheArgProGlyGlyGlyAspMetArgAspAsnTrpArgSerGluLeuTyrLys  483
           GAGGTCTTCAGACCTGGAGGAGGAGATATGAGGGACAATTGGAGAAGTGAATTATATAAA
```

FIG. 5F

```
      TyrLysValIleLysIleGluProLeuGlyIleAlaProThrLysAlaLysArgArgVal
 7228 TATAAAGTAATAAAAATTGAACCATTAGGAATAGCACCCACCAAGGCAAAGAGAAGAGTG

ValGlnArgGluLysArgAlaValGlyIleValGlyAlaMetPheLeuGlyPheLeuGly 523
      GTGCAGAGAGAAAAAAGAGCAGTGGGAATAGTAGGAGCTATGTTCCTTGGGTTCTTGGGA

AlaAlaGlySerThrMetGlyAlaValSerLeuThrLeuThrValGlnAlaArgGlnLeu
 7348 GCAGCAGGAAGCACTATGGGCGCAGTGTCATTGACGCTGACGGTACAGGCCAGACAATTA

LeuSerGlyIleValGlnGlnGlnAsnAsnLeuLeuArgAlaIleGluAlaGlnGlnHis 563
      TTGTCTGGTATAGTGCAACAGCAGAACAATTTGCTGAGGGCTATTGAGGCGCAACAACAT

LeuLeuGlnLeuThrValTrpGlyIleLysGlnLeuGlnAlaArgValLeuAlaValGlu
 7468 CTGTTGCAACTCACAGTCTGGGGCATCAAGCAGCTCCAGGCAAGAGTCCTGGCTGTGGAA

ArgTyrLeuArgAspGlnGlnLeuLeuGlyIleTrpGlyCysSerGlyLysLeuIleCys 603
      AGATACCTAAGGGATCAACAGCTCCTAGGGATTTGGGGTTGCTCTGGAAAACTCATTTGC

ThrThrAlaValProTrpAsnAlaSerTrpSerAsnLysSerLeuGluAspIleTrpAsp
 7588 ACCACTGCTGTGCCTTGGAATGCTAGTTGGAGTAATAAATCTCTGGAAGACATTTGGGAT

AsnMetThrTrpMetGlnTrpGluArgGluIleAspAsnTyrThrAsnThrIleTyrThr 643
      AACATGACCTGGATGCAGTGGGAAAGAGAAATTGACAATTACACAAACACAATATACACC

LeuLeuGluGluSerGlnAsnGlnGlnGluLysAsnGluGlnGluLeuLeuGluLeuAsp
 7708 TTACTTGAAGAATCGCAGAACCAACAAGAAAAGAATGAACAAGAATTATTAGAATTGGAT

LysTrpAlaSerLeuTrpAsnTrpPheSerIleThrAsnTrpLeuTrpTyrIleLysIle 683
      AAGTGGGCAAGTTTGTGGAATTGGTTTAGCATAACAAACTGGCTGTGGTATATAAAGATA

PheIleMetIleValGlyGlyLeuValGlyLeuArgIleValPheAlaValLeuSerIle              E
 7828 TTCATAATGATAGTAGGAGGCTTGGTAGGTTTAAGAATAGTTTTTGCTGTGCTTTCTATA

ValAsnArgValArgGlnGlyTyrSerProLeuSerPheGlnThrArgLeuProValPro 723
      GTGAATAGAGTTAGGCAGGGATACTCACCATTGTCATTTCAGACCCGCCTCCCAGTCCCG              N

ArgGlyProAspArgProAspGlyIleGluGluGluGlyGlyGluArgAspArgAspArg
 7948 AGGGGACCCGACAGGCCCGACGGAATCGAAGAAGAAGGTGGAGAGAGAGACAGAGACAGA

SerValArgLeuValAspGlyPheLeuAlaLeuIleTrpGluAspLeuArgSerLeuCys 763    V
      TCCGTTCGATTAGTGGATGGATTCTTAGCACTTATCTGGGAAGATCTGCGGAGCCTGTGC

LeuPheSerTyrArgArgLeuArgAspLeuLeuLeuIleAlaAlaArgThrValGluIle
 8068 CTCTTCAGCTACCGCCGCTTGAGAGACTTACTCTTGATTGCAGCGAGGACTGTGGAAATT

LeuGlyHisArgGlyTrpGluAlaLeuLysTyrTrpTrpSerLeuLeuGlnTyrTrpIle 803
      CTGGGGCACAGGGGGTGGGAAGCCCTCAAATATTGGTGGAGTCTCCTGCAGTATTGGATT

GlnGluLeuLysAsnSerAlaValSerTrpLeuAsnAlaThrAlaIleAlaValThrGlu
 8188 CAGGAACTAAAGAATAGTGCTGTTAGCTGGCTCAACGCCACAGCTATAGCAGTAACTGAG

GlyThrAspArgValIleGluValAlaGlnArgAlaTyrArgAlaIleLeuHisIleHis 843
      GGGACAGATAGGGTTATAGAAGTAGCACAAAGAGCTTATAGAGCTATTCTCCACATACAT

ArgArgIleArgGlnGlyLeuGluArgLeuLeuLeuOC
 8308 AGAAGAATTAGACAGGGCTTGGAAAGGCTTTTGCTATAAGATGGGTGGCAAGTGGTCAAA

ACGTAGTATGGGTGGATGGTCTGCTATAAGGGAAAGAATGAGACGAGCTGAGCCACGAGC
```

FIG. 5G

8428 TGAGCCAGCAGCAGATGGGGTGGGAGCAGTATCTCGAGACCTGGAAAAACATGGAGCAAT
     CACAAGTAGCAATACAGCAGCTACTAATGCTGATTGTGCCTGGCTAGAAGCACAAGAGGA
8548 GGAAGAGGTGGGTTTTCCAGTCAGACCTCAGGTACCTTTAAGACCAATGACTTACAAGGC
                                                      U3→
     AGCTTTAGATATTAGCCACTTTTTAAAAGAAAAGGGGGGA CTGGAAGGGCTAATTTGGT    L
8667 CCCAAAGAAGACAAGAGATCCTTGATCTGTGGATCTACCACACACAAGGCTACTTCCCTG
     ATTGGCAGAATTACACACCAGGGCCAGGGATCAGATATCCACTGACCTTTGGATGGTGCT    T
8787 TCAAGCTAGTACCAGTTGAGCCAGAGAAGGTAGAAGAGGCCAATGAAGGAGAGAACAACA
     GCTTGTTACACCCTATGAGCCTGCATGGGATGGAGGACGCGGAGAAAGAAGTGTTAGTGT    R
8907 GGAGGTTTGACAGCAAACTAGCATTTCATCACATGGCCCGAGAGCTGCATCCGGAGTACT
     ACAAAGACTGCTGACATCGAGCTTTCTACAAGGGACTTTCCGCTGGGGACTTTCCAGGGA
9027 GGCGTGGCCTGGGCGGGACTGGGGAGTGGCGTCCCTCAGATGCTGCATATAAGCAGCTGC
           ←U3 R→
     TTTTTGCCTGTACTG GGTCTCTCTGGTTAGACCAGATCTGAGCCTGGGAGCTCTCTGGC
                                                         ←R U5→
9146 TAACTAGGGAACCCACTGCTTAAGCCTCAATAAAGCTTGCCTTGAGTGCTTCA AGTAGT
     GTGTGCCCGTCTGTTGTGTGACTCTGGTAACTAGAGATCCCTCAGACCCTTTTAGTCAGT
         ←U5
9265 GTGGAAAAATCTCTAGCAG      FIG. 5H

|ptac 5 Promotor| MetIleVal
ATGATCGTA

GlnAsnLeuGlnGlyGlnMetValHisGlnAlaIleSerProArgThrLeuAsnAlaTrp
748 CAGAATCTGCAGGGGCAAATGGTACATCAGGCCATATCACCTAGAACTTTAAATGCATGG

ValLysValValGluGluLysAlaPheSerProGluValIleProMetPheSerAlaLeu 181
GTAAAAGTAGTAGAAGAAAAGGCTTTCAGCCCAGAAGTAATACCCATGTTTTCAGCATTA

SerGluGlyAlaThrProGlnAspLeuAsnThrMetLeuAsnThrValGlyGlyHisGln
868 TCAGAAGGAGCCACCCCACAAGATTTAAACACCATGCTAAACACAGTGGGGGGACATCAA

AlaAlaMetGlnMetLeuLysGluThrIleAsnGluGluAlaAlaGluTrpAspArgVal 221
GCAGCCATGCAAATGTTAAAAGAGACTATCAATGAGGAAGCTGCAGAATGGGATAGAGTG

HisProValHisAlaGlyProIleAlaProGlyGlnMetArgGluProArgGlySerAsp
988 CATCCAGTGCATGCAGGGCCTATTGCACCAGGCCAAATGAGAGAACCAAGGGGAAGTGAC

IleAlaGlyThrThrSerThrLeuGlnGluGlnIleGlyTrpMetThrAsnAsnProPro 261
ATAGCAGGAACTACTAGTACCCTTCAGGAACAAATAGGATGGATGACAAATAATCCACCT

IleProValGlyGluIleTyrLysArgTrpIleIleLeuGlyLeuAsnLysIleValArg
1108 ATCCCAGTAGGAGAAATCTATAAAAGATGGATAATCCTGGGATTAAATAAAATAGTAAGA

MetTyrSerProThrSerIleLeuAspIleArgGlnGlyProLysGluProPheArgAsp 301
ATGTATAGCCCTACCAGCATTCTGGACATAAGACAAGGACCAAAGGAACCCTTTAGAGAT

TyrValAspArgPheTyrLysThrLeuArgAlaGluGlnAlaSerGlnAspValLysAsn
1228 TATGTAGACCGGTTCTATAAAACTCTAAGAGCCGAACAAGCTTCACAGGATGTAAAAAAT

TrpMetThrGluThrLeuLeuValGlnAsnAlaAsnProAspCysLysThrIleLeuLys 341
TGGATGACAGAAACCTTGTTGGTCCAAAATGCAAACCCAGATTGTAAGACTATTTTAAAA

AlaLeuGlyProAlaAlaThrLeuGluGluMetMetThrAlaCysGlnGlyValGlyGly
1348 GCATTGGGACCAGCAGCTACACTAGAAGAAATGATGACAGCATGTCAGGGAGTGGGGGGA

ProGlyHisLysAlaArgValLeu Stop    Stop
CCCGGGCATAAAGCAAGAGTTTTGTGATAG          |ptac 5|

FIG. 8

|ptac 5 Promotor| MetIleVal 141
ATGATCGTA

GlnAsnLeuGlnGlyGlnMetValHisGlnAlaIleSerProArgThrLeuAsnAlaTrp
748 CAGAATCTGCAGGGGCAAATGGTACATCAGGCCATATCACCTAGAACTTTAAATGCATGG

ValLysValValGluGluLysAlaPheSerProGluValIleProMetPheSerAlaLeu 181
GTAAAAGTAGTAGAAGAAAAGGCTTTCAGCCCAGAAGTAATACCCATGTTTTCAGCATTA   G

SerGluGlyAlaThrProGlnAspLeuAsnThrMetLeuAsnThrValGlyGlyHisGln
868 TCAGAAGGAGCCACCCCACAAGATTTAAACACCATGCTAAACACAGTGGGGGGACATCAA

AlaAlaMetGlnMetLeuLysGluThrIleAsnGluGluAlaAlaGluTrpAspArgVal 221
GCAGCCATGCAAATGTTAAAAGAGACTATCAATGAGGAAGCTGCAGAATGGGATAGAGTG

HisProValHisAlaGlyProIleAlaProGlyGlnMetArgGluProArgGlySerAsp
988 CATCCAGTGCATGCAGGGCCTATTGCACCAGGCCAAATGAGAGAACCAAGGGGAAGTGAC   A

IleAlaGlyThrThrSerThrLeuGlnGluGlnIleGlyTrpMetThrAsnAsnProPro 261
ATAGCAGGAACTACTAGTACCCTTCAGGAACAAATAGGATGGATGACAAATAATCCACCT

IleProValGlyGluIleTyrLysArgTrpIleIleLeuGlyLeuAsnLysIleValArg
1108 ATCCCAGTAGGAGAAATCTATAAAAGATGGATAATCCTGGGATTAAATAAAATAGTAAGA   G

MetTyrSerProThrSerIleLeuAspIleArgGlnGlyProLysGluProPheArgAsp 301
ATGTATAGCCCTACCAGCATTCTGGACATAAGACAAGGACCAAAGGAACCCTTTAGAGAT

TyrValAspArgPheTyrLysThrLeuArgAlaGluGlnAlaSerGlnAspValLysAsn
1228 TATGTAGACCGGTTCTATAAAACTCTAAGAGCCGAACAAGCTTCACAGGATGTAAAAAAT

TrpMetThrGluThrLeuLeuValGlnAsnAlaAsnProAspCysLysThrIleLeuLys 341
TGGATGACAGAAACCTTGTTGGTCCAAAATGCAAACCCAGATTGTAAGACTATTTTAAAA

AlaLeuGlyProAlaAlaThrLeuGluGluMetMetThrAlaCysGlnGlyValGlyGly
1348 GCATTGGGACCAGCAGCTACACTAGAAGAAATGATGACAGCATGTCAGGGAGTGGGGGGA

ProGlyHisLysAlaArgValLeuAlaGluAlaMetSerGlnValThrAsnProAlaAsn 381
CCCGGCCATAAAGCAAGAGTTTTGGCTGAAGCCATGAGCCAAGTAACAAATCCAGCTAAC

IleMetMetGlnArgGlyAsnPheArgAsnGlnArgLysThrValLysCysPheAsnCys
1468 ATAATGATGCAGAGAGGCAATTTTAGGAACCAAAGAAAGACTGTTAAGTGTTTCAATTGT

GlyLysGluGlyHisIleAlaLysAsnCysArgAlaProArgLysLysGlyCysTrpArg 421
GGCAAAGAAGGGCACATAGCCAAAAATTGCAGGGCCCCTAGGAAAAAGGGCTGTTGGAGA

CysGlyArgGluGlyHisGlnMetLysAspCysThrGluArgGlnAlaAsnPheLeuGly
                                                  PhePheArgG
1588 TGTGGAAGGGAAGGACACCAAATGAAAGATTGCACTGAGAGACAGGCTAATTTTTTAGGG

LysIleTrpProSerTyrLysGlyArgProGlyAsnPheLeuGlnSerArgProGluPro 461
luAspLeuAlaPheLeuGlnGlyLysAlaArgGluPheSerSerGluGlnThrArgAla 23
AAGATCTGGCCTTCCTACAAGGGAAGGCCAGGGAATTTTCTTCAGAGCAGACCAGAGCCA

ThrAlaProProGluGluSerPheArgPheGlyGluGluLysThrThrProSerGlnLys
AsnSerProThrArgArgGluLeuGlnValTrpGlyGlyGluAsnAsnSerLeuSerGluA
1708 ACAGCCCCACCAGAAGAGAGCTTCAGGTTTGGGGAGGAGAAAACAACTCCCTCTCAGAAG

GlnGluProIleAspLysGluLeuTyrProLeuThrSerLeuArgSerLeuPheGlyAsn 501
laGlyAlaAspArgGlnGlyThrValSerPheAsnPheProGlnIleThrLeuTrpGln 63
CAGGAGCCGATAGACAAGGAACTGTATCCTTTAACTTCCCTCAGATCACTCTTTGGCAAC

FIG. 9A

```
                AspProSerSerGlnOC
        ArgProLeuValThrIleArgIleGlyGlyGlnLeuLysGluAlaLeuLeuAspThrGlyA
   1828 GACCCCTCGTCACAATAAGGATAGGGGGGCAACTAAAGGAAGCTCTATTAGATACAGGAG laAspAspThrValLeuGluGluMetAsnLeuProGlyLysTrpLysProLysMetIle 103
        CAGATGATACAGTATTAGAAGAAATGAATTTGCCAGGAAAATGGAAACCAAAAATGATAG

GlyGlyIleGlyGlyPheIleLysValArgGlnTyrAspGlnIleProValGluIleCysG
   1948 GGGGAATTGGAGGTTTTATCAAAGTAAGACAGTACGATCAGATACCTGTAGAAATCTGTG lyHisLysAlaIleGlyThrValLeuValGlyProThrProValAsnIleIleGlyArg  143
        GACATAAAGCTATAGGTACAGTATTAGTAGGACCTACACCTGTCAACATAATTGGAAGAA

AsnLeuLeuThrGlnIleGlyCysThrLeuAsnPheProIleSerProIleGluThrValP
   2068 ATCTGTTGACTCAGATTGGTTGTACTTTAAATTTCCCCATTAGTCCTATTGAAACTGTAC roValLysLeuLysProGlyMetAspGlyProLysValLysGlnTrpProLeuThrGlu  183
        CAGTAAAATTAAAGCCAGGAATGGATGGCCCAAAAGTTAAGCAATGGCCATTGACAGAAG

GluLysIleLysAlaLeuValGluIleCysThrGluMetGluLysGluGlyLysIleSerL
   2188 AAAAAATAAAAGCATTAGTAGAGATATGTACAGAAATGGAAAAGGAAGGGAAAATTTCAA ysIleGlyProGluAsnProTyrAsnThrProValPheAlaIleLysLysLysAspSer  223
        AAATTGGGCCTGAAAATCCATACAATACTCCAGTATTTGCTATAAAGAAAAAAGACAGTA

ThrLysTrpArgLysLeuValAspPheArgGluLeuAsnLysArgThrGlnAspPheTrpG
   2308 CTAAATGGAGAAAACTAGTAGATTTCAGAGAACTTAATAAAAGAACTCAAGACTTCTGGG luValGlnLeuGlyIleProHisProAlaGlyLeuLysLysLysLysSerValThrVal  263
        AAGTTCAGTTAGGAATACCACACCCCGCAGGGTTAAAAAAGAAAAAATCAGTAACAGTAT

LeuAspValGlyAspAlaTyrPheSerValProLeuAspLysAspPheArgLysTyrThrA
   2428 TGGATGTGGGTGATGCATACTTTTCAGTTCCCTTAGATAAAGACTTTAGAAAGTATACTG laPheThrIleProSerIleAsnAsnGluThrProGlyIleArgTyrGlnTyrAsnVal  303
        CATTTACCATACCTAGTATAAACAATGAGACACCAGGGATTAGATATCAGTACAATGTGC

LeuProGlnGlyTrpLysGlySerProAlaIlePheGlnSerSerMetThrLysIleLeuG
   2548 TGCCACAGGGATGGAAAGGATCACCAGCAATATTCCAAAGTAGCATGACAAAAATCTTAG luProPheArgLysGlnAsnProAspIleValIleTyrGlnTyrMetAspAspLeuTyr  343
        AGCCTTTTAGAAAACAGAATCCAGACATAGTTATCTATCAATACATGGATGATTTGTATG

ValGlySerAspLeuGluIleGlyGlnHisArgThrLysIleGluGluLeuArgGlnHisL
   2668 TAGGATCTGACTTAGAAATAGGGCAGCATAGAACAAAAATAGAGGAACTGAGACAGCATC euLeuArgTrpGlyPheThrThrProAspLysLysHisGlnLysGluProProPheLeu  383
        TGTTGAGGTGGGGATTTACCACACCAGACAAAAAACATCAGAAAGAACCTCCATTCCTTT

TrpMetGlyTyrGluLeuHisProAspLysTrpThrValGlnProIleMetLeuProGluL
   2788 GGATGGGTTATGAACTCCATCCTGATAAATGGACAGTACAGCCTATAATGCTGCCAGAAA ysAspSerTrpThrValAsnAspIleGlnLysLeuValGlyLysLeuAsnTrpAlaSer  423
        AAGACAGCTGGACTGTCAATGACATACAGAAGTTAGTGGGAAAATTGAATTGGGCAAGTC

GlnIleTyrAlaGlyIleLysValLysGlnLeuCysLysLeuLeuArgGlyThrLysAlaL
   2908 AGATTTATGCAGGGATTAAAGTAAAGCAGTTATGTAAACTCCTTAGAGGAACCAAAGCAC euThrGluValIleProLeuThrGluGluAlaGluLeuGluLeuAlaGluAsnArgGlu  463    P
        TAACAGAAGTAATACCACTAACAGAAGAAGCAGAGCTAGAACTGGCAGAAAACAGGGAGA         O
                                                                            L
```

FIG. 9B

```
      IleLeuLysGluProValHisGluValTyrTyrAspProSerLysAspLeuValAlaGluI
3028  TTCTAAAAGAACCAGTACATGAAGTATATTATGACCCATCAAAAGACTTAGTAGCAGAAA leGlnLysGlnGlyGlnGlyGlnTrpThrTyrGlnIleTyrGlnGluProPheLysAsn 503
      TACAGAAGCAGGGGCAAGGCCAATGGACATATCAAATTTATCAAGAGCCATTTAAAAATC

LeuLysThrGlyLysTyrAlaArgMetArgGlyAlaHisThrAsnAspValLysGlnLeuT
3148  TGAAAACAGGAAAGTATGCAAGGATGAGGGGTGCCCACACTAATGATGTAAAACAGTT hrGluAlaValGluLysValSerThrGluSerIleValIleTrpGlyLysIleProLys 543
         ptac 5
```

FIG. 9C

ARV GAG p16 - synthetic Parts A and B

```
5'      arv 234          3'
        MetGlnArgGlyAsnPheArgAsnGlnArgLysThrValLysCysPheAsnCysGlyLys
     TATTATGCAAAGAGGTAACTTCAGGAATCAAAGAAAGACCGTTAAGTGTTTCAACTGTGGTAAG
     ATAATACGTTTCTCCATTGAAGTCCTTAGTTTCTTTCTGGCAATTCACAAAGTTGACACCATTC
        3'      arv 235   5'
        10 mnll, 23 hinfl, GluGlyHisIleAlaLysAsnCysArgAlaProArgLysLysAlaCysTrpArgCysGly
     63 GAAGGTCACATCGCTAAGAACTGTAGAGCTCCAAGAAAGAAGGCTTGTTGGAGATGTGGT
        CTTCCAGTGTAGCGATTCTTGACATCTCGAGGTTCTTTCTTCCGAACAACCTCTACACCA 76 ddel, 88 ban2 hgiA hgiJll sacl sdul, 89 alul, ArgGluGlyHisGlnMetLysAspCysThrGluArgGlnAlaAsnPheLeuGlyLysIle
    123 AGAGAAGGTCACCAAATGAAGGACTGTACCGAAAGACAAGCTAACTTCTTGGGTAAGATC
        TCTCTTCCAGTGGTTTACTTCCTGACATGGCTTTCTGTTCGATTGAAGAACCCATTCTAG 129 bstE2, 131 hph, 148 rsal, 161 alul, 178 bglll xho2, 179
        sau3a, TrpProSerTyrLysGlyArgProGlyAsnPheLeuGlnSerArgProGluProThrAla
    183 TGGCCATCTTACAAGGGTAGACCAGGTAACTTCTTGCAATCCAGACCAGAACCAACCGCT
        ACCGGTAGAATGTTCCCATCTGGTCCATTGAAGAACGTTAGGTCTGGTCTTGGTTGGCGA 183 ball cfrl hael, 184 haelll, 199 accl, 204 apyl ecorll sc
        rFl, ProProGluGluSerPheArgPheGlyGluGluLysThrThrProSerGlnLysGlnGlu
    243 CCACCTGAAGAAAGTTTCAGGTTCGGTGAAGAAAAGACCACCCCATCTCAAAAGCAAGAA
        GGTGGACTTCTTTCAAAGTCCAAGCCACTTCTTTTCTGGTGGGGTAGAGTTTTCGTTCTT 249 mboll, 267 hph, 270 mboll, ProIleAspLysGluLeuTyrProLeuThrSerLeuArgSerLeuPheGlyAsnAspPro
    303 CCAATCGACAAGGAATTGTACCCATTGACCTCTTTGAGATCCTTGTTCGGTAACGATCCC
        GGTTAGCTGTTCCTTAACATGGGTAACTGGAGAAACTCTAGGAACAAGCCATTGCTAGGG 307 taql, 320 rsal, 331 mnll, 339 xho2, 340 sau3a, 357 sau3a,
        361 mnll, 362 aval xhol, SerSerGlnOP AM
    363 TCGAGCCAATGATAG
        AGCTCGGTTACTATCAGCT 363 taql, 377 accl hindll sall
```

FIG. 10

```
                                                              MetSer
        ┌─────────────────┐                                   ATGTCT
        │  PYK Promoter   │
        └─────────────────┘
     ArgIleAspCysSerAlaThrGluLysLeuTrpValThrValTyrTyrGlyValProVal  51
     AGAATCGAT GTAGTGCTACAGAAAAATTGTGGGTCACAGTTTATTATGGAGTACCTGTG TrpLysGluAlaThrThrThrLeuPheCysAlaSerAspAlaArgAlaTyrAspThrGlu
5908 TGGAAAGAAGCAACTACCACTCTATTTTGTGCATCAGATGCTAGAGCATATGATACAGAG ValHisAsnValTrpAlaThrHisAlaCysValProThrAspProAsnProGlnGluVal  91
     GTACATAATGTTTGGGCCACACATGCCTGTGTACCCACAGACCCCAACCCACAAGAAGTA ValLeuGlyAsnValThrGluAsnPheAsnMetTrpLysAsnAsnMetValGluGlnMet
6028 GTATTGGGAAATGTGACAGAAAATTTTAACATGTGGAAAAATAACATGGTAGAACAGATG GlnGluAspIleIleSerLeuTrpAspGlnSerLeuLysProCysValLysLeuThrPro 131
     CAGGAGGATATAATCAGTTTATGGGATCAAAGCCTAAAGCCATGTGTAAAATTAACCCCA LeuCysValThrLeuAsnCysThrAspLeuGlyLysAlaThrAsnThrAsnSerSerAsn
6148 CTCTGTGTTACTTTAAATTGCACTGATTTGGGGAAGGCTACTAATACCAATAGTAGTAAT TrpLysGluGluIleLysGlyGluIleLysAsnCysSerPheAsnIleThrThrSerIle 171
     TGGAAAGAAGAAATAAAAGGAGAAATAAAAAACTGCTCTTTCAATATCACCACAAGCATA ArgAspLysIleGlnLysGluAsnAlaLeuPheArgAsnLeuAspValValProIleAsp
6268 AGAGATAAGATTCAGAAAGAAAATGCACTTTTTCGTAACCTTGATGTAGTACCAATAGAT AsnAlaSerThrThrThrAsnTyrThrAsnTyrArgLeuIleHisCysAsnArgSerVal 211
     AATGCTAGTACTACTACCAACTATACCAACTATAGGTTGATACATTGTAACAGATCAGTC IleThrGlnAlaCysProLysValSerPheGluProIleProIleHisTyrCysThrPro
6388 ATTACACAGGCCTGTCCAAAGGTATCATTTGAGCCAATTCCCATACATTATTGTACCCCG AlaGlyPheAlaIleLeuLysCysAsnAsnLysThrPheAsnGlyLysGlyProCysThr 251
     GCTGGTTTTGCGATTCTAAAGTGTAATAATAAAACGTTCAATGGAAAAGGACCATGTACA
```

FIG. 11A

```
              AsnValSerThrValGlnCysThrHisGlyIleArgProIleValSerThrGlnLeuLeu
6508 AATGTCAGCACAGTACAATGTACACATGGAATTAGGCCAATAGTGTCAACTCAACTGCTG

LeuAsnGlySerLeuAlaGluGluGluValValIleArgSerAspAsnPheThrAsnAsn 291
     TTAAATGGCAGTCTAGCAGAAGAAGAGGTAGTAATTAGATCTGACAATTTCACGAACAAT

AlaLysThrIleIleValGlnLeuAsnGluSerValAlaIleAsnCysThrArgProAsn
6628 GCTAAAACCATAATAGTACAGCTGAATGAATCTGTAGCAATTAACTGTACAAGACCCAAC

AsnAsnThrArgLysSerIleTyrIleGlyProGlyArgAlaPheHisThrThrGlyArg 331
     AACAATACAAGAAAAAGTATCTATATAGGACCAGGGAGAGCATTTCATACAACAGGAAGA

IleIleGlyAspIleArgLysAlaHisCysAsnIleSerArgAlaGlnTrpAsnAsnThr
6748 ATAATAGGAGATATAAGAAAAGCACATTGTAACATTAGTAGAGCACAATGGAATAACACT

LeuGluGlnIleValLysLysLeuArgGluGlnPheGlyAsnAsnLysThrIleValPhe 371
     TTAGAACAGATAGTTAAAAAATTAAGAGAACAGTTTGGGAATAATAAAACAATAGTCTTT

AsnGlnSerSerGlyGlyAspProGluIleValMetHisSerPheAsnCysArgGlyGlu
6868 AATCAATCCTCAGGAGGGGACCCAGAAATTGTAATGCACAGTTTTAATTGTAGAGGGGAA

PhePheTyrCysAsnThrThrGlnLeuPheAsnAsnThrTrpArgLeuAsnHisThrGlu 411       E
     TTTTTCTACTGTAATACAACACAACTGTTTAATAATACATGGAGGTTAAATCACACTGAA

GlyThrLysGlyAsnAspThrIleIleLeuProCysArgIleLysGlnIleIleAsnMet
6988 GGAACTAAAGGAAATGACACAATCATACTCCCATGTAGAATAAAACAAATTATAAACATG

TrpGlnGluValGlyLysAlaMetTyrAlaProProIleGlyGlyGlnIleSerCysSer 451       N
     TGGCAGGAAGTAGGAAAAGCAATGTATGCCCCTCCCATTGGAGGACAAATTAGTTGTTCA

SerAsnIleThrGlyLeuLeuLeuThrArgAspGlyGlyThrAsnValThrAsnAspThr
7108 TCAAATATTACAGGGCTGCTATTAACAAGAGATGGTGGTACAAATGTAACTAATGACACC

GluValPheArgProGlyGlyGlyAspMetArgAspAsnTrpArgSerGluLeuTyrLys 491       V
     GAGGTCTTCAGACCTGGAGGAGGAGATATGAGGGACAATTGGAGAAGTGAATTATATAAA

TyrLysValIleLysIleGluProAsnSerValSer             PYK Terminator
7228 TATAAAGTAATAAAAATTGAACCAAATTCGGTATCTTGA
```

FIG. 11B

```
Nucleotide                    MetIleAspLysAlaGlnGluGluHisGluLysTyrHisSerAsnTrp
positions    1 AGGXAACAG:::::ATGAT:GA:AAGGCACAAGAAGAACATGAGAAATATCACAGTAATTGG
relative to    TCCXTTGTC:::::TACTA:CT:TTCCGTGTTCTTCTTGTACTCTTTATAGTGTCATTAACC
Figure 5.
               32 mboII, 38 nlaIII, ArgAlaMetAlaSerAspPheAsnLeuProProValValAlaLysGluIleValAlaSer
  3820     62 AGAGCCATGGCTAGTGATTTTAACCTGCCACCTGTAGTAGCAAAAGAAATAGTAGCCAGC
               TCTCGGTACCGATCACTAAAATTGGACGGTGGACATCATCGTTTTCTTTATCATCGGTCG
               66 ncoI, 67 nlaIII, 118 nspBII pvuII, 119 aluI, CysAspLysCysGlnLeuLysGlyGluAlaMetHisGlyGlnValAspCysSerProGly
  3880    122 TGTGATAAATGTCAGCTAAAAGGAGAAGCCATGCATGGACAAGTAGACTGTAGTCCAGGA
               ACACTATTTACAGTCGATTTTCCTCTTCGGTACGTACCTGTTCATCTGACATCAGGTCCT
               135 aluI, 151 nlaIII, 152 nsiI ava3, 155 nlaIII, 164 accI, 1
               76 apyI bstXI ecoRII scrFI, IleTrpGlnLeuAspCysThrHisLeuGluGlyLysIleIleLeuValAlaValHisVal
  3940    182 ATATGGCAACTAGATTGTACACATCTAGAAGGAAAAATTATCCTGGTAGCAGTTCATGTA
               TATACCGTTGATCTAACATGTGTAGATCTTCCTTTTTAATAGGACCATCGTCAAGTACAT
               198 rsaI, 205 xbaI, 223 apyI ecoRII scrFI, 236 nlaIII, AlaSerGlyTyrIleGluAlaGluValIleProAlaGluThrGlyGlnGluThrAlaTyr
  4000    242 GCCAGTGGATATATAGAAGCAGAAGTTATTCCAGCAGAGACAGGGCAGGAAACAGCATAT
               CGGTCACCTATATATCTTCGTCTTCAATAAGGTCGTCTCTGTCCCGTCCTTTGTCGTATA
               263 xmnI, PheLeuLeuLysLeuAlaGlyArgTrpProValLysThrIleHisThrAspAsnGlySer
  4060    302 TTTCTCTTAAAATTAGCAGGAAGATGGCCAGTAAAAACAATACATACAGACAATGGCAGC
               AAAGAGAATTTTAATCGTCCTTCTACCGGTCATTTTGTTATGTATGTCTGTTACCGTCG
               321 mboII, 326 baII cfrI haeI, 327 haeIII, 357 bbv fnu4hI, AsnPheThrSerThrThrValLysAlaAlaCysTrpTrpAlaGlyIleLysGlnGluPhe
  4120    362 AATTTCACCAGTACTACGGTTAAGGCCGCCTGTTGGTGGGCAGGGATCAAGCAGGAATTT
               TTAAAGTGGTCATGATGCCAATTCCGGCGGACAACCACCCGTCCCTAGTTCGTCCTTAAA
               366 hph, 371 scaI, 372 rsaI, 385 haeIII, 386 fnu4hI nsbII, 4
               05 binI, 406 dpnI sau3a, GlyIleProTyrAsnProGlnSerGlnGlyValValGluSerMetAsnAsnGluLeuLys
  4180    422 GGCATTCCCTACAATCCCCAAAGTCAAGGAGTAGTAGAATCTATGAATAATGAATTAAAG
               CCGTAAGGGATGTTAGGGGTTTCAGTTCCTCATCATCTTAGATACTTATTACTTAATTTC
               423 bsmI, 458 hinfI, LysIleIleGlyGlnValArgAspGlnAlaGluHisLeuLysThrAlaValGlnMetAla
  4240    482 AAAATTATAGGACAGGTAAGAGATCAGGCTGAACACCTTAAGACAGCAGTACAAATGGCA
               TTTTAATATCCTGTCCATTCTCTAGTCCGACTTGTGGAATTCTGTCGTCATGTTTACCGT
               503 dpnI sau3a, 518 afIII, 530 rsaI, ValPheIleHisAsnPheLysArgLysGlyGlyIleGlyGlyTyrSerAlaGlyGluArg
  4300    542 GTATTCATCCACAATTTTAAAAGAAAAGGGGGGATTGGGGGATACAGTGCAGGGGAAAGA
               CATAAGTAGGTGTTAAAATTTTCTTTTCCCCCCTAACCCCCTATGTCACGTCCCCTTTCT
               547 fokI, 557 ahaIII,
```

FIG. 12A

```
                IleValAspIleIleAlaThrAspIleGlnThrLysGluLeuGlnLysGlnIleThrLys
4360    602     ATAGTAGACATAATAGCAACAGACATACAAACTAAAGAACTACAAAAGCAAATTACAAAA
                TATCATCTGTATTATCGTTGTCTGTATGTTTGATTTCTTGATGTTTTCGTTTAATGTTTT
                605 accl, IleGlnAsnPheArgValTyrTyrArgAspAsnLysAspProLeuTrpLysGlyProAla
4420    662     ATTCAAAATTTTCGGGTTTATTACAGGGACAACAAAGATCCCCTTTGGAAAGGACCAGCA
                TAAGTTTTAAAAGCCCAAATAATGTCCCTGTTGTTTCTAGGGGAAACCTTTCCTGGTCGT
                697 xho2, 698 dpnl sau3a, 713 asul ava2, LysLeuLeuTrpLysGlyGluGlyAlaValValIleGlnAspAsnSerAspIleLysVal
4480    722     AAGCTTCTCTGGAAAGGTGAAGGGGCAGTAGTAATACAAGATAATAGTGACATAAAAGTA
                TTCGAAGAGACCTTTCCACTTCCCCGTCATCATTATGTTCTATTATCACTGTATTTTCAT
                722 hindlll, 723 alul, 737 hph, ValProArgArgLysAlaLysIleIleArgAspTyrGlyLysGlnMetAlaGlyAspAsp
4540    782     GTGCCAAGAAGAAAAGCAAAAATCATTAGGGATTATGGAAAACAGATGGCAGGTGATGAT
                CACGGTTCTTCTTTTCGTTTTTAGTAATCCCTAATACCTTTTGTCTACCGTCCACTACTA
                789 mboll, 833 hph, CysValAlaSerArgGlnAspGluAspAM
4600    842     TGTGTGGCAAGTAGACAGGATGAGGATTAGTCGACGGAATTCTTTAGTAAAACACC
                ACACACCGTTCATCTGTCCTACTCCTAATCAGCTGCCTTAAGAAATCATTTTGTGG
                852 accl, 859 fokl, 863 mnll, 871 accl hindll sall, 872 taql
                , 878 ecorl,
```

FIG. 12B

```
       SOD
      ┌──►
      MetAlaThrLysAlaValCysValLeuLysGlyAspGlyProValGlnGlyIleIleAsn
  1   CATGGCGACGAAGGCCGTGTGCGTGCTGAAGGGCGACGGCCCAGTGCAGGGCATCATCAAT
      GCTGCTTCCGGCACACGCACGACTTCCCGCTGCCGGGTCACGTCCCGTAGTAGTTA

PheGluGlnLysGluSerAsnGlyProValLysValTrpGlySerIleLysGlyLeuThr
 62   TTCGAGCAGAAGGAAAGTAATGGACCAGTGAAGGTGTGGGGAAGCATTAAAGGACTGACT
      AAGCTCGTCTTCCTTTCATTACCTGGTCACTTCCACACCCCTTCGTAATTTCCTGACTGA

GluGlyLeuHisGlyPheHisValHisGluPheGlyAspAsnThrAlaGlyCysThrSer
122   GAAGGCCTGCATGGATTCCATGTTCATGAGTTTGGAGATAATACAGCAGGCTGTACCAGT
      CTTCCGGACGTACCTAAGGTACAAGTACTCAAACCTCTATTATGTCGTCCGACATGGTCA

AlaGlyProHisPheAsnProLeuSerArgLysHisGlyGlyProLysAspGluGluArg
182   GCAGGTCCTCACTTTAATCCTCTATCCAGAAAACACGGTGGGCCAAAGGATGAAGAGAGG
      CGTCCAGGAGTGAAATTAGGAGATAGGTCTTTTGTGCCACCCGGTTTCCTACTTCTCTCC

HisValGlyAspLeuGlyAsnValThrAlaAspLysAspGlyValAlaAspValSerIle
242   CATGTTGGAGACTTGGGCAATGTGACTGCTGACAAAGATGGTGTGGCCGATGTGTCTATT
      GTACAACCTCTGAACCCGTTACACTGACGACTGTTTCTACCACACCGGCTACACAGATAA

GluAspSerValIleSerLeuSerGlyAspHisCysIleIleGlyArgThrLeuValVal
302   GAAGATTCTGTGATCTCACTCTCAGGAGACCATTGCATCATTGGCCGCACACTGGTGGTC
      CTTCTAAGACACTAGAGTGAGAGTCCTCTGGTAACGTAGTAACCGGCGTGTGACCACCAG

HisGluLysAlaAspAspLeuGlyLysGlyGlyAsnGluGluSerThrLysThrGlyAsn
362   CATGAAAAAGCAGATGACTTGGGCAAAGGTGGAAATGAAGAAAGTACAAAGACAGGAAAC
      GTACTTTTTCGTCTACTGAACCCGTTTCCACCTTTACTTCTTTCATGTTTCTGTCCTTTG

ENV 5B
                                                   ┌──►
      AlaGlySerArgLeuAlaCysGlyValIleGlyIleAlaMetAlaIleGluAlaGlnGln
422   GCTGGAAGTCGTTTGGCTTGTGGTGTAATTGGGATCGCCATGGCTATCGAAGCTCAACAA
      CGACCTTCAGCAAACCGAACACCACATTAACCCTAGCGGTACCGATAGCTTCGAGTTGTT

HisLeuLeuGlnLeuThrValTrpGlyIleLysGlnLeuGlnAlaArgValLeuAlaVal
482   CACTTGCTGCAGTTGACCGTTTGGGGTATCAAGCAGTTGCAGGCTAGAGTTTTGGCTGTT
      GTGAACGACGTCAACTGGCAAACCCCATAGTTCGTCAACGTCCGATCTCAAAACCGACAA

GluArgTyrLeuArgAspGlnGlnLeuLeuGlyIleTrpGlyCysSerGlyLysLeuIle
542   GAAAGATACTTGAGAGATCAACAATTGTTGGGTATCTGGGGTTGTTCTGGTAAGTTGATT
      CTTTCTATGAACTCTCTAGTTGTTAACAACCCATAGACCCCAACAAGACCATTCAACTAA

CysThrThrAlaValProTrpAsnAlaSerTrpSerAsnLysSerLeuGluAspIleTrp
602   TGTACCACCGCTGTTCCCTGGAACGCTTCTTGGTCTAACAAGTCTTTGGAAGACATCTGG
      ACATGGTGGCGACAAGGGACCTTGCGAAGAACCAGATTGTTCAGAAACCTTCTGTAGACC

AspAsnMetThrTrpMetGlnTrpGluArgGluIleAspAsnTyrThrAsnThrIleTyr
662   GACAACATGACCTGGATGCAATGGGAAAGAGAAATCGACAACTACACCAACACCATCTAC
      CTGTTGTACTGGACCTACGTTACCCTTTCTCTTTAGCTGTTGATGTGGTTGTGGTAGATG

ThrLeuLeuGluGluSerGlnAsnGlnGlnGluLysAsnGluGlnGluLeuLeuGluLeu
722   ACCTTGTTGGAGGAATCTCAAAACCAACAAGAAAAGAACGAACAAGAATTGTTGGAATTG
      TGGAACAACCTCCTTAGAGTTTTGGTTGTTCTTTTCTTGCTTGTTCTTAACAACCTTAAC

AspLysTrpAlaSerLeuTrpAsnTrpPheSerIleThrAsnTrpAM
782   GACAAGTGGGCAAGCTTGTGGAACTGGTTCTCTATCACCAACTGGTAG
      CTGTTCACCCGTTCGAACACCTTGACCAAGAGATAGTGGTTGACCATCAGCT

Translated Mol. Weight = 30414.22

FIG. 15
```

```
     1                                        10
    Met Pro Ile Val Gln Asn Leu Gln Gly Gln Met Val His Gln
C   ATG CCT ATA GTG CAG AAT CTG CAG GGG CAA ATG GTA CAT CAG

20
Ala Ile Ser Pro Arg Thr Leu Asn Ala Trp Val Lys Val Val Glu
GCC ATA TCA CCT AGA ACT TTA AAT GCT TGG GTA AAA GTA GTA GAA 30                                            40
Glu Lys Ala Phe Ser Pro Glu Val Ile Pro Met Phe Ser Ala Leu
GAA AAG GCT TTC AGC CCA GAA GTA ATA CCC ATG TTT TCA GCA TTA

50
Ser Glu Gly Ala Thr Pro Gln Asp Leu Asn Thr Met Leu Asn Thr
TCA GAA GGA GCC ACC CCT CAA GAT TTA AAC ACC ATG CTA AAC ACA 60                                            70
Val Gly Gly His Gln Ala Ala Met Gln Met Leu Lys Glu Thr Ile
GTG GGG GGA CAT CAA GCA GCC ATG CAA ATG TTA AAA GAG ACT ATC

80
Asn Glu Glu Ala Ala Glu Trp Asp Arg Val His Pro Val His Ala
AAT GAG GAG GCT GCC GAA TGG GAT AGA GTG CAT CCA GTG CAT GCA 90                                           100
Gly Pro Ile Ala Pro Gly Gln Met Arg Glu Pro Arg Gly Ser Asp
GGG CCT ATT GCA CCA GGC CAA ATG AGA GAA CCA AGG GGA AGT GAC
```

FIG. 22A

```
                                    110
Ile Ala Gly Thr Thr Ser Thr Leu Gln Glu Gln Ile Gly Trp Met
ATA GCA GGA ACT ACT AGT ACC CTT CAG GAA CAA ATA GGA TGG ATG 120                                     130
Thr Asn Asn Pro Pro Ile Pro Val Gly Glu Ile Tyr Lys Arg Trp
ACA AAT AAT CCA CCT ATC CCA GTA GGA GAA ATC TAT AAA AGA TGG

140
Ile Ile Leu Gly Leu Asn Lys Ile Val Arg Met Tyr Ser Pro Thr
ATA ATC CTG GGA TTA AAT AAA ATA GTA AGA ATG TAT AGC CCT ACC 150                                     160
Ser Ile Leu Asp Ile Arg Gln Gly Pro Lys Glu Pro Phe Arg Asp
AGC ATT CTG GAC ATA AGA CAA GGA CCA AAG GAA CCC TTT AGA GAT

170
Tyr Val Asp Arg Phe Tyr Lys Thr Leu Arg Ala Glu Gln Ala Ser
TAT GTA GAC CGG TTC TAT AAA ACT CTA AGA GCC GAA CAA GCT TCA 180                                     190
Gln Asp Val Lys Asn Trp Met Thr Glu Thr Leu Leu Val Gln Asn
CAG GAT GTA AAA AAT TGG ATG ACA GAA ACC TTG TTG GTC CAA AAT

200
Ala Asn Pro Asp Cys Lys Thr Ile Leu Lys Ala Leu Gly Pro Ala
GCA AAC CCA GAT TGT AAG ACT ATT TTA AAA GCA TTG GGA CCA GCA 210                                     220
Ala Thr Leu Glu Glu Met Met Thr Ala Cys Gln Gly Val Gly Gly
GCT ACA CTA GAA GAA ATG ATG ACA GCA TGT CAG GGA GTG GGG GGA 230     232
Pro Gly His Lys Ala Arg Val Leu OP
CCC GGG CAT AAA GCA AGA GTT TTG TGA TAG
```

Translated Mol. Weight = 25700.75

FIG. 22B

```
                                              SOD-->
                                              MetAlaThrLysAla
                                              ATGGCTACAAAGGCT
                                              TACCGATGTTTCCGA

ValCysValLeuLysGlyAspGlyProValGlnGlyIleIleAsnPheGluGlnLysGlu
1383   GTTTGTGTTTTGAAGGGTGACGGCCCAGTTCAAGGTATTATTAACTTCGAGCAGAAGGAA
       CAAACACAAAACTTCCCACTGCCGGGTCAAGTTCCATAATAATTGAAGCTCGTCTTCCTT

SerAsnGlyProValLysValTrpGlySerIleLysGlyLeuThrGluGlyLeuHisGly
1443   AGTAATGGACCAGTGAAGGTGTGGGGAAGCATTAAAGGACTGACTGAAGGCCTGCATGGA
       TCATTACCTGGTCACTTCCACACCCCTTCGTAATTTCCTGACTGACTTCCGGACGTACCT

PheHisValHisGluPheGlyAspAsnThrAlaGlyCysThrSerAlaGlyProHisPhe
1503   TTCCATGTTCATGAGTTTGGAGATAATACAGCAGGCTGTACCAGTGCAGGTCCTCACTTT
       AAGGTACAAGTACTCAAACCTCTATTATGTCGTCCGACATGGTCACGTCCAGGAGTGAAA

AsnProLeuSerArgLysHisGlyGlyProLysAspGluGluArgHisValGlyAspLeu
1563   AATCCTCTATCCAGAAAACACGGTGGGCCAAAGGATGAAGAGAGGCATGTTGGAGACTTG
       TTAGGAGATAGGTCTTTTGTGCCACCCGGTTTCCTACTTCTCTCCGTACAACCTCTGAAC

GlyAsnValThrAlaAspLysAspGlyValAlaAspValSerIleGluAspSerValIle
1623   GGCAATGTGACTGCTGACAAAGATGGTGTGGCCGATGTGTCTATTGAAGATTCTGTGATC
       CCGTTACACTGACGACTGTTTCTACCACACCGGCTACACAGATAACTTCTAAGACACTAG

SerLeuSerGlyAspHisCysIleIleGlyArgThrLeuValValHisGluLysAlaAsp
1683   TCACTCTCAGGAGACCATTGCATCATTGGCCGCACACTGGTGGTCCATGAAAAAGCAGAT
       AGTGAGAGTCCTCTGGTAACGTAGTAACCGGCGTGTGACCACCAGGTACTTTTTCGTCTA

AspLeuGlyLysGlyGlyAsnGluGluSerThrLysThrGlyAsnAlaGlySerArgLeu
1743   GACTTGGGCAAAGGTGGAAATGAAGAAAGTACAAAGACAGGAAACGCTGGAAGTCGTTTG
       CTGAACCCGTTTCCACCTTTACTTCTTTCATGTTTCTGTCCTTTGCGACCTTCAGCAAAC linker -->              p31 -->
       AlaCysGlyValIleGlyIleAlaGlnAsnSerGlyValGlyAlaMetAlaMetAlaSer
1803   GCTTGTGGTGTAATTGGGATCGCCCAGAATTCAGGTGTTGGAGCCATGGCCATGGCTAGT
       CGAACACCACATTAACCCTAGCGGGTCTTAAGTCCACAACCTCGGTACCGGTACCGATCA AspPheAsnLeuProProValValAlaLysGluIleValAlaSerCysAspLysCysGln
1863   GATTTTAACCTGCCACCTGTAGTAGCAAAAGAAATAGTAGCCAGCTGTGATAAATGTCAG
       CTAAAATTGGACGGTGGACATCATCGTTTTCTTTATCATCGGTCGACACTATTTACAGTC LeuLysGlyGluAlaMetHisGlyGlnValAspCysSerProGlyIleTrpGlnLeuAsp
1923   CTAAAAGGAGAAGCCATGCATGGACAAGTAGACTGTAGTCCAGGAATATGGCAACTAGAT
       GATTTTCCTCTTCGGTACGTACCTGTTCATCTGACATCAGGTCCTTATACCGTTGATCTA
```

FIG. 24A

```
     CysThrHisLeuGluGlyLysIleIleLeuValAlaValHisValAlaSerGlyTyrIle
1983 TGTACACATCTAGAAGGAAAAATTATCCTGGTAGCAGTTCATGTAGCCAGTGGATATATA
     ACATGTGTAGATCTTCCTTTTTAATAGGACCATCGTCAAGTACATCGGTCACCTATATAT

GluAlaGluValIleProAlaGluThrGlyGlnGluThrAlaTyrPheLeuLeuLysLeu
2043 GAAGCAGAAGTTATTCCAGCAGAGACAGGGCAGGAAACAGCATATTTTCTCTTAAAATTA
     CTTCGTCTTCAATAAGGTCGTCTCTGTCCCGTCCTTTGTCGTATAAAAGAGAATTTTAAT

AlaGlyArgTrpProValLysThrIleHisThrAspAsnGlySerAsnPheThrSerThr
2103 GCAGGAAGATGGCCAGTAAAAACAATACATACAGACAATGGCAGCAATTTCACCAGTACT
     CGTCCTTCTACCGGTCATTTTTGTTATGTATGTCTGTTACCGTCGTTAAAGTGGTCATGA

ThrValLysAlaAlaCysTrpTrpAlaGlyIleLysGlnGluPheGlyIleProTyrAsn
2163 ACGGTTAAGGCCGCCTGTTGGTGGGCAGGGATCAAGCAGGAATTTGGCATTCCCTACAAT
     TGCCAATTCCGGCGGACAACCACCCGTCCCTAGTTCGTCCTTAAACCGTAAGGGATGTTA

ProGlnSerGlnGlyValValGluSerMetAsnAsnGluLeuLysLysIleIleGlyGln
2223 CCCCAAAGTCAAGGAGTAGTAGAATCTATGAATAATGAATTAAAGAAAATTATAGGACAG
     GGGGTTTCAGTTCCTCATCATCTTAGATACTTATTACTTAATTTCTTTTAATATCCTGTC

ValArgAspGlnAlaGluHisLeuLysThrAlaValGlnMetAlaValPheIleHisAsn
2283 GTAAGAGATCAGGCTGAACACCTTAAGACAGCAGTACAAATGGCAGTATTCATCCACAAT
     CATTCTCTAGTCCGACTTGTGGAATTCTGTCGTCATGTTTACCGTCATAAGTAGGTGTTA

PheLysArgLysGlyGlyIleGlyGlyTyrSerAlaGlyGluArgIleValAspIleIle
2343 TTTAAAAGAAAAGGGGGGATTGGGGGATACAGTGCAGGGGAAAGAATAGTAGACATAATA
     AAATTTTCTTTTCCCCCCTAACCCCCTATGTCACGTCCCCTTTCTTATCATCTGTATTAT

AlaThrAspIleGlnThrLysGluLeuGlnLysGlnIleThrLysIleGlnAsnPheArg
2403 GCAACAGACATACAAACTAAAGAACTACAAAAGCAAATTACAAAAATTCAAAATTTTCGG
     CGTTGTCTGTATGTTTGATTTCTTGATGTTTTCGTTTAATGTTTTTAAGTTTTAAAAGCC

ValTyrTyrArgAspAsnLysAspProLeuTrpLysGlyProAlaLysLeuLeuTrpLys
2463 GTTTATTACAGGGACAACAAAGATCCCCTTTGGAAAGGACCAGCAAAGCTTCTCTGGAAA
     CAAATAATGTCCCTGTTGTTTCTAGGGGAAACCTTTCCTGGTCGTTTCGAAGAGACCTTT

GlyGluGlyAlaValValIleGlnAspAsnSerAspIleLysValValProArgArgLys
2523 GGTGAAGGGGCAGTAGTAATACAAGATAATAGTGACATAAAAGTAGTGCCAAGAAGAAAA
     CCACTTCCCCGTCATCATTATGTTCTATTATCACTGTATTTTCATCACGGTTCTTCTTTT

AlaLysIleIleArgAspTyrGlyLysGlnMetAlaGlyAspAspCysValAlaSerArg
2583 GCAAAAATCATTAGGGATTATGGAAAACAGATGGCAGGTGATGATTGTGTGGCAAGTAGA
     CGTTTTTAGTAATCCCTAATACCTTTTGTCTACCGTCCACTACTAACACACCGTTCATCT

GlnAspGluAspAM
2643 CAGGATGAGGATTAG
     GTCCTACTCCTAATC
```

FIG. 24B

Sequence of SOD/env-4

```
    SOD -->
    MetAlaThrLysAlaValCysValLeuLysGlyAspGlyProValGlnGlyIleIleAsn
  1 CATGGCGACGAAGGCCGTGTGCGTGCTGAAGGGCGACGGCCCAGTGCAGGGCATCATCAAT
    GCTGCTTCCGGCACACGCACGACTTCCCGCTGCCGGGTCACGTCCCGTAGTAGTTA

PheGluGlnLysGluSerAsnGlyProValLysValTrpGlySerIleLysGlyLeuThr
 62 TTCGAGCAGAAGGAAAGTAATGGACCAGTGAAGGTGTGGGGAAGCATTAAAGGACTGACT
    AAGCTCGTCTTCCTTTCATTACCTGGTCACTTCCACACCCCTTCGTAATTTCCTGACTGA

GluGlyLeuHisGlyPheHisValHisGluPheGlyAspAsnThrAlaGlyCysThrSer
122 GAAGGCCTGCATGGATTCCATGTTCATGAGTTTGGAGATAATACAGCAGGCTGTACCAGT
    CTTCCGGACGTACCTAAGGTACAAGTACTCAAACCTCTATTATGTCGTCCGACATGGTCA

AlaGlyProHisPheAsnProLeuSerArgLysHisGlyGlyProLysAspGluGluArg
182 GCAGGTCCTCACTTTAATCCTCTATCCAGAAAACACGGTGGGCCAAAGGATGAAGAGAGG
    CGTCCAGGAGTGAAATTAGGAGATAGGTCTTTTGTGCCACCCGGTTTCCTACTTCTCTCC

HisValGlyAspLeuGlyAsnValThrAlaAspLysAspGlyValAlaAspValSerIle
242 CATGTTGGAGACTTGGGCAATGTGACTGCTGACAAAGATGGTGTGGCCGATGTGTCTATT
    GTACAACCTCTGAACCCGTTACACTGACGACTGTTTCTACCACACCGGCTACACAGATAA

GluAspSerValIleSerLeuSerGlyAspHisCysIleIleGlyArgThrLeuValVal
302 GAAGATTCTGTGATCTCACTCTCAGGAGACCATTGCATCATTGGCCGCACACTGGTGGTC
    CTTCTAAGACACTAGAGTGAGAGTCCTCTGGTAACGTAGTAACCGGCGTGTGACCACCAG

HisGluLysAlaAspAspLeuGlyLysGlyGlyAsnGluGluSerThrLysThrGlyAsn
362 CATGAAAAAGCAGATGACTTGGGCAAAGGTGGAAATGAAGAAAGTACAAAGACAGGAAAC
    GTACTTTTTCGTCTACTGAACCCGTTTCCACCTTTACTTCTTTCATGTTTCTGTCCTTTG

Env4 -->
    AlaGlySerArgLeuAlaCysGlyValIleGlyIleAlaMetGluValValIleArgSer
422 GCTGGAAGTCGTTTGGCTTGTGGTGTAATTGGGATCGCCATGGAGGTAGTAATTAGATCT
    CGACCTTCAGCAAACCGAACACCACATTAACCCTAGCGGTACCTCCATCATTAATCTAGA

AspAsnPheThrAsnAsnAlaLysThrIleIleValGlnLeuAsnGluSerValAlaIle
482 GACAATTTCACGAACAATGCTAAAACCATAATAGTACAGCTGAATGAATCTGTAGCAATT
    CTGTTAAAGTGCTTGTTACGATTTTGGTATTATCATGTCGACTTACTTAGACATCGTTAA

AsnCysThrArgProAsnAsnAsnThrArgLysSerIleTyrIleGlyProGlyArgAla
542 AACTGTACAAGACCCAACAACAATACAAGAAAAAGTATCTATATAGGACCAGGGAGAGCA
    TTGACATGTTCTGGGTTGTTGTTATGTTCTTTTTCATAGATATATCCTGGTCCCTCTCGT
```

FIG. 26A

```
       PheHisThrThrGlyArgIleIleGlyAspIleArgLysAlaHisCysAsnIleSerArg
602    TTTCATACAACAGGAAGAATAATAGGAGATATAAGAAAAGCACATTGTAACATTAGTAGA
       AAAGTATGTTGTCCTTCTTATTATCCTCTATATTCTTTTCGTGTAACATTGTAATCATCT

AlaGlnTrpAsnAsnThrLeuGluGlnIleValLysLysLeuArgGluGlnPheGlyAsn
662    GCACAATGGAATAACACTTTAGAACAGATAGTTAAAAAATTAAGAGAACAGTTTGGGAAT
       CGTGTTACCTTATTGTGAAATCTTGTCTATCAATTTTTTAATTCTCTTGTCAAACCCTTA

AsnLysThrIleValPheAsnGlnSerSerGlyGlyAspProGluIleValMetHisSer
722    AATAAAACAATAGTCTTTAATCAATCCTCAGGAGGGGACCCAGAAATTGTAATGCACAGT
       TTATTTTGTTATCAGAAATTAGTTAGGAGTCCTCCCCTGGGTCTTTAACATTACGTGTCA

PheAsnCysArgGlyGluPhePheTyrCysAsnThrThrGlnLeuPheAsnAsnThrTrp
782    TTTAATTGTAGAGGGGAATTTTTCTACTGTAATACAACACAACTGTTTAATAATACATGG
       AAATTAACATCTCCCCTTAAAAAGATGACATTATGTTGTGTTGACAAATTATTATGTACC

ArgLeuAsnHisThrGluGlyThrLysGlyAsnAspThrIleIleLeuProCysArgIle
842    AGGTTAAATCACACTGAAGGAACTAAAGGAAATGACACAATCATACTCCCATGTAGAATA
       TCCAATTTAGTGTGACTTCCTTGATTTCCTTTACTGTGTTAGTATGAGGGTACATCTTAT

LysGlnIleIleAsnMetTrpGlnGluValGlyLysAlaMetTyrAlaProProIleGly
902    AAACAAATTATAAACATGTGGCAGGAAGTAGGAAAAGCAATGTATGCCCCTCCCATTGGA
       TTTGTTTAATATTTGTACACCGTCCTTCATCCTTTTCGTTACATACGGGGAGGGTAACCT

GlyGlnIleSerCysSerSerAsnIleThrGlyLeuLeuLeuThrArgAspGlyGlyThr
962    GGACAAATTAGTTGTTCATCAAATATTACAGGGCTGCTATTAACAAGAGATGGTGGTACA
       CCTGTTTAATCAACAAGTAGTTTATAATGTCCCGACGATAATTGTTCTCTACCACCATGT

AsnValThrAsnAspThrGluValPheArgProGlyGlyGlyAspMetArgAspAsnTrp
1022   AATGTAACTAATGACACCGAGGTCTTCAGACCTGGAGGAGGAGATATGAGGGACAATTGG
       TTACATTGATTACTGTGGCTCCAGAAGTCTGGACCTCCTCCTCTATACTCCCTGTTAACC

ArgSerGluLeuTyrLysTyrLysValIleLysIleGluProLeuGlyIleAlaProThr
1082   AGAAGTGAATTATATAAATATAAAGTAATAAAAATTGAACCATTAGGAATAGCACCCACC
       TCTTCACTTAATATATTTATATTTCATTATTTTTAACTTGGTAATCCTTATCGTGGGTGG

LysAlaLysArgArgValValGlnArgGluLysArgOP OP
1142   AAGGCAAAGAGAAGAGTGGTGCAGAGAGAAAAAAGATGATGAAGCTTG
       TTCCGTTTCTCTTCTCACCACGTCTCTCTTTTTTCTACTACTTCGAACAGCT
```

IMMUNOASSAYS FOR ANTIBODY TO HUMAN IMMUNODEFICIENCY VIRUS USING RECOMBINANT ANTIGENS

CROSS-REFERENCE TO RELATED APPLICATIONS

This application is a continuation-in-part of U.S. patent application Ser. No 773,447, filed Sep. 6, 1985, now abandoned, which is a continuation-in-part of U.S. patent application Ser. No. 696,534, filed Jan. 30, 1985, now abandoned, which is a continuation-in-part of U.S. patent application Ser. No. 667,501, filed Oct. 31, 1984, now abandoned. The disclosures of the above application are incorporated herein by reference.

TECHNICAL FIELD

The present invention is directed to nucleotide sequences, such as DNA, encoding human immunodeficiency virus polypeptides, the use of such nucleotide sequences in diagnostic procedures and in the production of recombinant protein, as well as the use of such proteins in diagnostic, prophylactic, and therapeutic applications.

BACKGROUND OF THE INVENTION

Acquired immune deficiency syndrome (AIDS) is now recognized as one of the greatest health threats facing modern medicine. There is, as yet, no cure for this almost invariably fatal disease. This state of affairs has made the prevention of the disease an extremely high priority in the medical community. An individual who is infected with human immunodeficiency virus (HIV), the etiologic agent of AIDS, can transmit the disease, and yet remain asymptomatic for many years. The ability to accurately screen large numbers of asymptomatic individuals (e.g., healthy appearing blood donors) for HIV infection is of great importance. Furthermore, the development of a vaccine would be particularly desirable, since it would afford some protection against transmission of AIDS by individuals who either are not detected by a diagnostic test, or evade such a test.

In 1983-1984, three groups independently identified the suspected etiological agent of AIDS. See, e.g., Barre-Sinoussi et al. (1983) *Science* 220:868-871; Montagnier et al., in *Human T-Cell Leukemia Viruses* (Gallo, Essex & Gross, eds., 1984); Vilmer et al. (1984) *The Lancet* 1:753; Popovic et al. (1984) *Science* 224:497-500; Levy et al. (1984) *Science* 225:840-842. These isolates were variously called lymphadenopathy-associated virus (LAV), human T-cell lymphotropic virus type III (HTLV-III), or AIDS-associated retrovirus (ARV). All of these isolates are strains of the same virus, and were later collectively named human immunodeficiency virus (HIV). With the isolation of a related AIDS-causing virus, the strains originally called HIV are now termed HIV-1 and the related virus is called HIV-2 See, e.g., Guyader et al. (1987) *Nature* 326:662-669; Brun-Vezinet et al. (1986) *Science* 233:343-346; Clavel et al. (1986) *Nature* 324:691-695.

Initially, HIV was propagated in culture in human mitogen-activated T cells. This method, however, could not produce the large quantities of virus required for serology assays on the scale required to protect public health and safety. It was not until immortalized cell lines capable of becoming chronically infected in vitro were discovered that HIV could be produced in any substantial quantities. See, e.g., Montagnier et al. (1984) *Science* 225:63-66; Levy et al., supra; Popovic et al., supra. The ability to grow the virus in culture led to the development of immunoassays for the detection of anti-HIV antibodies in the blood of patients suspected of having been infected, as well as for screening blood donors. See, e.g., Schupback et al. (1984) *Science* 224:503-505; Sarngadharan et al. (1984) *Science* 224:506-508; Feorino et al. (1984) *Science* 225:69-72; Kalyanaraman et al. (1984) *Science* 225:321-323; Culliton et al. (1984) *Science* 226:1128-1131; Groopman et al. (1984) *Science* 226:447-449; Ho et al. (1984) *Science* 226:451-453; U.S. Pat. No. 4,520,113.

Due to the great hazard of cultivating HIV in vitro, the number of facilities and individuals capable of working with the virus is necessarily limited. Furthermore, while tissue culture may provide viral polypeptides suitable for use in diagnostic assays, it is highly undesirable to employ polypeptides produced by tissue culture in vaccine compositions due to the risk of infectivity posed by live, intact virus.

While production of viral polypeptides by recombinant means could be considered to be a solution to the problems described above, the production of recombinant proteins was not possible prior to the present invention. For example, HIV nucleotide sequences were not available and sequenced so as to enable the production of recombinant proteins. Even more importantly, it was unknown whether recombinantly produced viral protein would be sufficiently similar in antigenic properties to native HIV polypeptides so as to be generally useful in diagnostic assays or vaccine production. In addition, homology between the genome of HIV and human T-cell leukemia virus type I and type II (HTLV-I and -II) had been reported. See, e.g., Arya et al. (1984) *Science* 225:927-930. Thus, it was unclear that sufficiently unique epitopes of HIV could be produced by recombinant means to distinguish HIV from HTLV-I or HTLV-II. Furthermore, it was unclear prior to the present invention whether the various HIV isolates possessed sufficiently related epitopes so that a recombinant polypeptide based on one isolate could be useful in a general diagnostic assay or vaccine composition.

Prior to the present invention, therefore, recombinant HIV polypeptides could not be produced and it was not clear that such polypeptides would be generally useful in diagnostic, prophylactic, or therapeutic methods or products.

SUMMARY OF THE INVENTION

Nucleotide sequences and expression of nucleotide sequences are provided for detecting the presence of complementary sequences associated with a retroviral etiologic agent (HIV, e.g., HIV-1 or -2) for lymphadenopathy syndrome (LAS), acquired immune deficiency syndrome (AIDS) or AIDS-related complex (ARC), and for producing polypeptides. The single-stranded sequences are at least 20, more usually of at least about 50 nucleotides in length, and may find use as probes. The double-stranded sequences may find use as genes coding for expression of polypeptides, either fragments or complete polypeptides expressed by the virus or fused proteins, for use in diagnosis of HIV infection or evaluating stage of infection, the production of antibodies to HIV, and the production of vaccines. Based on the nucleotide sequences, synthetic peptides may also be prepared.

Specific aspects of the invention include:

1. A DNA construct comprising a replication system recognized by a unicellular microorganism and a DNA sequence coding for at least 20 bp of a human immunodeficiency virus (HIV) genome, said replication system being a non-HIV replication system;

2. A DNA construct comprising a replication system recognized by a unicellular microorganism and a DNA sequence of at least about 21 bp having an open reading frame and having a sequence substantially complementary to a sequence found in the gag, env, or pol region of an HIV, coding for a polypeptide which is immunologically non-cross-reactive with HTLV-I and HTVL-II, and reactive with an HIV;

3. A restriction endonuclease fragment of at least about 1.5 kbp derived from restriction enzyme digestion by at least one restriction endonuclease of a DNA sequence coding for an HIV of the class HIV-1;

4. A DNA sequence comprising a fragment of at least about 20 bp, wherein the strands are complementary to a restriction endonuclease fragment described in 3 above, said sequence duplexing with an HIV nucleic acid sequence and not duplexing with HTLV-I or HTLV-II under comparable selective hybridization conditions;

5. A method for detecting the presence of an HIV nucleic acid sequence present in a nucleic acid sample obtained from a physiological sample, which comprises:
    (a) combining said nucleic acid sample with a single-stranded nucleic acid sequence of at least about 20 bases complementary to a sequence in said HIV and non-cross-reactive with HTLV-I and -II under conditions of predetermined stringency for hybridization; and
    (b) detecting duplex formation between said DNA sequence and nucleic acid present in said sample;

6. A method for cloning DNA specific for an HIV, which comprises growing a unicellular microorganism containing the above-described DNA construct, whereby said DNA sequence is replicated;

7. A method for producing an expression product of HIV which comprises:
    (a) transforming a unicellular microorganism host with a DNA construct having transcriptional and translational initiation and termination regulatory signals functional in said host and an HIV DNA sequence of at least 21 bp having an open reading frame and under the regulatory control of said signals; and
    (b) growing said host in a nutrient medium, whereby said expression product is produced;

8. A method for producing an expression product of HIV which comprises growing mammalian host cells having a DNA construct comprising transcriptional and translational initiation and termination regulatory signals functional in said host cells and a DNA sequence of at least 21 bp and less than the whole HIV genome, said sequence having an open reading frame and an initiation codon at its 5'-terminus and under the transcriptional and translational control of said regulatory signals, whereby a polypeptide encoded by said sequence is expressed;

9. A method of detecting antibodies to HIV in a sample suspected of containing said antibodies comprising:
    (a) providing a support with at least one antigenic recombinant HIV polypeptide bound thereto;
    (b) contacting said sample with said support-bound polypeptide;
    (c) washing the support;
    (d) contacting the support with labeled antibody to human immunoglobulin; and
    (e) detecting the presence of said antibodies to HIV on said support via said label;

10. Recombinant HIV polypeptides including, but not limited to:
    (a) p16gag;
    (b) p25gag;
    (c) an env polypeptide;
    (d) p31pol;
    (e) a fusion protein of p16gag and p25gag;
    (f) a fusion protein of a gag polypeptide and an env polypeptide;
    (g) a fusion protein comprising an env polypeptide;
    (h) a fusion protein comprising p31pol;
    (i) gp120env;
    (j) gp41env;
    (k) a fusion protein comprising env-5b; and
    (l) reverse transcriptase.

11. An article of manufacture for use in an assay for anti-HIV antibodies comprising at least one of the above-described HIV polypeptides bound to a solid support.

12. A vaccine composition, and a method of producing antibodies in a mammal comprising administering to said mammal said vaccine composition wherein the vaccine composition comprises an antigenically effective amount of a recombinant HIV polypeptide.

Other embodiments will also be apparent from the description below.

BRIEF DESCRIPTION OF THE DRAWINGS

FIG. 4 is a complete nucleotide sequence of ARV-2, derived from partial sequences of several ARV clones. Corresponding amino acid sequences are indicated for the open reading frames of the individual genes.

FIG. 5 is the nucleotide sequence of ARV-2(9B). The amino acid sequences for the products of the gag, pol, and env genes are indicated. The U3, R, and U5 regions of the LTRs are also designated. The cap site is position +1. The nucleotides at the beginning of each line are numbered, and the amino acids at the end of each line are indicated. FIG. 5 herein shows the same sequence as that in FIG. 5 of both U.S. Ser. No. 773,447 (filed Sep. 6, 1985) and U.S. Ser. No. 696,534 (filed Jan. 30, 1985), the nucleotides in the figure of the earlier applications being numbered from the beginning of the integrated sequences.

FIG. 8 is the nucleotide sequence of the p25gag gene cloned in plasmid pGAG25-10 and the amino acid sequence encoded by that gene.

FIG. 9 is the coding strand of the nucleotide sequence cloned in pGAG41-10 for producing the fusion protein p41gag and the corresponding amino acid.

FIG. 10 is a nucleotide sequence coding for p16gag protein that was cloned into plasmid ptac5 to make an expression plasmid for producing p16gag in bacteria.

FIG. 11 is a nucleotide sequence that encodes ARV-2 env protein that was used to prepare plasmid pDPC303.

FIG. 12 is a nucleotide sequence that encodes ARV-2 p31 protein and is contained in plasmid pTP31.

FIG. 15 is the synthetic nucleotide sequence env-5b, which encodes the amino acid sequence of the ARV env-5 region.

FIG. 22 shows the DNA and amino acid sequences of the p25gag structural region in pC1/ 1-p25-ADH-GAP.

FIG. 24 shows the DNA and amino acid sequences of the SOD/p31pol structural region in pC1/ 1-pSP31-ADH-GAP.

FIG. 26 shows the nucleotide sequence and putative amino acid sequence of the SOD/env-4 fusion construct in pBS24/SOD-SFenv4.

FIG. 29 is a restriction map of pCMV6a.

FIG. 30 is an immunoblot performed with AIDS patient serum on env-1 (lanes A, B), env-2 (lanes C, D) and env-3 (lanes E, F). Lanes A, C and E are immunoblots with normal sera, while lanes B, D and F are immunoblots with serum from an AIDS patient.

MODES FOR CARRYING OUT THE INVENTION

Figure 1:
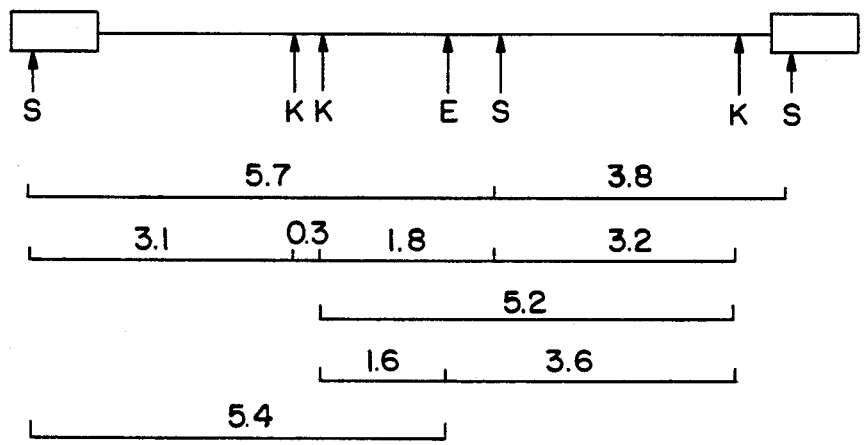
FIG. 1 is a restriction map of proviral DNA from HIV strain ARV-2.

Nucleotide sequences are provided which are at least in part specific for sequences present in HIV retroviruses, which are the etiological agent of AIDS. HIV is an art-recognized family of viruses, e.g., HIV-1 and HIV-2. The original isolates of these viruses were variably referred to as lymphadenopathy virus (LAV) [Barre- Sinoussi et al. (1983) Science 220:868-871], human T-cell lymphotropic virus-III (HTLV-III) [Popovic et al. (1984) Science 224:497] and AIDS-associated retrovirus (ARV) [Levy et al. (1984) Science 225 840-842]. Applicants originally termed these isolates "human T-cell lymphotropic retrovirus (hTLR)". Subsequently, the name HIV has been given to these retroviruses by an international committee. Thus, HIV (and particularly HIV-1) shall be used herein as an equivalent to hTLR. Examples of HIV-1 were previously called LAV, ARV and HTLV-III. Among the identifying characteristics of HIV retroviruses are (i) being an etiologic of AIDS, (ii) being cytopathic in vitro, (iii) having a tropism for CD4-bearing cells, and (iv) having elements trans-activating the expression of viral genes acting at the LTR level.

New HIVs may be shown to be of the same class by being similar in their morphology, serology, reverse transcriptase optima, cytopathology, amino acid sequence, and nucleotide sequence as known HIV strains. Coffin et al. (1986) Nature 321:10. Within different HIV-1 isolates, for example, the gag and pol proteins shows about 90-95% homology at the amino acid level, and the env precursor shows about 65-85% homology (most of the variations being confined to certain "hypervariable" regions), with all 23 env cysteines being conserved. Alizon et al. (1986) Cell 46:63-74. HIV-2, however, is a new class of the HIV family that is not a strain of HIV-1 according to the recommended criteria of the international taxonomy committee. See, e.g., Guyader et al. (1987) Nature 326:662-669. HIV-1 and HIV-2 show an overall approximate amino acid homology of about 42%, with about 60% amino acid homology for the gag and pol proteins, and about 40% for the env precursor.

The nucleotide sequences of this invention may be the entire sequence of the retrovirus and/or the provirus or may be fragments thereof based on restriction enzyme digestion of HIV (provirus and/or other dsDNA homologous to retrovirus RNA), which fragments may be all or part of the LTR, gag, pol, env, and/or other open reading frames, such as Q (or sor), R, tat, and art (or trs) (sometimes referred to by the designation "orf" herein), untranslated regions intermediate coding regions, and fragments and combinations thereof. The minimum size single-stranded fragment will be at least 20 bases and usually at least 50 bases and may be 100 bases or more, where the entire HIV is about 9.5 kb. The sequence may be obtained as a fragment from the HIV or be synthesized.

The fragments can be used in a wide variety of ways, depending upon their size, their natural function, the use for which they are desired, and the degree to which they can be manipulated to modify their function. Thus, sequences of at least 20 bases, more usually at least 50 bases, and usually not exceeding about 1000 bases, more usually not exceeding about 500 bases, may serve as probes for detection of the presence of HIV in a host cell, including the genome, or in a physiological fluid, such as blood, lymph, saliva, spinal fluid, or the like. These sequences may include coding and/or non-coding sequences. The coding sequences may involve the gag, pol, env or other open reading frames, either in whole or in part. Where splicing occurs between, for example, a region in the LTR sequence and a coding sequence in another region, the joined DNA from the provirus, linked by in vitro manipulation, or from cDNA or cloned cDNA, may be employed.

It is found that HIV is highly polymorphic. Therefore, not only may DNA prepared from various isolates vary by one or more point mutations, but even the passage of a single isolate may result in variation in the progeny. Thus, where the nucleotide sequences are used for duplex formation, hybridization, or annealing, for example, for diagnosis or monitoring of the presence of the virus in vivo or in vitro, complete base pairing will not be required. One or more mismatches are permissible. To ensure that the presence of one or a few, usually not more than three, mismatches still allows for stable duplexes under the predetermined stringency of hybridizing or annealing conditions, probes will normally be greater than 20 bases, preferably at least about 50 bases or more.

The method of detection will involve duplex formation by annealing or hybridization of the oligonucleotide probe, either labeled or unlabeled, depending upon the nature of the detection system, with the DNA or RNA of a host suspected of harboring the provirus or virus. A physiological sample may include tissue, blood, saliva, serum, etc. Particularly, blood samples will be taken, more particularly blood samples containing peripheral mononuclear cells, which may be lysed and the DNA or RNA isolated in accordance with known techniques. Cells may be cultured to amplify virus in vitro, or treated to stimulate PBLs, thereby producing more virus. Conveniently, the cells are treated with a detergent, nucleic acids are extracted with organic solvents and precipitated in an appropriately buffered medium, and the DNA or RNA isolated. Depending upon the particular protocol, the DNA may be fragmented by mechanical shearing or restriction endonuclease digestion.

The sample polynucleotide mixture obtained from the human host can be bound to a support or may be used in solution depending upon the nature of the protocol. The well-established Southern technique [(1975) *J. Mol. Biol.* 98:503] may be employed with denatured DNA, by binding the single-stranded fragments to a nitrocellulose filter. Alternatively, RNA can be blotted on nitrocellulose following the procedure described by Thomas, (1980) *Proc. Natl. Acad. Sci. (USA)* 77:5201. Desirably, the fragments will be electrophoresed prior to binding to a support, so as to be able to select for various sized fractions. Other techniques may also be used such as described in Meinkoth & Wahl, (1984) *Anal. Biochem.* 138:267–284.

The oligonucleotide probe may be DNA or RNA, usually DNA. The oligonucleotide sequence may be prepared synthetically or in vivo by cloning, where the complementary sequence may then be excised from the cloning vehicle or retained with the cloning vehicle. Various cloning vehicles are available, such as pBR322, M13, Charon 4A, or the like, desirably a single-stranded vehicle, such as M13.

As indicated, the oligonucleotide probe may be labeled or unlabeled. A wide variety of techniques exist for labeling DNA and RNA. As illustrative of such techniques, is radiolabeling using nick translation, tailing with terminal deoxytransferase, or the like, where the bases which are employed carry radioactive $^{32}P$. Alternatively, radioactive nucleotides can be employed where carbon, nitrogen or other radioactive atoms may be part of the nucleoside structure. Other labels which may be used include fluorophores, enzymes, enzyme substrates, enzyme cofactors, enzyme inhibitors, or the like. Alternatively, instead of having a label which provides for a detectable signal by itself or in conjunction with other reactive agents, ligands can be used to which receptors bind, where the receptors are labeled such as with the above-indicated labels, which labels provide detectable signals by themselves or in conjunction with other reagents See, e.g., Leary et al. (1983) *Proc Natl. Acad. Sci. (USA)* 80:4045–4049; Cosstick et al. (1984) *Nucleic Acids Res.* 12:1791–1810; PCT Pub. No. WO 83/02277.

The oligonucleotide probes are hybridized with the denatured human host nucleic acid, substantially intact or fragmented, or fractions thereof, under conditions of predetermined stringency. The stringency will depend upon the size and composition of the probe, the degree of mismatching, the desired cross reactivity with other strains of the subject HIV, and the like. Usually, an organic solvent such as formamide will be present in from about 30 to 60 vol percent, more usually from about 40 to 50 vol percent, with salt concentration from 0.5 to 1M. Temperatures will generally range from about 30° C to 65° C., more usually from about 35° C. to 50° C. The times for duplex formation may be varied widely, although minimum times will usually be at least about one hour and not more than about 72 hours, the time being selected in accordance with the amount of DNA or RNA available, the proportion of DNA or RNA as compared to total DNA or RNA, or the like. Stringency may also be modified by ionic strength and temperature. The hybridization and annealing can be carried out in two stages: a first stage in a hybridization medium; and, a second stage, involving washings at a higher stringency, by varying either or both temperature and ionic strength.

As understood in the art, the term "stringent hybridization conditions" as used herein refers to hybridization conditions which allow for closely related nucleic acid sequences to duplex (e.g., greater than about 90% homology), but not unrelated sequences. The appropriate conditions can be established by routine procedures, such as running Southern hybridization at increasing stringency until only related species are resolved and the background and/or control hybridization has disappeared (i.e., selective hybridization).

The oligonucleotide probe may be obtained in a variety of ways. Viral RNA from HIV may be isolated from the supernatant of cells infected (e.g., HIV-1 or HIV-2) in culture, and the high molecular weight materials precipitated and the DNA removed, for example, employing DNase. The residual RNA may then be divided into molecular weight fractions, where the fraction associated with the molecular weight of the retrovirus is isolated. This fraction will be from about 8 to 10 kb viral RNA. The viral RNA may be further purified by conventional techniques, such as electrophoresis, chromatography, or the like.

Nucleotide probes may be prepared employing reverse transcriptase using primers, e.g., random primers or specific primers. The cDNA may be prepared employing a radioactive label, e.g., $^{32}P$, present with one or more of the dNTPs. Reverse transcription will provide various sized fragments depending on the primers, the efficiency of transcription, the integrity of the RNA, and the like. The resulting cDNA sequences may be cloned, separated and used for detection of the presence of a provirus in the human genome or for isolation of pure retroviral RNA.

Using specific primers of 10 to 20 bases, or more, HIV may be reverse transcribed and the resulting ss DNA used as a probe specific for the region which hybridized to the primer. By employing one or more radionucleotide-labeled bases, the probes will be radiolabeled to provide a detectable signal. Alternatively, modified bases may be employed which will be randomly incorporated into the probe and may be used to provide for a detectable signal. For example, biotin-modified bases may be employed. The resulting biotin-containing probe may then be used in conjunction with labeled avidin to provide for a detectable signal upon hybridization and duplex formation.

Of particular interest is employing the region containing the gag or env genes, where fragments may be employed to screen proviral DNA in infected cells, to determine the identity of retroviruses associated with AIDS or LAS obtained from different human hosts. Probes providing for the desired degree of cross-reactivity or absence of cross-reactivity may then be prepared in a form, either labeled or unlabeled, useful for diagnostic assays employing hybridization and annealing.

The double-stranded DNA sequences, either isolated and cloned from proviral DNA or cDNA or synthesized, may be used for expression of polypeptides which may be a precursor protein subject to further manipulation by cleavage, or a complete mature protein or fragment thereof. The smallest sequence of interest, so as to encode an amino acid sequence capable of specific binding, for example, to a receptor or an immunoglobulin, will be 21 bp, usually at least 45 bp, exclusive of the initiation codon. The sequence may code for any greater portion of or the complete polypeptide, or may include flanking regions of a precursor polypeptide, so as to include portions of sequences or entire sequences coding for two or more different mature polypeptides. The sequence will usually be less than about 5 kbp, more usually less than about 3 kbp.

The sequences having open reading frames as numbered in FIG. 4 are the genes beginning at nucleotide (nt) 838 to 2298 (gag); 2347 to 2825 (small polypeptide between gag and pol regions); 2965 to 5103 (pol); and 6236 to 8800 (env). It is to be understood that the above sequences may be spliced to other sequences present in the retrovirus, so that the 5'-end of the sequence may not code for the N-terminal amino acid of the expression product. The splice site may be at the 5'-terminus of the open reading frame or internal to the open reading frame. The initiation codon for the protein may not be the first codon for methionine, but may be the second or third methionine, so that employing the entire sequence indicated above may result in an extended protein. However, for the gag and env genes there will be proteolytic processing in mammalian cells, which processing may include the removal of extra amino acids.

In isolating the different domains the provirus may be digested with restriction endonucleases, the fragments electrophoresed and fragments having the proper size and duplexing with a probe, when available, are isolated, cloned in a cloning vector, and excised from the vector. The fragments may then be manipulated for expression. Superfluous nucleotides may be removed from one or both termini using Ba131 digestion. By restriction mapping, convenient restriction sites may be located external or internal to the coding region. Primer repair or in vitro mutagenesis may be employed for defining a terminus, for insertions, deletion, point or multiple mutations, or the like, where codons may be changed, either cryptic or changing the amino acid, restriction sites introduced or removed, or the like. Where the gene has been truncated, the lost nucleotides may be replaced using an adaptor. Adaptors are particularly useful for joining coding regions to ensure the proper reading frame.

The env domain of HIV can be obtained by digestion of the provirus with EcoRI and KpnI and purification of a 3300 base pair (bp) fragment, which fragment contains about 400 bp of 5' non-coding and about 200 bp of 3' non-coding region. Three different methionines coded for by the sequence in the 5' end of the open reading frame may serve as translational initiation sites.

The open reading frame of the env gene of ARV-2 has a coding capacity of 863 amino acids. Portions of the env gene coding for the polypeptides shown in FIG. 5 were produced in *S. cerevisiae* using yeast expression vectors. See FIG. 13. Env-2, encompassing amino acid residues 26 to 510, corresponds to the major portion of the mature envelope glycoprotein, gp120, that is external to viral and infected cell membranes. Env-1 includes amino acid residues 26 to 276 and represents approximately the amino-terminal half of the gp120 polypeptide. Env-3, stretching between amino acid residues 529 to 855, corresponds to the portion of the env gene which encodes gp41, the viral glycoprotein that spans membranes and serves as an anchor for the envelope glycoprotein complex. Env-4, amino acid residues 272 to 509, correspond to the carboxyl terminal half of gp120. Env-5b, encompassing amino acid residues 557 to 677, corresponds to the region of gp41 stretching between the two hydrophobic domains. These various recombinant portions of the env domain are valuable in diagnostic assays for HIV infections, particularly env-2 and env-5b.

Digestion of proviral sequences with SacI and EcoRV provides a fragment of about 2300 bp which contains the gag domain and a second small open reading frame towards the 3' end of the gag region. The gag domain is about 1500 bp and codes for a large precursor protein which is processed to yield proteins of about 25,000 (p25), 16,000 (p16) and 12,000 (p12) daltons. Digestion with SacI and BglII may also be used to obtain exclusively the gag domain with p12, p25 and partial p16 regions.

Digestion of the previous with KpnI and SstI provides a fragment containing the portion of the pol domain that encodes p31. Native HIV reverse transcriptase (RT) is purified from virions in p66 and p51 forms. Both of these forms have identical N-termini, apparently differing at the C-termini. RT is encoded within a domain of the viral pol gene. The mature enzyme is derived by proteolytic processing from a large precursor polypeptide whose cleavage is thought to be mediated by a viral protease. This protease, by analogy with other retroviruses, also cleaves the gag gene precursor. For direct expression of the RT domain in yeast, the N- and C-termini of the mature protein were estimated by drawing on homology comparisons with the amino acid sequences of pol gene products of other retroviruses.

Precise amino acid choices for termini were based on the target specificities of retroviral proteases, including the AIDS virus protease, from known gag subunit sequences. Accordingly, the Phe-Pro at positions 155 and 156 of the ARV-2 pol open reading frame and the Val-Pro at positions 163 and 164 were selected as likely N-termini. A likely C terminal processing site was estimated at the Val-Pro of positions 691 and 692. See FIG. 5. Recombinant RT is valuable in diagnostic assays for HIV infections.

The polypeptides which are expressed by the above DNA sequences may find use in a variety of ways. The polypeptides or immunologically active fragments thereof, may find use as diagnostic reagents, being used in labeled or unlabeled form or immobilized (i.e., bound to a solid surface), as vaccines, in the production of monoclonal antibodies, e.g., inhibiting antibodies, or the like.

The DNA sequences may be joined with other sequences, such as viruses, e.g., vaccinia virus or adenovirus, to be used for vaccination. Particularly, the DNA sequence of the viral antigen may be inserted into the vaccinia virus at a site where it can be expressed, so as to provide an antigen of HIV recognized as an immunogen by the host. The gag, pol, or env genes or fragments thereof that encode immunogens could be used.

Another alternative is to join the gag, env, or pol regions or portions thereof to HBsAg gene or pre-S HBsAg gene or immunogenic portions thereof, which portion is capable of forming particles in a unicellular microorganism host, e.g., yeast or mammalian cells. Thus, particles are formed which will present the HIV immunogen to the host in immunogenic form, when the host is vaccinated with assembled particles.

As vaccines, the various forms of the immunogen can be administered in a variety of ways, orally, parenterally, intravenously, intra-arterially, subcutaneously, intramuscularly, or the like. Usually, these will be provided in a physiologically acceptable vehicle, generally distilled water, phosphate-buffered saline, physiological saline, buffers containing SDS or EDTA, and the like. Various adjuvants may be included, such as aluminum hydroxide, MTP in saline and Tween 80, and the dosages, number of times of administration and manner of administration determined empirically.

In order to obtain the HIV sequence (e.g., HIV-1 or HIV-2), virus can be pelleted from the supernatant of infected host cells. A 9 kb RNA species is purified by electrophoresis of the viral RNA in low-melting agarose gels, followed by phenol extraction. The purified RNA may then be used as a template with random primers in a reverse transcriptase reaction. The resulting cDNA is then screened for hybridization to polyA+ RNA from infected and uninfected cells, or to one of λ vectors containing HIV DNA disclosed herein. For the polyA+ RNA, hybridization occurring from infected, but not uninfected cells, is related to HIV.

Genomic DNA from infected cells can be digested with restriction enzymes and used to prepare a bacteriophage library. Based upon restriction analysis of the previously obtained fragments of the retrovirus, the viral genome can be partially digested with EcoRI and 9 kb-15 kb DNA fragments isolated and employed to prepare the library. The resulting recombinant phage may be screened using a double-lift screening method employing the viral cDNA probe, followed by further purification, e.g., plaque-purification and propagation in large liquid cultures. From the library, the complete sequence of the virus can be obtained and detected with the previously described probe.

HIV DNA (either provirus or cDNA) may be cloned in any convenient vector. Constructs can be prepared, either circular or linear, where the HIV DNA, either the entire HIV or fragments thereof, may be ligated to a replication system functional in a microorganism host, either prokaryotic or eukaryotic cells (mammalian, yeast, arthropod, plant). Microorganism hosts include *E. coli, B. subtilis, P. aerugenosa, S. cerevisiae, N. crassa*, etc. Replication systems may be derived from ColE1, 2 mµ plasmid, λ, SV40, bovine papilloma virus, or the like, that is, both plasmids and viruses. Besides the replication system and the HIV DNA, the construct will usually also include one or more markers, which allow for selection of transformed or transfected hosts. Markers may include biocide resistance, e.g., resistance to antibiotics, heavy metals, etc., complementation in an auxotrophic host to provide prototrophy, and the like.

To produce recombinant polypeptides, expression vectors will be employed. For expression in microorganisms, the expression vector may differ from the cloning vector in having transcriptional and translational initiation and termination regulatory signal sequences and may or may not include a replication system which is functional in the expression host. The coding sequence is inserted between the initiation and termination regulatory signals so as to be under their regulatory control. Expression vectors may also include the use of regulable promoters, e.g., temperature-sensitive or inducible by chemicals, or genes which will allow for integration and amplification of the vector and HIV DNA such as tk, dhfr, metallothionein, or the like.

The expression vector is introduced into an appropriate host where the regulatory signals are functional in such host. The expression host is grown in an appropriate nutrient medium, whereby the desired polypeptide is produced and isolated from cells or from the medium when the polypeptide is secreted.

Where a host is employed in which the HIV transcriptional and translational regulatory signals are functional, then the HIV DNA sequence may be manipulated to provide for expression of the desired polypeptide in proper juxtaposition to the regulatory signals.

The polypeptide products can be obtained in substantially pure form, particularly free of debris from human cells, which debris may include such contaminants as proteins, polysaccharides, lipids, nucleic acids, viruses, bacteria, fungi, etc., and combinations thereof. Generally, the polypeptide products will have less than about 10–15 weight percent, preferably less than about 5 weight percent, of contaminating materials from the expression host. Depending upon whether the desired polypeptide is produced in the cytoplasm or secreted, the manner of isolation will vary. Where the product is in the cytoplasm, the cells are harvested, lysed, the product extracted and purified, using solvent extraction, chromatography, gel exclusion, electrophoresis, or the like. Where secreted, the desired product will be extracted from the nutrient medium and purified in accordance with the methods described above.

In many cases it will be desirable to express the recombinant HIV polypeptide as a fusion protein. This is particularly true with polypeptides such as p31pol and the transmembrane region of gp41env (env-5), to obtain improved levels of expression. The fusion proteins approach allows the addition of a signal sequence to the HIV polypeptide so that the product is secreted by the expression host. Generally, the DNA sequence for the HIV polypeptide is in the C-terminal portion of the fused gene, the heterologous sequence making up the N-terminal. The choice of the appropriate heterologous sequence for fusion to the HIV sequence is a matter of choice within the skill of the art. Preferred heterologous sequences include the N-termini of β-galactosidase and human superoxide dismutase. It is usually preferable that the heterologous sequence be non-immunogenic to humans. In one embodiment, however, two HIV sequences from different immunogenic domains of the virus, such as gag and env, are fused together. This produces a single fusion protein with the immunogenic potential of the two parent polypeptides.

The expression products of the env, gag, and pol genes and immunogenic fragments thereof having immunogenic sites may be used for screening antisera from patients' blood to determine whether antibodies are present which bind to HIV antigens. One or more of the antigens may be used in the assay. Preferred modes of the assay employ a combination of gag and env antigens or pol and env antigens. A combination of p25gag, p16gag, or p31pol and env antigens is particularly preferred. A wide variety of assay techniques can be employed, involving labeled or unlabeled antigens or immobilized antigens. The label may be fluorescers, radionuclides, enzymes, chemiluminescers, magnetic particles, enzyme substrates, cofactors or inhibitors, ligands, or the like.

A particularly convenient technique is to bind the antigen to a support that will bind proteins, such as the surface of an assay tube, a well of an assay plate, or a strip of material like nitrocellulose or nylon, and then contact the sample with the immobilized antigen. After washing the support to remove non-specifically bound antisera, labeled antibodies to human Ig are added and specifically bound label determined.

ELISA and "dot-blot" assays are particularly useful for screening blood or serum samples for anti-HIV antibodies. The ELISA assay uses microtiter trays having wells that have been coated with the antigenic HIV polypeptides(s). The wells are also typically postcoated with a nonantigenic protein to avoid nonspecific binding of antibodies in the sample to the well surface. The sample is deposited in the wells and incubated therein for a suitable period under conditions favorable to antigen-antibody binding.

Anti-HIV antibodies present in the sample will bind to the antigen(s) on the well wall. The sample is then removed and the wells are washed to remove any residual, unbound sample. A reagent containing enzyme-labeled antibodies to human immunoglobulin is then deposited in the wells and incubated therein to permit binding between the labeled anti-human Ig antibodies and HIV antigen-human antibody complexes bound to the well wall. Upon completion of the incubation, the reagent is removed and the wells washed to remove unbound labeled reagent. A substrate reagent is then added to the wells and incubated therein. Enzymatic activity on the substrate is determined visually or spectrophotometrically and is an indication of the presence and amount of anti-HIV antibody-containing immune complex bound to the well surface.

The "dot-blot" procedure involves using HIV antigen(s) immobilized on a piece or strip of bibulous support material, such as nitrocellulose filter paper or nylon membrane, rather than antigen-coated microtiter trays. The support will also be treated subsequently with a nonantigenic protein to eliminate nonspecific binding of antibody to the support. The antigen-carrying support is contacted with (e.g., dipped into) the sample and allowed to incubate therein. Again, any anti-HIV antibodies in the sample will bind to the antigen(s) immobilized on the support. After a suitable incubation period the support is withdrawn from the sample and washed in buffer to remove any unbound sample from the paper. The support is then incubated with the enzyme-labeled antibody to human Ig reagent for a suitable incubation period. Following treatment with the labeled reagent the support is washed in buffer, followed by incubation in the substrate solution. Enzymatic activity, indicating the presence of anti-HIV antibody-containing complexes on the support, causes color changes on the support which may be detected optically.

Either of these techniques may be modified to employ labels other than enzymes, or to detect non-human anti-HIV antibodies (e.g., primate). The reading or detection phases will be altered accordingly.

The antigenic HIV polypeptide may also be used as immunogens by themselves or joined to other antigens for the production of antisera or monoclonal antibodies which may be used for therapy or diagnosis. When used as immunogens, the HIV polypeptides can be prepared as vaccine compositions, as is known in the art. The immunoglobulins may be from any mammalian source, e.g., rodent, such as rat or mouse, primate, such as baboon, monkey or human, or the like. For diagnosis, the antibodies can be used in conventional ways to detect HIV in a clinical sample.

EXAMPLES

The following examples are offered for illustrative purposes only, and are not intended to limit the scope of the claims in any way. The examples are organized as follows:

1. Isolation, Cloning and Characterization of HIV
   - 1.1. Purification and preparation of viral RNA
   - 1.2. Synthesis of labeled viral probe
   - 1.3. Detection of HIV RNA and DNA in mammalian cells
   - 1.4. Cloning of proviral HIV DNA
   - 1 5. Polymorphism of HIV
   - 1.6. Sequencing of proviral DNA
   - 1.7. Amino acid sequences of native HIV proteins
2. Expression of HIV Polypectides in Mammalian Cells
   - 2.1. Expression of env peptide
     - 2.1.1. Mammalian expression vector pSV-7c
     - 2.1.2. Transformation of cells with env sequences
     - 2.1.3. Detecting expression via immunofluorescence
   - 2.2 Expression of gp160env
     - 2.2.1. Mammalian expression vector pSV7d
     - 2.2.2. Expression of tPA/gp160
   - 2.3 Expression of gp120env
     - 2.3.1. Expression of tPA/gp120 in pSV7d
     - 2.3.2. Expression of gp120 using CMV IE-1 promoter
   - 2.4 Expression of gag peptides
   - 2.5 Expression of gag-env fusion protein
3. Expression of HIV Polypeptides in Bacteria
   - 3.1. Expression of p25gag
     - 3.1.1. Host-vector system
     - 3.1.2. Construction of pGAG25-10

3.1.3. Transformation and expression of gag peptide
3.1.4. Fermentation process
　3.1.4.1. Preparation of master seed stock
　3.1.4.2. Fermenter inoculum
　3.1.4.3. Fermentation and harvest
3.1.5. Purification of p25gag
3.1.6. Characterization of recombinant p25gag
　3.1.6.1. Protein gel electrophoresis
　3.1.6.2. Western analysis
　3 1.6.3. ELISA comparison of recombinant and native p25gag
3.2. Expression of p16gag
3.3. Expression of fusion protein p41gag
3.4. Expression of p31pol
　3.4.1. Host-vector system
　3.4.2. Construction of pTP31.2
　　3.4.2.1. Construction of M13 template 01100484
　　3.4.2.2. In vitro mutagenesis of 01100484
　　3.4.2.3. Isolation of DNA fragments containing p31
　　3.4.2.4. Cloning of p31 into plot 7
　　3.4.2.5. Construction of pTP31
　3.4.3. Screening of transformants
　3.4.4. Characterization of recombinant protein
3.5. Expression of SOD-p31 fusion protein
3.6. Expression of SOD-env5b fusion protein
　3.6.1. Host-Vector System
　3.6.2. Construction of pSOD/env5b
　3.6.3. Expression of SOD/env5b fusion protein
　3.6.4. Protein Purification
3.7. Expression of β-gal-env fusion proteins
　3.7.1. Host-vector system
　3.7.2. Construction of pII-3
　3.7.3. Expression and characterization of fusion protein
4. Expression of HIV Polypeptides in Yeast
　4.1. Expression of envH peptide
　　4.1.1. Host-vector system
　　4.1.2. Construction of pDPC303
　　4.1.3. Transformation and expression
　　4.1.4. Purification of envH protein
　　　4.1.4.1. Cell breakage
　　　4.1.4.2. SDS extraction of insoluble material
　　　4.1.4.3. Selective precipitation and gel filtration
　　4.1.5. Characterization of recombinant envH
　4.2. Expression of env subregion polypeptides
　　4.2 1. Env-1
　　　4.2.1.1. GAP promoter
　　4.2.2. Env-2
　　　4.2.2.1. Construction of pAB24-GAP-env2
　　　4.2.2.2. Transformation and expression
　　　4.2.2.3. Purification of env-2 protein
　　　4.2.2.4. Immunogenicity
　　4.2.3. Env-3
　　　4.2.3.1. GAP promoter
　　　4.2.3.2. ADH-2/GAPDH promoter
　　4.2.4. Env-4
　　　4.2.4.1. pBS24/SF2env4/GAP
　　　4.2.4.2. pBS24
　　　4.2.4.3. pBS24/SOD-SF2env4
　　4.2.5. ySOD/env-5b fusion protein
　　4.2.6. Env 4-5
　　　4.2.6.1. Construction of pBS24.1/SOD-SF2env 4-5
　　　4.2.6.2. Transformation and expression
　　　4.2.6.3. Protein purification
　4.3. p31pol
　　4.3.1. GAP/ADH2 promoter
　　4.3.2. GAP promoter
　　4.3.3. SOD-p31 fusion protein
　　　4.3.3.1. pC1/1-pSP31-GAP-ADH2
　　　4.3.3.2. Transformation and expression
　　　4.3.3.3. Purification and characterization
　4.4 Reverse transcriptase (RT)
　　4.4.1. pAB24/RT4 expression vector
　　4.4.2. Transformation and expression
　　4.4.3. Purification
　　4.4.4. Electrophoresis and immunoblotting
　　4.4.5. RT activity assay
　4.5. p25gag
　　4.5.1. Host-vector system
　　4.5.2. *Saccharomyces cerevisiae* AB110
　　4.5.3. pC1/1-p25-ADH-GAP
　　4.5.4. Transformation and expression
　　4.5.5. Protein Purification
　4.6. p53gag
　　4.6.1. Construction of pC1/1-GAP-p53
　　4.6.2. Transformation and expression
　　4.6.3. Protein purification
5. Immunoassays for Anti-HIV Abs Using Recombinant HIV Polypectides
　5.1. ELISA-A
　　5.1.1. Assay Protocol
　　5.1.2. Results
　5.2. ELISA-B
　　5.2.1. Assay Protocol
　　5.2.2 Results
　5.3. Dot Blot Assay
　5.4. Immunoblot Strip ELISA Assay
6. Serology Studies with Recombinant HIV Polypeptides
　6.1. Immunoblot with Env Polypeptides
　6.2. ELISA with Env Polypeptides
　6.3. ELISA with Gag Polypeptides
　6.4. Western and ELISA with Pol Polypeptides
7. HIV Immunization
　7.1. Immunization of mice
　7.2 Immunization of guinea pigs
7. Deposits of Biological Materials 1. Isolation, Cloning and Characterization of HIV The DNA and RNA sequences of HIV are provided, as well as fragments thereof, which find extensive use in the detection of the presence of HIV, for the expression of protein specific for HIV and the use of such proteins for the production of monoclonal antibodies for in vitro and in vivo use, in diagnostics, therapy, or the like. In addition, due to the observed polymorphism of HIV, probes are indicated which can be used to detect the presence of HIV or a particular polymorphism thereof. The probes are at least about 20 bases and will usually not be more than about 500 bases and may be in the gag, env or LTR region. Furthermore, a strategy is provided for analyzing the various polymorphisms, using restriction enzyme analysis, whereby different isolates can be related in accordance with different families.

1.1 Purification and preparation of viral RNA

HUT-78 cells infected with ARV-2 (ATCC Accession No. CRL 8597, deposited on August 7, 1984) were obtained from Dr. Jay Levy, University of California, San Francisco. Cultures were grown for two weeks in RPMI medium with 10% fetal calf serum. Cells were removed by low-speed centrifugation (1,000×g for 10 min), and the resulting supernatants centrifuged at 2 Krpm for 1 h at 4° C. using a SW-28 rotor. The pellet, containing the virus, was resuspended in 10 mM Tris-HCl, pH 7.5 on ice. The resuspended pellet was treated with 10 μg of DNase (Boehringer-Mannhein) and was layered onto a linear sucrose gradient (15–50% in 10 mM Tris-HCl, pH 7.5, 1 mM EDTA, 20 mM NaCl). The gradient was spun at 34 Krpm for 4 h at 4° C., in SW-41 rotor. Five 2.5 ml fractions were collected and an aliquot of each was electrophoresed in a 1% agarose, 5 mM methyl mercury hydroxide gel [Bailey et al. (1976) *Anal. Biochem* 70 75–85] to determine which contained the 9 kb viral RNA. The fraction containing the viral RNA (identified by gel analysis) was diluted to 10 ml in 10 mM Tris-HCl, pH 7.5, 1 mM EDTA and was centrifuged at 34 Krpm for 2 h at 4° C. The pellet was resuspended in 20 mM Tris-HCl, pH 7.6, 10 mM EDTA, 0.1% SDS, and 200 μg/ml proteinase K. Incubation was carried out for 15 min at room temperature. The mixture was extracted with phenol and the aqueous phase was made 400 mM NaCl and precipitated with ethanol. The pellet was resuspended in water and stored at −70° C.

To purify the viral RNA from the nucleic acid pellet obtained as described above, a sample was electrophoresed in a low-melting 1% agarose gel containing 5 mM Methyl mercury hydroxide. After electrophoresis, the gel was stained with 0.1% ethidium bromide and nucleic acid bands were visualized under UV light. The region corresponding to 9 kb was cut from the gel and the agarose was melted at 70° C. for 2 to 3 min in three volumes of 0.3M NaCl, 10 mM Tris, pH 7.5, 1 mM EDTA. The mixture was extracted with an equal volume of phenol. The aqueous phase was reextracted with phenol and was precipitated with ethanol. The pellet was washed with cold 95% ethanol, air dried, resuspended in water and stored at −70° C. until use. One hundred ml of culture medium yielded 0.5 to 1 μg of purified RNA.

1.2. Synthesis of labeled viral probe

A $^{32}$P-labeled cDNA was made to the gel purified viral RNA using random primers (calf thymus primers) prepared as described in Maniatis et al., *Molecular Cloning: A Laboratory Manual* (Cold Spring Harbor Laboratories 1982). The reaction mixture contained 2 μl of 0.5M MgCl$_2$; 5 μl of 0.1M dithiothreitol; 2.5 μl each of 10 mM dATP, 10 mM dGTP and 10 mM dTTP; 2.5 μl calf thymus primer (100A$_{260}$/ml); 0.5 μg viral RNA; 5 μl of actinomycin D (200 μg/ml); 10 μl of $^{32}$P-dCTP (>3000 Ci/mmole, 1 mCi/ml) and 1 μl of AMV reverse transcriptase (17 units/μl) in a 50 μl reaction volume. The reaction was incubated for 1 h at 37° C. The probe was purified away from free nucleotides by gel filtration using a Sephadex G50 column. The void volume was pooled, NaCl was added to a final concentration of 400 mM and carrier single-stranded DNA to 100 μg/ml, and the cDNA was precipitated with ethanol. The pellet was resuspended in water and incorporated $^{32}$P counts were determined.

1.3. Detection of HIV RNA and DNA in mammalian cells

PolyA+ RNA was prepared from HUT-78 cells infected with ARV-2, ARV-3 or ARV-4 (three different isolates from three different AIDS patients) and from uninfected HUT-78 cells. The polyA+ RNA was electrophoresed on 1% agarose gels containing 5 mM methyl mercury hydroxide (Bailey et al. supra), was transferred to nitrocellulose filters, and hybridized with the homologous probe prepared as described in Section 1.2. Hybridizations were carried out in 50% formamide, 3×SSC at 42° C. Washes were at 50° C. in 0.2 ×SSC. A 9 kbp band was present in all three samples of infected HUT-78 cells. This band was absent in polyA+ from uninfected cells.

High molecular weight DNA (chromosomal) was prepared from cultures of HUT-78 cells infected with ARV-2 and from non-infected HUT-78 cells following the procedure of Luciw et al. (1984) *Molec. & Cell Biol.* 4:1260–1269. The DNA was digested with restriction enzyme(s), electrophoresed in 1% agarose gels and blotted onto nitrocellulose following the procedure described by Southern, (1975), supra. Blots were hybridized with the $^{32}$P-labeled probe (10$^6$ cpm/blot) in a mixture containing 50% formamide, 3×SSC, 10 mM Hepes, pH 7.0, 100 μg/ml denatured carrier DNA, 100 μg/ml yeast RNA and 1×Denhardt×s for 36 h at 42° C. Filters were washed once at room temperature in 2×SSC and twice at 42° C. in 0.2×SSC, 0.1% SDS. Filters were air dried and exposed to X-Omat film using an intensifying screen.

The homologous $^{32}$P-probe to ARV-2 hybridized specifically to two bands in the DNA from infected cells restricted with SacI. These bands were absent when DNA of non-infected cells was used, indicating that the probe is hybridizing specifically to infected cells presumably to the provirus integrated in the chromosomal DNA. The molecular weight of the bands is approximately 5 kb and 3 kb.

In order to determine if different enzymes would cut the proviral sequence, several other restriction digestions of the cell DNA were carried out using EcoRI, SphI or KcnI or double digestions using two of them. Southern results show specific bands hybridizing when DNA of infected cells is used. FIG. 1 shows a schematic map of the positions of restriction enzyme sites in the proviral sequence, and indicates fragment sites.

1.4. Cloning of proviral HIV DNA

High molecular weight cell DNA from infected HUT-78 cells was prepared following the procedure of Luciw et al., supra. The DNA was digested with EcoRI, which cuts once in the provirus, centrifuged in a sucrose gradient and fractions corresponding to 8–15 kb were pooled, dialyzed and concentrated by ethanol precipitation. The bacteriophage λ derivative cloning vector, EMBL-4 [Karn et al. (1983) *Methods Enzymol.* 101:3–19] was digested to completion with a mixture of EcoRI, BamHI and SalI restriction enzymes and the DNA then deproteinized by phenol-chloroform extraction, precipitated with cold ethanol and resuspended in ligation buffer. The EMBL-4 phage DNA and EcoRI digest of cellular DNA were mixed and ligated and the resultant recombinant phage genomes packaged in vitro. After phage infection of λ-sensitive *E. coli* (DP50supF), about 500,000 phage plaques were transferred onto nitrocellulose filters, DNA was fixed and the filters were screened with a homologous $^{32}$P-probe prepared as described in Section 1.2. Eleven recombinant phage out of 500,000 phage annealed in the initial double-lift screening method (Maniatis et al., supra) to viral cDNA probe, and these were further plaque-purified and propagated in large liquid cultures for preparation of recombinant DNA. Plaque-purified phage containing ARV DNA were propagated in liquid culture in *E. coli* DP50supF; phage particles were harvested and banded in CsCl gradients and recombinant phage DNA was prepared by phenol extraction followed by ethanol precipitation (Maniatis et al., supra). One microgram of purified phage DNA was digested with restriction enzymes, electrophoresed on 1% agarose gels, and visualized with ethidium bromide under ultraviolet light. The DNA from these gels was transferred to nitrocellulose and annealed with viral cDNA probe.

Figure 2:
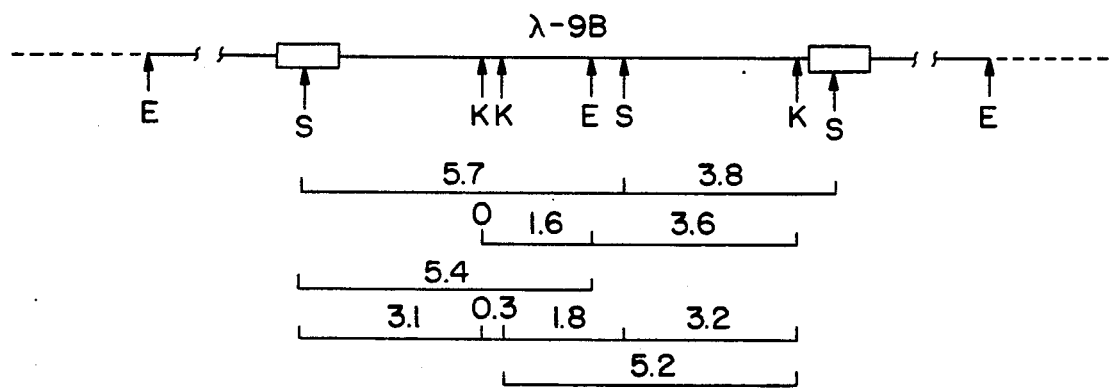
FIGS. 2 and 3 are restriction maps of recombinant λ phages containing ARV-2 sequences.

Described below is the analysis of the 11 recombinant phage DNA molecules utilizing restriction enzymes and viral cDNA probe. Two examples were selected for detailed description: λ-9B contained an insertion of full-length proviral DNA along with flanking cell sequences, and λ-7A harbored a full-length viral genome permuted with respect to the EcoRI site. Digestion of λ-9B DNA with SacI yielded viral DNA fragments of 3.8 kb and 5.7 kb (FIG. 2). EcoRI digestion of λ-9B produced virus containing DNA species at 6.4 kb and 8.0 kb; a double digest of SacI and EcoRI gave viral DNA fragments at 3.8 kb and 5.4 kb (FIG. 2). This pattern is consistent with that of a provirus linked to cell DNA. The patterns of the digestion with KcnI and with a mixture of KpnI and EcoRI support this conclusion for λ-9B. In particular, digestion of λ-9B DNA with KcnI showed a 5.2 kb species that represents the internal fragment seen in proviral DNA (FIGS. 1 and 2). Bacteriophage λARV-2(9B) was deposited at the ATCC on Jan. 25, 1985 and given Accession No. 40158. A second recombinant phage, λ-10C, also contained a full-length proviral DNA insertion.

Figure 3:
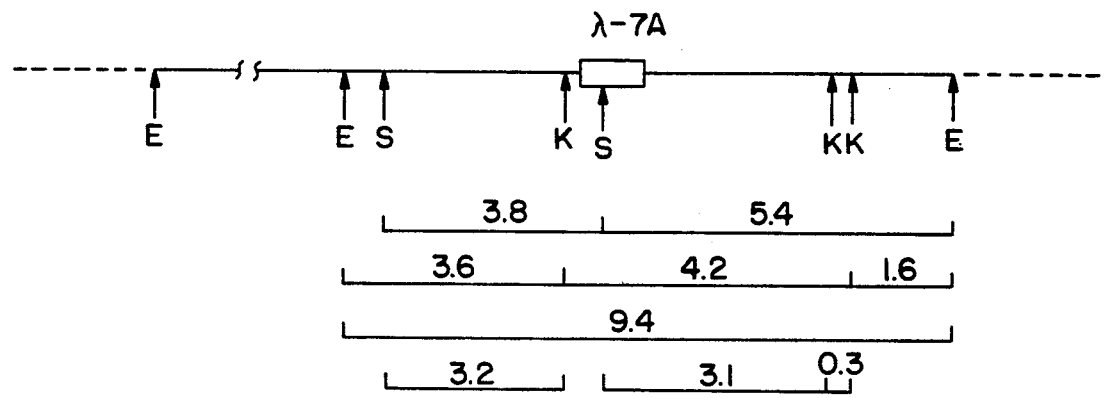

When the DNA of λ-7A phage was treated with SacI, two viral DNA fragments were observed at 3.8 kb and 6.6 kb (FIG. 3). EcoRI digestion of λ-7A DNA produced a 9.4 kb viral species, and a digestion with a mixture of EcoRI and SacI yielded two viral DNA fragments at 3.8 kb and 5.4 kb (FIG. 3). Thus, λ-7A should represent a recombinant phage clone containing a full-length linear HIV genome that is permuted with respect to the EcoRI site. Analyses with KpnI support this model. After digestion with KpnI a DNA fragment at 4.2 kb was observed as well as other DNA species. See FIG. 3. The data indicated that the 4.2 kb DNA fragment represents the circle junction and the others represent HIV DNA linked to cell DNA and bacteriophage vector DNA. The double digestion with KpnI and EcoRI left the 4.2 kb DNA intact and produced two fragments at 1.6 kb and 3.6 kb (FIG. 3); these three DNA species added up to 9.4 kb and constituted the HIV genome predicted from a permuted configuration.

In addition to the two types of recombinant phage containing HIV DNA described above, phage was obtained that (1) possessed the left half of the viral genome from the EcoRI site in viral DNA extending into flanking cell DNA [λARV-2(8A)] and (2) phage that had the right half of the viral genome [λARV-2(7D)] from the EcoRI site in viral DNA extending into flanking cell DNA. The four types of recombinant phage DNA structures are predicted from the analysis of viral DNA observed in infected cells. Maps of restriction enzyme sites are shown in FIGS. 1–3. The data for these maps were compiled from studies of proviral DNA in infected cells, from characterization of recombinant phage DNA, and from preliminary DNA sequence information. Bacteriophages λARV-2(7D) (right) and λARV-2(8A) (left) were deposited at the ATCC on Oct. 26, 1984 and given Accession Nos. 40143 and 40144, respectively.

To validate the cloned HIV DNA, a radioactive probe was prepared from two regions of the cloned HIV genome that represent about 70% of the genome and this probe was used to detect HIV DNA in restriction enzyme digests of DNA from infected cells. Whole-cell DNA was prepared from HUT-78 cell cultures infected with HIV-1 strains ARV-2, ARV-3 and ARV-4, and analyzed by digestion with restriction enzymes as described in Section 1.3. A probe to cloned ARV-2 DNA was prepared C as follows: DNA from recombinant phage λ-7A (FIG. 3) was digested with SacI or with a mixture of SacI and KpnI and digestion products were electrophoresed in 1% agarose gels (low-melting agarose); the 3.8 kb DNA fragment from the digestion with SacI and the 3.1 kb DNA fragment from the digestion with SacI and KpnI (FIG. 3) were eluted, pooled, denatured by boiling in water for 2 min, and used as templates with random DNA primers (calf thymus) with reverse transcriptase.

DNA from HUT-78 cells infected with ARV-2, ARV-3 or ARV-4 were digested with SacI, PstI or HindIII. Digested DNA was electrophoresed on 1% agarose gels, blotted onto nitrocellulose filters and annealed with probe to cloned ARV-2 DNA or to homologous cDNA probe prepared as described in Section 1.2. Results show that SacI, PstI, and HindIII fragments detected by both probes are identical in all isolates.

1.5. Polymorphism of HIV

To measure the relatedness of independent HIV isolates, restriction enzyme digests of DNA from HUT-78 cells infected with ARV-3 and ARV-4 were analyzed with the probe made from cloned ARV-2 DNA. The SacI digest of ARV-3 DNA was similar to that of ARV-2 whereas the HindIII digests displayed different patterns. The SacI digest and the PstI digest of ARV-4 DNA differed from the corresponding digests of ARV-2 DNA. The intensity of the annealing signals obtained with ARV-3 and ARV-4 samples was much lower (about 10-fold less) than that for ARV-2 DNA, probably as a result of the fact that fewer cells were infected in the ARV-3 and ARV-4 cultures. The viral-specific DNA fragments produced by SacI treatment of ARV-3 and ARV-4 DNA totaled 9.0–9.5 kbp, a value similar to that of ARV-2 and in consonance with the RNA genome sizes.

1.6. Sequencing of proviral DNA

Fragments or subfragments of ARV-2 DNA were prepared from the recombinant phages and cloned into M13 according to conventional procedures (Maniatis et al., supra). Sequencing was performed according to Sanger et al. [(1977) Proc. Natl. Acad. Sci. USA 74:5463], using the universal M13 primer or chemically synthesized primers complementary to ARV-2 sequence The sequence is shown in FIG. 4. Also indicated in this figure are the restriction sites present in the DNA and the open reading frames encoded by the sequence.

The sequence of the HIV-1 DNA from λ phage 9B was sequenced in a similar manner. This sequence is shown in FIG. 5. There are several differences between the sequences shown in FIGS. 4 and 5 which reflect the polymorphism in HIV and the fact that the sequence of FIG. 4 was derived as a composite from sequence data on several HIV isolates, whereas the sequence of FIG. 5 is from a single isolate. The main difference affecting polypeptide sequence is that the small open reading frame between the gag and pol genes in FIG. 4 is not independent, but is part of the pol gene in FIG. 5. This merger of these reading frames was the result of three base changes. The region of fusion and sequence change occurs roughly between nucleotides 2853 and 2941 in FIG. 5.

Furthermore, open reading frames in FIG. 4 were translated into amino acids beginning with the first methionine in the open reading frame, whereas in FIG. 5 translation into amino acids was begun immediately with the codon following the stop codon.

1.7. Amino acid sequences of native HIV proteins

ARV-2 was prepared and purified as described in Section 1.1. The viral proteins were electrophoresed on an acrylamide gel, and the band corresponding to a 24,000 dalton or 16,000 dalton protein was excised from the gel and used for sequencing. Micro-sequence analysis was performed using Applied Biosystems model 470A protein sequencer similar to that described by Hewick et al. (1981) *J. Biol. Chem.* 256:7990-7997. Phenylthiohydantoin amino acids were identified by HPLC using a Beckman Ultrasphere ODS column and a trifluoroacetic acid-acetonitrile buffer system as reported by Hawke et al. (1982) *Anal. Biochem.* 120:308-311. Table 1 shows the first 20 amino acids from the amino terminus determined for p25-gag protein and Table 2 shows the first 30 amino acids for p16-gag protein.

TABLE 1

| Amino-terminal sequence of p25gag | |
|---|---|
| Position | Amino acid |
| 1 | Pro |
| 2 | Ile |
| 3 | Val |
| 4 | Gln |
| 5 | Asn |
| 6 | Leu |
| 7 | Gln |
| 8 | Gly |
| 9 | Gln |
| 10 | Met |
| 11 | Val |
| 12 | (His) |
| 13 | Gln |
| 14 | Ala |
| 15 | Ile |
| 16 | (Ser) |
| 17 | Pro |
| 18 | (Arg, Lys) |
| 19 | Thr |
| 20 | (Leu) |

TABLE 2

| Amino-terminal sequence of p16gag | |
|---|---|
| Position | Amino acid |
| 1 | (Met) |
| 2 | Gln |
| 3 | Arg |
| 4 | Gly |
| 5 | Asn |
| 6 | Phe |
| 7 | Arg |
| 8 | Asn |
| 9 | Gln |
| 10 | Arg |
| 11 | Lys |
| 12 | Thr |
| 13 | Val |
| 14 | Lys |
| 15 | —(Cys) |
| 16 | Phe |
| 17 | Asn |
| 18 | —(Cys) |
| 19 | Gly |
| 20 | Lys |
| 21 | Glu |
| 22 | Gly |
| 23 | (His) |
| 24 | Ile |
| 25 | Ala |
| 26 | (Lys) |
| 27 | Asn |
| 28 | (Gly) |
| 29 | (Arg) |

TABLE 2-continued

| Amino-terminal sequence of p16gag | |
|---|---|
| Position | Amino acid |
| 30 | (Ala, Leu) |

The amino acid sequence of Table 1 is predicted by nucleotides 1195 to 1255, and from Table 2 by nucleotides 1930 to 2120, from the ARV-2 DNA sequence (indicated by bars in FIG. 4). Therefore, these results confirm that the indicated gag open reading frame is in fact being translated and identifies the N-termini of p25 and p16.

2. Expression of HIV Polypeptides in Mammalian Cells 2.1. Expression of env peptide 2.1.1. Mammalian expression vector pSV-7c Plasmid pSV-7c contains the SV40 early promoter, origin of replication and polyA processing signal, and was constructed as described below.

A 400 bp BamHI-HindIII fragment containing the SV40 origin of replication and early promoter was obtained by digestion of plasmid pSVgt1 (P. Berg, Stanford University, Palo Alto, Calif.) and purification through gel electrophoresis. A second 240 bp SV40 fragment containing SV40 polyA addition sites was obtained by digestion of pSV2/dhfr [Subramani et al. (1981) *J. Mol. Cell. Biol.* 1:854-864] with BclI and BamHI, and gel purification. Both fragments were fused together through a linker which provided for a HindIII overhang in the 5'-end, a BclI overhang in the 3'-end, three general restriction sites and three successive stop codons in all three reading frames. The sequence of the polylinker was the following:

```
                          Stop Codons
                          1     2    3
5'-AGCTAGATCTCCCGGGTCTAGATAAGTAAT-3'
    TCTAGAGGGCCCAGATCTATTCATTACTAG
HindIII  BglII  SmaI    XbaI    BclI
                                    overhang
```

The about 670 bp fragment, containing SV40 origin of replication, SV40 early promoter, polylinker with stop codons and SV40 polyadenylation site, was cloned into the BamHI site of pML [Lusky & Botchan, (1984) *Cell* 36:391], a pBR322 derivative with an about 2.5 kbp deletion, to yield pSV-6. To eliminate the EcoRI and EcoRV sites present in pML sequences of pSV-6, this plasmid was digested with EcoRI and EcoRV, treated with Ba131 nuclease to remove about 200 bp per end, religated and cloned to yield pSV-7a. The Ba131 resection also eliminated one BamHI restriction site flanking the SV40 region approximately 200 bp away from the EcoRV site. To further eliminate the other BamHI site flanking the SV40 region, pSV-7a was digested with NruI, which cuts in the SV40 sequence, and PvuII, which cuts in the pML sequence upstream from the origin of replication. The plasmid was recircularized by blunt end ligation and cloned to yield pSV-7b. To increase the number of cloning sites of pSV-7b, a new polylinker was cloned into the plasmid to replace the previous one but the stop codons in the three frames were still retained. For this purpose, pSV-7b was digested with StuI and XbaI, and a linker of the following sequence was ligated to the vector to yield pSV-7c.

```
  BglII    EcoRI      SmaI      KpnI  XbaI
5'-AGATCTCGAATTCCCCGGGGGTACCT-3'
   TCTAGAGCTTAAGGGGCCCCCATGGAGATC
```

2.1.2. Transformation of cells with env sequences

Figure 6:
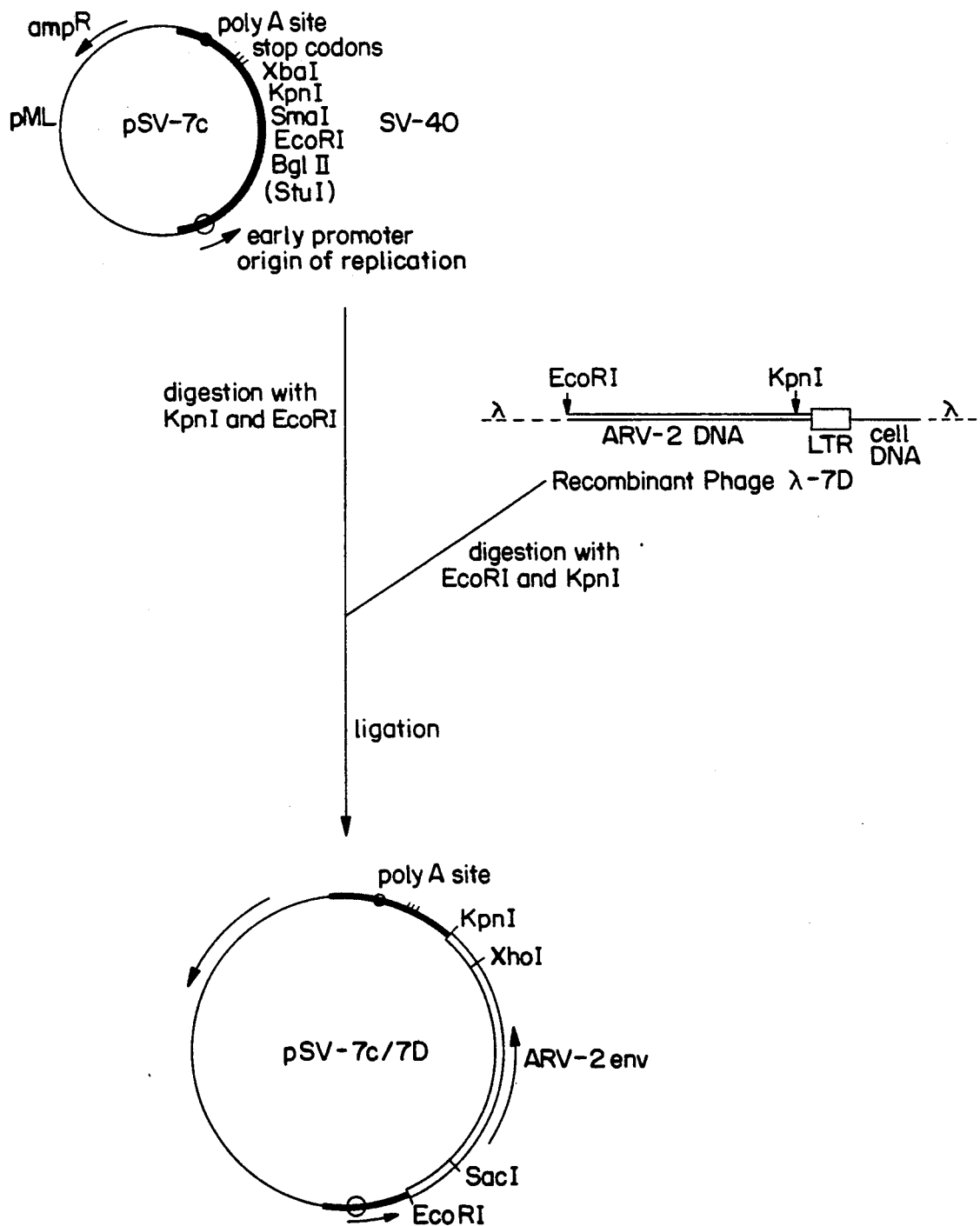
FIG. 6 is a flow diagram showing the procedure for making the plasmid of pSV-7c/env, an expression vector for ARV-2 env gene.

The HIV DNA coding for the env region was excised from a recombinant phage λARV-2(7D) [λ7D] which contains the right half of the provirus by digestion with KpnI and EcoRI and gel purification of about 3300 bp fragment. This fragment was cloned into plasmid pSV-7c as shown in FIG. 6. The recombinant vector (pSV7c/env) was used to transfect Cos cells [Mellon et al. (1981) *Cell* 27:279] following the procedure of van der Eb & Graham [(1980) *Methods in Enzymology* 65:826–839] as modified by Parker and Stark [(1979) *J. Virol.* 31:360369], in 60 mm plastic dishes ($5 \times 10^5$ cells per dish). Thirty-six hours later the cells were transferred to glass microscope slides and cultured for another 24 h ($5 \times 10^4$ cells per chamber in a 4-chamber Titer-tek slide). The cell sheet was rinsed in PBS and fixed by dipping in cold acetone for 5 sec.

2.1.3. Detecting expression via immunoflorescence

The fixed-cell monolayers in each chamber were incubated with AIDS patient sera (Reference serum EW511 obtained from Dr. Paul Feorino, Center for Disease Control) and with control normal human sera. Both sera were diluted 1/100 in PBS and 50 microliters were applied per chamber, incubated for 1 h at 37° C., and rinsed by dipping in PBS. Fluoresceinated goat anti-human antisera (Cappel Labs) was diluted 1/100 in PBS and 50 microliters were applied to each chamber and incubated for 30 min at 37° C. After washing in PBS, 75% glycerol in PBS was added to the cell sheets, a coverslip was placed on top, and the cells were observed in a fluorescence microscope. About five cells in 100 showed bright immunofluorescence with the AIDS sera. No cells stained with control normal human sera. Cells transfected with a control plasmid containing only SV40 vector sequences did not show any immunofluorescence with any antisera. Thus, the EcoRI-KpnI ARV-2 DNA fragment encodes a gene that can be expressed in mammalian cells and the expression product detected specifically by AIDS patient sera.

2.2. Expression of gp160env

2.2.1. Mammalian expression vector pSV7d pSV7c and pSV7d represent successive polylinker replacements. The polylinker in pSV7c was digested with BglII and XbaI, and then ligated with the following linker to yield pSV7d:

```
  BglII    EcoRI      SmaI       XbaI    BamHI   SalI
5'-GATCTCGAATTCCCCGGGTCTAGAGGATCCGTCGAC
   AGCTTAAGGGGCCCAGATCTCCTAGGCACGTGGATC
```

2.2.2. Expression of tPA/gp160

In order to achieve optimal secretion of gp160 from mammalian tissue culture cells, the 5' end of the coding sequence was modified to accept a heterologous signal sequence known to direct efficient secretion of both the homologous gene (human tissue plasminogen activator) and deletion variants of this gene. van Zonnefeld et al. (1986) *Proc. Natl. Acad. Sci. USA* 83:4670.

A portion of the HIV env gene was excised with SacI and StuI (positions 5555 and 6395) and was subcloned into the vector M13mp19 [Yanisch-Perron et al. (1985) *Gene* 33:103–109] between SacI and SmaI. Oligonucleotide-directed mutagenesis [Zoller et al. (1983) *Methods in Enzymology* 100:468–500] was used to create an NheI site at the junction of the natural signal peptide and the mature envelope polypeptide using the following oligonucleotide:

```
5'-GATGATCTGTTCAGCTAGCGAAAAATTGTGG-3'
```

This mutagenesis changes cytosine-5867 to guanine and adenine-5868 to cytosine, thereby creating an NheI site and altering the codon for threonine-30 to code for serine.

In parallel, the tPA gene was likewise mutagenized in 3 to place an NheI site near the carboxyl end of the tPA signal peptide. The following sequences show the 5' UT sequences and signal for wild type tPA leader and for the NheI variant.

Wild-type sequence of the tPA signal:
5' untranslated sequences

```
AGAGCTGAGATCCTACAGGAGTCCAGGGCTGGAGAGAAAACCTCTGCGAGGAAAGGGAAGGA

GCAAGCCGTGAATTTAAGGGACGCTGTGAAGCAATCATGGATGCAATGAAGAGAGGGCTC
                                    Met Asp Ala Met Lys Arg Gly Leu

TGCTGTGTGCTGCTGCTGTGTGGAGCAGTCTTCGTTTCGCCCAGCCAGGAAATCCATGCC
Cys Cys Val Leu Leu Leu Cys Gly Ala Val Phe Val Ser Pro Ser Gln Glu Ile His Ala mature   tPA
CGATTCAGAAGAGGAGCCAGA TCTTACCAAGTG
Arg Phe Arg Arg Gly Ala Arg Ser Tyr Gln Val
```

The NheI variant of the tPA signal:

5' untranslated sequences

```
AGAGCTGAGATCCTACAGGAGTCCAGGGCTGGAGAGAAAACCTCTGCGAGGAAAGGGAAGGA

GCAAGCCGTGAATTTAAGGGACGCTGTGAAGCAATCATGGATGCAATGAAGAGAGGGCTC
                                    Met Asp Ala Met Lys Arg Gly Leu

TGCTGTGTGCTGCTGCTGTGTGGAGCAGTCTTCGTTTCGCCCAGCGCTAGC
Cys Cys Val Leu Leu Leu Cys Gly Ala Val Phe Val Ser Pro Ser Ala Ser
```

Following mutagenesis and sequence verification, a 174 bp fragment containing 99 bp of 5' untranslated sequence and the signal sequence from tPa was excised from the tPA-containing M13 clone using SalI and NheI and fused to the 559 bp fragment containing the 5' end of the env gene which was excised from the env-containing M13 clone with NheI and HindIII (contributed by the M13 polylinker) and these fragments were subcloned into M13mp18 between SalI and HindIII. This plasmid is called M13tpaS.NheIenv.

The DNA and amino acid sequences of the tPA signal fused to the 5' end of gp160 is:

```
...tPA signal...                    5869   (amino acid 31 of env)
Phe Val Ser Pro Ser Ala Ser Glu Lys Leu Trp Val Thr Val
TTC GTT TCG CCC AGC GCT AGC GAA AAA TTG TGG GTC ACA GTT
                    NheI
```

From this M13 subclone, M13tpaS.NheIenv, the DNA fragment containing the heterologous signal and 5' untranslated sequences fused to the 5' end of the env gene was excised using the XbaI site from the M13 polylinker and the unique NdeI site found at position 5954 in the env gene. This 268 bp fragment was ligated with a 2506 bp NdeI-XhoI fragment, encoding the remainder of the env gene, from NdeI at position 5954 through the stop codon at position 8344, and 116 additional bases to the XhoI site at position 8460 and at the same time with vector pSV7d cleaved with XbaI and SalI in order to generate a fully functional gp160 gene in the proper orientation for expression from the SV40 early promoter. This expression plasmid, called pSV7dARV160tpa, was used to transfect COS 7 cells as described by Sompayrac et al. (1981) *Proc. Natl. Acad. Sci. USA* 78:7575. Transfected cells were assayed for gp160 expression by immunofluorescence as described in Section 2.1.3 above. Approximately 5% of the cells showed bright fluorescence when exposed to the HIV infected human sera, and no cells stained with normal human serum. Positive sera employed were obtained from the Interstate Blood Bank.

Permanent cell lines were obtained by transfection of CHO cells lacking dihydrofolate reductase (dhfr). CHO dhfr− cells [Urlaub et al. (1980) *Proc. Natl. Acad. Sci. USA* 77:4216] were plated at a density of $5 \times 10^5$ to $10^6$ cells per 10 cm dish the day prior to transfection in nutrient medium (F12 supplemented with 1.18 mg/ml $Na_2CO_3$, 292 ug/ml glutamine, 110 ug/ml sodium pyruvate, 100 U/ml penicillin, 100 U/ml streptomycin, 150 ug/ml proline and 10% fetal calf serum). Cells were transfected using the calcium phosphate coprecipitation method described by Graham et al. (1973) *Virology* 52:456–467 with the gp160 expression plasmid, pSV7dARV160tpa; a plasmid bearing as a selectable marker, a dhfr gene driven by the adenovirus major late promoter, pAD-dhfr; and a plasmid bearing the human tissue plasminogen activator gene driven by the SV40 early promoter, pSV7tpa3, to serve as an easily screened gene marker. Plasmid pSV7tpa3 is a mammalian cell expression vector containing the full length tpa cDNA (with 99 bp 5' untranslated sequences) cloned into the SalI site of pSV7d, with the orientation such that the proper reading frame is transcribed from the SV40 early promoter.

Samples were added to the dishes of cells fed with fresh medium and allowed to settle for 6 h in an incubator (5% $CO_2$, 95% air) at 37° C. Six hours later, the supernatants were aspirated, the cells rinsed gently with calcium and magnesium-free phosphate buffered saline (PBS-CMF), and the dishes exposed to 15% glycerol in HEPES-buffered saline as an adjuvant for 3.5 to 4 min. After rinsing, the medium on the cells was replaced with fresh F12 as described. Forty-eight hours after the addition of DNA to the cells, the cells were trypsinized and split 1:20 into selective medium, Dulbecco's Modified Eagle Medium (DMEM) supplemented with 4.5 mg/ml glucose, 3.7 mg/ml $Na_2CO_3$, 292 ug/ml glutamine, 110 ug/ml sodium pyruvate, 100 U/ml penicillin, 100 U/ml streptomycin, 150 ug/ml proline, and 10% dialyzed fetal calf serum. After growth in selective medium for 1-2 weeks, colonies appeared. These colonies were assayed for production of tPA by the casein-plasminogen-agar overlay assay. Granelli-Piperno et al. (1978) *J. Exp. Med.* 148:223–234. Individual clones were transferred to microwell plates and expanded to T75 flasks. Twenty-four cell lines that were the highest tPA producers were screened by immunofluorescence for gp160 expression as described for COS cells above and in Section 2.1.3. Of these, seven lines fluoresced brightly when reacted with HIV-positive serum. These seven gp160-positive lines were pooled by mixing equal numbers of each cell line and plating in 10 cm dishes at a cell density of $1 \times 10^5$ cells per dish. Replicate dishes were fed with DMEM supplemented as described above with the addition of varying amounts of methotrexate (amethopterin, Sigma): 0.01, 0.02, 0.05, 0.1 and 0.2 micromolar. After growth in the amplification medium containing methotrexate for 2 to 3 weeks, colonies appeared on the 0.1 and 0.2 micromolar methotrexate dishes. These colonies were transferred to microwell plates and expanded to T75 flasks.

Clones were screened and scored for increased tPA production. Lysates of the cells were prepared in order to examine any gp160 expressed and found in the cell membranes, as is found in HIV infected human lymphocytic lines. Lysates were prepared from cell monolayers by rinsing in cold PBS-CMF and adding lysis buffer consisting of 100 mM NaCl, 20 mM Tris pH 7.5, 1 mM EDTA, 0.5% NP40, 0.5% sodium deoxycholate, 1% BSA, 1 ug/ml pepstatin, 1 mM PMSF, and 17 ug/ml aprotinin. Lysates were collected, incubated on ice for 10 min with occasional vortexing, spun 5 min at 14000 x g in a microcentrifuge, and supernatants transferred to new tubes for storage at −70° C. These samples were assayed by an ELISA specific for envH derived from yeast (see Sections 4.1.2 and 4.1.5).

Immunoblot analysis was done by standard Western transfer of proteins from 8% denaturing gels [Laemmli (1970) *Nature* 227:680–685] and analysis with human immune sera or mouse monoclonal antibodies raised against yeast-expressed envH and env-2 (see Sections 4.1.2 and 4.1.5). The blocking solution is 0.3% Tween-20, 2% normal goat serum in phosphate buffered saline, and all incubations and washes were done in this solution. The human imune sera (Interstate Blood Bank) were diluted 1:100, and Tago goat anti-human horse radish peroxidase (HRP) conjugate was diluted 1:250. Development was with 4-chloro-1-napthol (BioRad). Mouse monoclonal antibody 98B3 [Stephans et al., in *Viruses and Human Cancer*, pp. 29–41 (R. C. Gallo et al., eds., 1987)] was used undiluted as ascites fluid or diluted to 50 ug/ml from a stock of ammonium sulfate purified 1 g. Goat anti-mouse HRP conjugate (Tago) was diluted 1:200.

ELISA analysis was done using the cellular lysates. Plates were coated with mouse monoclonal IgM antibody 95C9 [Stephans et al., supra] at a concentration of 250 ng per 100 microliters per well in PBS. After 2h at 37° C. or overnight at 4° C., the plates were washed 6 times in wash buffer (0.137M NaCl, 0.05% Triton X-100) and the samples added to the wells in casein diluent (100 mM sodium phosphate, 0.1% casein, 1 mM EDTA, 1% Triton X-100, 0.5M NaCl, 0.01% thimerosol pH7.5), and plates were incubated overnight at 4° C. and 4 h at 37. Samples were aspirated, then plates were washed 6 times as above. Rabbit anti-env-2 polyclonal serum [Barr et al. (1987) Vaccine 5:90-101] is diluted 1:100 in the diluent above and added to the plates (100 microliters per well). Plates were incubated for 1 h at 37° C., and then aspirated and washed as described above. Goat anti-rabbit HRP conjugate (Tago) was diluted 1:1000 in the diluent buffer, and 100 microliters were added to each well. Plates were incubated 1h at 37. Samples were aspirated and the plates were washed as described above. Plates were developed with ABTS color reagent and H₂O₂ for 30 min at 37. ABTS was dissolved in citrate buffer and 100 microliters per well were added to the plate. The reaction was stopped by adding 50 ul per well 10% SDS, and the plates were read at 415 nm, 600 nm reference beam. Env-2 was used as a standard using serial 2-fold dilutions starting with 100 ng/ml to 11 places.

Six CHO clones positive by the ELISA assay were amplified in a pool in methotrexate as described above, except that after isolation of colonies from the first round of amplification, cells were again pooled and set up for a consecutive round of amplification. For the first round, methotrexate levels were 0.25, 0.5, 0.75, 1.0, 1.25, and 1.75 micromolar. Colonies from the 0.5 and 0.75 micromolar dishes were pooled and set up in 0.75, 1.0, 2.0, 3.0, 4.0, and 5 micromolar. Clones were isolated from 3, 4, and 5 micromolar levels, expanded and assayed for gp160 production by the ELISA. Increases in expression were observed for these clones as compared to the clones grown in 0.1 and 0.2 micromolar methotrexate, and this expression level represents an improvement over the levels of gp160 in HIV-infected HUT cells.

2.3 Expression of gp120env 2.3.1. Expression of engineered gp120 in pS7Vd

In order to express a secreted form of the envelope polypeptide in mammalian cells, the env gene was modified by in vitro mutagenesis to eliminate any potential transmembrane domains and to provide a stop codon following the processing site between the gp120 and gp41 domains of the gp160 protein. This mutagenesis was accomplished by subcloning the fragment which encodes the env gene from clone pSV7c/env (Section 2.1.2.) by excising with HindIII and XhoI (positions 5582 to 8460) and inserting the 2.8 kb fragment into M13 mp19 previously digested with HindIII and SalI. A 37 bp oligonucleotide of the following sequence was used to alter the sequence at the gp120/gp41 processing site at position 7306 to encode 2 stop codons and two restriction endonuclease sites.

5'-GAACATAGCTGTCGACAAGCTTCATCATCTTTTTTCT-3'

The sequence of the wild-type gene and the mutant are shown below:

Wild-type sequence:

```
                                        Processing site
Position:    7288      7294      7300                    7318
Amino acid:  Val Gln Arg Glu Lys Arg Ala Val Gly Ile Val
DNA:         GTG CAG AGA GAA AAA AGA GCA GTG GGA ATA GTA
``` gp120 mutant:

```
Position:    7288      7294      7300  7306            7317
Amino acid:  Val Gln Arg Glu Lys Arg OP  OP
DNA:         GTG CAG AGA GAA AAA AGA TGA TGA AGC TTG TCG AC
Restriction site:                            HindIII    SalI
```

Following mutagenesis, the gene was engineered for optimal secretion into the medium utilizing the same procedure that was used for gp160. The 268 bp XbaI-NdeI fragment containing the heterologous 5' untranslated sequences and signal sequences from human tPA fused to the 5' end of env was excised from the M13 clone M13tpaS.NheIenv described in Section 2.2.2. This fragment was ligated with a 1363 bp NdeI-SalI fragment encoding the remainder of the gp120 coding region which was isolated from the gp120 mutant (positions 5954 and 7317) described above, and both fragments were inserted into the vector pSV7d previously digested with XbaI and SalI.

This plasmid, pSV7dARV120tpa, has a gene encoding gp120 that ends precisely at the processing site between gp120 and gp41, Arginine-509, expressed from the SV40 early promoter. Plasmid pSV7dARV120 was used to transfect COS7 cells as described in Section 2.2.2. Transfected cells were assayed for expression and secretion of gp120 into the culture medium by immunoblot analysis of conditioned cell medium from the transfected cells. Immunoblot analysis was done using both HIV-positive human serum and mouse monoclonal antibodies described in Section 2.2.2. Using both antibody sources, the gp120 transfected cells secreted into the medium a polypeptide of the size of gp120 that reacted with these immunological reagents, while mock transfected or pSV7dARV160tpa transfected COS cell supernatants showed no such polypeptide. These results are consistent with the production of authentic gp120 in COS cells.

2.3.2. Expression of gp120env using CMV IE-1 promoter

In an effort to improve the expression of gp120 in COS and other mammalian cell types, the gp120 coding region was excised from pSV7dARV120tpa using SalI and inserted into the unique SalI site of the CMV IE-1 expression vector pCMV6a (described below) and screened for insertion in the proper orientation for expression from the CMV IE-1 promoter. The resulting plasmid, pCMV6ARV120tpa, was used to transfect COS 7 cells as described in Sections 2.2.2. and 2.3.1. The conditioned cell medium from the transfected cells was assayed by immunoblot and by ELISA, as described in Sections 2.2.2.and 2.3.1. The CMV6ARV120-tpa-transfected cells expressed gp120 at levels of 60-250 ng/ml and the pSV7ARV120tpa-transfected cells expressed less than 0.5 ng/ml. These results indicate a significant increase in expression of the gp120 polypeptide using the CMV expression plasmid relative to the SV40 expression plasmid described in Section 2.3.1, 50 to 100-fold in magnitude as measured by the ELISA.

Figure 29:
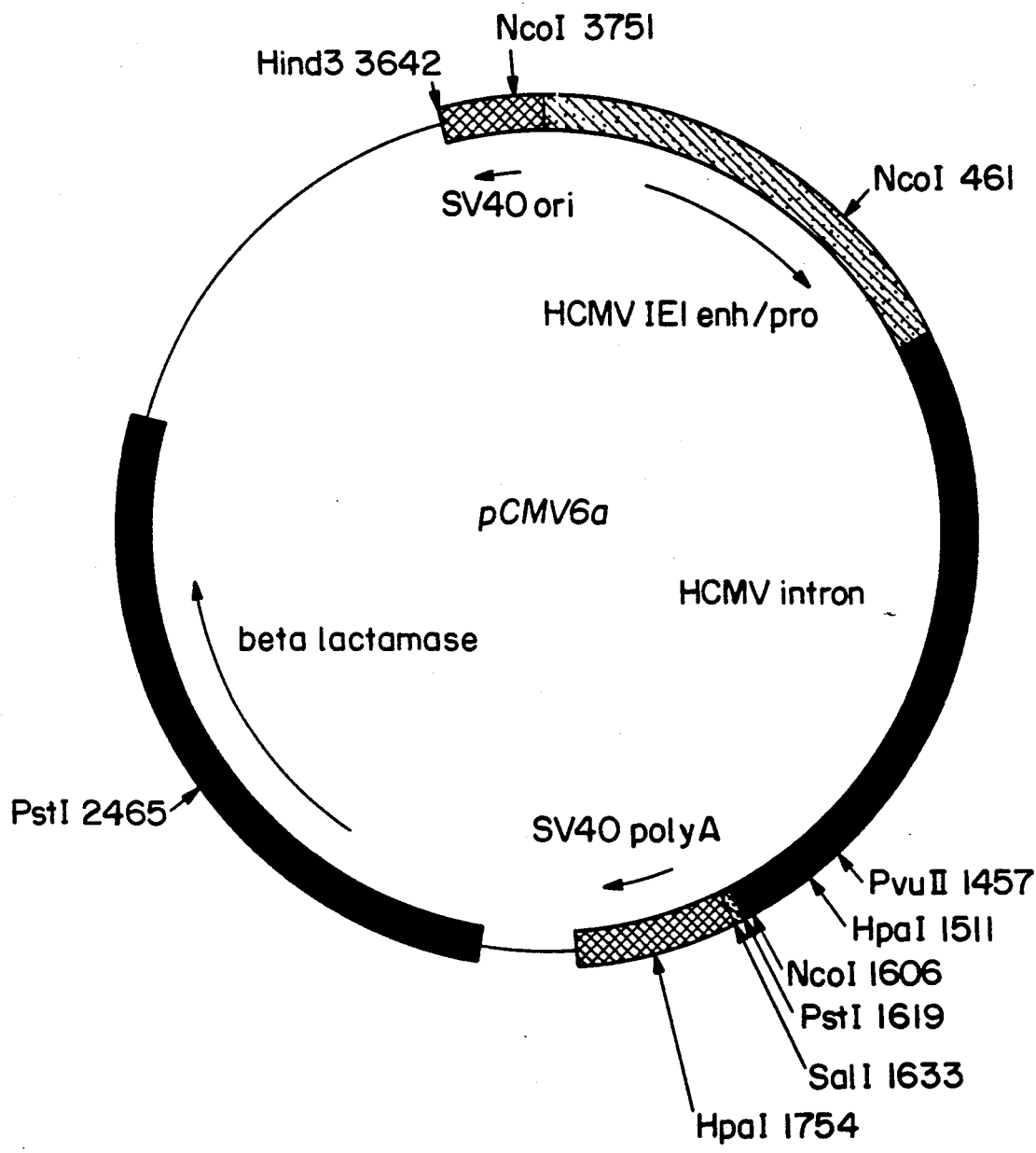

Plasmid pCMV6a is a mammalian cell expression vector which contains the transcriptional regulatory region from human cytomegalovirus immediate early region, HCMV IE1. The plasmid contains the SV40 polyadenylation region derived from pSV7d (Section 2.2.1.) as a 700 bp PvuI-SalI fragment; the SV40 origin of replication derived for pSVT2 [Meyers et al. (1981) Cell 25:373 ∝ 384; Rio et al. (1983) Cell 32:1227-1240] as a 1.4 kb PvuI-EcoRI (filled in with Klenow fragment); and the HCMV IE1 promoter as a 1.7 kbp SspI-SalI fragment derived from a subclone of the human cytomegalovirus (Towne strain). The HCMV IE1 promoter region contains the region encoding the first exon (5' untranslated), the first intron and the start of the second exon (where the SalI site was created by in vitro mutagenesis). The map of pCMV6a is shown in FIG. 29.

2.4. Expression of gag peptides

The ARV-2 DNA coding for the gag region was excised from a recombinant phage (7A; FIG. 3) by digestion with KpnI and SacI and gel purification of a fragment of about 3200 bp. This gag containing fragment was cloned into KpnI and SacI digested pSV-7c/envΔES (described below) to yield pSV-7c/gag. The recombinant vector was used to transfect Cos cells. Expression of gag protein was detected as previously described for the env protein (Section 2.1). About 5 percent of the cells transfected with SV40 vector containing the ARV-2 gag fragment showed bright immunofluorescence when incubated with the AIDS sera and a second fluoresceinated goat anti-human antisera. Cells transfected with a control plasmid containing only SV40 vector sequences did not show any immunofluorescence with any antisera.

Plasmid pSV-7c/envΔES was constructed as follows: Plasmid pSV-7c/env (described in section 2.1.2) was digested with EcoRI and SacI. A linker of the following sequence, which regenerates both the EcoRI and SacI sites and provides for a BamHI site between them was ligated to the linearized vector.

```
     AATTCGGATCCGAGCT
         GCCGAGGC
EcoRI    BamHI    SacI
```

This vector was digested with KpnI and SacI, the fragment corresponding to linearized plasmid was purified by gel electrophoresis and ligated to the 3200 bp KpnI-SacI fragment containing the gag region.

2.5 Expression of gag-env fusion protein

A mammalian cell expression vector containing a fused sequence of nt 225 to nt 1650 encoding for a gag region and nt 5957 to nt 8582 for an env region (FIG. 5) was constructed as follows. Plasmid pSV-7c/gag (described in Section 2.4) was digested with BglII. The overhangs were filled in with reverse transcriptase, and the resulting two fragments were subsequently digested with SacI. The 1390 SacI-BglII bp fragment coding for gag was purified by gel electrophoresis and cloned into pSV-7c/env (Section 2.1.2) prepared as follows.

Vector pSV-7c/env was digested with NdeI which cuts 59 codons downstream from the N-terminal ATG of env. Ends were filled in with reverse transcriptase and the linearized vector was digested with SacI. The SacI-NdeI vector fragment was purified by gel electrophoresis and ligated to the gag fragment obtained as indicated above. The ligation mixture was used to transform HB101, and plasmid pSV-7c/gagΔenv was thus obtained.

Plasmid pSV-7c/gagΔenv was used to transform Cos cells using the procedure described in Section 2.1.2 above. Expression was detected by immunofluorescence using an AIDS patient serum and following the procedure described previously (Section 2.1.3). About 5 cells in 100 showed bright immunofluorescence with the immune serum. No cells stained with control normal human serum.

3. Expression of HIV Polyceptides in Bacteria 3.1. Expression of p25gag 3.1.1. Host-vector system The p25gag protein is synthesized by *E. coli* strain D1210 transformed with plasmid pGAG25-10. Plasmid pGAG25-10 is a pBR322 derivative which contains the sequence coding for p25gag under transcriptional control of a hybrid tac promoter [De Boer et al. (1983) Proc. Natl. Acad. Sci. USA 80:21-25] derived from sequences of the trp and the lac UV5 promoters. Expression of p25gag is induced in bacterial transformants with isopropylthiogalactoside (IPTG).

*E. coli* D1210, a lac-repressor overproducing strain, carries the lacI$^q$ and lacY$^+$ alleles on the chromosome but otherwise is identical to *E. coli* HB101 (F$^-$ lacI$^+$, lacO$^+$, lacZ$^+$, lacY$^-$, gal$^-$, pro$^-$, leu$^-$, thi$^-$, end$^-$, hsm$^-$, hsr$^-$, recA$^-$, rpsL$^-$) from which it was derived.

3.1.2. Construction of pGAG25-10.

Figure 7:
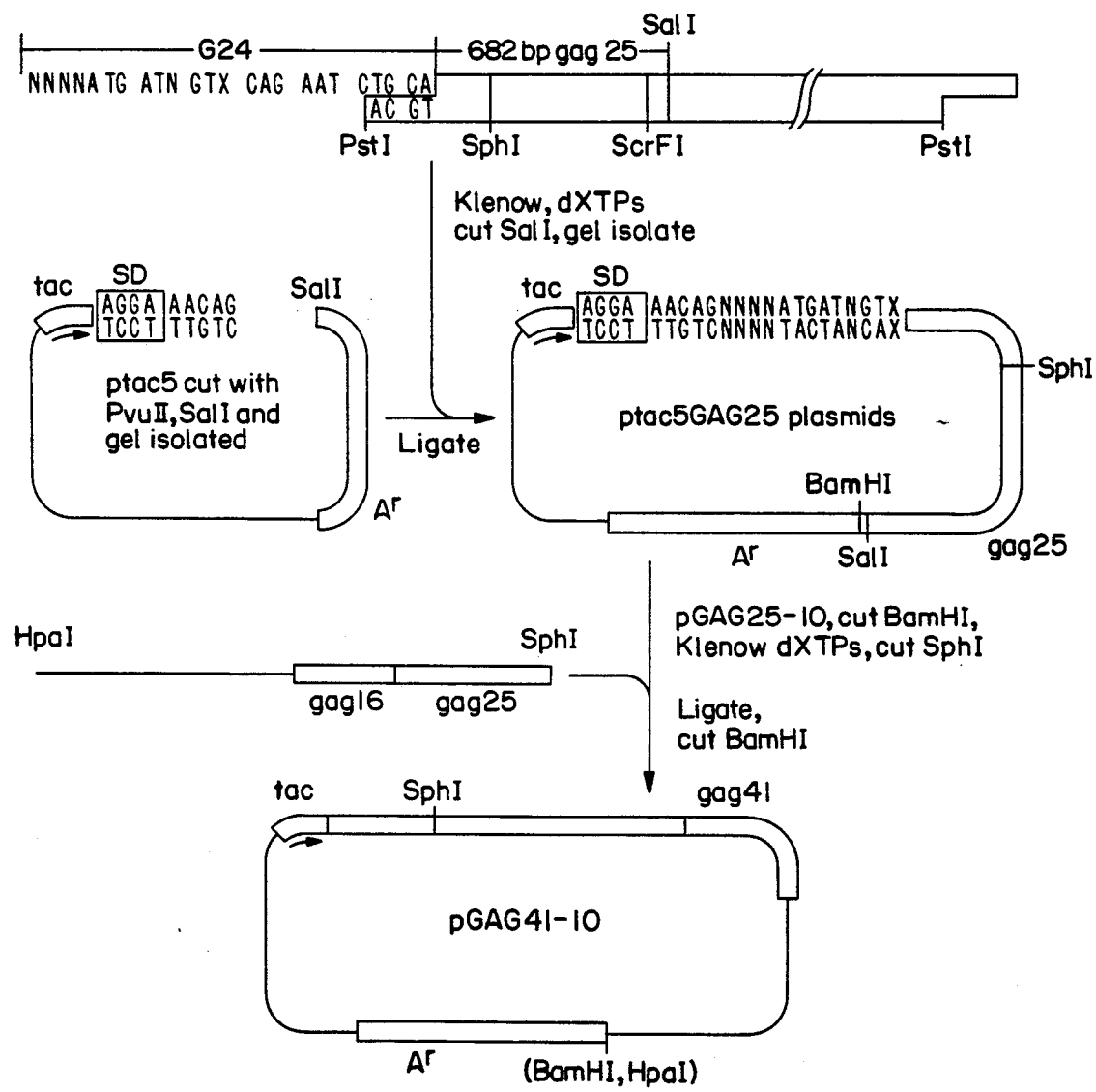
FIG. 7 is a flow diagram showing the procedures for making the plasmids pGAG25-10 and pGAG41-10.

Plasmid pGAG25-10 was constructed by cloning a 699 bp DNA fragment coding for p25gag into plasmid ptac5, according to the scheme shown in FIG. 7. The vector ptac5 is a pBR322 derivative which contains the tac promoter, Shine Delgarno sequences, and a polylinker as a substitution of the original pBR322 sequences comprised between the EcoRI and PvuII restriction sites.

The 699 bp DNA fragment codes for the complete p25gag protein (amino acid residues 136 to 365 as numbered in FIG. 5), the only difference being that a methionine was added as the first amino acid in pGAG25-10 to allow for translational initiation. This change, as well as other changes in nucleotide sequence as indicated below, were achieved by using chemical synthesis of parts of the DNA fragment. The DNA fragment also includes two stop codons at the 3' end of the sequence.

FIG. 8 shows the nucleotide sequence cloned in pGAG25-10 and the amino acid sequence derived from it. DNA sequences that are not underlined in the figure were derived directly from the λARV-2(9B) DNA. All other sequences were chemically synthesized or derived from vector ptac5. Changes were introduced in this DNA sequence, with respect to the original DNA, to create or delete restriction sites, to add a methionine prior to the isoleucine (second residue of p25) or to include stop codons after the last codon of p25gag. However, as previously indicated, all changes in the DNA sequence, except those in the first codon, do not alter the amino acid sequence of p25gag.

3.1.3. Transformation and expression of gag peptide

*E. coli* D1210 cells are made competent for transformation following a standard protocol [Cohen et al. (1982) *Proc. Natl. Acad. Sci. USA* 69:2110]. Transformation is performed as indicated in the protocol with 25-50 ng of pGAG25-10. The transformation mix is plated on agar plates made in L-Broth containing 100 μg/ml ampicillin. Plates are incubated for 12 h at 37° C.

Single ampicillin resistant colonies are transferred into 1 ml L-Broth containing 100 μg/ml ampicillin and grown at 37° C. Expression of p25gag protein is induced by adding 10 μl of 100 mM IPTG (Sigma) to a final concentration of 1 mM followed by incubation at 37° C. for 2 h.

Cells from 1 ml of induced cultures are pelleted and resuspended in 100 μl Laemmli sample buffer. After 3 cycles of boiling and freezing, portions of resultant lysates are analyzed on standard denaturing acrylamide gels. Proteins are visualized by staining with Coomassie blue.

The extent of expression is initially determined by appearance of new protein bands for induced candidate samples compared with control. Proteins of molecular weights expected for the genes expressed comprised 2%-5% of total cell protein in the highest expressing recombinants as determined by visual inspection with reference to a standard protein of known amount.

Authenticity of the expressed proteins is determined by standard Western transfer of proteins to nitrocellulose and analysis with appropriate human or rabbit immune sera or mouse monoclonal antibodies or by comparing ELISA assays of purified recombinant and natural proteins using human immune sera from AIDS patients (see Section 3.1.6).

3.1.4. Fermentation process

3.1.4.1. Preparation of master seed stock

Transformant cells from a culture expressing high levels (3%) of p25gag are streaked onto an L-Broth plate containing 100 μg/ml ampicillin and the plate is incubated overnight at 37° C. A single colony is inoculated into 10 ml of L-Broth, 100 μg/ml ampicillin and grown overnight at 37° C. An aliquot is used to verify plasmid structure by restriction mapping with SalI and PstI. A second aliquot is used to induce expression of p25gag and the rest of the culture is made 15% glycerol by adding ¼ volume of 75% sterile glycerol. Glycerol cell stocks are aliquoted in 1 ml and quickly frozen in liquid nitrogen or dry-ice ethanol bath. These master seed stocks are stored at −70° C.

3.1.4.2. Fermenter inoculum

The master seed stock is scraped with a sterile applicator which is used to streak an L-Broth plate containing 100 μg/ml ampicillin. Single colonies from this plate are used to inoculate 20-50 ml of L-Broth/amp, which is incubated at 37° C. overnight.

An aliquot of the overnight culture is used to inoculate larger volumes (1-6 liters) of L-Broth/amp. Cells are incubated at 37° C. overnight and reach an $O.D._{650}$ of approximately 5 prior to use as inoculum for the fermenter run.

3.1.4.3. Fermentation and harvest

Fermenters (capacity: 16 liters) containing 10 l of L-Broth and 1 ml of antifoam are inoculated with 100-500 ml from the inoculum culture. Cells are grown at 37° C. to an O.D. of about 1. Expression of p25gag is induced by addition of 100 ml of an IPTG solution (100 mM) to yield a 1 mM final concentration in the fermenter. Cells are grown for 3 additional hours and subsequently harvested using continuous flow centrifugation. At this step cells may be frozen and kept at −20° C. until purification of p25gag proceeds. Alternatively, 250 l fermenters are inoculated with 1-5 l from the inoculum culture. Growth, induction, and harvest are as indicated before.

3.1.5. Purification of p25gag

Frozen *E. coli* cells are thawed and suspended in 2.5 volumes of lysis buffer (0.1M sodium phosphate (NaPi), pH 7.5, 1 mM EDTA, 0.1 M NaCl). Cells are broken in a non-continuous system using a 300 ml glass unit of a Dyno-mill at 3000 rpm and 140 ml of acid-washed glass beads for 15 min. The jacketed chamber is kept cool by a −20° C. ethylene glycol solution. Broken cells are centrifuged at 27,000×g for 25 minutes to remove debris and glass beads. The supernatant is recovered and kept at 4° C.

The cell extract is made 30% $(NH_4)_2SO_4$ by slowly adding the ammonium sulfate at 4° C. The extract is stirred for 10 min after the final concentration is achieved, followed by contrifugation at 27,000×g for 20 min. The pellet is resuspended in 1M NaCl, 1 mM EDTA, 1% Triton X-100, and 5% SDS, and then boiled for 5 min.

The fraction obtained by selective precipitation is submitted to gel filtration using a G50 Sephadex column equilibrated in 0.03M NaPi, pH 6.8. Chromatography is developed in the same solution. Fractions are collected and absorbance at 280 nm is determined. Protein-containing fractions are pooled and characterized by protein gel electrophoresis, Western analysis, and ELISA.

3.1.6. Characterization of recombinant p25gag

3.1.6.1. Protein gel electrophoresis

SDS-polyacrylamide gel analysis (10%-20% gradient gels) of proteins from pGAG25-containing cells and control cells indicated that varying levels of a protein of a molecular weight of about 25,000 were specifically induced in cells containing p25gag expression plasmids after derepression of the tacI promoter with IPTG. Identity of the p25gag gene product was confirmed by both an enzyme-linked immunosorbent assay (ELISA; see Section 3.1.6.3) and Western immunoblot analysis (see Section 3.1.6.2) using both AIDS patient serum and a monoclonal antibody to viral p25gag.

3.1.6.2. Western analysis

Samples were electrophoresed under denaturing conditions on a 10%-20% polyacrylamide gradient gel. Samples were electroblotted onto nitrocellulose. The nitrocellulose paper was washed with a 1:250 dilution of AIDS patient reference serum (EW5111, obtained from P. Feorino, Centers for Disease Control, Atlanta, Ga.) and then with a 1:500 dilution of HRP-conjugated goat antiserum to human immunoglobulin (Cappel, No. 3201-0081). Alternatively, the nitrocellulose was washed with undiluted culture supernatant from 76C, a murine monoclonal antibody to HIV-1 p25gag, and then with a 1:500 dilution of HRP-conjugated goat antiserum to mouse immunoglobulin (TAGO, No. 6450). The substrate for immunoblots was HRP color development reagent containing 4-chloro-1-naphthol.

The p25gag protein reacted with both AIDS patient reference serum and with the monoclonal antibody, while it shows no reactivity with the nonimmune serum.

3.1.6.3. ELISA comparison of recombinant and native p25gag

The reactivity of sera with the purified p25gag (recombinant and native) was assayed by coating wells of microtiter plates with 0.25 μg/ml of purified antigen, adding dilutions of test sera, followed by a 1:1000 dilution of HRP-conjugated goat antiserum to human immunoglobulin. Finally, the wells received substrate solution (150 μg/ml 2,2'-azino-di-[3-ethylbenzyl-thiazoline sulfonic acid], 0.001% $H_2O_2$, 0.1M citrate pH 4). The reaction was stopped after incubation for 30 min at 37° C. by the addition of 50 μl/well of 10% SDS. The absorbance was read on a Flow Titertech ELISA reader at 414 nm. Samples were assayed in duplicate beginning at a dilution of 1:100 and by serial 2-fold dilutions thereafter.

As an example, a single sample of HIV antibody-positive serum and normal human serum were each titrated on both recombinant and native p25gag. The antibody-positive serum reacted equally with viral and recombinant antigen. There was no reaction seen with serum from a normal individual.

The reactivity of purified recombinant p25gag to various sera was then compared to that of natural p25gag protein purified by preparative polyacrylamide gel electrophoresis in an ELISA assay. For comparisons, assays were also done using disrupted gradient purified virus (5 μg/ml) as antigen. The table below summarizes the results of assays on 8 AIDS sera that scored positive in the assay with disrupted virus and 6 normal sera that were negative in the disrupted virus assay.

| SERUM NUMBER | ELISA ASSAY TITER[a] | | |
|---|---|---|---|
| | Disrupted Virus | Recomb. p26gag | Viral p25gag |
| Group I: Sera Scoring As Positive in Virus ELISA[b] | | | |
| 1 | 51,200 | 3,125 | 3,125 |
| 5 | 12,800 | 25 | 25 |
| 6 | 12,800 | 625 | 625 |
| 7 | 12,800 | 3,125 | 3,125 |
| 8 | 25,600 | 15,625 | 15,625 |
| 9 | 12,800 | 625 | 625 |
| 13 | 800 | 125 | 125 |
| 18 | 3,200 | 625 | 625 |
| Group II: Sera Scoring Negative in Virus ELISA[b] | | | |
| 15 | —[c] | — | — |
| 16 | — | — | — |
| 19 | — | — | — |
| 21 | — | — | — |
| 26 | — | — | — |
| 33 | — | — | — |

[a]Reported as the reciprocal of the serum dilution that gave a signal equivalent to 50% of the maximum.
[b]Results were confirmed by immunofluorescence and immunoblotting as described previously.
[c]No detectable signal at a 1:25 serum dilution.

These results show that p25gag purified from bacteria behaves identically to similarly purified p25gag from AIDS virus in an ELISA of the eight AIDS patient sera. The results of the ELISA show that there is a wide variation in the levels of anti-p25gag antibodies and suggests that antibodies to some virus-encoded proteins may not be detected using conventional virus-based assay systems.

3.2. Expression of p16gag

The sequence shown in FIG. 10 and coding for the p16gag protein was chemically synthesized [Warner et al. (1984) DNA 3:401] using yeast-preferred codons. The blunt-end to SalI fragment (381 bp) was cloned into -pvuII-SalI digested and gel-isolated ptac5 (see Section 3.1). The resulting plasmid, pGAG16, was used to transform E. coli D1210 cells, as in Section 3.1.3. Expression was induced with IPTG, and proteins were analyzed by polyacrylamide gel electrophoresis and Western analysis. A band of about 16,000 daltons was induced by IPTG in the transformed cells. This protein showed reactivity in Western blots with immune sera from AIDS patients. No reactivity was observed with sera from normal individuals.

3.3 Expression of fusion protein p41gag

A fusion protein of the p25gag and p16gag proteins of ARV-2, designated p41gag, was synthesized in E. coli strain D1210 transformed with plasmid pGAG41-10. pGAG41-10 was constructed from plasmid pGAG25-10 (see Section 3.1.2) as shown in FIG. 7 by inserting an SphI-HpaI fragment from the ARV-2 genome containing the sequences from the C-terminal p16gag portion of the p53gag precursor polyprotein and part of the p25gag protein between the SphI and BamHI sites of pGAG25-10. The coding strand of the DNA sequence cloned in pGAG41-10 is shown in FIG. 9. Transformation and induction of expression were effected by the procedures described above. The cells were treated and the p41gag protein was visualized on Coomassie-stained gel as described above. The approximate molecular weight of the observed protein was 41,000 daltons. The protein reacted with AIDS sera and monoclonal antibody to p25gag in Western and ELISA analyses carried out as above.

3.4. Expression of p31pol 3.4.1. Host-vector system

The C-terminal region of the polymerase gene (p31pol) is synthesized by E. coli strain D1210 transformed with plasmid pTP31.2. Plasmid pTP31.2 is a pBR322 derivation which contains the sequence coding for p31 under transcriptional control of the hybrid tac promoter (described in Section 3.1). Expression of p31 is induced in bacterial transformants by IPTG.

3.4.2. Construction of pTP31.2

3.4.2.1. Construction of M13 template 01100484

A 4.87 kb DNA fragment was isolated from a KpnI digest of ARV-2 (9b) containing the 3' end of the pol gene, orf-1, env and the 5' end of orf-2, that had been run on a 1% low melting point agarose (Sea-Pack) gel and extracted with phenol at 65° C., precipitated with 100% ethanol and resuspended in TE. Eight μl of this material were further digested with SstI for 1 h at 37° C. in a final volume of 10 μl. After heat inactivation of the enzyme, 1.25 μl of this digest were ligated to 20 ng of M13mp19 previously cut with KpnI and SstI, in the presence of ATP and in a final volume of 20 μl. The reaction was allowed to proceed for 2 h at room temperature. Five μl of this mixture were used to transform competent E. coli JM101. Clear plaques were grown and single-stranded DNA was prepared as described in Messing & Vieira, (1982) Gene 19:269–276. One of these plaques containing the 1848 bp fragment was designated 01100484.

3.4.2.2. In vitro mutagenesis of 01100484

The DNA sequence in 01100484 was altered by site-specific mutagenesis to generate a restriction site recognized by NcoI (CCATGG). An oligodeoxynucleotide that substitutes the A for a C at position 3845 (FIG. 5) and changes a T for an A at position 3851 (FIG. 5) was synthesized using solid phase phosphoramidite chemistry. Both of these changes are silent in terms of the amino acid sequence, and the second one was introduced to decrease the stability of the heterologous molecules. The oligomer was named ARV-216 and has the sequence: 5'-TTAAAATCACTTGCCATGGCTCT-CCAATTACTG and corresponds to the noncoding strand since the M13 derivative template 01100484 is single-stranded and contains the coding strand. The 5' phosphorylated oligomer was annealed to the 01100484 M13 template at 55° C. in the presence of M13 sequencing primer, 50 mM Tris-HCl pH 8, 20 mM KCl, 7 mM MgCl$_2$ and 0.1 mM EDTA. The polymerization reaction was done in 100 μl containing 50 ng/μl DNA duplex, 150 μM dNTPs, 1 mM ATP, 33 mM Tris-acetate pH 7.8, 66 mM potassium acetate, 10 mM magnesium acetate, 5 mM DTT, 12.5 units of T4 polymerase, 100 μg/ml T4 gene 32 protein and 5 units of T4 DNA ligase. The reaction was incubated at 30° C. for 30 min and was stopped by the addition of EDTA and SDS (10 mM and 0.2% respectively, final concentration).

Competent JM101 *E. coli* cells were transformed with 1, 2, and 4 μl of a 1:10 dilution of the polymerization product and plated into YT plates. Plaques were lifted by adsorption to nitrocellulose filters and denatured in 0.2N NaOH, 1.5M NaCl, followed by neutralization in 0.5M Tris-HCl pH 7.3, 3M NaCl and equilibrated in 6×SSC. The filters were blotted dry, baked at 80° C. for 2 h and preannealed at 37° C. in 0.2% SDS, 10×Denhardt's, 6×SSC. After 1 h, 7.5 million CPM of labeled ARV-216 were added to the filters and incubated for 2 additional h at 37° C. The filters were washed in 6×SSC at 42° C. for 20 min, blot-dried and used to expose film at −70° C. for 1 h using an intensifying screen. Strong hybridizing plaques were grown and single-stranded DNA was prepared from them and used low melting point agarose (Sea-Pack) gel and the DNAs were visualized by fluorescence with ethidium bromide. The 800 bp bands were cut and the DNAs were extracted from the gel as mentioned above and resuspended in 10 μl of TE. The fragments were called ARV248NR#2 and ARV248NL, respectively.

3.4.2.4. Cloning of p31 into plot 7

The vector plot #7 (3 μg) [Hallewell et al. (1985) *Nucl. Acid Res.* 13:2017-2034] was cut with NcoI and EcoRI in 40 μl final volume and the enzymes were heat-inactivated after 3 h. Two μl of this digest were mixed with 2 μl of ARV248NR#2 and ligated in 20 μl in the presence of ATP and T4 DNA ligase at 14° C. overnight, and 10 μl of this mixture were used to transform competent D1210 cells. Colonies resistant to 2 mM IPTG and 100 μg/ml ampicillin were selected and supercoiled DNA was extracted from each of them. The DNAs were then restricted with NcoI and EcoRI and analyzed by agarose gel electrophoresis. Clones with the appropriate 800 bp insert were selected for further use. They are designated pRSP248 numbers 3 and 4.

3.4.2.5. Construction of pTP31

The NcoI site introduced into 01100485 is 52 bp downstream from the putative start of p31. Three oligomers were synthesized as above that code for the first 17 amino acids of p31 and generate a cohesive NcoI end at the 3' end of the molecule. The 5' end of the molecule has been extended beyond the initiation codon to include a ribosome binding site. The oligomers that were synthesized have the sequences:

ARV-221
```
             CCCC       C  C
5'AGGXAACAGAAAAATGATAGATTAAGGCACAAGAA
             TTTT       T
```

ARV-222
5'GAACATGAGAAATATCACAGTAATTGGAGAGC

ARV-223
3'CGTGTTCTTCTTGTACTCTTTATAGTGTCATTAACCTCTCGGTAC as templates for sequencing. Sequencing showed that template 01021785 contains the NcoI site as well as the second substitution mentioned above.

A second oligomer was synthesized to insert sites for SalI and EcoRI immediately after the termination codon of the pol gene (position 4647, FIG. 5). This oligomer was called ARV-248 and has the sequence: 5'-GGTGTTTTACTAAAGAATTCCGTCGAC-TAATCCTCATCC. Using the template 01020785, site specific mutagenesis was carried out as described above except that the filter wash after the hybridization was done at 65° C. As above, 8 strong hybridizing plaques were grown and single-stranded DNA was sequenced. The sequence of template 01031985 shows that it contains the restriction sites for NcoI, SalI, and EcoRI as intended.

3.4.2.3. Isolation of DNA fragments containing p31

Replicative form (RF) of the 01031985 template was prepared by growing 6 clear plaques, each in 1.5 ml of 2×YT at 37° C. for 5 h. Double-stranded DNA was obtained as described by Maniatis et al., supra, pooled and resuspended in 100 μl final volume. Ten μl of RF were digested with NcoI and EcoRI in a final volume of 20 μl. This fragment was used for direct p31 expression in bacteria. An additional 20 μl of RF were cut with NcoI and SalI in 40 μl. This fragment was used for p31 expression in yeast. The samples were run on a 1%

One hundred fifty picomoles each of dephosphorylated ARV-221, phosphorylated ARV-222 and ARV-223 were ligated to 20 μg of pRSP248 previously cut with NcoI, at 14° C. for 18 h in a final volume of 62 μl. After phenol extraction and ethanol precipitation, the DNA was resuspended in 40 μl H$_2$O and incubated with 15 units of Klenow fragment in the presence of 0.5 mM dNTPs for 1 h at room temperature. The sample was phenol extracted, ethanol precipitated, resuspended in 40 μl H$_2$O, and digested with EcoRI. The DNA was then run on a low melting point agarose gel and the fragment of about 820 bp was extracted as described above and resuspended in a final volume of 20 μl of H$_2$O. After phosphorylating the ends, 5 μl of the sample were incubated for 18 h at 14° C. with 150 ng of plot7 that had been cut with PvuII and EcoRI and its ends dephosphorylated, in the presence of T4 DNA ligase, ATP and in a final volume of 31 μl. Five μl of ligation product were used to transform RR1ΔM15. Clones resistant to 100 μg/ml of ampicillin were selected and supercoiled DNA was extracted from them. The DNAs were digested with NcoI and EcoRI and resolved on a 1% agarose gel. Colonies with the appropriate size insert were obtained and named pTP31. The p31 sequence contained in the insert is shown in FIG. 12.

Underlined sequences were chemically synthesized. Others were derived from DNA.

3.4.3. Screening of transformants

Bacterial transformants containing either the vector alone, or the vector with the p31 DNA (pTP31.2) were grown in L-Broth with 0.02% ampicillin to an $OD_{650}$ of 0.5. Cultures were induced by the addition of IPTG to a final concentration of 2 mM and grown for 3 more hours. Bacteria from 1 ml cultures were pelleted and resuspended in 200 µl of gel sample buffer. The cells were disrupted by three cycles of freezing and thawing, boiled, and the extracts loaded onto 12.5% polyacrylamide-SDS minigels. Proteins were electrophoresed and transferred to nitrocellulose by electro-blotting. The nitrocellulose filters were reacted with serum EW5111 (diluted 1:100; positive reference serum from the CDC that reacts strongly with viral p31), horse radish peroxidase-conjugated goat anti-human IgG and HRP substrate. A prominent band at ~30,000 d and several lower molecular weight species were seen in gels of extracts from transformants with the p31 DNA, but not in extracts from bacteria transformed with the vector alone.

3.4.4. Characterization of recombinant protein

Lysozyme-NP40 extracts were prepared from bacteria transformed with pTP31.2 or vector alone. Five ml cultures were grown, the cells pelleted and resuspended in 1 ml of 50 mM Tris-HCl pH 8, 0.5 mM EDTA, 1 mg/ml lysozyme and incubated at 0° C. for 15 min NaCl, $MgCl_2$, and NP40 were added to final concentrations of 0.4, 5 mM and 0.5% respectively, mixed and incubated with DNAse I (100 µg/ml) at 0° C. for 30 min. When EW5111 serum (diluted 1:100) was preincubated with a 1:10 dilution of the cell extracts from bacteria transformed with pTP31.2, prior to reaction with a virus blot, the viral p31 band was completely eliminated, while reactivity with other viral proteins remained unaffected. In contrast, extracts from bacteria transformed with the vector alone did not absorb out the p31 reactive antibodies. The viral p31 protein is thus the product of the C-terminal or endonuclease region of the pol gene of HIV-1.

3.5. Expression of SOD-p31 fusion protein

In order to generate a fused protein SOD-p31 that can be expressed in *E. coli*, 2 μl of the fragment ARV248NL were ligated to 100 ng of a NcoI-SalI digest of pSODCF2 [Steimer et al. (1986) *J. Virol.* 58:9–16], a plasmid that contains the human SOD coding region under the regulation of the tacl promoter, in 20 μl final volume for 18 h at 14° C. Competent D1210 cells were transformed with 5 μl of the ligation mix and colonies were selected on L-broth ampicillin plates. Colonies with the correct insert were called *E. coli* D1210 (pTSp31). The expression of the fusion protein was analyzed in the same manner as the direct expression of p31. The analysis showed production of large amounts of a protein of about 47 kd that is immunoreactive with EW5111 but not with normal human sera. Further characterization of the recombinant protein is described in Section 4.3.3.3.

3.6. Expression of SOD-env5b fusion protein 3.6.1. Host-Vector System

A hybrid protein consisting of human superoxide dismutase (SOD) fused to a viral envelope (env-5b) protein is synthesized by *E. coli* strain D1210 transformed with plasmid pSOD/env5b. Plasmid pSOD/env5b is a bacterial expression vector which contains the sequence coding for human SOD [Hallewell et al. (1985) *Nucl. Acid. Res.* 13:2017] fused to the env-5b region of the viral env gene [Sanchez-Pescador et al. (1985) *Science* 227:484] as well as pBR322 sequences including the ampicillin resistant ($amp^R$) gene.

Expression of SOD/env-5b fusion protein is non-constitutive and it is under transcriptional control of a hybrid tac promoter [De Boer et al. (1983) *Proc. Natl Acad. Sci. USA* 80:21–25] derived from sequences of the trp and the lac UV5 promoters. Expression of SOD/env-5b is induced in bacterial transformants with IPTG.

*E. coli* D1210, a lac-repressor overproducing strain, carries the lacI and $lacY^+$ alleles on the chromosome but otherwise is identical to *E. coli* HB101 ($F^+$, $lacO^+$, $lacY^-$, $gal^-$, $pro^-$, $leu^-$, $thi^-$, $end^-$, $hsm^-$, $hsr^-$, $recA^-$, $rpsL^-$) from which it was derived [Sadler et al. (1980) *Gene* 8:279–300].

3.6.2. Construction of pSOD/env5b

Plasmid pSOD/env5b is a pBR322 derivative which contains the sequences coding for env-5b [Sanchez-Pescador et al. (1985) supra] under transcriptional control of a hybrid tac promoter. De Boer et al. (1983) supra.

Plasmid pSOD/env5b (FIG. 25) was constructed by cloning a 322 base pairs synthetic DNA fragment coding for env-5b into plasmid pSODCF2 [Steimer et al. (1986) *J. Virol.* 58:9–16], a vector containing the human SOD gene under the control of the tacI promoter. Plasmid pSODCF2 is derived from vector ptac5 [Hallewell et al. (1985) *Nucl. Acid. Res.* 13:2017] a pBR322 derivative which contains the tac promoter, Shine Delgarno sequences and a polylinker as a substitution of the original pBR322 sequences comprised between the EcoRI and PvuII restriction sites.

The 322 base pairs synthetic DNA fragment codes for the env-5b fragment (amino acid residues 557 to 677 as numbered in FIG. 5) with an additional methionine to allow for translational initiation site. The synthetic gene was prepared by synthesizing oligonucleotides varying in length between 34 and 48 bases, and purifying and kinasing them individually according to standard procedures. Warner et al. (1984) *DNA* 3:401. The solution was phenol extracted and ethanol precipitated. The pellet was redissolved in 30 μl of a buffer containing 20 mM Tris-HCl (pH 8.0), 10 mM $MgCl_2$, and 10 mM dithiothreitol, and heated to 90° C. After allowing to cool over 3 hours, the solution was made 3 mM in ATP, brought up to a volume of 45 μl, and 5 μl of T4 DNA ligase ($4\times10^5$ U/ml Biolabs) added. The ligation was stopped after 10 minutes at 25° C. by phenol extraction and ethanol precipitation. The pellet was redissolved in 80 μl $H_2O$ in 10 μl of 10× high salt restriction buffer and digested for 2 hours at 37° C. with 5 μl each of NcoI and SalI (Biolabs). The full-length gene was then purified on a 7% native polyacrylamide gel, electroeluted, and cloned into NcoI/SalI-digested pBS-100.

The cloned env-5b gene was isolated as an NcoI/SalI fragment from the resulting plasmid and cloned into NcoI/SalI-digested pSODCF2 to give plasmid pSOD/env5b. The resulting bacterial expression vector was used to express the SOD/env-5b fusion protein in *E. coli* under the control of the tac-1 promoter. Hallewell et al. (1985) *Nucleic Acids Res.* 13:2017.

FIG. 15 shows the nucleotide sequence of the SOD/env-5b insert cloned in pSOD/env5b and the amino acid sequences derived for it. Sequences coding for human SOD were derived from a human cDNA isolated as described in Hallewell et al. (1985), supra. Sequences coding for env-5b were chemically synthesized by the phosphoramidite method as originally described by Beaucage & Caruthers, (1981) *Tetrahedron Lett.* 22:1859.

3.6.3. Expression of SOD/env-5b fusion protein

*E. coli* D1210 cells were made competent for transformation following a standard procedure and transformed with pSOD/env5b. The transformation mix was plated on agar plates made with L-broth containing 100 μg/ml ampicillin. Plates were incubated for 12 hours at 37° C.

Single ampicillin resistant colonies were transferred into L-broth containing 100 μg/ml ampicillin and grown at 37° C. Expression of env-5b was induced by adding 100 mM IPTG to a final concentration of 1 mM followed by incubation at 37° C. for 2 hours.

Cells from induced cultures were pelleted and resuspended in Laemmli sample buffer. Laemmli (1970) *Nature* 227:680. After 3 cycles of boiling and freezing, portions of resultant lysates were analyzed on standard denaturing acylamide gels. Laemmli (1970), supra. Proteins were visualized by staining with Coomassie blue.

The extent of expression was initially determined by appearance of new protein bands for induced candidate samples compared with controls. Proteins of molecular weights expected for the cloned DNA were determined by visual inspection of the gel lanes with reference to a standard protein band of known amount.

Authenticity of the expressed proteins was determined by standard western transfer of proteins to nitrocellulose and analysis with appropriate human or rabbit immune sera or mouse monoclonal antibodies or by ELISA assays of soluble *E. coli* proteins using human immune sera from AIDS patients.

3.6.4. Protein purification

Single colonies of D1210 (pSOD/env5b) were inoculated into 2 ml aliquots of L-broth containing 100 μg/ml ampicillin and the cultures were grown overnight at 37° C. The culture was made 15% glycerol by adding ¼ volume of 75% sterile glycerol. The glycerol cell stocks aliquoted and quickly frozen in liquid nitrogen. The aliquots were stored at −70° C.

A frozen aliquot of the seed stock (200 μl) was thawed and used to inoculate 110 ml of L-broth with 0.01% ampicillin medium. The culture was grown to saturation at 37° C. with agitation. A 15 ml portion of the culture was added to each of six (6) flasks containing 1.5 L of L-broth with 0.01% ampicillin medium. The cultures were grown at 37° C. with agitation. During late log phase (after approximately 6 h.), env-5b expression was induced by addition of IPTG to a final concentration of 1 mM. Incubation was continued for an additional 2–4 h. at 37° C.

After the cells had completed the growth period they were harvested by centrifugation and pooled. The packed cells were stored at either 4° C. or −20° C. The frozen (or refrigerated) cells were thawed and suspended in 2 volumes of cell lysis solution (1.0 mM PMSF, 0.18 mM EDTA, 230 mM tris-HCl, 0.425 mg/ml Lysozyme) on ice for 1 h. Approximately 1.5 volumes of DNA Digestion Solution (1.0 mM PMSF, 30 units/ml DNAse I, 1.0 mM MgCl2) was added and then the cell lysate was sonicated at room temperature for 30 minutes. The lysate was centrifuged at 113,000×g for 15 minutes.

The supernatant was discarded and the pellet was suspended in solubilization buffer (0.1% β-mercaptoethanol in 7M guanidine-HCl) and rocked for 3 h. at 2°–8° C. The solution was subjected to ultracentrifugation at 25,500×g for 4 h. at 2°–8° C. The pellet was discarded, and the supernatant was diluted with 6 volumes of water, and then incubated at room temperature for 1–2 h. The diluted supernatant was centrifuged at 11,300×g for 30 minutes. Following centrifugation, the supernatant was discarded and the pellet was resuspended in 10–15 volumes of elution and resuspension buffer (0.1% β-mercaptoethanol, 50 mM Tris-HCl in 3.5M guanidine-HCl, pH 7.4). The suspension was centrifuged at 2,000×g for 10 minutes at 2°–8° C. to remove any insoluble material.

The resolubilized fraction was chromatographed on a Sephacryl S-300 column and eluted with Elution and Resuspension Buffer. Fractions were collected and the absorbance was monitored at 280 nm. Fractions containing env-5b as determined by SDS-PAGE were pooled. The pooled fractions were concentrated to 1/5 the original volume by ultrafiltration in an Amicon unit under $N_2$ pressure.

The concentrate was dialyzed (MW cutoff 2000) against 50 to 100 volumes of urea-containing dialysis buffer (0.1% B-Mercaptoethanol, 50 mM Tris-HCl in 7.5M urea, pH 7.4) for 16–24 h. at 2°–8° C. The protein concentration of the dialyzed env-5b was adjusted to 1.02.0 mg/ml (based on modified Lowry assay).

3 7. Expression of β-gal-env fusion proteins.

3.7.1. Host-vector system

A partial env protein is synthesized by *E. coli* D1210 transformed with plasmid pII-3. Plasmid pII-3 (ATCC No. 67549) is a bacterial expression vector which contains the sequence for ⅔ (carboxyl end) of the env protein fused to *E. coli* b-galactosidase DNA in the vector pNL291. Expression of the β-gal-env fusion protein is induced with IPTG.

3.7.2. Construction of pII-3

Plasmid pII-3 was constructed by cloning a 1855 bp BglII-XhoI fragment coding for ⅔ of the env protein. The fragment extends from nt 6604 to nt 8460 (FIG. 5) and codes for env amino acid residues from number 276 to the end of the env protein.

To prepare the plasmid, the 1856bp fragment was isolated by gel electrophoresis. The BglII-XhoI fragment was cloned into pNL291 which had been previously digested with BamHI and XhoI. Plasmid pNL291 is a derivative pUR291 [Ruther et al. (1983) *EMBO J.* 2:1791–1794] in which a polylinker containing the additional restriction sites NcoI, PvuII and XhoI was substituted between the BamHI and SalI sites. Plasmid pUR291 is an inducible *E. coli* expression vector which produces β-galactosidase C-terminal fusion proteins.

3.7.3. Expression and characterization of fusion protein

*E. coli* D1210 cells were transformed with 25–50 ng of pII-3. The transformation mix was plated onto L-Broth agar plates containing 100 μg/ml ampicillin. Single $amp^R$ colonies were grown in L-Broth/amp and expression of the fusion protein was induced by IPTG addition (1 mM) followed by incubation. Cell extracts were prepared and analyzed by SDS gel electrophoresis and immunoassays using human immune sera or rabbit immune sera.

Results of this analysis showed that a large molecular weight protein is induced with IPTG. Expression levels are about 20 mg/l. This fusion protein reacted with human immune sera from AIDS patients in ELISA assays.

4. Expression of HIV Polypeptides in Yeast 4.1. Expression of envH peptide

4.1.1. Host-vector system

A partial env protein is synthesized by *S. cerevisiae* 2150-2-3 transformed with plasmid pDPC303. Plasmid pDPC303 is a yeast expression vector which contains the sequence coding for ⅔ of the env protein, envH, as well as pBR322 sequences including the amp$^R$ gene and 2-micron sequences including the yeast leu 2-04 gene. Expression of envH is under regulation of the yeast pyruvate kinase promoter and terminator sequences. Yeast strain *S. cerevisiae* 2150-2-3 has the following genotype: Mat a, ade 1, leu 2-112, cir°. This strain was obtained from Dr. Leland Hartwell, University of Washington.

4.1.2. Construction of pDPC303

Plasmid pDPC303 contains an "expression cassette" (described below) for envH cloned into the BamHI site of vector pC1/ 1. Vector pCl/1 contains pBR322 and 2 micron sequences including the amp$^R$ and yeast leu 2-04 markers. It was derived from pJDB219d [Beggs (1978) *Nature* 275:104] by replacing the pMB9 region with pBR322 sequences.

The "expression cassette" for envH consists of the following sequences fused together in this order (5' to 3'): yeast pyruvate kinase (PYK) promoter, envH coding region and PYK terminator. The PYK promoter and terminator regions were derived from the PYK gene isolated as described in Burke et al. (1983) *J. Biol. Chem* 258:2193-2201.

The envH fragment cloned into the expression cassette was derived from ARV-2 DNA and comprises a 1395 bp fragment which codes for env amino acid residues 27 through 491 coded by nt 5857 to nt 7242 (FIG. 5). In addition, there are 5 extra codons fused in reading frame in the 5' end, the first codon corresponding to a methionine, and 4 extra codons fused in reading frame at the 3' end followed by a stop codon. The extra codons were incorporated to facilitate cloning procedures exclusively.

FIG. 11 shows the coding strand of the nucleotide sequence cloned in pDPC303 and the amino acid sequence derived from it. DNA sequences that are not underlined in the figure were derived directly from the ARV-2 λ9B DNA described above. All other sequences were either chemically synthesized, or derived from the PYK vector.

4.1.3. Transformation and expression

Yeast cells *S. cerevisiae* 2150-2-3 (Mat a, ade 1, leu 2-04, cir°) were transformed as described by Hinnen et al. (1978) *Proc. Natl. Acad. Sci. USA* 75:1929-1933, and plated onto leu$^-$ selective plates. Single colonies were inoculated into leu$^-$ selective media and grown to saturation. Cells were harvested and the env protein was purified and characterized as described below.

4.1.4. Purification of envH protein

4.1.4.1. Cell breakage

Frozen *S. cerevisiae* 2150-2-3 (pDPC303) are thawed and suspended in 1 volume of lysis buffer (1 μg/ml pepstatin, 0.001M PMSF, 0.001M EDTA, 0.15M NaCl, 0.05M Tris-HCl pH 8.0), and 1 volume of acid-washed glass beads are added. Cells are broken in a noncontinuous system using a 300 ml glass unit of Dyno-mill at 3000 rpm for 10 min. The jacket is kept cool by a −20° C. ethylene glycol solution. Glass beads are decanted by letting the mixture set for 3 minutes on ice. The cell extract is recovered and centrifuged at 18,000 rpm (39,200×g) for 35 min. The supernatant is discarded and the precipitate (pellet 1) is further treated as indicated below.

4.1.4.2. SDS extraction of insoluble material

Pellet 1 is resuspended in 4 volumes of Tris-HCl buffer (0.01M Tris-HCl, pH 8.0, 0.01M NaCl, 0.001M PMSF, 1 μg/ml pepstatin, 0.001M EDTA, 0.1% SDS) and extracted for 2 h at 4° C. with agitation. The solution is centrifuged at 6,300×g for 15 min. The insoluble fraction (pellet 2) is resuspended in 4 volumes (360 ml) of PBS (per liter: 0.2 g KCl, 0.2 g KH$_2$PO$_4$, 8.0 g NaCl, 2.9 g Na$_2$HPO$_4$.12H$_2$O), 0.1% SDS, 0.001M EDTA, 0.001M PMSF, 1 μg/ml pepstatin, and centrifuged at 6,300×g for 15 min. The pellet (pellet 3) is suspended in 4 volumes of PBS, 0.2% SDS, 0.001M EDTA, 0.001M PMSF, 1 μg/ml pepstatin and is extracted for 12 h at 4° C. with agitation on a tube rocker. The solution is centrifuged at 6,300×g for 15 min. The soluble fraction is recovered for further purification as indicated below. (The pellet can be reextracted by resuspending it in 4 volumes of 2.3% SDS, 5% β-mercaptoethanol, and boiling for 5 min. After boiling, the solution is centrifuged at 6,300×g for 15 min. The soluble fraction is recovered for further purification.)

4.1.4.3. Selective precipitation and gel filtration

The soluble fraction is concentrated by precipitation with 30% ammonium sulfate at 4° C. The pellet (pellet 4) is resuspended in 2.3% SDS, 5% β-mercaptoethanol, and chromatographed on an ACA 34 (LKB Products) gel filtration column. The column is equilibrated with PBS, 0.1% SDS, at room temperature. Chromatography is developed in the same solution with a flow rate of 0.3 ml/min. Five ml fractions are collected, pooled and characterized by protein gel electrophoresis, Western analysis, and ELISA. If needed, pooled fractions are concentrated by vacuum dialysis on Spectrapor #2 (MW cutoff 12-14K).

4.1.5. Characterization of recombinant envH

SDS polyacrylamide gel analysis (12% acrylamide gels) showed that a new 55,000 dalton protein was being synthesized in yeast cells transformed with the env-containing vector. The 55,000 dalton protein is absent from cells transformed with control plasmid (vector without env insert). The identity of env was confirmed by both ELISA (Section 3.1.6.3.) and Western analysis using AIDS patient serum. In both assays the 55,000 dalton protein showed immunoreactivity. No reactivity was obtained with serum from a normal individual.

4.2. Expression of env subregion polypeptides

Figure 13:
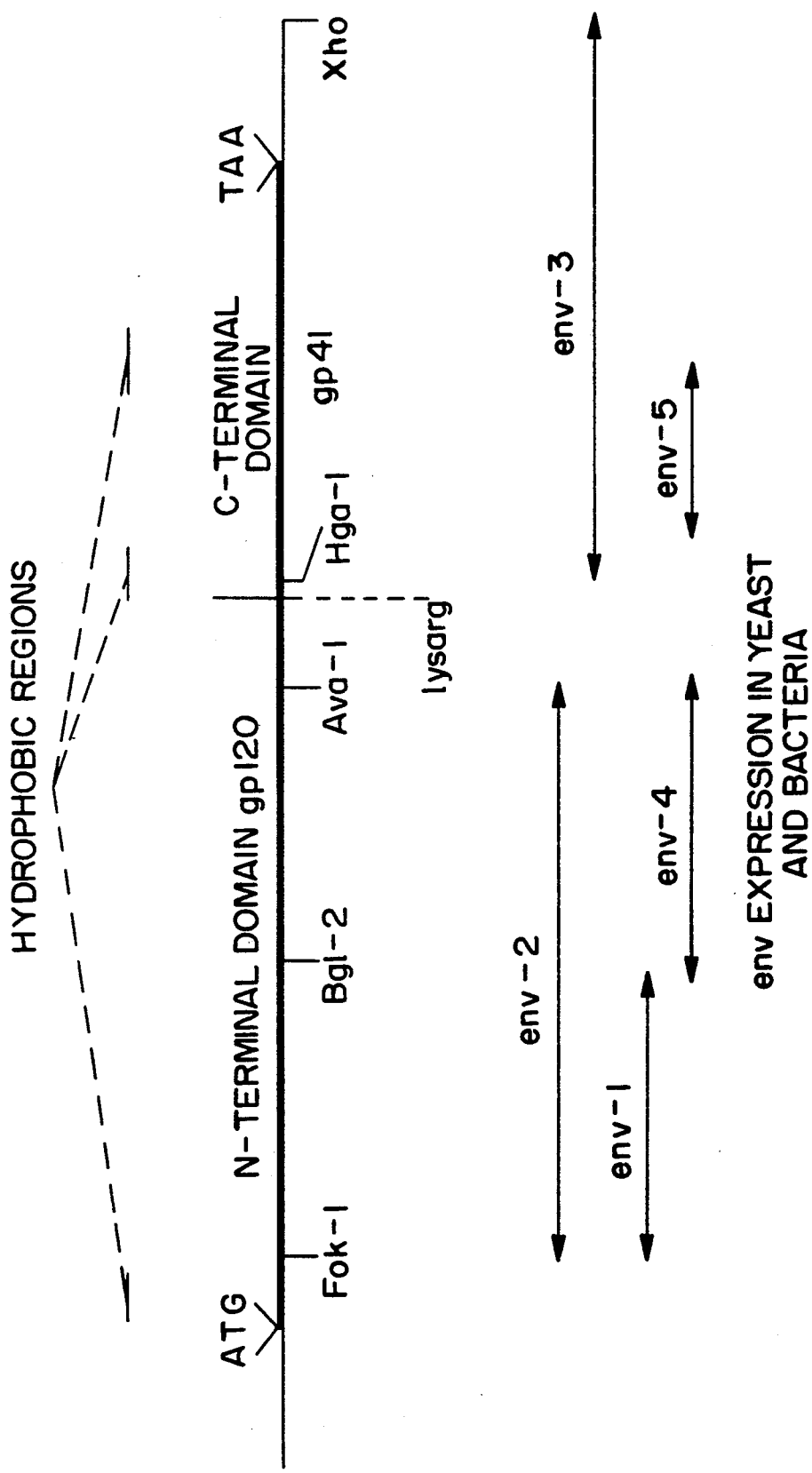
FIG. 13 is a map of the ARV env gene showing the regions env-1, env-2, env-3, env-4, and env-5.

The following example describes the expression of DNA coding regions defined as env-1, env-2, env-3, env-4 and env-5b (see FIG. 13). Env-1 and env-4 approximate the N- and C-terminal halves of gp120env, respectively. Env-2 and env-3 approximate the entire env polypeptide moieties of gp120 and gp41, respectively. Env-5b corresponds to the region of gp41env thought to be external to the cell membrane.

4.2.1. Env-1

4.2.1.1. GAP promoter

Proviral ARV-2 sequences were isolated from phage λARV-2 (7D) and subcloned into plasmid pUC19. Yanisch et al. (1985) *Gene* 33:103-119. The plasmid containing the proviral sequences was named pUC1-9ARV7D/7. To isolate the env-1 region, the plasmid was cut with FokI at cys27 of the env region (nt5857, FIG. 5) and with BglII at arg276 (nt6604, FIG. 5). This provided a nucleotide segment with a coding capacity for 28 kD from the N-terminus of gp120 without the 29 amino acid signal sequence of the env gene product. A synthetic, NcoI/FokI adaptor, with the following sequence, was ligated to the env-1 segment:

```
5'-CATGGCTATC
      CGATAGACAT-5'
```

A second adaptor, for BglII/SalI, was also ligated to the env-1 segment. This second adaptor had the following sequence:

```
5'-GATCTTGATAGG
      AACTATCCAGCT-5'
```

The first synthetic adaptor contains an in-frame initiation codon, and the second synthetic adaptor contains an in-frame stop codon.

The env-1 segment modified with the synthetic adaptors was then ligated into pPGAP1 previously linearized with NcoI and SalI. Plasmid pPGAP1 has been previously described. EPO Pub. No. 164,556. It contains a yeast glyceraldehyde-3-phosphate dehydrogenase (GAPDH) promoter and terminator sequences flanking NcoI and SalI cloning sites. The ligation of the modified env-1 segment into pPGAP1 produces plasmid pPGAP/FGenv, which contains the env-1 sequence fused directly to the GAPDH promoter and terminator sequences. The expression cassette containing GAPDH promoter-env-1-GAPDH terminator was excised by digestion of pPGAP/FGenv with BamHI and gel purification of the fragment. The expression cassette was cloned into BamHI-digested pCl/1 (see Section 4.1.2) to yield pCl/1FGenv.

Plasmid pCl/1FGenv was used to transform yeast strain AB110 (Matα, ura 3-52, leu 2-04 or both leu 2-3 and leu 2-112, pep 4-3, his 4-580, cir°; see EPO Pub. No. 620,662 and Section 4.5.2) as described previously. Hinnen et al. (1978) *Proc. Natl. Acad. Sci. USA* 75:1929. Yeast colonies transformed with the expression plasmid were grown in synthetic complete media lacking leucine at a concentration of 2% glucose. Large-scale cultures were grown in YEP medium with 2% glucose as described in Section 4.1.3. Lysates were prepared from yeast cultures as described previously, and were then separated into soluble and insoluble fractions by centrifugation, and analyzed by polyacrylamide gel electrophoresis, see Section 4.1.4. A heavily expressed protein corresponding to env-1 was readily discernible in the insoluble fraction by Coomassie blue staining. This protein also migrated at a molecular weight of approximately 28 kD, as predicted from the DNA sequence.

4.2.2. Env-2

The env-2 polypeptide is similar to the previously described envH (Section 4.1.1) and corresponds to the viral gp120 glycoprotein. Env-2 differs from envH in the 5 amino terminal residues and is under the regulatory control of the GAPDH promoter as described for the expression of env-1. Env-2 is a polypeptide having the amino acid sequence of gp120env residues 26510.

4.2.2.1. Construction of pAB24-GAP-env2

Figure 28:
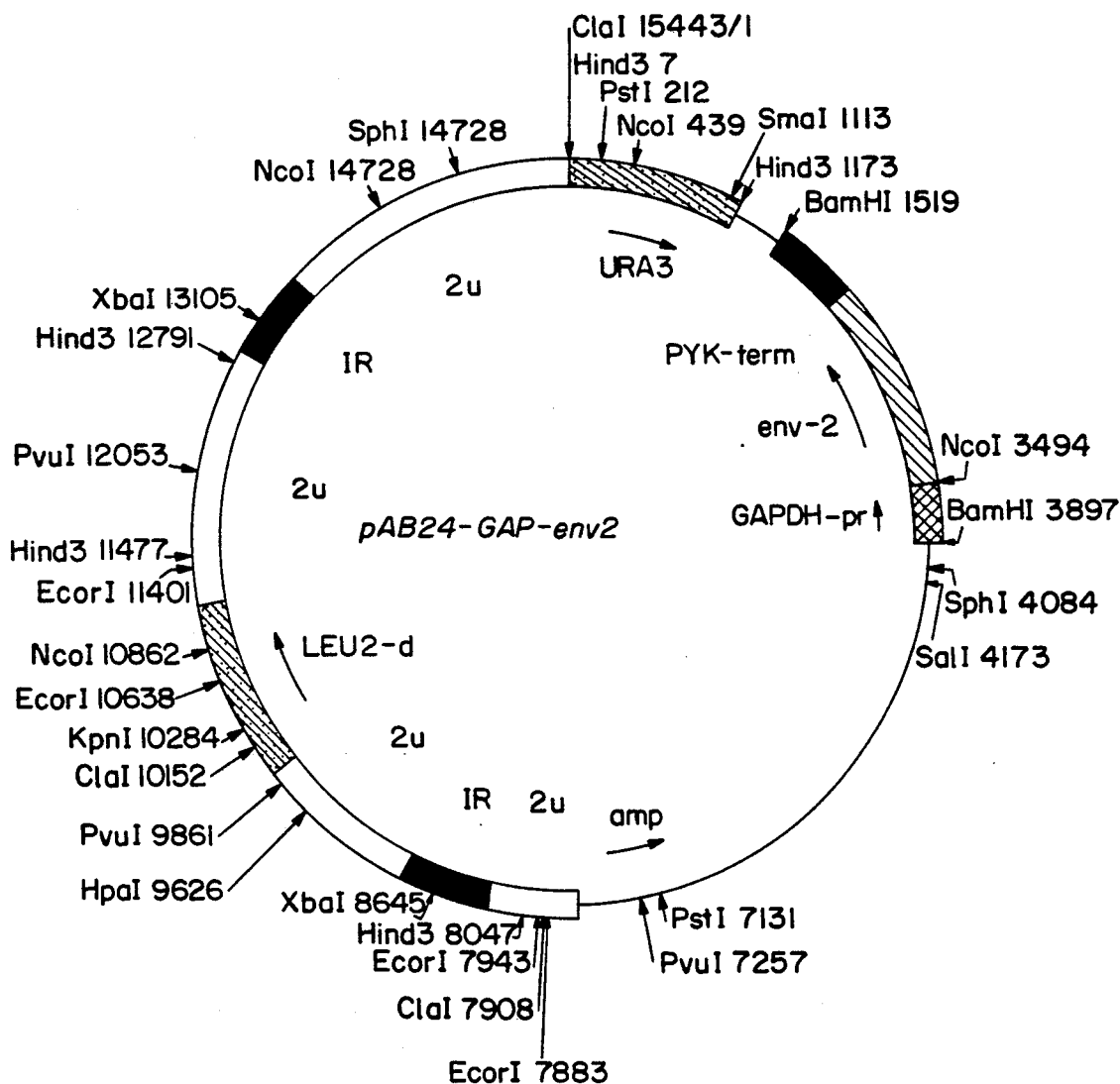
FIG. 28 is a restriction map for yeast expression vector pAB-GAP-env2.

Plasmid pAB24-GAP-env2 (FIG. 28) contains an "expression cassette" for the env gene cloned into the BamHI site of the yeast shuttle vector pAB24 (below). Expression of the env gene is under regulatory control of the GAPDH promoter and the PYK terminator. Construction of pAB24-GAP-env2 was accomplished by ligating (i) an approximately 952 bp BamHI-StuI fragment from plasmid pCl/1-FGenv (Section 4.2.1) which contains the GAPDH promoter and the envelope sequences coding for amino acids 26-267, and (ii) an approximately 1474 bp StuI-BamHI fragment from plasmid pDPC302 (which is similar to pDPC303 in Section 4.1.1. except that it extends 57 nucleotides in the 3' direction of the envelope coding region), which codes for env amino acids 267-510 and the PYK terminator, into plasmid pAB24 which had been previously digested with BamHI and treated with alkaline phosphatase. The direction of transcription in the "expression cassette" is in the opposite direction of the tetracycline gene of the pBR322 sequences.

Figure 27:
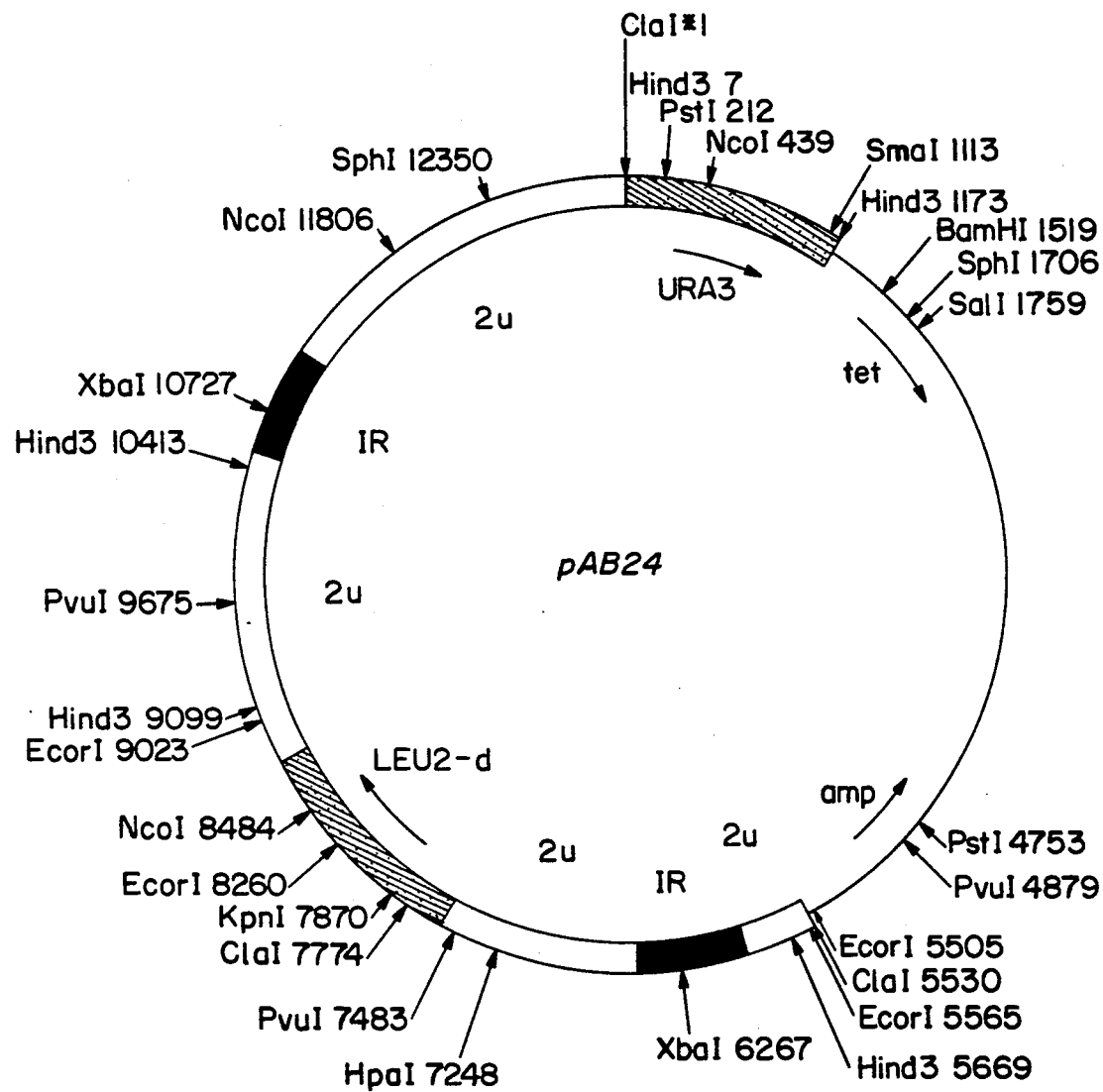
FIG. 27 is a restriction map for yeast shuttle vector pAB24.

Plasmid pAB24 (FIG. 27) is a yeast shuttle vector which contains the complete 2μ sequence [Broach, in: *Molecular Biology of the Yeast Saccharomyces*, Vol. 1, p. 445, Cold Spring Harbor Press (1981)] and pBR322 sequences. It also contains the yeast URA3 gene derived from plasmid YEp24 [Botstein et al. (1979) *Gene* 8:17] and the yeast LEU$^{2d}$ gene derived from plasmid pCl/1. EPO Pub. No. 116,201. Plasmid pAB24 was constructed by digesting YEp24 with EcoRI and religating the vector to remove the partial 2μ sequences. The resulting plasmid, YEp24ΔRI, was linearized by digestion with ClaI and ligated with the complete 2μ plasmid which had been linearized with ClaI. The resulting plasmid, pCBou, was then digested with XbaI and the 8605 bp vector fragment was gel isolated. This isolated XbaI fragment was ligated with a 4460 bp XbaI fragment containing the LEU$^2$d gene isolated from pCl/1; the orientation of the LEU$^2$d gene is in the same direction as the URA3 gene. Insertion of the expression cassette was in the unique BamHI site of the pBR322 sequences, this interrupting the gene for bacterial resistance to tetracycline.

4.2.2.2. Transformation and expression

Yeast cells *S. cerevisiae* 2150-2-3 (Mat a, ade 1, leu 2-04, cir°) were transformed as described by Hinnen et al. [(1978) Proc. Natl. Acad. Sci. USA 75:1929-1933] and plated onto leu-selective plates. Single colonies were inoculated into leu-selective media and grown to saturation. The culture was further inoculated into YEP 2% glucose media. Cells were harvested and the env-2 protein was purified and characterized as described below.

4.2.2.3. Purification of env-2 protein

Frozen *S. cerevisiae* 2150-2-3 (pAB24-GAP-env2) were thawed and suspended in 1 volume of lysis buffer (1 μg/ml pepstatin, 0.001M PMSF, 0.001M EDTA, 0.15M NaCl, 0.05M Tris-HCl pH 8.0), and 1 volume of acid-washed glass beads are added. Cells are broken in a non-continuous system using a 300 ml glass unit of Dyno-mill at 3000 rpm for 10-25 min. The jacket is kept cool by a −20° C. ethylene glycol solution. Glass beads are decanted by letting the mixture set for approximately 3 minutes on ice. The cell extract is recovered and centrifuged at 18,000 rpm (39,200×g) for 35 min. The supernatant is discarded and the precipitate (pellet 1) is further treated as indicated below.

Pellet 1 is resuspended in 4 volumes of Tris-HCl buffer (0.01M Tris-HCl, pH 8.0, 0.01M NaCl, 0.001M PMSF, 1 μg/ml pepstatin, 0.001M EDTA, 0.1% SDS) and extracted for 2 h at 4° C. with agitation. The solution is centrifuged at 6,300×g for 15 min. The insoluble fraction (pellet 2) is resuspended in 4 volumes of PBS (per liter: 0.2 g KCl, 0.2 g KH$_2$PO$_4$, 8.0 g NaCl, 2.9 g Na$_2$HPO$_4$.12H$_2$O), 0.1% SDS, 0.001M EDTA, 0.001M PMSF, 1 μg/ml pepstatin, and centrifuged at 6,300×g for 15 min. The pellet (pellet 3) is suspended in 4 volumes of PBS, 0.2% SDS, 0.001M EDTA, 0.001M PMSF, 1 μg/ml pepstatin and is extracted for 12±3 h at 4° C. with agitation on a tube rocker. The solution is centrifuged at 6,300×g for 15 min. The soluble fraction is recovered for further purification as indicated below. (The pellet can be reextracted by resuspending it in 4 volumes of 2.3% SDS, 5% β-mercaptoethanol, and boiling for 5 min. After boiling, the solution is centrifuged at 6,300×g for 15 min. The soluble fraction is recovered for further purification.)

The soluble fraction is concentrated by precipitation with 30% ammonium sulfate at 4° C. The pellet (pellet 4) is resuspended in 2.3% SDS, 5% β-mercaptoethanol, and chromatographed on an ACA 34 (LKB Products) gel filtration column. The column is equilibrated with PBS, 0.1% SDS, at room temperature. Chromatography is developed in the same solution with a flow rate of 0.3±0.1 ml/min. 5±2 ml fractions are collected, pooled and characterized by protein gel electrophoresis, Western analysis, and ELISA. If needed, pooled fractions are concentrated by vacuum dialysis on Spectrapor #2 (MW cutoff 12-14K), or by membrane filtration using an Amicon concentrator using a PM10 membrane.

SDS polyacrylamide gel analysis (12% acrylamide gels) showed that a new 55,000 dalton protein was being synthesized in yeast cells transformed with the env-containing vector. The 55,000 dalton protein is absent from cells transformed with control plasmid (vector without env insert). The identity of env-2 was confirmed by both ELISA and Western analysis using AIDS patient serum. In both assays the 55,000 dalton protein showed immunoreactivity. No reactivity was obtained with serum from a pool of normal individuals.

4.2.2.4. Immunogenicity

To determine the immunogenicity of polypeptides expressed in yeast, purified env-2 (Section 4.2.2.3) was used to immunize rabbits. Rabbits received perilymphnodal injections of 250 μg of purified env-2 polypeptide in complete Freund's adjuvant. Twenty-one days later, the rabbits were boosted with intramuscular injections of 250 μg of env-2 polypeptide in incomplete Freund's adjuvant. Ten days later the animals were bled and then set up on a schedule of boosting, bleeding 10 days later, and rebooting after 21 days. Antibody titers to env-2 polypeptide for the rabbits were measured using ELISA. Antibodies from the rabbits reacted specifically with env glycoproteins in virus (gp120) and in infected cells (gp160). Thus, the polypeptide moiety representing the N-terminal domain of the env region is immunogenic when expressed in a heterologous host species.

4.2.3. Env-3

4.2.3.1. GAP promoter

Env-3, the gp41env equivalent (AA 529-855 of env), was prepared by cutting the env insert of plasmid pUC19ARV7D/7 (Section 4.2.1.1) at the HgaI site (nt7401, FIG. 5) and at the XhoI site 3' to the env termination codon (nt8460, FIG. 5). The resulting env-3 segment was modified by the addition of synthetic adapters. The 5' end was modified by the addition of an NcoI/HgaI adapter which reintroduced the coding sequence to met529 (nt7817, FIG. 5). The linker had the following sequence:

5'-CATGGGCGCCGTTTCTTTGACCTTGACC-3'
3'-CCGCGGCAAAGAAACTGGAACTGGCATGT-5'

A second synthetic XhoI/SalI adapter molecule was prepared and ligated to the XhoI end of env-3, the adapter having the following sequence:

5'-TCGACCTCGAGG-3'
3'-GGAGCTCCAGCT-5'

The HgaI/XhoI fragment was cloned together with the above linkers into NcoI/SalI-digested pPGAP/FGenv (Section 4.2.1.1), and the resulting plasmid, pPGAP/HXenv, was digested with BamHI. The BamHI expression cassette was cloned into pC1/ 1. The resulting expression vector pCl/1GAP/HXenv was expressed as described above after transformation of yeast strain AB110 (Section 4.2.1). Extreme toxicity, as evidenced by slow growth of cells, was observed when this gene was expressed constitutively in yeast under control of the GAPDH promoter.

4.2.3.2. ADH-2/GAPDH promoter

In order to express env-3 under the control of the glucose-regulable ADH-2/GAPDH (or ADH-2/GAP) promoter, the Nco-I/BamHI fragment containing the env-3 coding region and the GAPDH terminator was excised from pPGAP/HXenv. This was cloned together with the ADH-2/GAPDH promoter as a BamHI/Nco-I fragment (from pJS103) into BamHI-digested and phosphatized pC1/ 1. The resulting expression vector, pCl/1ADH-2/GAP/HXenv, was expressed as described below after transformation of yeast strain AB110.

Plasmid pJS103, which contains the hybrid ADH-2/GAPDH promoter employed above, was constructed as follows. The ADH-2 portion of the promoter was constructed by cutting a plasmid containing the wild-type ADH2 gene from plasmid pADR2 [Beier et al. (1982) Nature 300:724-728] with restriction enzyme EcoR5, which cuts at position +66 relative to the ATG start codon, as well as in two other sites in pADR2, outside of the ADH2 region. The resulting mixture of a vector fragment and two smaller fragments was resected with Bal31 exonuclease to remove about 300 bp. Synthetic XhoI linkers were ligated onto the Bal31-treated DNA. The resulting DNA linker vector fragment (about 5 kb) was separated from the linkers by column chromatography, cut with restriction enzyme XhoI, religated, and used to transform E. coli to ampicillin resistance. The positions of the XhoI linker were determined by DNA sequencing. One plasmid which contained an XhoI linker within the 5' nontranscribed region of the ADH2 gene (position −232 from ATG) was cut with the restriction enzyme XhoI, treated with nuclease S1, and subsequently treated with the restriction enzyme EcoRI to create a linear vector molecule having 1 blunt end at the site of the XhoI linker and an EcoRI end. The GAP portion of the promoter was constructed by cutting plasmid pPGAP with the enzymes BamHI and EcoRI, followed by the isolation of the 0.4 Kbp DNA fragment. This purified fragment was then completely digested with the enzyme AluI and an approximately 200 bp fragment was isolated. This GAP promoter fragment was ligated to the ADH-2 fragment present on the linear vector described above to give plasmid pJS103.

S. cerevisiae AB110 was transformed with the ADH-2/GAPDH constructions, and the cultures grown initially in synthetic complete media lacking leucine with 8% glucose. Env-3 was induced by diluting the culture 1:25 into YEP with 1% glucose and allowing growth at 30° C. for 24 hours. Normal cell growth was observed; however, complex expression products were observed. In an immunoblot assay with AIDS sera, the protein appeared as a multiplet of immunoreactive bands, including a major band at about 37 kD and five additional bands of increasing molecular weight. As demonstrated by treatment with endoglycosidase-H prior to gel and immunoblot analysis, these additional bands were due to glycosylation. Inspection of the gp41 DNA sequence shows five potential N-linked carbohydrate addition sites. Since env-3 encodes a polypeptide with a calculated molecular weight of 40.5 kD, the gel mobility of env-3 at around 37 kD may indicate either aberrant electrophoresis properties, or C-terminal processing analogous to that proposed for infected T-cell-derived gp41.

4.2.4. Env-4

The env-4 region approximates the carboxy-terminal half of the gp120 glycoprotein from the envelope gene and corresponds to amino acids Glu-272 to Arg-509 (FIG. 5). Env-4 also contains a methionine at the N-terminus which serves as an initiation codon for the yeast expression system.

Expression of the env-4 protein was initially attempted as a direct expression product in yeast which failed to provide any detectable product. Successful expression of the env-4 protein was achieved as an SOD fusion product in yeast.

4.2.4.1. pBS24/SF2env4/GAP

The 3' end of the env-4 coding sequence was modified by M13 mutagenesis to generate 2 stop codons in frame after Arg-509, and by adding restriction sites for HindIII and SalI. Plasmid pSV-7c/env (Section 2.1.2) was digested with HindIII and XhoI and an approximate 2830 bp fragment was gel isolated The fragment was cloned into M13-mp19 and single stranded template was generated. M13 mutagenesis was performed using the following primer:

5'-GAACATAGCTGTCGACAAGCTTCATCATCTTTTTTTCT-3'.

A single plaque designated M13Fenv3-447 was isolated and confirmed by M13 sequencing to contain the inserted stop codons and new restriction sites for HindIII and SalI. M13 replicative-form DNA was prepared for M13Fenv3-447 by standard methods, and an approximately 713 bp BglII (position 6604, FIG. 5) to SalI fragment was excised and gel purified. This fragment was ligated to the following NcoI-BglII linker, which codes for a methionine initiation codon and the first four amino acids of the env-4 protein:

Met Glu Val Val Ile Arg
5'-CATGGAGGTAGTAATTA-3'
     CTCCATCATTAATCTAG and then cloned into pPGAP1 [EPO Pub. No. 164,556] which was previously digested with NcoI and SalI and gel isolated. The approximate 1130 bp BamHI-SalI fragment containing the GAPDH promoter and the env-4 gene was excised and cloned into pBS24 (below), which was previously digested with BamHI and SalI and gel isolated, to give plasmid pBS24/SF2env4-/GAP.

Plasmid pBS24/SF2env4/GAp was transformed into S. cerevisiae strains 2150-2-3 and AB110 as described previously. Cultures from single colonies were grown and analyzed for expression by SDS polyacrylamide gel electrophoresis. No env-4 protein was detected by either Coomassie stained gels or western blot analysis.

4.2.4.2. pBS24

Plasmid pBS24 is a derivative of pAB24 as described in Section 4.2.2.1. Plasmid pAB24 was digested with BamHI and SalI (which cut within the tetracycline gene of the pBR322 sequences) and gel purified. The vector was then ligated with a synthetic adapter of the following sequence which created new unique BglII and BamHI sites:

BglII                            BamHI
5'-GATCAGATCTAAATTTCCCGGATCC-3'
       TCTAGATTTAAAGGGCCTAGGAGCT
  (BamHI)                         (SalI)

The resulting vector, pAB24ΔBL was then digested with BamHI and BglII and gel purified. The linearized vector was ligated with the BamHI cassette excised and purified from pSOD/env-5b (Section 4.2.5) to give pBS24. The cassette contains the hybrid ADH-2/GAPDH promoter and α-factor terminator with an NcoI-SalI insert of the SOD/env-5b fusion gene. The cassette is oriented in pBS24 such that the direction of transcription from the ADH-2/GAPDH promoter is in the opposite direction to that of the inactivated tetracycline gene of the pBR322 sequences.

4.2.4.3. pBS24/SOD-SF2env4

Since there was no detectable expression of env-4 from the direct expression system, an SOD/env-4 fusion gene was constructed. Plasmid pBS24/SF2env4/GAP was digested with NcoI and SalI and the approximate 713 bp env-4 gene was gel isolated. The env-4 gene was ligated into pSODCF-2 (Section 3.5) which was previously digested with NcoI and SalI and gel purified, to give pCF2-SODenv4. Plasmid pSODCF2 is a bacterial expression vector which allows for the C-terminal fusions of heterologous genes with the human SOD gene and is under the control of the tacI promoter. When plasmid pCF2-SODenv4 was transformed into E. coli strains D1210 and RR1ΔM15 and analyzed for expression as described previously (Sections 3.4.4 and 3.6), no expression of SOD/env-4 fusion protein was detected. Plasmid pCF2-SODenv4 was digested with StuI and SalI to isolate the 3' half of the SOD gene fused with the env-4 gene. This fragment was ligated to pSI8 which had been previously digested with StuI and SalI and gel isolated to give plasmid pSI8-SODenv4. Plasmid pSI8 (Section 4.2.5) contains the hybrid ADH-2/GAPDH promoter and the α-factor terminator sequences flanking the SOD-insulin fusion gene. The resulting plasmid pSI8-SOD/env-4 was digested with BamHI and SalI to excise a fragment containing the ADH-2/GAPDH promoter and SOD/env-4 fusion gene. This fragment was gel isolated and cloned into pBS24 which had been previously digested with BamHI and SalI and gel isolated to give pBS24/SOD-SF2env4 (FIG. 26).

4.2.4.4. Transformation and Expression.

The plasmid pBS24/SOD-SF2env4 was transformed into yeast cells S. cerevisiae 2150-2-3 and S. cerevisiae AB116 (mat a, leu 2, trp 1, ura 3-58, pro 1-1122 (prot. B), pep 4-3 (prot. A), pre 1-407 (prot. C), cir°) as described previously [Hinnen et al. (1978) Proc. Natl. Acad. Sci.

USA 75:1929-1933] and plated onto Leu⁻ sorbitol plates. Strain AB116 was isolated by curing *S. cerevisiae* strain BJ2168 of its 2 micron plasmid by standard methods. BJ2168 is available from the Yeast Genetic Stock Center, Department of Biophysics and Medical Physics, University of California, Berkeley 94720.

Cultures were grown as follows: a loopfull of cells from the individual colonies were inoculated into 3 ml of Leu⁻, 8% glucose media and incubated in an air shaker at 30° C. for 16-18 h. The 3 ml culture was transferred to 40 ml of fresh Leu⁻, 8% glucose media and incubated in an air shaker at 30° for 24 h. The 40 ml culture was transferred to 1 liter of YEP, 1% glucose media (or YEP, 2.5% Ethanol media for 2150-2-3 cells) and incubated in an air shaker at 30° for an additional 48 h. The cells were harvested by centrifugation and stored at −20 °C.

Expression of the SOD/env-4 fusion protein was analyzed by both polyacrylamide gel electrophoresis and western blot. Cells are disrupted by glass bead lysis method in 0.1M NaPo₄ (pH 7.4), 0.1% Triton lysis buffer. After lysis the soluble and insoluble fractions are separated by centrifugation. The insoluble pellet is solubilized in Laemmli gel loading buffer and run on a 12.5% acrylamide SDS gel. Laemmli (1970) *Nature* 227:680. A band migrating at approximately 44 Kd molecular weight (expected size of SOD/env-4 fusion protein) was observed. This same band also reacted on a western blot with AIDS positive human sera but not with control sera. Expression levels of SOD/env-4 fusion protein were approximately equal for the two different strains. Protein purification was carried out essentially as described in Section 4.2.2.3. for env-2.

4.2.5. ySOD/env-5b fusion protein

The region of the envelope gene corresponding to amino acids alanine-557 through tryptophan-677 is termed env-5b as described in Section 3.6 and is also expressed as a stable fusion protein with hSOD in yeast. A StuI-SalI fragment containing most of the SOD gene fused to the env-5b gene was removed from pSOD-/env5b (Section 3.6) and cloned into pSI8 which had been previously digested with StuI and SalI and gel isolated to give pSI8/SOD-env5b. Plasmid pSI8 (described below) contains the ADH-2/GAPDH hybrid promoter and α-factor terminator sequences flanking the SOD-insulin fusion gene. The resulting plasmid, designated pSI8/SOD-env5b, was digested with BamHI and the fragment containing the promoter-ySODenv-5b fusion-terminator was isolated and cloned into the BamHI cut and phosphatased pAB24 to give pYSOD/env-5b, which was used to transform the yeast strain 2150, as described above. Expression of the ySOD/env-5b fusion protein was induced by diluting a starter culture into YEP containing 1% ethanol.

Lysates were isolated and prepared as described above. A heavily expressed protein corresponding to the SOD/env-5 fusion was readily discerned in the insoluble fraction by Coomassie blue staining. This protein migrated at a molecular weight of approximately 30.6 kD, as predicted from its DNA sequence. This fusion protein was also subsequently shown to have a high proportion of reactivity to AIDS patients' sera.

Plasmid pSI8 is a derivative pYASI1, the latter being described in commonly owned U.S. patent application Ser. No. 845,737, filed on Mar. 28, 1986 by Cousens et al. and EPO Pub. No. 196,056, the disclosures of which are expressly incorporated herein by reference. Essentially, pSI8 contains: The hybrid ADH-2/GAPDH promoter (as a 1.3 kb Bam-Nco fragment) derived from plasmid pJS104 (described below); an SOD-insulin fusion gene (as a 736 bp Nco-Sal fragment) derived from a derivative of pYSI1 (U.S. Ser. No. 845,737); and the α-factor terminator isolated as a 277 bp SalI-EcoRI fragment in which the EcoRI site has been filled in with Klenow fragment and BamHI linkers ligated to give a SalI-BamHI fragment [Brake et al. (1984) *Proc. Natl. Acad. Sci. USA* 81:4642-4646]; all cloned into a pBR322 derivative in which the segment between EcoRI and SalI is deleted and Bam linkers attached. Plasmid pJS104 is the same as plasmid pJS103 (Section 4.2.3.2), except that the GAPDH fragment of the ADH-2/GAPDH promoter is about 400 bp, as opposed to 200 bp. The construction of pJS104 was the same as pJS103, except that during the preparation of the GAPDH portion of the promoter, the 0.4 Kbp BamdI-EcoRI fragment was partially digested with AluI to create a blunt-end near the BamHI site.

4.2.6. Env 4-5

The env 4-5 polypeptide corresponds to the region of the envelope gene which approximates the C-terminus of gp120 and the N-terminus of gp41, amino acids 272 to 673 (FIG. 5). Plasmid pBS24.1/SOD-SF2env4-5 was used to express the env 4-5 polypeptide as an SOD fusion protein under the regulatory control of the ADH-2/GAPDH promoter in yeast.

4.2.6.1. Construction of pBS24.1/SOD-SF2env4-5

To construct plasmid pBS24.1/SOD-SF2env4-5 a 1.2 kbp BglII-SalI fragment which corresponds to nucleotides 6603-7795 (see FIG. 5) was isolated from pSV7dARV160T-tpa and ligated into pBS24/SOD-SF2env4 (see Section 4.2.4.3.) which had previously been digested with BglII and SalI. Plasmid pSV7dARV160T-tpa is a plasmid which contains the HIV envelope gene to which two stop codons, a HindIII, and SalI site had been introduced at position 7798 by M13 mutagenesis with the following mutagenic primer:

5'-CTTTATATACGTCGACAAGCTTCATCAGCTAAACCAA-3'

4.2.6.2. Transformation and expression

The plasmid pBS24.1/SOD-SF2env 4-5 was transformed into yeast cells *S. cerevisiae* AB116 [mat a, leu 2, trp 1, ura 3-58, pro 1-1122 (prot. B), pep 4-3 (prot A), pre 1-407 (prot. c), cir°] as described previously [Hinnen, et al. (1978) *Proc. Natl. Acad. Sci. USA* 75:1929-1933] and plated on Leu⁻ sorbitol plates. The cultures were grown and expression analyzed as previously described in Section 4.2.4.4. Expression levels of the SOD/env4-5 fusion protein were approximately 15-20% of the insoluble protein fraction as estimated by Coomassie-blue staining of PAGE-treated samples.

4.2.6.3. Protein purification

Cultures of AB116 (pBS24.1/SOD-SF2env4-5) were grown in 3 ml Leu (−), 8% glucose medium overnight at 30° C. The 3 ml was inoculated into 50 ml Leu⁻, 8% glucose medium for 24 h at 30° C. The 50 ml was then inoculated into 1 liter of YEP, 1% glucose and grown 30-48 h for induction of protein expression. The cells expressing SOD/env 4-5 were harvested and further processed as described for the purification of env-2 (Section 4.2.2.3.).

4.3. p31pol

4.3.1. GAP/ADH2 promoter

The ARV248NL fragment (Section 3.4.2.3) was cloned into pBS100 previously cut with NcoI and SalI. pBS100 (below) is a bacterial vector derived from pAB12 with a BamHI cassette consisting of the GAP-ADH2 promoter (i.e., the ADH-2/GAPDH promoter), an ARV-env gene as an NcoI-SalI fragment, and the GAP terminator. The BamHI cassette from a positive clone of pBS100/p31/GAP-ADH2 was cloned into pAB24 (Section 4.2.2.1), a yeast vector with both ura and leu selection capabilities. Both orientations of the cassette in this vector were screened for and used to transform the yeast strain AB110 (Mat a, ura 3-52. leu 2-04, or both leu 2-3 and leu 2-112. pep 4-3, his 4-580, cir°). These cells were plated in both ura⁻ and leu⁻ plates. Also, ura⁻ cells were plated onto leu⁻ plates.

Three different induction procedures were done: (1). Ura⁻ colonies patched on ura⁻ plates were induced for 24 h ih YEP/1% glucose. Both a Western and a polyacrylamide gel were run on these samples. Both results were negative. (2). Colonies from ura⁻ plates patched on leu⁻ plates were induced in either leu⁻/3% ethanol or YEP/1% glucose for 24 h. A Western and a polyacrylamide gel were run on these samples and the results were also negative. (3). Colonies from leu⁻ plates patched on leu⁻ plates were induced in either leu⁻/3% ethanol or YEP/1% glucose for 24 h. The polyacrylamide gel showed a negative result. No Western was run on these samples.

Plasmid pBS100 is a yeast expression cassette vector cloned into a pBR322 derivative, pAB12. The expression cassette contains the hybrid ADH-2/GAPDH promoter and the GAPDH terminator flanking a gene segment from the envelope gene. The ADH-2/GAPDH promoter is a 1200 bp BamHI-NcoI fragment isolated from pJS103 (Section 4.2.3.2) and the GAPDH terminator is a 900 bp SalI-BamHI fragment isolated from plasmid pPGAP1 (Section 4.2.1.1). Plasmid pBS100 also contains a non-essential fragment between the NcoI and SalI sites which is replaced by gene fragments of interest. The expression cassette can be removed from pBS100 by digestion with BamHI and cloned into yeast shuttle vectors for introduction into yeast cells.

Plasmid pAB12 is a pBR322 derivative lacking the region between the single HindIII and SalI sites and containing a BamHI linker inserted between the unique EcoRI site. This vector was constructed by digesting pBR322 to completion with HindIII and SalI, followed by limited digestion with Bal31 nuclease, repair of the ends so created with the Klenow fragment of *E. coli* DNA polymerase I, and blunt-end ligation with T4 DNA ligase to reform closed covalent circles. The plasmid was then opened up with EcoRI, treated with the Klenow fragment of *E. coli* DNA polymerase I (to fill-in the 5' overhangs), blunt-end ligated with BamHI linkers, digested with BamHI to remove excess linkers, and then ligated to form closed circles.

4.3.2. GAP promoter

The pBS100/p31/GAP-ADH2 plasmid was cut with BamHI and NcoI and the fragment containing the p31 gene (NcoI-SalI) and the GAP terminator (SalI-BamHI) was gel purified. pC1/1-alpha 1 antitrypsin/GAP was also cut with NcoI and SalI and the fragment including the GAP promoter (NcoI-BamHI) and a portion of pC1/1 (BamHI-SalI) was gel isolated as well. Both fragments were ligated with the yeast vector pC1/1 previously cut with BamHI and SalI. The BamHI cassette can only be cloned in a single orientation in this case. The resulting DNA was used to transform yeast strains AB110 and PO17 (Mat a, leu 2-04, cir°) and the cells were plated on leu⁻ plates. The transformation using strain PO17 gave no transformants.

Colonies from leu⁻ plates were grown in 3 ml of leu⁻/2% glucose for 24 h. Yeast was analyzed on polyacrylamide gels stained by Coomassie Blue with negative results. No Western was run on these samples.

4.3.3. SOD-c31 fusion protein

Figure 23:
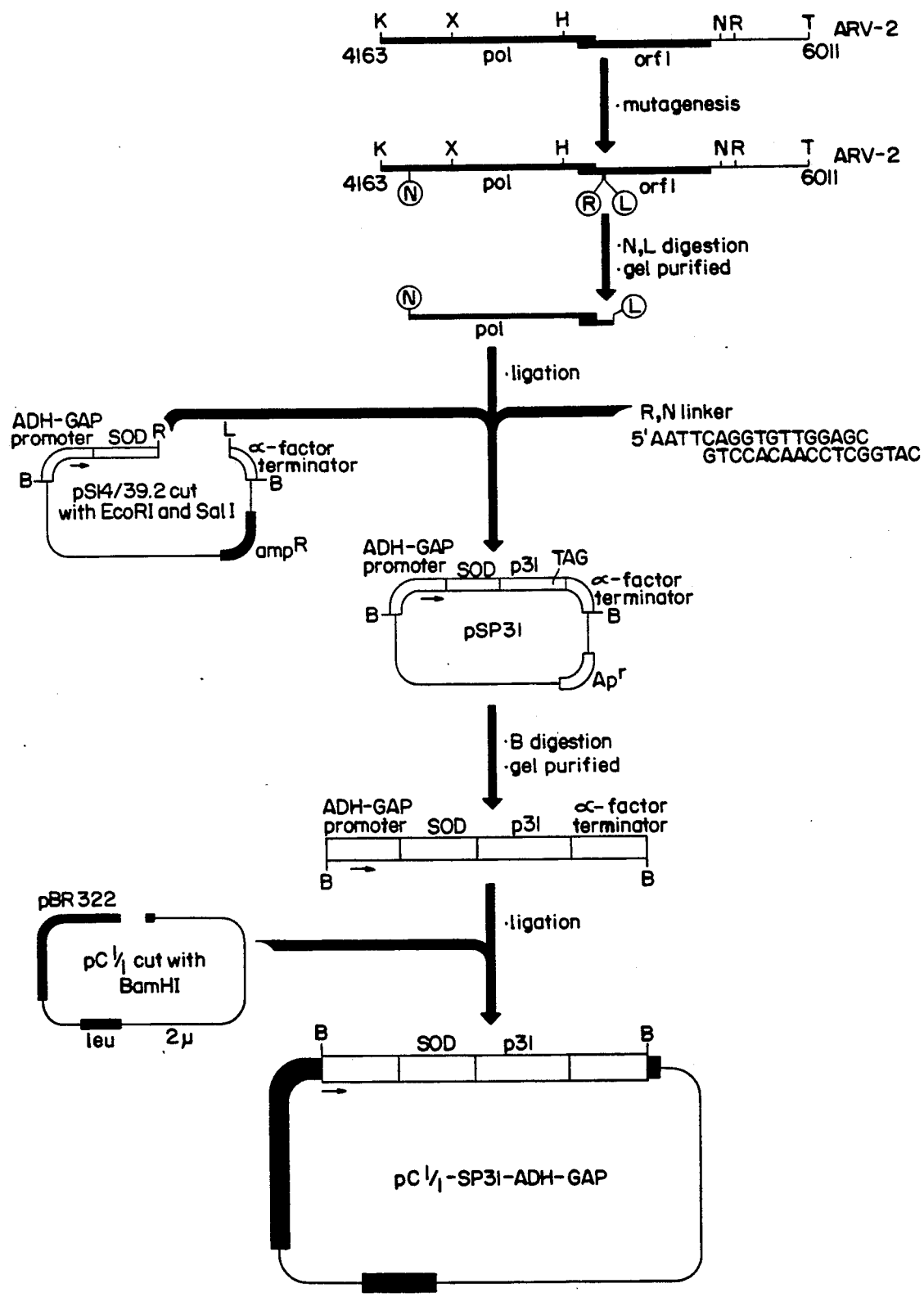
FIG. 23 is a flow diagram showing the construction of pC1/ 1-pSP31-ADH-GAP (pC1/ 1-pSP31-GAP-ADH2), a yeast expression vector for a SOD/p31pol fusion protein.
Figure 25:
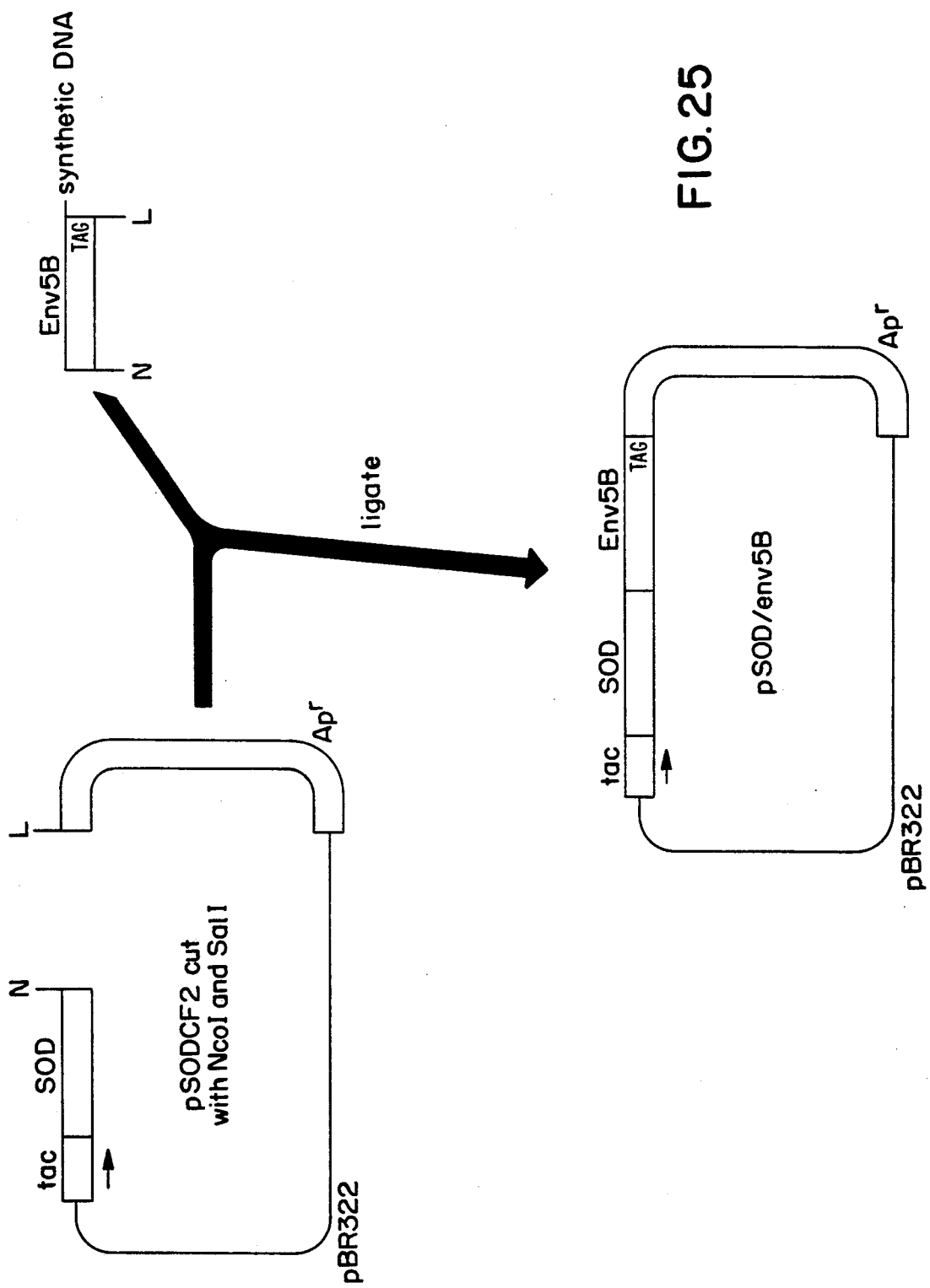
FIG. 25 is a flow diagram showing the construction of pSOD/env5b from pSODCF2 and a synthetic env-5b sequence.

The construction of the p31pol expression vector is shown schematically in FIG. 23. The DNA and amino acid sequences of the SOD/p31 insert are shown in FIG. 24.

4.3.3.1. pC1/1-pSP31-GAP-ADH2

For the construction of a gene for a fused protein SOD-p31 to be expressed in yeast, plasmid pSI4/392 was used. This plasmid contains the SOD gene fused to the proinsulin gene under the regulation of the ADH-2/GAP promoter. The proinsulin gene is located between EcoRI and SalI restriction sites. To substitute the proinsulin gene with the ARV248NL (Section 3.4.2.3) fragment, two oligomers designated ARV-300 and ARV-301, respectively, were synthesized using phosphoramidite chemistry. The sequences generate cohesive ends for EcoRI and NcoI on each side of the molecule when the two oligomers are annealed. ARV-300 and ARV-301 have the sequences:

```
ARV-300  5'AATTCAGGTGTTGGAGC
              GTCCACAACCTCGGTAC 5'  ARV-301
```

Two micrograms of pSI4/39-2 linearized with EcoRI were ligated to 100 picomoles each of phosphorylated ARV-300 and dephosphorylated ARV-301 in the presence of ATP and T4 DNA ligase in a final volume of 35 μ. The reaction was carried out at 14° C. for 18 h. The DNA was further digested with SalI and the fragments were resolved on a 1% low melting point agarose gel and a fragment containing the vector plus the SOD gene (~6.5 kb) was purified as described above and resuspended in 50 μl of TE. Five μl of this preparation were ligated to 5 μl of ARV248NL in 20 μl final volume for 18 h at 14° C. and 5 μl used to transform competent HB101 cells. The resultant plasmid was called pSP31. Twenty μg of this plasmid were digested with BamHI and a fragment of about 2900 bp was isolated by gel electrophoresis, resuspended in TE and ligated to pC1/1 previously cut with BamHI. This DNA (the pC1/1-pSP31-GAP-ADH2 derivative) was used to transform HB101 and transformants with the BamHI cassette were obtained.

4.3.3.2. Transformation and expression

Yeast strains 2150, PO17, and AB110 were transformed with the pC1/1-pSP31-GAP-ADH2 derivative, both short and long orientations. The strain 2150 gave no transformants. All other transformants were patched on leu⁻ plates.

Yeast strain PO17 (Mat a, leu 2-04, cir°) was obtained by isolating a spontaneous revertant strain 21502-3 (Mat a, ade 1, leu 2-04, cir°). To isolate the revertant PO17, 2150-2-3 yeast cells were grown in YEPD, washed in medium without adenine and about $6 \times 10^8$ cells were plated onto six adenine minus (ade⁻) plates. Four candidate revertants were tested for other genetic markers by steaking on plates without uracyl (ura⁻), plates with no leucine (leu⁻), and minimal plates plus leucine. Growth was observed on ura⁻ and minimal plus leu plates; no growth was observed on leu− plates. Revertants were crossed with strain AB103.1 (Mat a, pep 4-3, leu 2-3, leu 2-112, ura 3.52, his 4-580) to determine if the reversion was due to extragenic suppression. Based on tetrad analysis, none of the four independent ade+ revertants were due to extragenic suppression. Based on good growth and high spore viability, one of the revertants was selected and named PO17.

Three different kinds of inductions were tried: (1). PO17 colonies were induced in either a 10 ml culture of YEP/1% glucose or a leu−/3% ethanol culture for 24 h. The yeast pellets were analyzed by both polyacrylamide gels and Westerns and even though the Coomassie-stained gel showed a negative result, the Western did light up a band of the correct molecular weight with both induction methods. (2). PO17 colonies were induced in a 30 ml culture of YEP/1% ethanol for 48 h. Aliquots were analyzed by PAGE at various time points during the induction. The Coomassie-stained gel shows a band in the correct molecular weight range (47–50 kd) that appears after 14 h in YEP/1% ethanol and reaches a maximum intensity at 24 h of induction. The Western result correlates well with the Coomassie-stained gel, showing strong bands at 24 and 48 h. (3). AB110 colonies were induced in either leu−/3% ethanol or YEP/1% glucose for 24 h. PAGE and Westerns were run and the results were negative for the PAGE and positive for the Western, in both induction methods.

Expression and immunoreactivity were characterized as described below.

Cells from one patch PO17 (pC1/ 1-pSP31-GAP-ADH2) were inoculated in 50 ml of leu−/7.1% glucose and grown overnight at 30° C. The saturated culture was inoculated into 500 ml of the same leu−/7 1% glucose medium and incubated overnight at 30° C. The saturated 500 ml culture was used to inoculate a 10 L fermenter with YEPD. Cells were then harvested about five days later.

A sample of cells from the fermenter were analyzed by PAGE electrophoresis to determine expression levels of p31-SOD. In addition, Western analysis using a Trimar serum was performed on the samples to determine its immunoreactivity.

The following procedure was used to prepare samples for PAGE and Westerns:

a. Cells (4 g) were resuspended in 7 ml of lysis buffer (50 mM Tris-HCl, pH 8.0, 1 mM EDTA, 150 mM NaCl, 1 mM PMSF) in a centrifuge tube and 4 ml of yeast-size glass beads were added.

b Cells were vortexed at top speed in a VWR vortex for 10 minutes (1 min. on ice, 1 min. vortexing).

c. The cell lysate was centrifuged at 18,000 rpm (39,000×g) for 10 minutes in a JA 20 rotor. Both insoluble (pellet) and soluble (supernatant) fractions were further analyzed.

d. The supernatant was diluted in sample buffer (¼ dilution), boiled 10 minutes and cooled to room temperature.

e. The pellet obtained in "c" was boiled during 10 minutes in sample buffer (5 ml) and cooled to room temperature. The mixture was centrifuged at 18,000 rmp (39,000×g) for 15 minutes in a JA 20 rotor. The supernatant was recovered and was diluted ¼ in sample buffer.

f. Samples from the supernatant (obtained in "d") and solubilized pellet (obtained in "e") were loaded on a 12% PAGE. A band corresponding to SOD-p31 (between MW 68 and 43 Kd) was present in the insoluble fraction (samples of solubilized pellet).

Immunoreactivity of SOD-p31 band was tested by Western Analysis using serum Trimar 0036 from an AIDS patient. For this purpose, proteins were fractionated on a 12% PAGE as previously described and transferred to nitrocellulose filter paper. The filter paper was then treated with serum 0036, followed by a second goat anti-human antibody conjugated with horseradish peroxidase (HRP). Color was developed using an HRP substrate. Bands corresponding to p31-SOD were present in samples corresponding to the insoluble (Pellet) fractions. Bands of smaller size, present in both soluble and insoluble fractions, also react with the sera and most probably correspond to degradation products of SOD-p31.

4 3.3.3. Purification and characterization

Frozen bacteria (Section 3.5) or yeast cells expressing the p31-SOD fusion protein are thawed at room temperature and suspended in 1.5 volumes of lysis buffer (20 mM Tris-Cl, pH 8.0, 2 mM EDTA, 1 mM PMSF, for bacteria; 50 mM Tris-Cl, pH 8.0, 2 mM EDTA, 1 mM pMSF for yeast), and mixed with 1 volume of acid-washed glass beads.

Cells are broken for 15 min in a non-continuous mode using the glass chamber of a Dynomill unit at 3,000 rpm, connected to a −20° C. cooling unit. Glass beads are decanted for 2-3 min on ice, the cell lysate is removed. The decanted glass beads are washed twice with 30 ml of lysis buffer at 4° C. The cell lysate is centrifuged at 39,000×g for 30 min.

The pellet obtained from the above centrifugation is washed once with lysis buffer, after vortexing and suspending it at 4° C. (same centrifugation as above). The washed pellet is treated with 0.2% SDS (for bacteria) or 0.1% SDS (for yeast) in lysis buffer and agitated by rocking at 4° C. for 10 min. The lysate is centrifuged at 39,000×g for 30 min. The pellet is boiled in sample buffer (67.5 mM Tris-Cl, pH 7.0, 5% B-mercaptoethanol, 2.3% SDS) for 10 min and centrifuged for 10 min at 39,000×g. The supernatant is recovered and further centrifuged at 100,000×g for 60 min (60 Ti rotor). This step is replaced by a 0.45 μm filtration when yeast is used. The supernatant from the above centrifugation is loaded (maximum 50 mg of protein) on a gel filtration column (2.5×90 cm, ACA 34 LKB) with a flow rate of 0.3–0.4 ml/min, equilibrated with phosphate-buffered saline (PBS), 0.1% SDS. The fractions containing SOD-p31 are pooled and concentrated either by vacuum dialysis or using a YM5 Amicon membrane at 40 psi. The protein is stored at −20° C. as concentrated solution.

Gel electrophoresis analysis shows that the SOD-p31 protein migrates having a molecular weight of about 46 kd and is over 90% pure.

4.4. Reverse transcriptase (RT)

The AIDS retroviral reverse transcriptase (RT) is an RNA-dependent DNA polymerase found in virions in low quantities. RT is encoded within a domain of the viral pol gene. The mature enzyme is derived by proteolytic processing from a large polypeptide precursor whose cleavage is thought to be mediated by a viral protease.

The amino terminal sequence of HIV RT has been reported [Veronese et al. (1986) *Science* 231:1289–1291] and corresponds to proline-156 of the polymerase gene (nucleotide 2403, FIG. 5). The carboxy terminal end of the RT gene is estimated to be at valine-691 (nucleotide 3708).

4.4.1. pAB24/RT4 expression vector

A 6.1 kb EcoRI fragment of cloned proviral DNA was cloned into pUC19 at the EcoRI site and designated pUC-ARV8A. plasmid pUC-ARV8A was digested with BalI and KpnI which liberates a 1535 bp fragment containing coding sequence for amino acids proline-180 through tryptophane-690. This fragment was extended, using synthetic oligonucleotides, to include proline-164 at the N-terminus and alanine-693 at the C-terminus. The synthetic DNA also provides a methionine initiation codon.

The RT-encoding fragment was modified by the addition of synthetic oligonucleotide adapters. The 5' synthetic DNA has the following sequence:

```
5'-CATGCCTATCTCTCCAATCGAAACCGTC
3'-GGATAGAGAGGTTAGCTTTGGCAG

CCAGTCAAGCTTAAACCAGGTATGGATGGG
GGTCAGTTCGAATTTGGTCCATACCTACCC

CCCAAGGTCAAGCAGTGG-3'
GGGTTCCAGTTCGTCACC-5'
```

The 3' adaptor was a KpnI/SalI adaptor with an inframe stop codon having the following sequence

```
5'-CAGCATAG-3'
3'-CATGGTCGTATCAGCT-5'
```

The 5' adaptor contains a HindIII site within the initiation codon so that digestion with HindIII and SalI can facilitate subsequent cloning of the RT sequence into additional expression vectors.

Figure 20:
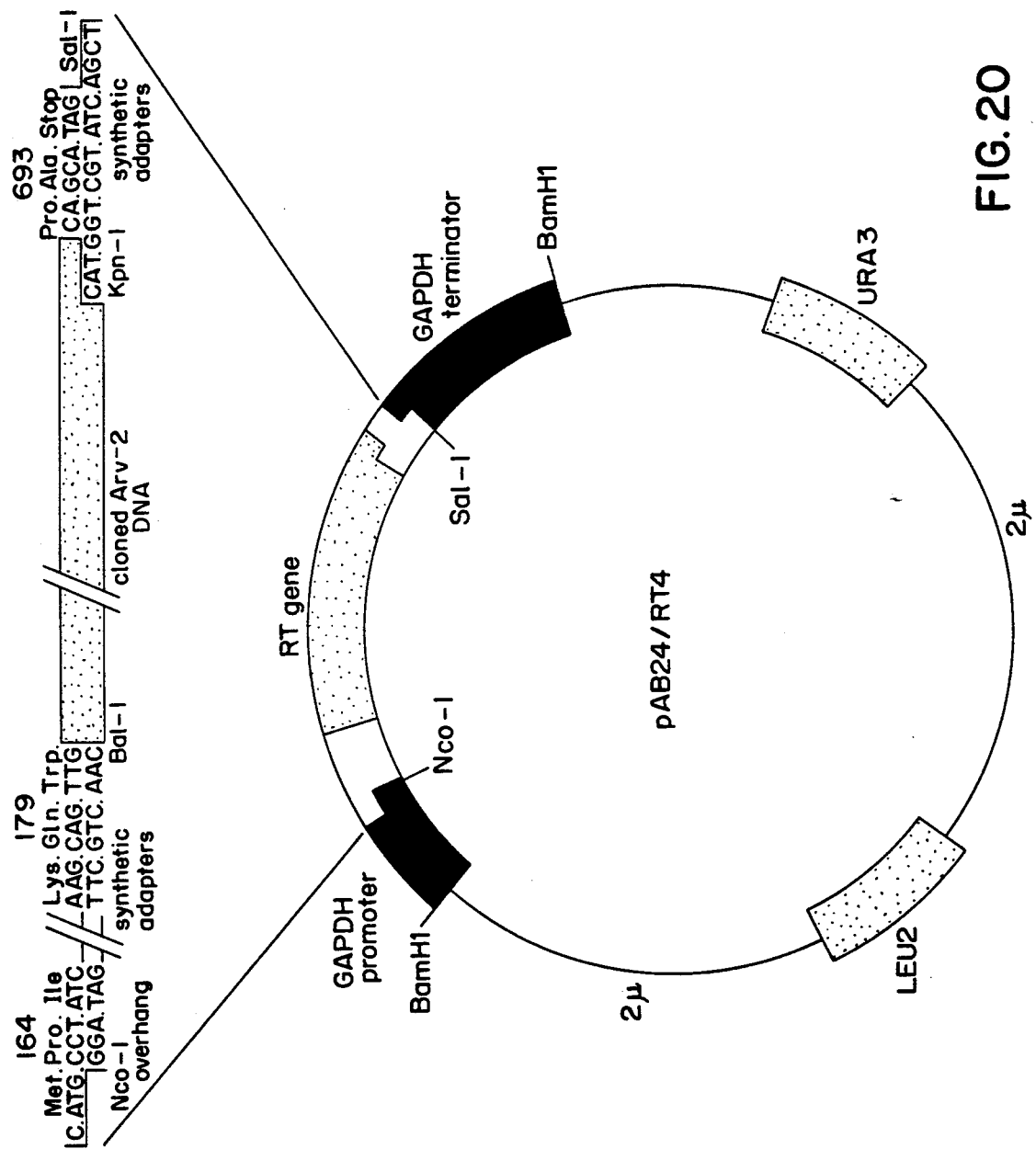
FIG. 20 is a flow diagram showing the procedure for making plasmid pAB24/RT4, an expression vector for HIV reverse transcriptase.

The synthetic linkers and the cloned DNA were ligated by standard techniques into the vector pPGAP1 (Section 4.2.1.1) which had been previously digested with NcoI-SalI and gel isolated. The resulting expression cassette containing the GAPDH promoter, the RT gene, and GAPDH terminator was excised with BamHI and cloned into pAB24 which had been previously digested with BamHI and treated with alkaline phosphatase. The resulting expression plasmid was designated pAB24/RT4 and is shown in FIG. 20.

4.4.2. Transformation and expression

Plasmid pAB24-RT4 was used to transform yeast strain AB110, and leucine prototrophs grown in leucindeficient media to 3ml, followed by growth in YEPD to the 1 l level. Travis et al. (1985) *J. Biol. Chem.* 260:4384–4389.

4.4.3. Purification

Cells from a 1 l culture were pelleted by centrifugation at 2,500 rpm for 10 min. The cell pellet was resuspended in 300 ml of 50 mM Tris-HCl, pH 7.5, 14 mM B-mercaptoethanol, 1.2M sorbitol, and 200 μg/ml Zymolyase. Spheroplast formation, monitored by light microscopy, was allowed to proceed for 90 min at 30° C. After a low speed centrifugation, the pelleted spheroplasts were lysed in 40 ml of a buffer containing 50mM Tris-HCl, pH 7.5, 0.1% Triton X-100, and 1 mM DTT at room temperature The yeast lysate was clarified by centrifugation at 20,000 rpm for 2 hours and the supernatant was fractionated by stepwise NH4SO4 precipitation. Greater than 90% of RT activity was in the 0-30% NH4SO4 insoluble fraction. This NH4SO4 pellet was resuspended in 20 ml of reverse transcriptase buffer (RTB; 50 mM Tris-HCl, pH 7.5, 2 mM B-mercaptoethanol, 0.2 mM EDTA, 0.1% Triton X-100, 20% vol/vol glycerol) containing 50 mM KCl. An Amicon pressure filtration device was used for desalting. The extract was then applied to a cellulose phosphate column (Sigma C-2383) (2.5 cm×30 cm) preequilibrated in RTB containing 50 mM KCl. The column was washed with 100 ml of the same buffer. A linear gradient of 50 to 800 mM KCl in RTB was used for elution. Individual fractions were monitored for RT activity. The peak fractions of RT activity were between 150 and 225 mM KCl. This material (about 15 ml total) was pooled, desalted by Amicon filtration using RTB containing 50 mM KCl, and then applied to a single-stranded DNA cellulose column (Sigma D-8273) (1.0 cm×10cm) preequilibrated in RTB at 50 mM KCl. The column was washed with 30 ml of this buffer and eluted with a linear gradient of RTB from 50 to 800 mM KCl. Fractions were monitored for RT activity and peak fractions were pooled.

4.4.4. Electrophoresis and immunoblotting

Recombinant RT was analyzed by polyacrylamide gel electrophoresis and immunoblotting techniques using AIDS patients' sera. The recombinant protein gave an apparent gel mobility of approximately 66 kD, indicating an extremely close approximation to the native p66 species, and in good agreement with the calculated molecular weight of 62.5 kD. It was also noted that during purification, processing of this 66 KD protein occurred giving a second major species with an estimated molecular weight of 51±1.5 KD. This processing is presumably due to a yeast protease since the region thought to encode ARV protease was not included in this expression construction. Previously, HIV gag-pol fusions expressed in yeast were shown to be processed when this protease region was included. Kramer et al. (1986) *Science* 231:1580–1584. That the p66 and p51 species produced in yeast had identical N-termini (Pro.Ile,Ser.pro.Ile, etc.) was confirmed by gas phase sequence analysis of the purified proteins (15 cycles; as a mixture, Panel A, lane 3). Thus, yeast may mimic the natural maturation processes for HIV RTs, giving rise to both p66 and p51. The sequence analysis also showed that the N-termini methionine derived from the synthetic initiation codon was removed in vivo. Interestingly, the processing observed in yeast may indicate that HIV protease is not necessarily required for this processing event in vivo. Preliminary immunoblot analysis of recombinant RT also indicates a high degree of reactivity with AIDS sera. Of 20 sera tested, 19 scored positive.

4.4.5. RT activity assay

Analysis of recombinant RT activity by enzymatic assay was performed on crude yeast lysates and the purified enzyme. Cruse lysate was prepared as follows. Cells from 25 ml culture were pelleted by centrifugation at 2,500 rpm for 10 min. The cell pellet was resuspended in 7.5 ml of 50 mM Tris-HCl, pH 7.5, 14 mM B-mercaptoethanol, 1.2M sorbitol, and 200 μg/ml Zymolyase. Spheroplast formation, monitored by light microscopy, was allowed to proceed for 90 min at 30° C. After a low speed centrifugation, the pelleted spheroplasts were lysed in 1 ml of a buffer containing 50 mM Tris-HCl, pH 7.5, 0.1% Triton X-100, and 1 mM DTT at room temperature. The yeast lysate was clarified by centrifugation.

Using the assay conditions described for RT isolated from virions [Veronese (1986) *Science* 231:1289–1292], the relative activity of yeast-derived RT was assayed using various primer template combinations. Thus, relative to (dT)~5·(rA)$_n$ (100%), the enzyme activity with (dT)~5·(dA)$_n$ was 4.3%, with (dG)~15·(rC)$_n$ was 71.1%, and with (dG)~15·(rC$^m$)$_n$ was 2.4%. Yeast extracts form cells containing control plasmids gave background levels of incorporation, excluding the possibility of host-encoded RT activity. In all cases, the enzyme reactions were linear for greater than 90 minutes. The results are shown in the following table:

| Time | cpm Incorporated |
|---|---|
| 10′ | 860 |
| 20′ | 2110 |
| 30′ | 2720 |
| 40′ | 4046 |
| 50′ | 3834 |
| 60′ | 5360 |
| 90′ | 8284 |
| 120′ | 10626 |
| 160′ | 11814 |
| 180′ | 11750 |

Kinetics of recombinant reverse transcriptase activity: 6 μl of RT sample incubated at 37° C. with 50 mM Tris-HCl, pH 7-8; 10 mM MgCl$_2$; 10 mM DTT; 0.1M NaCl; 0.1 mM [$^3$H] dTTP and 15 μg of (dT)~15 · (rA)$_n$ in a total volume of 300 μl. 25 μl aliquots were removed at indicated times and trichloroacetic acid precipitated on glass filters, washed, and dried, and their radioactivity was determined with a Beckman scintillation counter.

4.5. p25gag
4.5.1. Host-vector system

Protein p25gag is synthesized by *Saccharomyces cerevisiae* AB110 transformed with plasmid pC1/ 1-p25-ADH-GAP. Plasmid pC1/ 1-p25-ADH-GAP is a yeast expression vector which contains the sequence coding for p25gag Sanchez-Pescador et al. (1985) *Science* 227:484] as well as pBR322 sequences including the ampicillin-resistant (amp$^R$) gene and 2 micron (2μ) sequences [Broach, in *Molecular Biology of the Yeast Saccharomyces*, Vol. 1, p. 445 (Cold Spring Harbor Press, 1981)], including the yeast leucine (leu) 2-04 gene.

Expression of p25 is non-constitutive and it is under regulation of a hybrid ADH-2/GAPDH promoter derived from promoter sequences of the yeast alcohol dehydrogenase gene (ADH2) [Beier et al. (1982) *Nature* 300:724–728] and glyceraldehyde-3-phosphate dehydrogenase (GAPDH) [EPO Pub. No. 120,551] and of the GAPDH terminator. Induction of p25 expression is achieved by low concentration of glucose in the growth medium Yeast strain *S. cerevisiae* AB110 has the following genotype: Mat α, ura3-52, leu2-04, or both leu2-3 and leu2-112, pep4-3, his4-580, cir°. This strain was obtained as described below.

4.5.2. *Saccharomyces cerevisiae* AB110

Yeast strain *S. cerevisiae* 2150-2-3 (available from Lee Hartwell, University of Washington) was crossed with yeast *S. cerevisiae* strain AB103.1 transformant containing pC1/ 1 derivative. The diploids were sporulated and the tetrads dissected. Strains were maintained on leucine selective plates in order to ensure maintenance of the plasmid, since the parents are auxotrophs. A series of colonies were screened for their genotype with respect to a number of markers (Mat α, ura3, leu2, pep4-3).

The strain AB110 has the following genotype: Mat α, ura3-52, leu2-04 or both leu2-3 and leu2-112, pep4-3, his4-580, cir°, and is obtained by curing the above strain AB110 (pC1/ 1 derivative) of its resident plasmid by growth in the presence of leucine (absence of selective pressure) and then selection for leu− colonies by replica plating.

4.5.3. pC1/ 1-p25-ADH-GAP

Plasmid pC1/ 1-p25-ADH-GAP is a yeast expression vector which contains an "expression cassette" (see below) for p25gag cloned into the BamHI site of vector pC1/ 1. Vector pC1/ 1 was previously described (Section 4.1.2).

Figure 21:
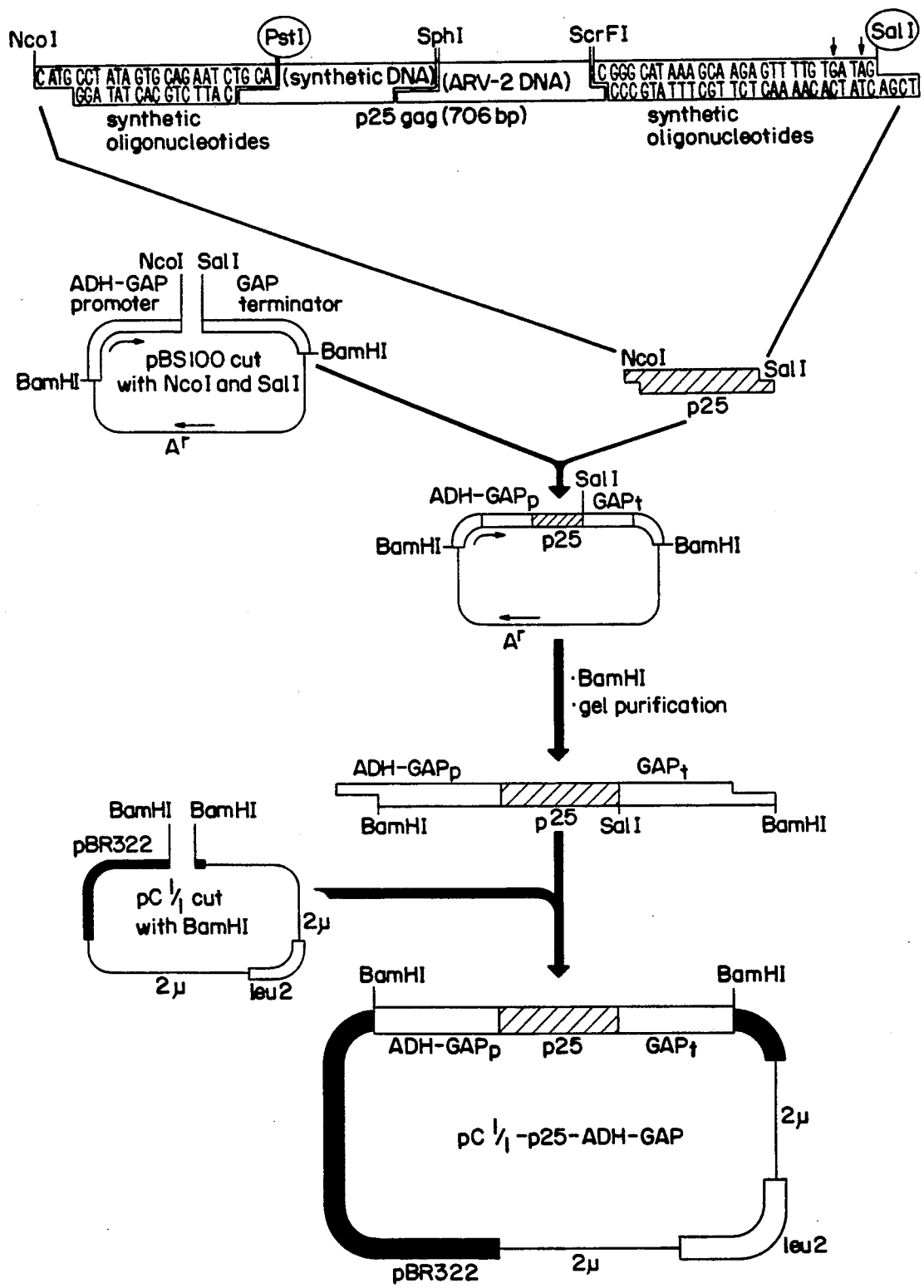
FIG. 21 is a flow diagram showing the construction of pC1/ 1-p25-ADH-GAP, a yeast expression vector for p25gag.

An "expression cassette" for p25gag consists of the following sequences fused together in this order (5' to 3') yeast hybrid ADH-2/GAPDH promoter, a gene for p25gag, and GAPDH terminator. FIG. 21 shows a schematic of the construction of pC1/ 1-p25-ADH-GAP. The fragment shown at the top of the figure, containing p25gag, was constructed from ARV-2 DNA, in which the sequences coding for leu (position 7) to an SphI site at gly (position 90) (see FIG. 22 for amino acid numbers) were repeated by synthetic DNA. A PstI site (encircled in the figure) was inserted at leu (position 7) by replacing the natural CTA with a CTG codon. A natural PstI site at Ala79 was removed by making a silent third position change (dA to dC) in this codon. Two stop codons (indicated by an arrow) and a SalI site (circled) were placed adjacent to the C-terminal leu (position 232) codon by substituting synthetic DNA from the ScrFI site at pro (position 225) to the SalI using synthetic oligonucleotides. An additional methionine codon (indicated with an asterisk) was used as the initiation codon. The PstI-SalI fragment had been previously cloned in the construction of pGAG25-10 (see Section 3.1.2. and FIGS. 7 and 8).

To construct the yeast expression vector, a 682 bp PstI-SalI fragment containing the p25gag gene was isolated from plasmid pGAG25-10 (Section 3.1.2) and ligated with a synthetic NcoI-PstI linker, which has the following sequence:

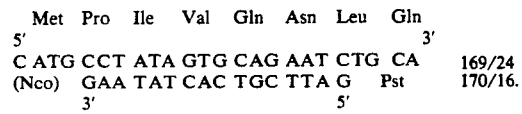

This was cloned into pBS100 (Section 4.3.2) which had been previously digested with NcoI and SalI and gel isolated. The BamHI expression cassette was excised from the resulting plasmid and ligated into BamHI digested and phosphatased treated pC1/ 1 to yield pC1/ 1-p25-ADH-GAP. The p25gag produced in yeast differs from that produced in *E. coli* (Section 3.1.) by the presence of the naturally occurring proline after the methionine at the N-terminus.

FIG. 22 shows the nucleotide sequence of the p25gag insert cloned in pC1/ 1-p25-ADH-GAP and the amino acid sequence derived from it. DNA sequences that are not underlined in the p25 region are derived directly from the ARV-2 proviral DNA Underlined sequences were chemically synthesized by the phosphoramidite method as originally described by Beaucage & Caruthers, (1981) *Tetrahedron Lett.* 22:1859.

4.5.4. Transformation and expression

Yeast cells were transformed following the procedure of Hinnen et al. (1978) *Proc. Natl. Acad. Sci. USA* 75:1929. The transformation mix was plated onto selective leu− agar plates. Plates were incubated at 30° C. for 2 to 4 days.

Single transformant colonies were transferred into leu−, 8% glucose medium and grown at 30° C. until saturation. For induction of expression, a 1/25 dilution of the saturated culture into YEP/1% glucose was made and the cells were grown to saturation. Cells were harvested, lysed with glass beads and the insoluble material was collected by centrifugation. The pellet was resuspended in gel sample buffer and boiled. Extracts were fractionated on standard denaturing acrylamide gels. Laemmli (1970) *Nature* 227:680. Proteins were visualized by staining with Coomassie blue.

The extent of expression was initially determined by appearance of a new protein of the expected molecular weight in extract of transformants harboring pC1/ 1-p25-ADH-GAP as compared with control extracts (cells transformed with vector without p25gag insert). Immunoreactivity of the p25 protein was determined by standard western analysis [Towbin et al. (1979) *Proc. Natl. Acad. Sci. USA* 76:4350] using human serum from an AIDS patient. The western analysis showed immune reaction of a protein of about 25,000 daltons. No reaction was observed with non-immune serum.

For preparation of a master seed stock, transformant cells were streaked onto a leu⁻ plate and incubated at 30° C. for 2 days. Five single colonies were picked and individually inoculated into 5 ml of leu⁻, 8% glucose liquid medium and grown overnight at 30° C. A 1 ml aliquot was used to test expression of p25 and 15% glycerol was added to the rest of each culture. Glycerol cell stocks were aliquoted into 1 ml vials, labeled and quickly frozen in liquid nitrogen. Aliquots of the culture corresponding to the highest expressor were selected as the master seed stock and stored at −70° C. The seed stock was tested for absence of bacterial contamination.

4.5.5. Protein Purification.

Cells from the patch which gives highest expression of p25 were used to inoculate 40-60 ml of leu⁻, 7.1% glucose medium. Cultures were grown to saturation at 25°-35° C. with agitation. An aliquot (10-50 ml) of the first culture were added to 400-600 ml of leu⁻ 7.1% glucose medium. Cultures were grown to saturation at 25°-35° C. with agitation. An aliquot (100-500 ml) of the second inoculum was added to 8-12 L of YEP/1% glucose containing 1 ml of antifoam in a 16 L fermentor. Cultures were grown for 24 to 48 hours at 25°-35° C. with agitation. Following fermentation, the approximately 8-12 L of yeast culture were centrifuged through a continuous flow centrifuge, and the cells were harvested.

Frozen (or refrigerated) packed cells (50-150 g portions) were thawed and suspended in Lysis Buffer (1 mM PMSF, 2 mM EDTA, 150 mM NaCl, 50 mM Tris-HCl, pH 8.0; total volume of cells and Lysis Buffer=280 ml), and 160-170 g of acid-washed glass beads were added. Cells were broken in a non-continuous system using a 300 ml glass unit of a Dyno-mill at 3,000±500 rpm for 10-25 minutes. The exterior jacket temperature of the Dynamill was maintained at −15° to −20° C. by an ethylene glycol solution. Glass beads were allowed to settle by letting the mixture sit on ice. The cell lysate was decanted. Glass beads were washed with Lysis Buffer and the wash was added to the cell lysate. The lysate was centrifuged at 39,000×g (30-70 minutes, depending on rotor) for 30 minutes. The pellet was discarded, and the soluble fraction was further centrifuged at 100,000 ×g for 60 minutes at 2°-8° C. The fatty layer (about ¼ of total volume) was aspirated off. The supernatant was decanted, and the pellet was discarded.

The soluble fraction obtained in the previous step was diluted ten fold by adding 9 volumes of 0.03M Tris-HCl, 1 mM EDTA, pH 9.0. The pH of the diluted soluble fraction was adjusted to 9.0±0.5, then the material was chromatographed at 4°-8° C. on a DEAE Sephacel column equilibrated with 0.03M Tris-HCl, 1 mM EDTA, pH 9.0. Material was eluted using the same buffer; absorbance of the eluate was monitored at 280 nm, and 20-25 ml fractions were collected. Fractions were assayed by SDS-PAGE, and those containing p25 protein were pooled.

The pooled fractions were concentrated to a protein concentration of 20-25 mg/ml by ultrafiltration in an Amicon unit under N₂ pressure. The concentrate was chromatographed on an ACA54 (LKB) column equilibrated with at least 1 column volume of 0.03M TrisHCl, 1 mM EDTA, pH 9.0. Material was eluted using the same buffer; absorbance of the eluate was monitored at 280 nm, and 10-30 ml fractions were collected. Fractions containing p25 protein as determined by SD-PAGE were pooled. The fraction pool was concentrated to approximately 1-2 mg/ml total protein by ultrafiltration in an Amicon unit under N₂ pressure. Protein concentration of the Bulk p25 was adjusted to 1.2-1.8 mg/ml (based on Lowry assay).

4.6. p53gag

The gag proteins from the HIV retrovirus are derived from a gag precursor polypeptide, designated p53gag. By combining HIV DNA derived from pUC-8A, (a subclone containing the insert from λARV-2 (8A) cloned into pUC19) with synthetic oligonucleotides and cloning into a yeast expression vector the complete p53gag precursor protein was synthesized by yeast.

4.6.1. Construction of pC1/ 1-GAP-p53

A 1424 bp SacI-BclII fragment was gel isolated from pUC-8A. This fragment corresponds to nucleotides 225 to 1650 as shown in FIG. 5. The SacI-BglII fragment was further digested with HgaI and then ligated with the following oligonucleotide linker:

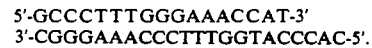

5'-GCCCTTTGGGAAACCAT-3'
3'-CGGGAAACCCTTTGGTACCCAC-5'.

The ligated linker fragment was digested with NcoI and BglII and then cloned into pPGAP-IGF1 which had previously been digested with NcoI and BglII. The NcoI site of the linker functions to regenerate the N-terminal methionine of p53. Plasmid pPGAP-IGF1 is plasmid pPGAP1 as described in Section 4.2.1.1. with a 220 bp NcoI-SalI fragment encoding IGF-I. The IGF-I sequences only serve as a matter of convenience due to the presence of a BglII site 60 bp from the 3' end of the insert. The resulting plasmid, pPGAP-p53/IGF1, was digested with BglII and SalI and ligated with a 201 bp synthetic oligonucleotide fragment which encodes the C-terminus of the p53 protein to give plasmid pPGAP-p53. The 1505 bp NcoI-SalI fragment contains the entire coding region of p53 from amino acid methionine-1 to glutamine-502. Plasmid pPGAP-p53 was digested with BamHI to isolate the expression cassette containing the GAPDH promoter -p53 gene -GAPDH terminator as a 2843 bp BamHI fragment which was then cloned into pC1/ 1 which had previously been digested with BamHI. The resulting plasmid was called pC1/ 1-GAP-p53.

4.6.2. Transformation and expression

Figure 14:
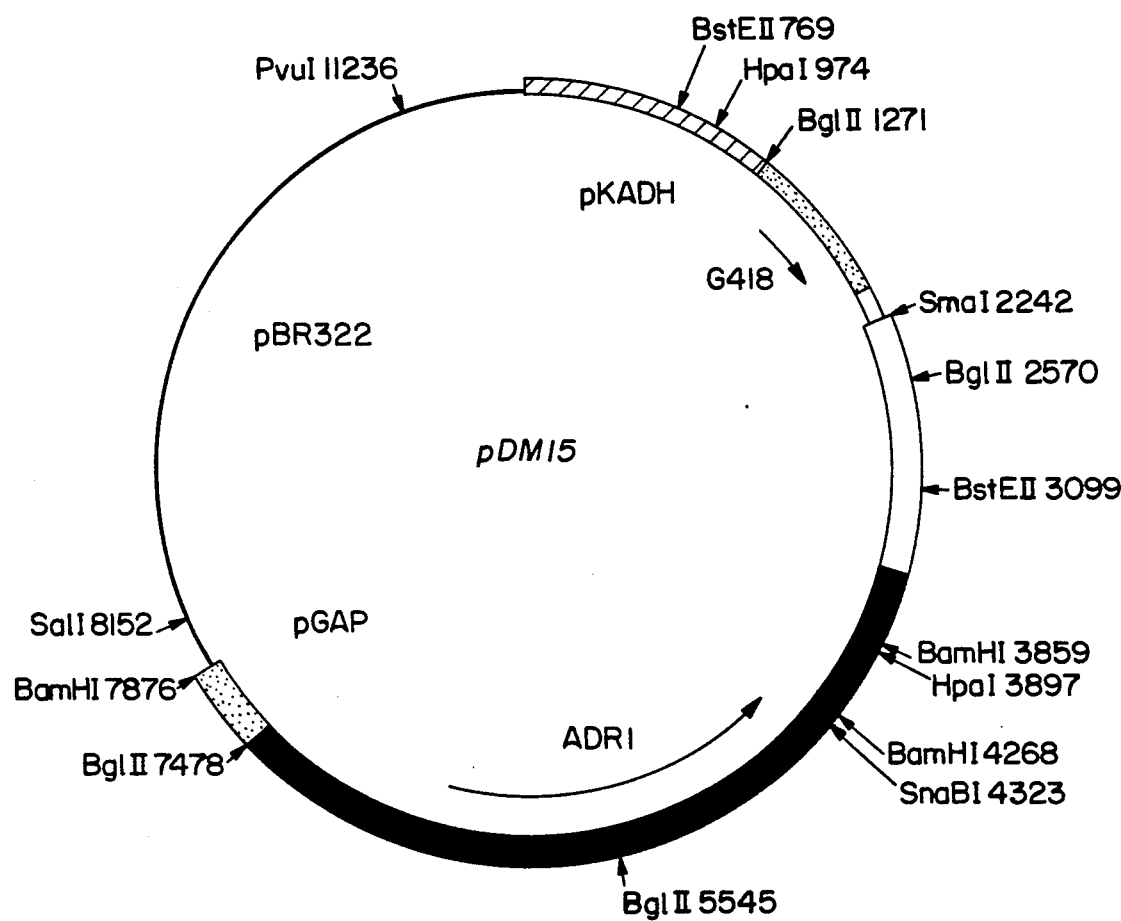
FIG. 14 is a restriction map of plasmid pDM15, which was used to construct S. cerevisiae strain JSC302.

*S. cerevisiae* strain JSC302 was constructed by transforming strain AB116 to G418 resistance with plasmid pDM15 (FIG. 14). Plasmid pDM15 consists of

*Kluyveromyces lactis* ADH1 promoter and terminator sequences flanking the G418 gene, pBR322 sequences, and a GAP promoter-ADR1 expression cassette. This integrating plasmid was targeted to the ADR1 locus.

Plasmid pC1/ 1-GAP-p53 was transformed into yeast strain *S. cerevisiae* JSC302 following the procedure of Hinnen et al.(1978) *Proc. Natl. Acad. Sci. USA* 75:1929. The transformation mix was plated onto selective leu$^-$ agar plates. The plates were incubated at 30° C. for 2 to 4 days. Single transformant colonies were transferred into leu$^-$, 8% glucose medium and grown at 80° C. until saturation. For induction of expression, a 1/25 dilution of the saturated culture into YEP, 1% glucose was made and the cells were grown to saturation. Cells were harvested, lysed with glass beads and the insoluble material was collected by centrifugation. The pellet was resuspended in gel sample buffer and boiled. Extracts were fractionated on standard denaturing polyacrylamide gels. Proteins were visualized by staining with Coomassie blue dye. A band of the appropriate molecular weight for p53 was present in the cultures transformed with pC1/ 1-GAP-p53 but not in control extracts of JSC302.

4.6.3. Protein purification

Cultures of JSC302 (pC1/ 1-GAP-p53) were grown under the conditions described above except that the culture in YEP, 1% glucose was allowed to grow for only 24 hours. Cells were harvested and processed using the glass bead lysis procedure with Triton lysis buffer. Triton Lysis Buffer (0.1%, Triton X-100 (10 mM Tris HCl 8.0), 62.5 mM EDTA pH 8.0, 50 mM, Tris HCl pM 8.0). The proteins were precipitated with 40% NH$_2$SO$_4$. The pellet was resuspended in H$_x$O and dialyzed with 50 mM phosphate pH 7.0, 1 mM EDTA, 1 µg/ml Leupeptin, 1 µg/ml Leupeptin, 1 µg/ml Aprotinin, 1 mM PMSF (Phenylmethyl-sulfonylfluoride).

The solution is applied to a Mono-Q resin (Pharmacia) on a FPLC column (Pharmacia). The column is eluted with a 0–1M NaCl gradient. Fractions are collected and analyzed by Coomassie staining western blot analysis for the presence of p53. The peak fraction is made up to 20% glycerol. The column may be repeated to obtain higher purity of the protein.

5. Immunoassay for Anti-HIV Abs Using Recombinant HIV Polypeptides

Diagnostic assays based on the ELISA technique and employing recombinantly produced viral antigens have been developed for the detection of antibodies to HIV. Micro titer plate based ELISAs and an immunoblot strip ELISAs have been configured which use either three or four recombinant viral antigens: the major core protein p25gag, the endonuclease region of the viral polymerase gene p31pol, and one or two polypeptides from the envelope gene, either from gp120 and/or gp41 coding regions.

5.1. ELISA-A 5.1.1. Assay Protocol

Stock solutions of purified p25gag protein (Section 3.1.5) (1.25 mg/ml in 20 mM sodium phosphate, 0.1% SDS, pH 7.2), purified env-2 protein (Section 4 2.2) (2 mg/ml in 20 mM sodium phosphate, 0.1% SDS, pH 7.2), and purified SOD-p31 fusion protein (Section 4.3.3) (2 mg/ml in 20 mM sodium phosphate, 0.1% SDS, pH 7.2) were prepared.

For coating microtiter plates (Dynatech Immulon I), 1 part each of the stock solutions of p25gag, env, and SOD-p31 were added to 997 parts of borate coating buffer (0.05M borate, pH 9.0). One hundred microliters of the coating solution was added to each well, and the plates were covered and incubated 2 h at 37° C. or 12 h at 4° C. The coating solution was then aspirated from the wells and the plates washed 6 x with wash solution (0.137M 0.8% NaCl, 0.05% Triton X-100).

Serum samples were diluted 1:100 in dilution solution (0.1% casein, 1 mM EDTA, 1% Triton X-100, 0.5M NaCl, 0.01% thimerosal, pH 7.5) with yeast protein (strain AB103.1) extract (1:40 dilution, approximately 2 mg protein per ml in PBS containing 1% Triton X-100, 2 mM PMSF, 0.01% thimerosal) and *E. coli* protein extract (1:40 dilution, approximately 1 mg protein per ml in PBS containing 1% Triton X-100, 2 mM PMSF, 0.01% thimerosal) added to the dilution solution. Extraction procedures were similar to those described in 16 and 18 above but using nonrecombinant strains. One hundred microliters of diluted serum was added to each well and incubated 30 min at 37° C. The plates were then washed 6 x with wash solution.

Goat anti-human Ig labeled with horseradish peroxidase (Cappel) diluted 1:8000 in dilution solution without added yeast and *E. coli* extracts were added at 100 µl/well to the plates and incubated 30 min at 37° C. The plates were then washed 6× with wash solution. Substrate solution (10 ml citrate buffer, 10.5 g citric acid/liter dH$_2$O, pH to 4.0 with 6M NaOH), 0.1 ml ABTS [15 mg/ml 2,2'-azino-di-(3-ethylbenzthiazolene sulfonic acid) in dH$_2$O] and 3.33 µl H$_2$O$_2$ at 100 µl/well was then added to the plates and the plates wrapped in foil and incubated at 37° C. for 30 min. The reaction was then stopped by adding 50 µl/well of 10% SDS. Readings were made with a Dynatech ELISA reader set for dual wavelength reading: absorbance wavelength of 1 (410 nm) and reference wavelength of 4.

5.1.2. Results

The following sera were tested:

A. 89 consecutive blood donors from the Kansas City Blood Bank ("normal blood donors"): log nos. 1001–1081, 1085–1092.

B. 52 sera from patients with lymphadenopathy syndrome (LAD) or AIDS or sexual partners of persons with LAD or AIDS (referred to as "contacts")—all obtained from UCSF AIDS Serum Bank panel: log nos. 4601–4652.

The positive/negative cut-off used was 5×(average background signal signal with diluent alone) and was determined to be 0.195. Thus, sera with signals below 0.195 were rated (−); those above were rated (+). Each sample was also evaluated by the commercially available ABBOTT HTLV III EIA kit (Abbott Labs) and by Western analysis.

Tests on the normal blood donor samples indicated all except one were negative in the invention ELISA. This normal serum scored negative in the ABBOTT HTLV III EIA test, but was actually positive, as confirmed by Western analysis.

The results of the tests on the 52 sera from LAD and AIDS patients and contacts are tabulated below:

| Serum No. | Diagnosis | ABBOTT EIA | Invention ELISA | | Western |
|---|---|---|---|---|---|
| 4601 | Contacts | + | 1.89 | + | + |
| 02 | Contacts | − | 0.04 | − | − |
| 03 | Contacts | + | 1.44 | + | + |
| 04 | Contacts | + | 1.92 | + | + |
| 05 | Contacts | − | 0.04 | − | − |
| 06 | Contacts | + | >2 | + | + |
| 07 | Contacts | + | 1.37 | + | + |

-continued

| Serum No. | Diagnosis | ABBOTT EIA | Invention ELISA | | Western |
|---|---|---|---|---|---|
| 08 | Contacts | + | 1.60 | + | + |
| 09 | Contacts | + | >2 | + | + |
| 10 | Contacts | + | >2 | + | + |
| 11 | Contacts | + | 1.94 | + | + |
| 12 | Contacts | + | >2 | + | + |
| 13 | Contacts | + | >2 | + | + |
| 14 | Contacts | + | >2 | + | + |
| 15 | Contacts | + | 1.97 | + | + |
| 16 | AIDS | + | 0.61 | + | + |
| 17 | AIDS | + | >2 | + | + |
| 18 | AIDS | + | >2 | + | + |
| 19 | AIDS | + | 1.58 | + | + |
| 20 | AIDS | + | 1.58 | + | + |
| 21 | AIDS | + | 0.76 | + | + |
| 22 | AIDS | + | 1.74 | + | + |
| 23 | LAD | + | 1.26 | + | + |
| 24 | LAD | + | >2 | + | + |
| 25 | AIDS | + | 1.04 | + | + |
| 26 | AIDS | + | 1.24 | + | + |
| 27 | AIDS | + | 1.40 | + | + |
| 28 | AIDS | − | 0.07 | − | − |
| 29 | LAD | + | 1.93 | + | + |
| 30 | Contacts | + | 1.96 | + | + |
| 31 | AIDS | + | 1.76 | + | + |
| 32 | AIDS | + | 0.90 | + | + |
| 33 | AIDS | + | 1.69 | + | + |
| 34 | LAD | + | 1.09 | + | + |
| 35 | AIDS | + | 1.54 | + | + |
| 36 | AIDS | + | 1.22 | + | + |
| 37 | AIDS | + | 1.96 | + | + |
| 38 | AIDS | − | >2 | + | + |
| 39 | LAD | + | 1.85 | + | + |
| 40 | LAD | + | >2 | + | + |
| 41 | LAD | + | 0.84 | + | + |
| 42 | LAD | + | 1.59 | + | + |
| 43 | LAD | + | 1.71 | + | + |
| 44 | AIDS | + | 1.40 | + | + |
| 45 | LAD | + | >2 | + | + |
| 46 | AIDS | + | 1.38 | + | + |
| 47 | AIDS | + | 1.29 | + | + |
| 48 | LAD | + | 1.93 | + | + |
| 49 | LAD | +/− | 0.48 | + | + |
| 50 | LAD | − | 0.04 | − | − |
| 51 | LAD | − | 0.07 | − | − |
| 52 | LAD | + | 1.92 | + | + |

The above results show that the ELISA-A, using recombinant HIV proteins, is at least as good as the ABBOTT HTLV EIA test or Western analysis.

In the ELISA-A reported in this example, the yeast and bacterial extracts were added to the serum to bind serum antibodies to yeast and bacteria to prevent such antibodies from binding to minor contaminants in the recombinant HIV-1 protein preparations. Both yeast and bacterial extracts were required since the recombinant polypeptides included polypeptides expressed in yeast and polypeptides expressed in bacteria. If all the polypeptides were expressed in the same type of organism, only one extract would be needed. For instance, if a p25gag polypeptide expressed in yeast was substituted for the bacterially produced p25gag polypeptide of the example, only yeast extract would be added to the serum samples.

5.2. ELISA-B 5.2.1. Assay Protocol

Frozen stocks of the following purified proteins were thawed and used to make a solution containing: p25gag (Section 4.5) 1.25 μg/ml, SOD-p31 (Section 4.3.3) 1.00 μg/ml, SOD-env5b (Section 3.6) 1.25 μg/ml, and env-2 (Section 4.2.2) 0.50 μg/ml in 0.05M sodium borate, pH 9.0. For coating microtiter plates, 100 μl of the above solution was pipetted into each well of Immulon I round bottom microtiter plates (Dynatech Laboratories), and incubated for 2 h at 37° C. The coating solution was then aspirated from the wells. The plates were washed three times with 200 μl/well Wash Buffer [100 mM Sodium Phosphate pH 7.4, 140 mM Sodium Chloride, 0.1% Casein (Sigma), 0.05% Triton X-100 (Sigma), 0.01% (w/v) Thimerosal (Sigma)] and then washed two times with 200 μl/well PBS (10 mM Sodium Phosphate pH 6.7, 150 mM Sodium Chloride). The plates were then post coated by incubating with 200 μl/well of Postcoat solution [PBS, 0.1% (w/v) Casein, 2 mM PMSF (phenylmethyl-sulfonylfluoride)] for 30 minutes at 15°–30° C. The Postcoat solution was aspirated off. The plates were dried in a lyophilizer (such as: Virtis Unitop 600 SL lyophilizer, Virtis Company) overnight or by incubating for 2 h at 25° C.

To assay samples in the ELISA-B assy, 100 μl of Samples Diluent [100 mM Sodium Phosphate, pH 7.4, 0.5M Sodium Chloride, 1 mM EDTA, 0.1% casein, 1% Triton X-100, 100 μg/ml yeast extract (see below), 100 μg/ml E. coli extract (see below), and 0.01% Thimerosal] was added to each of the coated wells on the plates. Ten μl of the samples to be assayed or controls were pipetted into the wells. The plates were then sealed and incubated for 1 h at 37° C. The sample was then aspirated and the plates were washed three times with 200 μl/well of distilled water. The plates were then incubated with a goat anti-human IgG-HRP (horseradish peroxidase) conjugated antibody (available from commercial sources, i e., Tago or Cappel, or the conjugate may be synthesized by the Nakane procedure). The anti-human IgG-HRP conjugate was diluted 1/3200 in Conjugate Solution I [PBS, 5% noral goat serum, 0.01% ANS (8-Anilino-1-naphthalene sulfonic acid, ammonium salt), 0.01% Thimerosal]. A final dilution to 1/32000 was made in Conjugate Diluent MT [116 mM Sodium Phosphate, pH 7.4, 0.622M Sodium Chloride, 0.56% BSA, 2.22% normal goat serum, 1.11% Triton X-100, 0.11% Casein, 0.0044% ANS, 0.01% Thimerosal] immediately before use. One hundred μl of the diluted conjugate was added per well (except for blank wells). The plates were sealed and incubated for 1 h at 37° C. The conjugate solution was aspirated off and the plates were washed three times with 200 μl/well of distilled water. Then 100 μl of Developer [made fresh: 50 mM Sodium Citrate adjusted to pH 5.1 with 1M Phosphoric Acid, 0.6 μl/ml 30% $H_2O_2$, OPD tablet (Sigma) (1 tablet/5 ml of buffer)] was added to each well and incubated thirty minutes at room temperature (15°–30° C). The reaction was stopped by the addition of 50 μl of 4N $H_2SO_4$ to each well.

The microtiter plates were analyzed on a standard ELISA reader (such as Biotek EIA Autoreader Model EL310, Biotek Instruments) by reading the absorbance of developed color at 492 nm. The results were analyzed by comparing the values generated for the samples against an assay cutoff valve (cutoff=0.5×average absorbance value for the positive controls.)

Yeast and E. coli extracts used in the Sample Diluent were prepared in an analogous manner to the purification process for recombinant polypeptides in Sections 3.1.4.2–3.2.5 and 4.1.4.1–4.1.4.3, except non-recombinant strains S. cerevisiae AB103.1 and E. coli D1210 were used.

5.2.2. Results

The ability of ELISA-B to detect the presence of antibodies directed against HIV was compared to a licensed and commercially available ELISA produced by DuPont.

493 serum samples were run in ELISA-B and the DuPont screening ELISA. The panel of sera was composed of specimens from various sources: 205 samples from CDC (clinically categorized as AIDS, ARC, contact, false positive from licensed screening ELISA, and 4 negative); 101 samples from UCSF (clinically categorized as AIDS, ARC, and contact); 187 samples obtained from Interstate Blood Bank, PA, (initially scored positive on licensed screening ELISA). In this group of samples there were eight (8) discrepancies. Four (4) samples were found positive by ELISA-B and negative in the DuPont ELISA. Correlation between the DuPont assay and ELISA-B was 98.4%. Concensus data indicated that of the four (4) samples found positive by ELISA-B and negative by the DuPont ELISA, three (3) (LW 47, 4202, and 4225) were true positives (DuPont ELISA false negatives) and one (4279) was an ELISA-B false positive. Concensus data also indicated that the four samples found negative in ELISA-B and positive in the DuPont ELISA (LW 12, 20061, 20145, 20162) were negative (DuPont ELISA false positives). For the eight (8) discrepant samples ELISA-B differed from the concensus data in one (1) case and the DuPont ELISA differed in seven (7) cases. Also note that one sample was false positive in both assays.

The positivity or negativity of a specimen in these panels was determined from the concensus results of commercial viral ELISAs, the microtiter plate assay using recombinant antigens, the strip ELISA, Western Blot data (when available) and clinical data, if available.

or more. The strips are then post-coated in a 5% solution of Carnation non-fat dry milk in PBS, 0.01% Thimerosal, for 15-60 min at room temperature. Each test solution sample is diluted 1:50 in 0.5 ml of the post-coating solution in a test tube. A post-coated strip is then placed in the tube and incubated in the sample with rocking at 37° C. for 1 h. The strip is then removed from the tube and washed with post-coating solution. The strip is then incubated for 15 min at room temperature in goat anti-human Ig reagent labeled with horse radish peroxidase diluted 1:500 in post-coating solution. After incubation in the labeled antibody, the strip is washed serially with PBS, 1% Triton, and distilled water. The strips are developed by incubating them in substrate solution (see 23 above) for 15 min at room temperature.

Positive samples will cause a visually perceptible color change at the spotting site. Normal (negative) sera sample yield no color change or give a faint signal that is discernible from a positive signal. Competition assays may be run on sera giving faint signals to verify that they are negative. In the competition assay, polypeptide (10-25 $\mu$g/ml) is added to the test sample and incubated from 1 h at 37° C. before the strip is incubated in the sample. With authentic positive sera the signal is completely blocked by the added polypeptide, whereas with normal (negative) sera there is no change in signal.

5.4. Immunoblot Strip ELISA Assay

In the immunoblot strip ELISA, recombinant derived viral antigens are individually coated in bands on a nitrocellulose strip and reacted with samples to bind anti-HIV specific antibodies.

Frozen aliquots of the individual recombinant polypeptides were thawed and diluted to the appropriate

TABLE

Correlation of ELISA-B with the DuPont Screening ELISA Discrepant Samples

| Panels | ELISA-B | | DuPont ELISA | | Strip ELISA | | | |
|---|---|---|---|---|---|---|---|---|
| | OD$_{490nm}$ | S/CO | OD$_{490nm}$ | S/CO | P-24 | P-31 | GP-41 | GP-120 |
| UCSF | | | | | | | | |
| (N = 100) | | | | | | | | |
| CDC | | | | | | | | |
| (N = 205) | | | | | | | | |
| 4110 | 2.25 | 4.4 | 1.66 | 4.22 | — | 4+ | 4+ | ± |
| 4133 | 1.21 | 2.4 | 1.25 | 3.18 | ± | — | 2+ | — |
| 4204 | .56 | 1.1 | .33 | .90 | — | — | — | — |
| 4218 | .60 | 1.2 | 2.37 | 6.4 | — | — | — | — |
| 4225 | .54 | 1.1 | .07 | .2 | — | — | — | — |
| 4279 | .98 | 3.6 | .18 | .5 | — | — | — | — |
| Interstate (LW) | | | | | | | | |
| (N = 58) | | | | | | | | |
| 12 | .28 | .5 | 1.17 | 2.0 | — | — | — | — |
| 47 | .46 | .90 (1.7) | .46 | .80 (.54) | 1+ | — | — | — |
| Interstate I | | | | | | | | |
| (N = 67) | | | | | | | | |
| 20061 | .22 | .48 | 1.71 | 2.5 (2.1) | — | — | — | — |
| Interstate II | | | | | | | | |
| (N = 62) | | | | | | | | |
| 20145 | .13 | .22 | >3.00 | 4.4 (3.2) | — | — | — | — |
| 20162 | .18 | .32 | .94 | 1.4 (1.0) | — | + | + | + |

S/CO = signal: cut off ratio
if = or > 1.0 samples is positive

5.3. Dot Blot Assay

Nitrocellular strips (0.5×5 cm) are spotted with 50 ng polypeptide in PBS (spotting volume 2 $\mu$l). After spotting the strips are dried at room temperature for 1 h concentration in Coating Solution [PBS pH adjusted to 7.4, 375 mg/l Napthiol Blue Black (used only as an inert marker)] as follows: p25gag (Section 4.5) 3-4 $\mu$g/ml, SOD-p31 (Section 4.3.3) 1–1.6 μg/ml, SOD/env-5b (Section 3.6) 1.0 μg/ml, env-2 (Section 4.2.2) 0.5 μg/ml. The individual protein solutions were coated as individual bands on a sheet of nitrocellulose paper; BA85 NC ™; Schleicher & Schuell, Inc., Keene, NH, (pre-wetted with PBS buffer). The coating apparatus can be any apparatus which allows for solutions to be applied to filter paper under vacuum pressure as discrete bands, such as Minifold ® II Slot-Blot System; Schleicher & Schuell.

The coated sheets are dried overnight. The dried, coated sheets are immersed for five minutes in Blocking Buffer (PBS, 1% (w/v) Casein, 0.01% Thimerosal, pH adjusted to 7.4) and then dried overnight. The coated and blocked nitrocellulose sheets were attached to a backing sheet of paper with double faced tape and then cut into individual strips which contain the individual bands corresponding to each of the recombinant viral antigens.

The sample to be assayed was diluted 1/100 with Sample Diluent by adding 10 μl of the sample to 1 ml of Sample Diluent [PBS, 0.1% Casein, 1 mM EDTA, 2.0% Triton X-100, 1 mg/ml Yeast extract, 500 μg/ml E. coli extract, 0.2 μg/ml YP45 extract, 0.01% Thimerosal, pH adjusted to 7.4]. The strips were then individually soaked in the diluted sample solution with agitation for 2 h at room temperature (15° to 30° C). The strips were removed from the diluted sample solution and washed four times with water. The strips were then incubated with 1 ml/strip of Goat anti-human IgG-HRP conjugate diluted in Conjugate Buffer [PBS pH 7.2, 0.3% Casein, 5% normal goat serum, 0.01% ANS, 0.01% Thimerosal] with agitation for 30 minutes at room temperature (15°–30° C).

The strips were removed from the conjugate solution and then washed three times with water. The strips were then incubated with 1 ml/strip of Developer Buffer [10 mM Sodium Phosphate, 20 mM Sodium Chloride, 0.8 μl/ml 30% hydrogen peroxide, 0.05% (w/v) 4-chloro-1-naphthol, 16.6% methanol] with agitation for 15 minutes at room temperature (15°–30° C). The reaction was stopped by removing the strips from the Developer Buffer and washing two times in water. The color developed on the band is compared with positive control bands (IgG applied at 0.25 μg/ml and 1.25 μg/ml).

Yeast and bacterial proteins were used to preabsorb antisera for cross-reactive antibodies. Yeast extract was prepared by processing bulk yeast S. cerevisiae (Red Star Yeast, grade 1; Red Star, Oakland, Calif.) through the standard lysis procedure as described previously for the purification of yeast recombinant proteins. The insoluble cellular debris was separated from the soluble protein fraction. The E. coli extract was prepared by growing E. coli strain D1210 (pSODCF2), lysing the cells, and solubilizing the pellet as described in Section 3.6.4. YP45 extract is a yeast protein and was prepared by growing S. cerevisiae AB110 and following the purification procedure described in Section 4.3.3.3. A 45 kd yeast protein was purified which helps in preabsorbing nonspecific cross-reactive antibodies found in some area.

6. Serology Studies with Recombinant HIV Polypeptides 6.1 Immunoblot with Env Polypeptides Recombinant polypeptides originating from different regions of the env gene of the ARV-2 isolate of HIV (Section 4.2) were used to characterize the antienvelope antibody response of virus seropositive individuals. The sera characterized included specimens from AIDS patients, ARC patients and clinically healthy homosexual men with documented exposure to the virus through sexual contact with AIDS or ARC patients (contacts).

Regions of the envelope gene of the ARV-2 isolate of HIV were cloned into yeast expression vectors (env-1, env-2, env-3) or bacterial expression vectors (env-5b), and used to produce recombinant proteins as described in Sections 3 and 4.

Extracts of yeast for SDS polyacrylamide gel electrophoresis were prepared as follows: 1 ml of yeast grown to 20 O.D. (A450) were pelleted and suspended in 200 μl of electrophoresis sample buffer. The mixture was boiled for 10 min and then centrifuged at 12,000 g for 2 min to remove cell debris prior to electrophoresis. To prepare bacterial extracts for gel electrophoresis, bacterial cells from 1 ml of culture were pelleted, suspended in 200 μl of electrophoresis sample buffer, and disrupted by 3 cycles of freezing and thawing. The mixture was boiled for 10 minutes prior to electrophoresis.

Yeast or bacterial extracts were electrophoresed on standard Laemmli discontinuous SDS-polyacrylamide (12% acrylamide) gels using a Biorad Laboratories minigel apparatus. Laemmli (1970) Nature 227:680–685. The extracts (100 μl) were loaded into an 8 cm well in the stacking gel prior to electrophoresis. Following electrophoresis, proteins were transferred to nitrocellulose filters. Towbin et al. (1979) Proc. Natl. Acad. Sci. USA 76:4350–4355. Strips of the filter with the electroblotted lysates were cut and each strip reacted with an individual serum sample diluted 1/100.

Sera from 85 seropositive individuals, including AIDS patients, ARC patients, contacts and clinically healthy individuals, as well as a pool of sera from normal human blood donors, were assayed on env-1, env-2 and env-3. The blots were processed with Carnation nonfat dry milk as described previously. Johnson et al. (1984) Gene Anal. Techn. 1:3–8. The enzyme conjugate (diluted 1/200) was goat antiserum to human immunoglobulin G (Cappel Laboratories) and the chromogen was HRP color reagent (4-chloro-1-Napthol; Biorad Laboratories).

Positive immunoblot assays obtained with env-1, -2, and -3 are shown in FIG. 30. A prominent band at 28,000 was seen in the env-1 blot with a patient's serum with anti-env-1 antibodies. In the immunoblot of env-2, the antibody-positive serum reacted with a protein of approximately 55 kD. With env-3, the positive serum reacted with a series of bands migrating between 30,000 and 35,000. The multiple immunoreactive species in the env-3 immunoblot are due to differences in glycosylation (see Section 4.2.3) of this polypeptide during its synthesis in yeast. Five potential glycosylation sites are contained within the coding region for env-3.

The results of assays of the reactivity of sera obtained from the various patient groups in the 85 serum panel with the env-1, env-2 and env-3 are presented in table below:

| Clinical Group | Number Tested | Number Reacting With: | | |
|---|---|---|---|---|
| | | env-1 | env-2 | env-3 |
| Contacts | 21 | 4 (19%) | 21 (100%) | 21 (100%) |
| ARC | 26 | 3 (12%) | 26 (100%) | 26 (100%) |
| AIDS | 38 | 6 (16%) | 36 (95%) | 36 (95%) |

All of the specimens selected for this analysis were positive in an enzyme-linked immunosorbent assay (ELISA) for antibodies to the AIDS retrovirus. Wiess et al. (1985) *J.A.M.A.* 253:221-225. Sera from all of the contacts and ARC patients had antibodies that reacted with env-2 and env-3 indicating that they had antibodies to both gp120 and gp41 that could be detected with these non-glycosylated polypeptides in immunoblot assays. Thirty-six of the 38 AIDS patients (95%) had antibodies that reacted with env-2. The same thirty-six sera also reacted with env-3. The two AIDS sera that did not react in immunoblot assays with env-2 or env-3 either lacked antibodies detected using these recombinant antigens, or their antibody titers were below the limit of detection in these assays, at least in generating an immune response to sequential epitopes.

When these sera were tested in immunoblot assays with env-1, only a minority in each diagnostic group scored positive. The percentage of contacts, ARC patients and AIDS patients with antibodies to env-1 was 19%, 12% and 16%, respectively. Since env-1 corresponds to the amino-terminal half of env-2 (amino acids 26-491, the majority of gp120), this observation suggests that the carboxyl terminal portion of gp120 is much more immunogenic in infected individuals than the amino-terminal half of the polypeptide, at least in generating an immune response to sequential epitopes.

Because the env-1 polypeptide was also represented in env-2, it could not be determined directly from the immunoblot results if env-1 positive sera reacted exclusively with env-1 or were also reactive with the carboxyl-terminal half of env-2. To evaluate the reactivity of env-1 positive sera with the carboxyl-terminal half of env-2, competition experiments were carried out. Sera were reacted with env-1 and env-2 in immunoblot assays in the presence or absence of an excess of env-1 in the serum diluent. An env-1 positive serum, diluted 1/100, was incubated with: env-1 immunoblot with no addition, env-1 immunoblot with 50 µg/ml env-1 in diluent, env-2 immunoblot with no addition, env-2 immunoblot with 50 µg/ml of env-1 in diluent and env-2 immunoblot with 50 µg/ml of env-2 in diluent. The reactivity of the env-1 serum sample with the env-1 blot was completely eliminated by preincubation with env-1. However, reactivity with the env-2 blot was still evident. Similar results were observed with all of the env-1 positive sera, indicating that they all reacted with the carboxyl terminal as well as the amino terminal half of the gp120 polypeptide.

Immunoblots of extracts from bacteria expressing a subregion of gp41 (aa 557-667) as an hSOD fusion, referred to as env-5b, with an AIDS patient's serum, showed a prominent immunoreactive species at 32,000 daltons that was absent from immunoblots of extracts from bacteria transformed with the vector lacking the env insert (Section 3.6). This was approximately the molecular weight expected for a polypeptide coded for by the sum of the hSOD and env gp41 sequences. Twenty serum samples shown previously to contain antibodies that reacted with env-3 in immunoblot assays were reacted with env-5b immunoblots. All 20 specimens reacted with the fusion protein.

Immunoblot assays detect antibodies which recognize principally sequential determinants. The results presented here indicate that virus seropositive individuals frequently have mounted immune responses to sequential epitopes within the carboxyl terminal half of the gp120 polypeptide. In addition, such individuals have also mounted immune responses to sequential epitopes within gp41 (env-5b). The prevalence of antibodies to these two env regions detected by using recombinant polypeptides from a single virus isolate suggests that there are epitopes within both regions that are highly conserved. The failure of most virus seropositive specimens to react with the amino terminal half of gp120 represented by env-1 may indicate that there are not such highly conserved immunodominant sequential epitopes within this region. These data suggest that either the amino terminal region of gp120 is a poor immunogen in humans, or humans respond in a strain-specific fashion so that only those individuals infected with a highly homologous virus are detected with env-1 from ARV-2. Another explanation centers around the possibility that conformational epitopes may be a feature of the N-terminal portion of gp120; immunoblotting would miss antibodies directed at conformational determinants. Another possible explanation is that the immunogenicity of the amino terminal region of gp120 is masked by glycosylation or by structural constraints due to association of gp120 with gp41 and/or the viral membrane.

It was also found that all sera reacting in immunoblots with env-3 also reacted with the fusion protein env-5b. In fact, several sera that were only weakly positive on env-3 were clearly positive on env-5b. The sensitivity of an immunoblot assay is limited by the amount of antigen that is present in the preparation. Since env-5b expression levels were high compared to the levels of expression of env-3 in yeast (env-5b represented approximately 2-5% of the total bacterial protein, whereas env-3 was less than 0.1% of the total yeast protein), it was not unexpected the env-5b immunoblot assays were more sensitive than the env-3 immunoblot assays.

6.2 ELISA with Env Polypeptides

To provide a quantitative assessment of the antibody response detected using these recombinant polypeptides representing regions of two subunits of the HIV envelope glycoprotein complex, env recombinant polypeptides (Section 4.2) were purified and enzyme-linked immunosorbent assays (ELISA) configured.

Test sera were the same as described in Section 6.1. The ELISA procedures were modifications of those described previously. See Brun-Vezinet et al. (1984) *Lancet I*:1253-1256; Saxinger et al. (1983) *Lab. Invest.* 49:371-377; Weiss et al. (1985) *J.A.M.A.* 253:221-225; Steimer et al. (1986) *J. Virol.* 58:9-160.

For virus ELISAs, microtiter plates (Dynatech, Immulon I) were coated with 5 µg/ml of SDS-disrupted sucrose gradient purified ARV-2 virus. Human serum samples, diluted 1/100, were added to the wells and the plates incubated at 37° C. After 1 h, the plates were washed and goat antiserum to human immunoglobulin conjugated with horseradish peroxidase (Cappel Laboratories) and diluted 1/4000 was added to the wells. The plates were incubated for 30 min. at 37° C., washed and the substrate solution (150 µg/ml, 2,2'-azino-di-3'-ethyl-benzylthiazoline sulfate in 0.1M citrate, 0.001% $H_2O_2$, pH 4.0) was added for 30 minutes. The plates were read on a ELISA reader at 415 nm with a reference wavelength of 600 nm. Samples were scored as positive when their assay result was greater than five times the absorbance obtained with the negative control pooled normal human serum (NHS).

For recombinant env polypeptide ELISAs, microtiter plates were coated with 2 µg/ml of purified env-2 or env-5b (Section 7.1). Serum samples were assayed for antibodies to these antigens by the procedure described above. Included in the serum diluent for the env-2 antibody ELISA was included extract (final concentration 100 μg/ml) from yeast transformed with the vector alone lacking the env-2 insert. Similarly, 100 μg/ml of an extract from untransformed *E. coli* was added to the diluent for the env-5b antibody ELISA.

Figure 16A:
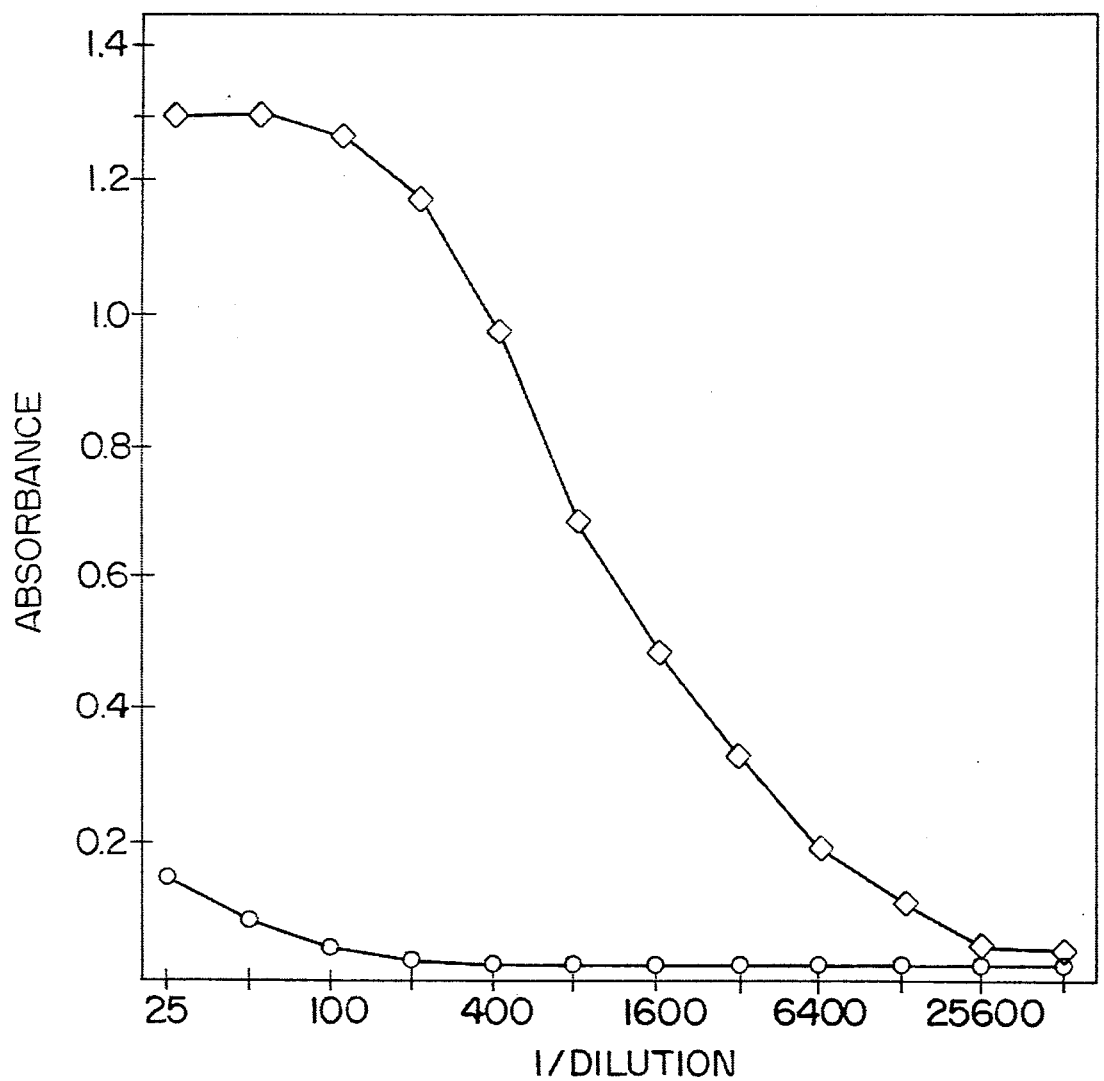
FIG. 16 is the results of an indirect ELISA in which an AIDS patient's serum was ( ) titrated against microtiter plates coated with recombinant polypeptides from env regions. A pool of serum samples from random blood donors was used as a control (o). Panel A shows the results for purified, recombinant env-2. panel B shows the results with purified, recombinant env-5b. The insert in each panel shows a Coomassie-stained gel (lane 1) and an immunoblot with the AIDS patient's serum (lane 2) of the purified antigens used in these ELISAs.
Figure 16B:
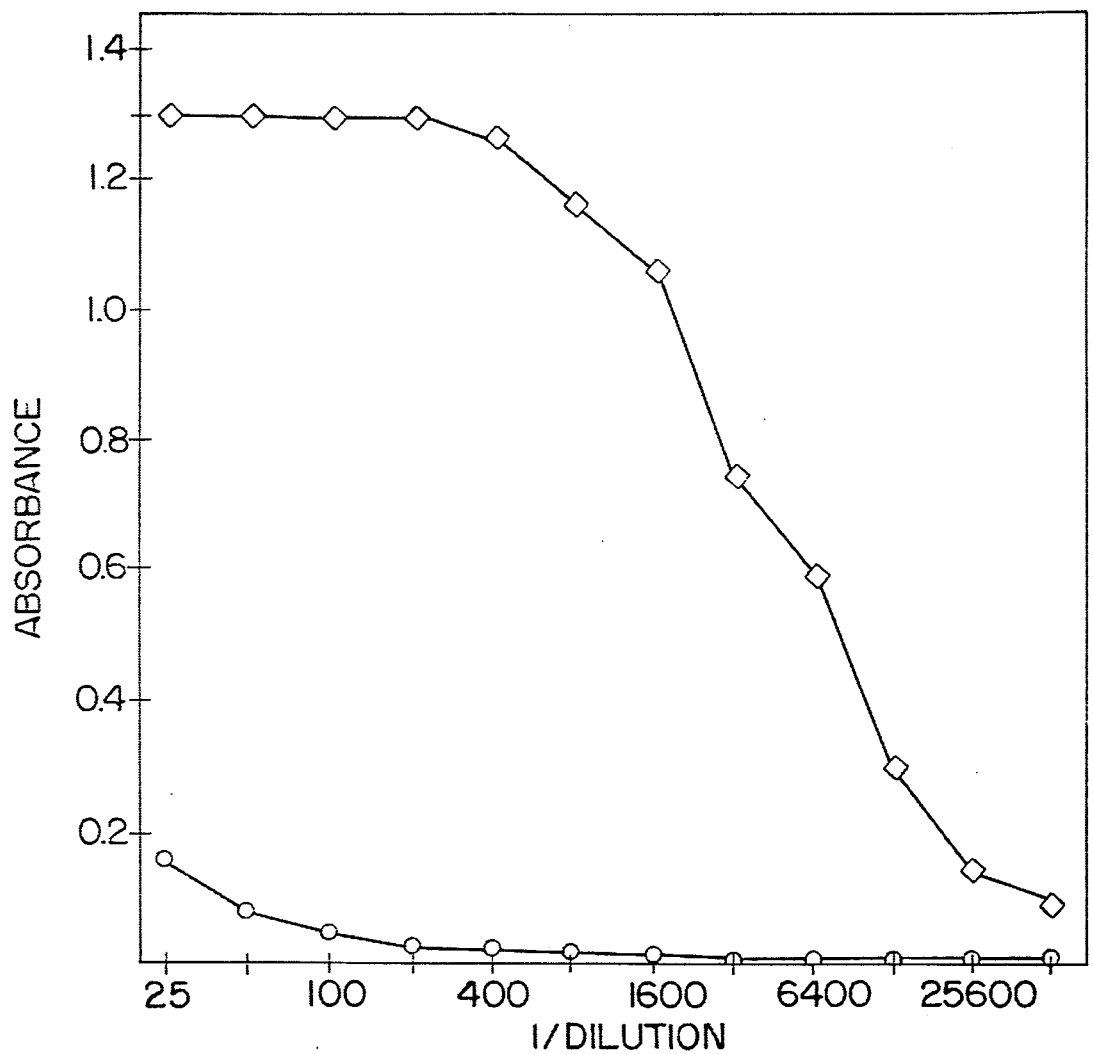

FIG. 16 (panel A) shows the results of a titration of antibodies in an AIDS patient's serum that reacted with env-2. Pooled normal human serum (NHS) (0) and serum 0036 from an AIDS patient ( ) were diluted 1/25 and then by serial 2-fold dilutions. The titer of env-2 antibodies in this particular serum specimen was approximately 1400. The signal with the control sample (NHS) was low at all dilutions.

Env-5b was purified and used as antigen in an ELISA for antibodies to the gp41 polypeptide. FIG. 16 (panel B) shows the results of a titration of env-5b antibodies in the same serum sample that was titered previously in the env-2 ELISA. No appreciable signal was seen with NHS.

Figure 17:
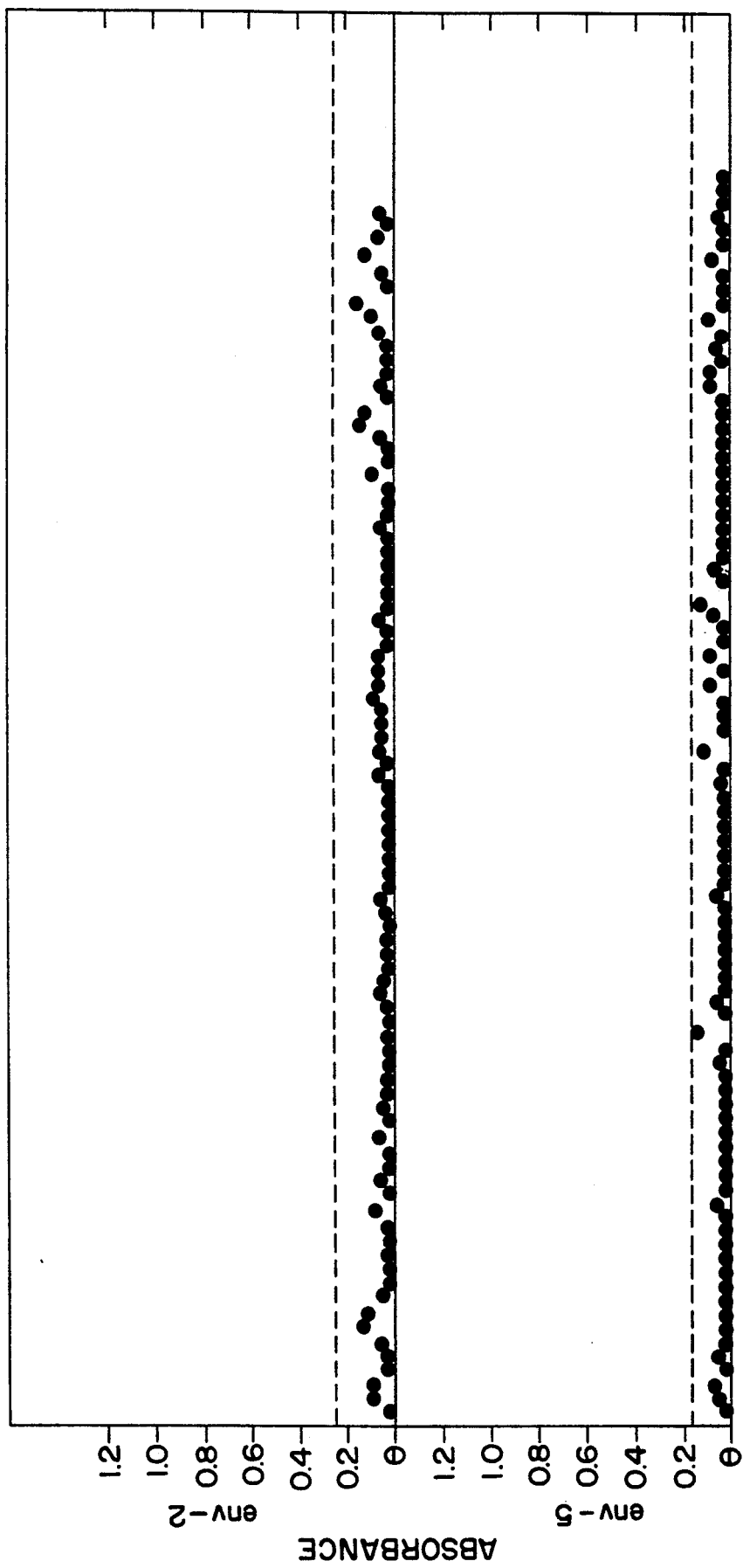
FIG. 17 shows the results of an ELISA, employing recombinant env-2 (top panel) and env-5b (bottom panel) polypeptides, run on seronegative blood donors.

Serum samples from 88 blood donors, all seronegative in an ELISA for AIDS retrovirus antibodies were tested at a dilution of 1/100 in the env-2 and env-5b antibody ELISAs (FIG. 17). The average signal in the env-2 antibody ELISA was 0.045±0.033 with a range of 0 to 0.149. In the env-5b ELISA these same sera yielded an average signal of 0.034±0.030 with a range of 0 to 0.144. The cut-off for both assays was set at five times the average signal of these 88 seronegative specimens. For the env-2 antibody ELISA the cut-off was 0.225, and for the env-5b assay it was 0.170.

Figure 18:
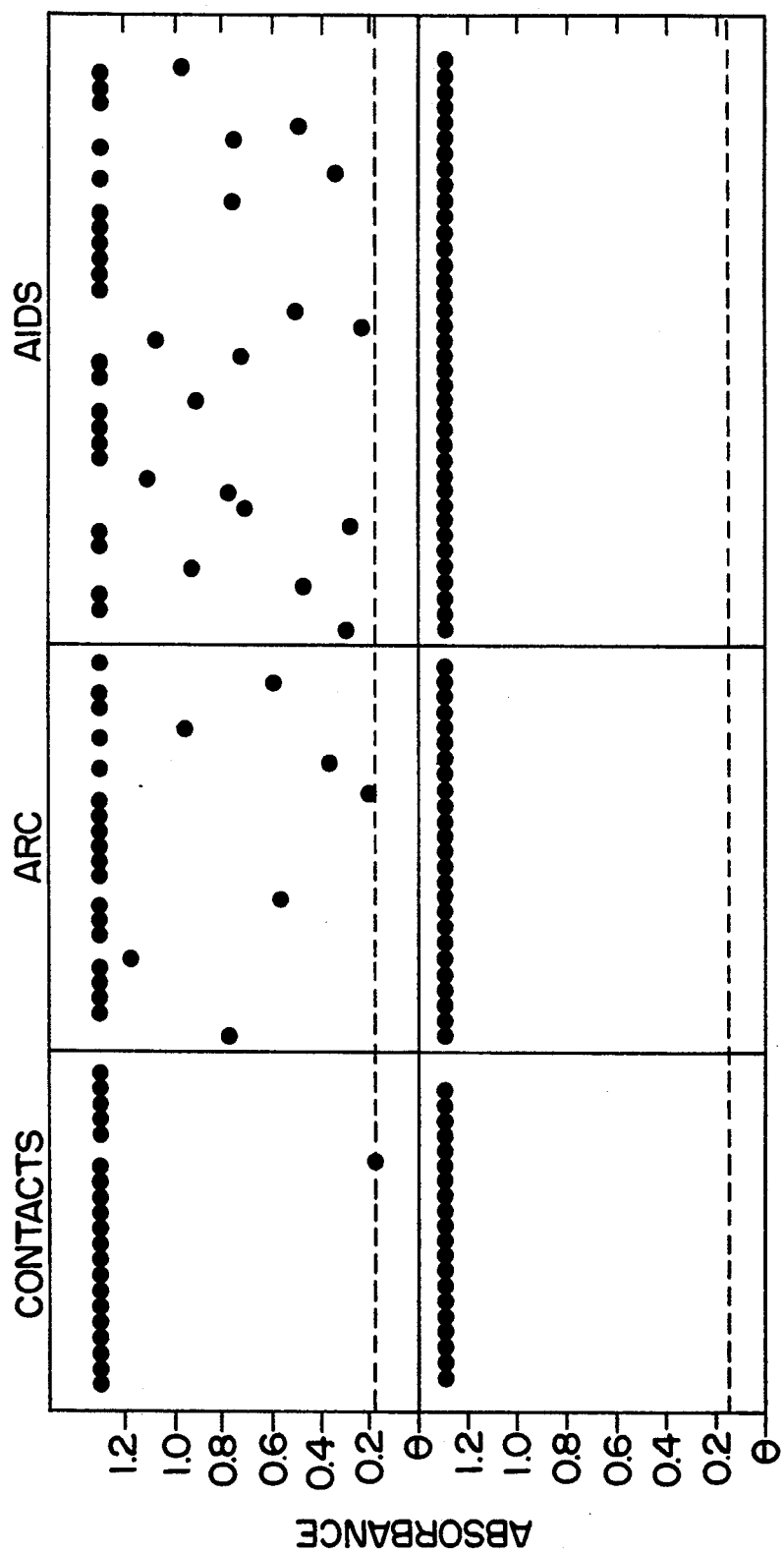
FIG. 18 shows the results of an ELISA, employing recombinant env-2 (top panel) and env-5b (bottom panel) polypeptides, run on HIV seropositive patients, including those diagnosed as having AIDS or AIDS-related complex (ARC), as well as those having contacts with AIDS patients.

The results of the env-2 and env-5b ELISAs with the same panel of virus seropositive specimens described previously (see the table in Section 7.1) are presented in FIG. 18. The dotted line in the top panel designates the cut-off (0.174) in the env-2 ELISA. The dotted line in the bottom panel (0.154) is the cut-off in env-5b antibody ELISA. Each data point is the average of duplicate assays. All of the sera, regardless of diagnosis, yielded the maximum signal in the env-5b antibody ELISA.

Serum antibodies were clearly detected in the env-2 ELISA with specimens from 20 of the 21 contacts, 24 of the 25 ARC patients, and 35 of the 38 AIDS patients. The remaining five sera, one from a contact, one from an ARC patient and three from AIDS patients, are considered to be borderline. The contact and ARC sera scored just below the assay cut-off while the three AIDS sera scored just above the cut-off. These same sera were all clearly positive in the env-5b antibody ELISA.

Figure 19:
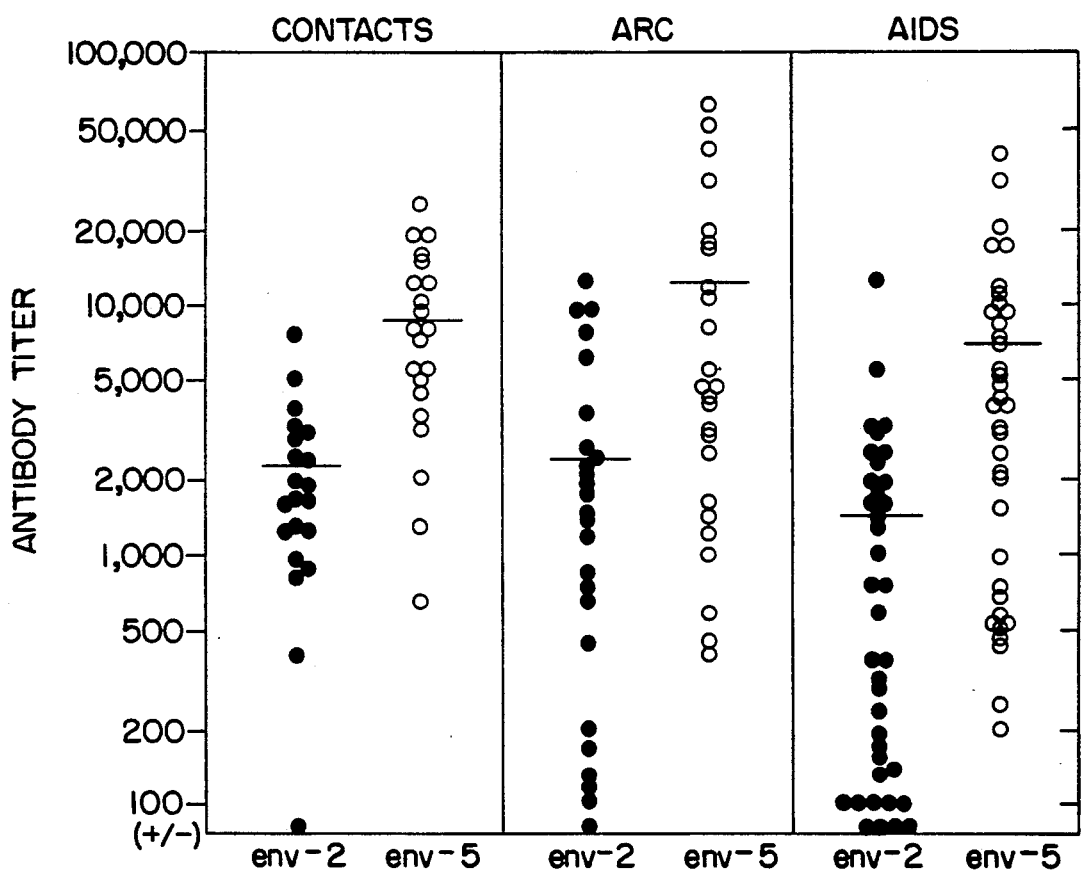
FIG. 19 shows the results of ELISAs used to measure antibody titers in the AIDS seropositive patients of FIG. 18.

FIG. 19 compares antibody titers of the above sera for both env-2 and env-5b. These serum samples were assayed in the env-2 and env-5b ELISAs at dilutions ranging from 1/100 to 1/51,200. The titers reported are the dilution at which half-maximum absorbance was attained. The env-2 titers are shown as dark circles, and the env-5 titers are open circles. The horizontal lines show the mean titers of sera in each group. Borderline sera (less than 0.15 above assay cut-off) are shown as "±". Sera with titers below 1/100, but not borderline, are plotted as having titers of 1/100.

Antibody titers in sera obtained from all three groups were higher to env-5b than to env-2). The average titer of env-2 antibodies in sera obtained from contacts was 2224 (range <100–7975) compared to an average titer of env-5b antibodies of 8988 (range 650–25,000). Among the ARC patients the average env-2 and env-5b antibody titers were 2480 (range<100–12,800) and 12,560 (range 42062,000), respectively. Finally, for AIDS patients the average env-2 antibody titer was 1394 (range <100–12,800) compared to an average env-5b antibody titer of 7059 (range<100–42,000).

The ratio of env-5b to env-2 antibody titers was 5.06, 4.04 and 5.06 for contacts, ARC patients and AIDS patients respectively. Since these ratios remain constant, regardless of diagnosis, it is unlikely that there is a selective decline in the antibody titer to one or the other of the env polypeptides with progressive disease. Instead, it indicates that individuals with low titer antibodies to one env polypeptide tend to have low titers of antibodies to the other polypeptide. Examining the env-5b antibody titers of those individuals with low (<200) titers of env-2 antibodies (table below) supported this conclusions; these sera all had correspondingly low env-5b antibody titers.

| Serum Number | Clinical Group | Env-2 Antibody Titer | Env-5b Antibody Titer |
|---|---|---|---|
| 4687 | C* | <100 | 1300 |
| 4623 | ARC | 115 | 3100 |
| 4648 | ARC | 125 | 1000 |
| 4672 | ARC | <100 | 590 |
| 4677 | ARC | <100 | 450 |
| 4685 | ARC | 170 | 420 |
| 4616 | AIDS | <100 | 430 |
| 4619 | AIDS | 100 | 900 |
| 4620 | AIDS | 130 | 620 |
| 4625 | AIDS | <100 | 1500 |
| 4626 | AIDS | 100 | 4300 |
| 4627 | AIDS | 100 | 200 |
| 4631 | AIDS | 170 | 500 |
| 4637 | AIDS | 190 | 480 |
| 4653 | AIDS | <100 | 2500 |
| 4654 | AIDS | 100 | 400 |
| 4660 | AIDS | 100 | 760 |
| 4664 | AIDS | 155 | 300 |
| 4667 | AIDS | 100 | 680 |

*Contacts.

6.3 ELISA with Gag Polypeptides

Large-scale purification of p25gag from bacterial extracts (Section 3.1.5) provided sufficient antigen for a survey of p25gag seropositivity among various risk and patient groups. These sera were tested first in a virus ELISA to identify those with antibodies to the virus and then in the p25gag ELISA to determine the proportion of virus seropositive individuals with antibodies to p25gag.

Ninety-six sera from random blood donors, all of whom were negative for AIDS virus antibodies in the virus ELISA, scored negative in the ELISA for p25gag antibodies. The average signal in the p25gag ELISA of these sera was 0.034±0.016 optical density units (OD) with a range of 0.011 to 0.089 (not shown).

A panel of 100 sera was then examined, consisting of 28 specimens from high-risk individuals with no symptoms of the disease, but with potential exposure to the virus through sexual contact with AIDS patients (contacts), 33 sera from patients with AIDS-related complex (ARC), and samples from 39 patients with AIDS. Eighty-six of the 100 specimens were positive in the virus ELISA, an indication that these individuals had mounted an immune response to one or more viral antigens. The number of virus ELISA positive contacts was 21 (75%), ARC patients was 27 (81.8%), and AIDS patients was 38 (97.4%). The results of the p25gag antibody ELISA of these specimens are summarized in the table below. Of the 86 sera from the total panel that were positive in the virus ELISA, only 34 (39.5%) scored positive in the p25gag ELISA. When the results were grouped according to diagnosis, however, the contacts had the highest number of virus seropositive individuals with antibodies to p25gag (71%), the ARC patients were intermediate (48%), and the AIDS patients were the lowest (16%). Also tested were the 14 virus ELISA negative specimens from this panel of 100 sera in the p25gag ELISA, and all scored negative (not shown).

The data presented in the table suggest that with an increase in the severity of the disease, there is a decline in the proportion of virus seropositive individuals with antibodies to p25gag. To determine the significance of the observed differences in p25gag seropositivity between groups, we used an $X^2$ test with pairwise comparison of groups. This analysis shows that the probability that the observed differences in frequency of p25gag seropositivity between the contacts and AIDS patients could have been due to chance was less than 1 in 2000. Similarly, the probability that the difference between ARC and AIDS patients was due to chance was very small (1 in 200). A comparison of contacts and ARC patients, however, gave a higher probability (1 in 10) that the observed difference was due to chance. A larger sample size would be required to establish the significance of this difference with greater certainty.

These results suggest that monitoring p25gag seropositivity of individuals infected with the AIDS retrovirus might be of diagnostic value. Although patients with more severe forms of the disease clearly have antibodies to other viral antigens, such as the envelope glycoproteins [Barin et al. (1985) *Science* 228 1097; Montagnier et al. (1985) *Virology* 144:283], they are less likely than those in earlier stages to have antibodies to p25gag.

The above results were obtained with p25gag antigen produced in *E. coli*. Similar results have been seen with the antigen produced in yeast.

| p25gag Antibody ELISA of Virus Seropositive Specimens[a] | | |
|---|---|---|
| Category or diagnostic (number in group) | Number scoring positive | Percentage[b] positive |
| Contacts (21) | 15 | 71 |
| ARC patients (27) | 13 | 48 |
| AIDS patients (38) | 6 | 16 |
| total (86) | 34 | 39 |

[a]Samples were categorized as virus seropositive if they yielded greater than five times the signal obtained with normal human serum (NHS) in a virus ELISA assay using disrupted ARV-2 virus as antigen. The p25gag antibody ELISA procedure was as follows: ELISA plates were coated with 5 μg/ml of p25gag purified from bacterial extracts. In the diluent was included a lysate from untransformed *E. coli*. All were diluted 1/100 for assay. The conjugate was horseradish peroxidase conjugated goat antiserum to human immunoglobulin (Cappel, No. 321-0081).
[b]A sample was scored as positive when the average OD reading was greater than five times the signal with pooled normal human serum (NHS). In this particular assay this was $OD_{414} = 0.200$.

6.4. Western and ELISA with Pol Polypeptides

A panel of 10 sera that scored positive in the ELISA for vial antibodies with disrupted virus as the antigen was selected to compare the immunoreactivity of viral p31 with those of the two recombinant pretains. This panel included eight sera that were positive and two sera that were negative for antibodies to viral p31 in virus immunoblots. Lysates of pTP31.2 )Section 3.4.2) and pTSp31 (Section 3.5) transformants were electrophoresed and electroblotted, and strips of the blots were reacted with individual serum samples (see table below). The eight sera that were positive on viral p31 also reacted with the 30- and 48-kDa bands in lysates of bacterial cells containing pTP31.2 (expressing p31pol) and pTSp31 (expressing SOD-p31pol fusion), respectively. The two sera that were negative on viral p31 were also negative on both of the recombinant proteins. Pooled normal human serum was negative in all three Western blot assays.

The SOD-p31 fusion protein was purified and used as a source of antigen for an ELISA for testing sera for antibodies to p31. Prior to deciding to pursue the fusion protein as a source of antigen for the assay, sera from 300 random blood donors and a panel of 100 sera obtained from high-risk, AIDS, and ARC patients was screened for antibodies to purified human SOD in an ELISA. None of these sera scored positive (data not shown).

The ELISA protocol was as follows: Microtiter plates were coated with 2 μg/ml of SOD-p31 in borate buffer (pH 9). In the diluent was included extract from *E. coli* (pTAC7). This extract was necessary to absorb out antibodies in human sera that reacted with minor contaminants in the purified SOD-p31. The ELISA protocol from this point was identical to the procedure described for other recombinant HIV antigens described above.

Figure 31A:
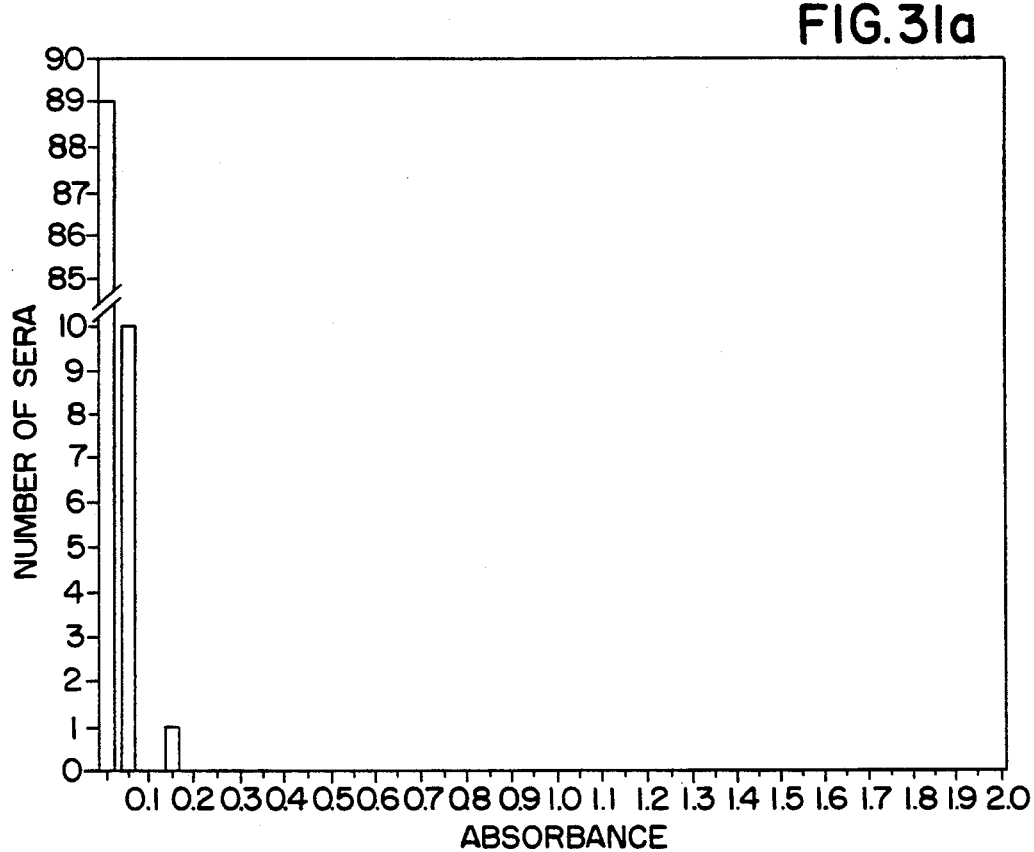
FIG. 31 shows an ELISA survey for p31 antibodies. Panel (a) shows the results for random, normal blood donors. Panel (b) shows the results for virus-seropositive individuals. The shaded bars are for sera that scored negative in the virus immunoblot assays.
Figure 31B:
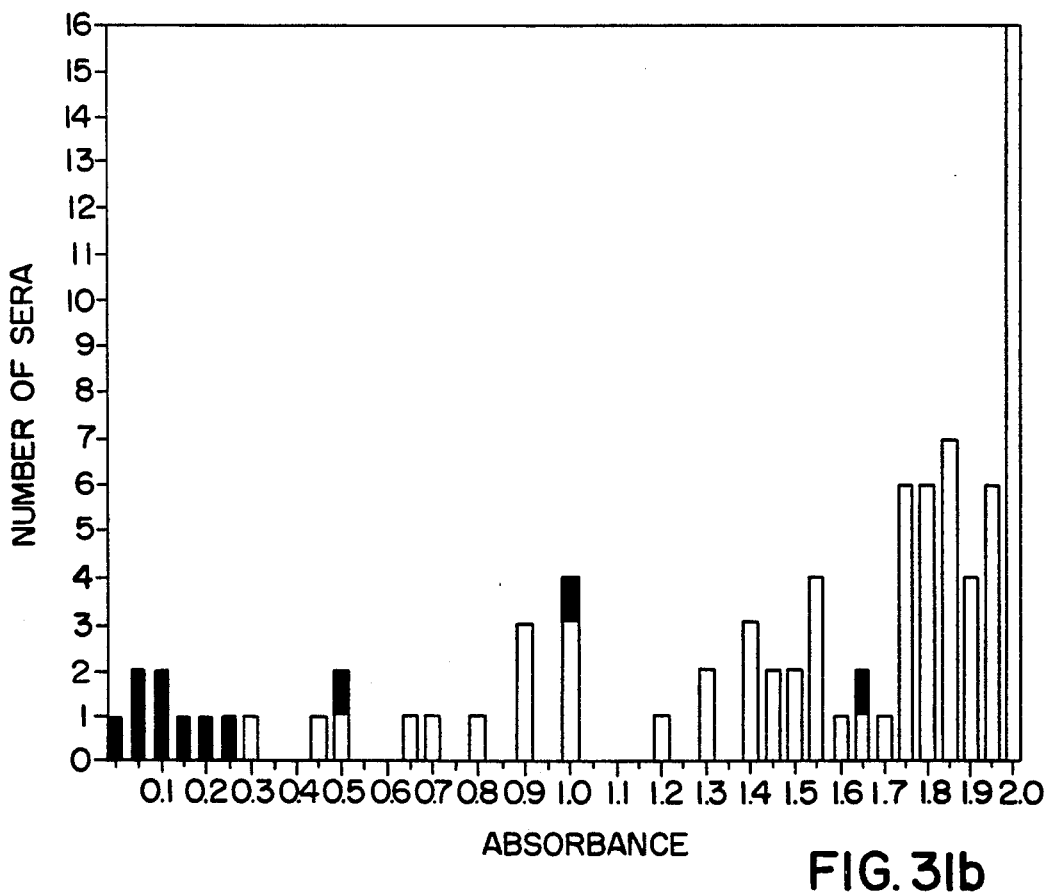

A panel of sera from 100 consecutive blood donors that were all seronegative in the virus ELISA was tested in the p31 ELISA. These sera all scored very low in the assay (FIG. 31a). The average ELISA result for these sera when they were assayed at a 1/100 dilution was 0.026 with a range of 0.001 to 0.117 and a standard deviation of 0.012. The results obtained with 85 virus-seropositive samples are presented in FIG. 31b. The ELISA results with sera that did not react with the p31 band in the virus Western blot assay are indicated by shading. In general, sera that were positive in virus Western blots for p31 antibodies were clearly positive in the p31 antibody ELISA. There were, however, three sera that did not react with p31 in virus immunoblots that were clearly positive in the p31 ELISA.

Three possible explanations for viral p31 immunoblot-negative sera scoring positive in the p31 ELISA were considered. First, the ELISA may have been more sensitive than the virus immunoblot assay for detecting antibodies to p31. Second, these sera may have scored positive in the ELISA owing to immunological reactivity with *E. coli* proteins contaminating the SOD-p31 preparation that were not absorbed out by the bacterial lysate in the antibody diluent. Third, these sera may have scored positive in the ELISA because they contained antibodies to the SOD portion of the fusion protein.

To clarify this, these three sera were tested on blots of directly expressed p31 by using the pTP31.2 lysate, which should contain a much higher concentration of p31 antigen than virus. All three of these sera reacted with the p31 species in this assay (data not shown). Thus, these sera scored positive in the ELISA because of its greater sensitivity than virus immunoblots for detecting p31 antibodies, not because of reaction with *E. coli* contaminants or SOD.

We also tested the remaining eight viral p31 Western blot-negative sera in immunoblot assays of pTP31.2 lysates. The five sera scoring lowest in the ELISA (FIG. 31b) failed to react with p31 in this assay. However, the three remaining sera, scoring between 0.15 and 0.3 in the ELISA, reacted in immunoblots with directly expressed p31 (data not shown). Thus, we concluded that of this panel of 85 seropositive samples, 80 (95%) had detectable antibodies to the p31 antigen.

These data clearly demonstrate the utility of the HIV pol endonuclease polypeptide in serodiagnosing HIV infection. It should be noted that serological results were identical when SOD-p31 produced in yeast was used instead of the bacterially expressed protein.

| Comparison of Western blot results of various virus-seropositive samples in viral p31, recombinant p31 expressed directly in E. coli and as a fusion protein with human SOD | | | |
|---|---|---|---|
| | Reactivity with: | | |
| Serum | Viral p31 | Recombinant p31 | Recombinant SOD-p31 |
| 4607 | + | + | + |
| 4608 | + | + | + |
| 4620 | + | + | + |
| 4625 | + | + | + |
| 4626 | + | + | + |
| 4642 | − | − | − |
| 4643 | + | + | + |
| 4646 | + | + | + |
| 4659 | − | − | − |
| 0036 | + | + | + |
| NHS[b] | − | − | − |

[a]Strips from immunoblots of electrophoresed virus, pTP31.2 extracts, and pTS31 extracts were reacted with a 1/100 dilution of each serum.
[b]NHS, pooled normal human sera obtained from Medical Specialities Laboratories.

7. HIV Immunization

Recombinantly produced viral envelope protein was used to generate anti-HIV antibodies in experimental animals which were capable of neutralizing the infectivity of the virus. The purified env-2 (Section 4.2.2) was injected into both mice and guinea pigs and the sera had neutralizing activity in an in vitro neutralization assay.

The HIV neutralization assay that was developed measures the ability of serum specimens to neutralize directly the infectivity of HIV in a tissue culture system (described in commonly owned, co-pending U.S. patent application Ser. No. 946,539, the disclosure of which is hereby incorporated by reference). Diluted sera are mixed with an equal volume of virus inoculum, the mixture is incubated for 30 minutes at room temperature and then 0.1 ml of the mixture is added to a 1 ml culture of permissive HUT-78 cells ($1 \times 10^4$ cells/ml) in 24-well microtiter plates. Seven days later the cells are harvested, lysed with 1% Triton X-100 in PBS.

Infection is monitored by measuring the levels of intracellular p25gag antigen with a capture enzyme-linked immunosorbent assay (ELISA) Steimer et al. (1986) Virology 150:283-290. This assay uses a murine monoclonal antibody immobilized on the assay plate to capture p25gag and a rabbit polyclonal antiserum as the detecting reagent. The virus inoculum that was used for all strains of HIV was adjusted to yield 40-80 ng/ml of intracellular p25gag and approximately 10% of the HUT-78 cells in the culture were infected under these conditions.

7.1. Env-2 immunization of mice

In order to test if env-2 polypeptide derived from yeast was capable of eliciting neutralizing antibodies, mice were immunized with env-2 (Section 4.2.2).

Three Balb/c mice were injected three times with 10 μg of env-2 in alum at two week intervals. The mice were bled one week following the third injection and their sera tested for env-2 antibodies in ELISA. Normal mouse serum from a pool of sera obtained from unimmunized Balb/c mice, was included as a control. The sera was diluted 1:10, and by serial 2-fold dilutions, and reacted in the env-2 ELISA. All three mice had mounted an antibody response to the injected env-2 (see below). The sera were then tested in the neutralization assay at a 1:20 dilution. Sera from two of the immunized mice showed significant neutralization of HIV at a 1:20 dilution (see below).

| Serum sample | Env-2 antibody titer | Neutralization activity (percent neutralization) |
|---|---|---|
| normal | <10 | 18 |
| mouse 1 | 420 | 97 |
| mouse 2 | 230 | 4 |
| mouse 3 | 200 | 76 |

7.2. Env-2 immunization of guinea pigs

Twelve Hartley guinea pigs were used to study the effectiveness of the env-2 polypeptide (Section 4.2.2) in eliciting neutralizing antibodies. The sera were also tested for their ability to neutralize different strains of the HIV virus.

Six of the guinea pigs were immunized with 50 μg of antigen with adjuvant (see below) and six were immunized with the adjuvant alone according to the following protocol:

Adjuvant: contains 0.5 mg Monophosphoryl Lipid A (MPL), 0.5 mg Trehalose Dimycolate (TDM), 0.5 mg Cell Wall Skeleton (CWS) (isolated from attenuated tubercle bacillus: Bacillus-Calmette-Guerin) lyophilized in 40 μl of oil (Squalene) and 0.2% Tween 80 in water (adjuvant obtained from Ribi Immunochem Research, Inc., Hamilton, Mont.).

Vaccine: Reconstitute the adjuvant by adding 600 μl of PBS and vortexing vigorously for 2-3 minutes. Mix 300 μl of the adjuvant with 300 μg of the env-2 polypeptide and PBS to bring total volume to 600 μl. Vortex vigorously for 2-3 minutes. Inject each guinea pig with 100 μl of vaccine in foot pad.

Control: Dilute remaining 300 μl of adjuvant with 300 μl of PBS and vortex vigorously for 2-3 minutes. The six control guinea pigs are injected with 100 μl each in foot pad.

Immunization: Two to four days prior to immunization Schedule: obtain "prebleed" blood sample for guinea pigs:
Day 0: Primary immunization;
Day 21: second immunization;
Day 28: obtain first blood sample;
Day 42: third immunization;
Day 49: obtain second blood sample.

| | Results: | | |
|---|---|---|---|
| | ELISA Titers[2] Bleed 1 | against env-2 Bleed 2 | Neutralization Titer[2] of Bleed 2 |
| Immunized Guinea pigs[1] | | | |
| A | 81 | n.d. | n.d. |
| B | 171 | 605 | <10 |
| C | 111 | n.d. | n.d. |
| D | 510 | 1,274 | <10 |

-continued

| | Results: | | |
|---|---|---|---|
| | ELISA Titers[2] Bleed 1 | against env-2 Bleed 2 | Neutralization Titer[2] of Bleed 2 |
| E | 501 | 10,756 | 220 |
| F | n.d. | 4,050 | 40 |
| Control Guinea Pigs[1] | | | |
| A' | <25 | <25 | <10 |
| B' | <25 | <25 | <10 |
| C' | <25 | <25 | <10 |
| D' | <25 | <25 | <25 |
| E' | <25 | <25 | n.d. |
| F' | <25 | <25 | n.d. | n.d. = not determined
[1]sera was heat inactivated
[2]dilution that gives 50% of inhibition of viral inoculum (ARV-2)

The sera from guinea pigs E and F were tested for their ability to neutralize various isolates of HIV which have been associated with AIDS.

| HIV Isolate | Neutralizing Titer of Guinea Pig E, Bleed 2 | Neutralizing Titer of Guinea Pig F, Bleed 2 |
|---|---|---|
| LAV[1] | 70 | 30 |
| ARV-2[2] | 220 | 40 |
| ARV-3[3] | <10 | n.d. |
| ARV-33[3] | <10 | n.d. |
| HIV-Zr6[4] | <10 | n.d. |

[1]Barre-Sinoussi et al. (1983) Science 220:868-871.
[2]Levy et al. (1984) Science 225:740-842.
[3]Staben et al. (1986) in: Vaccines 86, Cold Spring Harbor Laboratory, New York, pp. 345-350.
[4]Srinivassen et al. (1987) Gene 52:71-82.

8. Deposits of Biological Materials

Samples of organisms that contain HIV clones or express the above-described hTLR polypeptides were deposited at the American Type Culture Collection (ATCC), 12301 Parklawn Drive, Rockville, Md. under the provisions of the Budapest Treaty. The accession numbers and dates of these deposits are listed below.

| Deposited Material | ATCC Accession No. | Deposit Date |
|---|---|---|
| λ-ARV-2(7D) | 40143 | 26 October 1984 |
| λ-ARV-2(8A) | 40144 | 26 October 1984 |
| λ-ARV-2(9B) | 40158 | 25 January 1985 |
| E. coli HB101 (pSV7c/env) | 67593 | 23 December 1987 |
| E. coli HB101 (pCMV6ARV120tpa) | — | — |
| E. coli D1210 (pGAG25-10) | 53246 | 27 August 1985 |
| E. coli D1210 (pSOD/env5b) | — | — |
| E. coli D1210 (pTP31.2) | — | — |
| E. coli D1210 (pII-3) | 67549 | 28 October 1987 |
| Saccharomyces cerevisiae P017 (pC1/1 (pSP31-GAP-ADH2) | 20768 | 27 August 1985 |
| Saccharomyces cerevisiae 2150 (pDPC303) | 20769 | 27 August 1985 |
| Saccharomyces cerevisiae 2150-2-3 (pAB24-GAP-env2) | 20827 | 23 December 1986 |
| Saccharomyces cerevisiae 2168 (pBS24/SOD-SF2env4) | — | — |
| Saccharomyces cerevisiae AB110 (pC1/1-p25-ADH-GAP) | — | — |
| Saccharomyces cerevisiae AB116 (pBS24.1/SOD-SF2env4-5) | — | — |
| Saccharomyces cerevisiae (pAB24/RT4) | — | — |
| Saccharomyces cerevisiae JSC302 (pC1/1-GAP-p53) | — | — |

These deposits are provided for the convenience of those skilled in the art. These deposits are neither an admission that such deposits are required to practice the present invention, nor that equivalent embodiments are not within the skill of the art in view of the present disclosure. The public availability of these deposits is not a grant of a license to make, use or sell the deposited materials under this or any other patent. The nucleic acid sequences of the deposited materials are incorporated in the present disclosure by reference and are controlling if in conflict with any sequence described herein.

Although the foregoing invention has been described in some detail by way of illustration and example for purposes of clarity of understanding, it will be obvious that changes and modifications may be practiced within the scope of the appended claims.

We claim:

1. In an immunoassay to detect the presence of antibodies to a human immunodeficiency virus (HIV) in a human sample comprising contacting said sample with an immunogenic polypeptide comprising an amino acid sequence from the envelope (env) domain of said HIV and determining whether antibodies are bound to said immunogenic polypeptide, the improvement comprising employing as said immunogenic polypeptide a recombinant polypeptide that is the expression product of cellular hosts transformed by a heterologous expression vector comprising a DNA sequence encoding said recombinant polypeptide under the control of transciptional and translational initiation and termination regulatory sequences functional in said cellular hosts.

2. A method of detecting antibodies to a human immunodeficiency virus (HIV) in a human sample comprising:
   a) providing a solid support having bound thereto a recombinant polypeptide comprising at least an immunogenic portion of the envelope (env) domain of said HIV, wherein said recombinant polypeptide is the expression product of cellular hosts transformed by a heterologous expression vector comprising a DNA sequence encoding said recombinant polypeptide under the control of transciptional and translation initiation and termination regulatory sequences functional in said cellular hosts;
   b) contacting said solid support with said human sample to provide a sample-contacted support;
   c) washing said sample-contacted support to provide a washed support; and
   d) determining whether human antibodies are bound to said washed support.

3. The method claim 1 wherein said cellular hosts are microorganisms.

4. The method claim 2 wherein said cellular hosts are microorganisms.

5. The method of claim 3 wherein said microorganisms are *E. coli*.

6. The method of claim 4 wherein said microorganisms are *E. coli*.

7. The method of claim 3 wherein said microorganisms are *S. cerevisiae*.

8. The method of claim 4 wherein said microorganisms are *S. cerevisiae*.

9. The method of claim 1 wherein said cellular hosts are mammalian cells.

10. The method of claim 2 wherein said cellular hosts are mammalian cells.

11. The method of claim 1 wherein said recombinant polypeptide is not glycosylated.

12. The method of claim 2 wherein said recombinant polypeptide is not glycosylated.

13. The method of claim 1 wherein said human sample comprises serum.

14. The method of claim 2 wherein said human sample comprises serum.

15. The method of claim 2 wherein step (d) comprises contacting said washed support with labeled antibodies to human Ig and the specific binding of said labeled antibodies to said washed support is measured.

16. The method of claim 15 wherein said labeled antibodies bound to said washed support are measured by an enzyme label.

17. An article of manufacture adapted for use in an immunoassay for antibodies to a human immunodeficiency virus (HIV) comprising a solid support having bound thereto a recombinant polypeptide comprising at least an immunogenic portion of the envelope (env) domain of said HIV, wherein said recombinant polypeptide is the expression product of cellular hosts transformed by a heterologous expression vector comprising a DNA sequence encoding said recombinant polypeptide under the control of transciptional and translation initiation and terminator regulatory sequences functional in said cellular hosts.

18. The article of manufacture of claim 17 wherein said recombinant polypeptide is not glycosylated.

19. The article of manufacture of claim 17 wherein said cellular hosts are microorganisms.

20. The article of manufacture of claim 19 wherein said microorganisms are *E. coli*.

21. The article of manufacture of claim 19 wherein said microorganisms are *S. cerevisiae*.

22. The article of manufacture of claim 17 wherein said cellular hosts are mammalian cells.

* * * * *

UNITED STATES PATENT AND TRADEMARK OFFICE
CERTIFICATE OF CORRECTION

PATENT NO. : 5,156,949
DATED : October 20, 1992
INVENTOR(S) : P. Luciw et al

Page 1 of 4

It is certified that error appears in the above-indentified patent and that said Letters Patent is hereby corrected as shown below:

On the title page: Item [56]

under U.S. PATENT DOCUMENTS, insert (after 4,520,113 5/1985 Gallo et al.) --436/504--. On page 1, right hand column, under OTHER PUBLICATIONS, the page citation for "Shaw et al. in *AIDS: Papers from Science, 1982-1985*, pp. 356-268 (R. Kulstad ed. 1986)" should be --Shaw et al. in *AIDS: Papers from Science, 1982-1985*, pp. 356-368 (R. Kulstad ed. 1986).--.
On page 2, "Montagomier, et al.," should be --Montagnier, et al.,--; and "Leciw, et al," should be --Luciw, et al,--.
Column 5, line 11, change "( )" to --(◊)--.
Column 6, line 14, change "225 840" to --225:840--.
Column 8, line 15, change "reagents  See" to --reagents. See--.
Column 16, line 24, change "Polypectides" to --Polypeptides--.
Column 18, line 16, change "Denhardt x s" to --Denhardt's-- and, at line 32, change "KcnI" to --KpnI--.
Column 19, line 18, change "KcnI" to --KpnI-- and, at line 21, change "KcnI" to --KpnI--.
Column 20, line 5, change "prepared C as" to --prepared as--.
Column 22, line 40, change "...TCTATTC..." to --...TCTAATTC...-- and, at line 42, change "BqlII" to --BglII--.
Column 24, line 39, change "3" to --M13--.
Column 25, line 3, change "tPa" to --tPA--.
Column 29, line 19, change "373∝384;" to --373-384;--.
Column 30, line 21, change "Polyceptides" to --Polypeptides--.
Column 33, line 34, change "p26gag" to --p25gag--.
Column 36, line 35, change "...AGATTAAGG..." to --...AGATAAGG...--.
Column 38, line 14, change "F+" to --F--.
Column 39, line 60, change "MgCl2" to --$MgCl_2$--.
Column 40, line 31, change "b-galactosidase" to --β-galactosidase--.
Column 47, line 66, change "...env4/GAp" to --...env4/GAP--.
Column 48, line 10, change "Bql" to --Bgl-- and, in column 48, at line 16, "(SalI)" should be under "A" of final "AGCT".

UNITED STATES PATENT AND TRADEMARK OFFICE
CERTIFICATE OF CORRECTION

PATENT NO. : 5,156,949
DATED : October 20, 1992
INVENTOR(S) : P. Luciw et al.

It is certified that error appears in the above-indentified patent and that said Letters Patent is hereby corrected as shown below:

```
Column 51, line 12, change "3-52. leu" to --3-52, leu--; at line 13,
     change "2-112. pep" to --2-112, pep--; at line 18, change "24 h
     ih YEP" to --24 h in YEP--.
Column 52, line 9, change "SOD-c31" to --SOD-p31--.
Column 53, line 35, change "leu-/7 1%" to --leu-/7.1%--.
Column 54, line 24, change "pMSF" to --PMSF--.
Column 56, line 19, change "immunoblottinq" to --immunoblotting--.
Column 57, line 3, change "(dT)-5•(dA)n" to --(dT)-5•(dA)n--;  at line 4,
     change "(dG)-15•(rCm)n"   to  --(dG)-15•(rCm)n--.
Column 58, line 39, change "(Nco) GAA TAT" to --(Nco) GGA TAT--.
Column 60, line 34, change "SacI-BclII" to --SacI-BglII--.
Column 73, line 57, change "No. 321-0081)." to --No. 3201-0081).--;
     at line 63, change "vial" to --viral--; at line 65, change
     "pretains" to --proteins--
Column 75, line 15, change "directly in E. coil" to --directly in E.
     coli--.
```

Signed and Sealed this

Twentieth Day of December, 1994

Attest:

BRUCE LEHMAN

*Attesting Officer*       *Commissioner of Patents and Trademarks*

UNITED STATES PATENT AND TRADEMARK OFFICE
CERTIFICATE OF CORRECTION

PATENT NO. : 5,156,949
DATED : October 20, 1992
INVENTOR(S) : P. Luciw et al.

It is certified that error appears in the above-indentified patent and that said Letters Patent is hereby corrected as shown below:

Substitute the following table for that spanning column 77, line 45 through column 78, line 13:

| Deposited Material | ATCC Accession No. | Deposit Date |
|---|---|---|
| λ-ARV-2(7D) | 40143 | 26 October 1984 |
| λ-ARV-2(8A) | 40144 | 26 October 1984 |
| λ-ARV-2(9B) | 40158 | 25 January 1985 |
| *E. coli* HB101 (pSV7c/env) | 67593 | 23 December 1987 |
| *E. coli* HB101 (pCMV6ARV120tpa) | 68249 | 8 March 1990 |
| *E. coli* D1210 (pGAG25-10) | 53246 | 27 August 1985 |
| *E. coli* D1210 (pSOD/env5b) | 74159 | 12 June 1992 |
| *E. coli* D1210 (pTP31.2) | 69014 | 16 June 1992 |
| *E. coli* D1210 (pII-3) | 67549 | 28 October 1987 |
| *Saccharomyces cerevisiae* PO17 (pC1/1 pSP31-GAP-ADH2) | 20768 | 27 August 1985 |
| *Saccharomyces cerevisiae* 2150 (pDPC303) | 20769 | 27 August 1985 |
| *Saccharomyces cerevisiae* 2150-2-3 (pAB24-GAP-env2) | 20827 | 23 December 1986 |

UNITED STATES PATENT AND TRADEMARK OFFICE
CERTIFICATE OF CORRECTION

PATENT NO. : 5,156,949
DATED : October 20, 1992
INVENTOR(S) : P. Luciw et al.

It is certified that error appears in the above-indentified patent and that said Letters Patent is hereby corrected as shown below:

| Deposited Material | ATCC Accession No. | Deposit Date |
|---|---|---|
| *Saccharomyces cerevisiae* [2168] (pBS24/SOD--SF2env4) | 74162 | 16 June 1992 |
| *Saccharomyces cerevisiae* AB110 (pC1/1-p25-ADH-GAP) | 74160 | 12 June 1992 |
| *Saccharomyces cerevisiae* AB116 (pBS24.1/SOD-*SF2env4-5*) | 74158 | 11 June 1992 |
| *Saccharomyces cerevisiae* (pAB24/RT4) | 74163 | 17 June 1992 |
| *Saccharomyces cerevisiae* JSC302 | 74161 | 16 June 1992 |